(12) United States Patent
Nakamura et al.

(10) Patent No.: US 10,679,731 B2
(45) Date of Patent: *Jun. 9, 2020

(54) METHOD FOR DESIGNING RNA BINDING PROTEIN UTILIZING PPR MOTIF, AND USE THEREOF

(71) Applicant: KYUSHU UNIVERSITY, NATIONAL UNIVERSITY CORPORATION, Fukuoka-shi, Fukuoka (JP)

(72) Inventors: Takahiro Nakamura, Fukuoka (JP); Yusuke Yagi, Fukuoka (JP); Keiko Kobayashi, Fukuoka (JP)

(73) Assignee: KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,429

(22) Filed: Jun. 4, 2019

(65) Prior Publication Data

US 2019/0311783 A1  Oct. 10, 2019

Related U.S. Application Data

(62) Division of application No. 15/962,127, filed on Apr. 25, 2018, now Pat. No. 10,340,028, which is a division of application No. 15/335,243, filed on Oct. 26, 2016, now Pat. No. 9,984,202, which is a division of application No. 14/352,697, filed as application No. PCT/JP2012/077274 on Oct. 22, 2012, now Pat. No. 9,513,283.

(30) Foreign Application Priority Data

Oct. 21, 2011 (JP) ................. 2011-231346

(51) Int. Cl.
| | |
|---|---|
| *A61K 38/00* | (2006.01) |
| *G16B 30/00* | (2019.01) |
| *G16B 15/00* | (2019.01) |
| *G16B 35/00* | (2019.01) |
| *G16C 20/60* | (2019.01) |
| *C07K 14/415* | (2006.01) |
| *C12N 15/82* | (2006.01) |
| *C12Q 1/68* | (2018.01) |
| *G01N 33/53* | (2006.01) |
| *G16B 20/00* | (2019.01) |

(52) U.S. Cl.
CPC ............ *G16B 30/00* (2019.02); *C07K 14/415* (2013.01); *C12N 15/8216* (2013.01); *C12N 15/8287* (2013.01); *C12N 15/8289* (2013.01); *C12Q 1/68* (2013.01); *G01N 33/5308* (2013.01); *G16B 15/00* (2019.02); *G16B 35/00* (2019.02); *G16C 20/60* (2019.02); *C07K 2319/85* (2013.01); *C12Q 2522/101* (2013.01); *G16B 20/00* (2019.02)

(58) Field of Classification Search
None
See application file for complete search history.

(56) References Cited

U.S. PATENT DOCUMENTS

| | | |
|---|---|---|
| 2004/0088749 A1 | 5/2004 | Imamura et al. |
| 2004/0117868 A1 | 6/2004 | Imamura et al. |
| 2010/0199376 A1 | 8/2010 | Imamura et al. |
| 2011/0060033 A1 | 3/2011 | Toriyama et al. |

FOREIGN PATENT DOCUMENTS

| | | |
|---|---|---|
| EP | 1382612 A1 | 1/2004 |
| EP | 1 586 652 A1 | 10/2005 |
| EP | 2258165 A1 | 12/2010 |
| JP | 2002355041 A | 12/2002 |
| JP | 2003-289879 A | 10/2003 |
| WO | 2002/088179 A1 | 11/2002 |
| WO | 2009/113249 A1 | 9/2009 |
| WO | 2011072246 A2 | 3/2011 |
| WO | 2011/111829 A1 | 9/2011 |
| WO | 2013/058404 A1 | 4/2013 |
| WO | 2013155555 A1 | 10/2013 |

OTHER PUBLICATIONS

Morgan L Maeder et al. Rapid "Open-Source" Engineering of Customized Zinc-Finger Nucleases for Highly Efficient Gene Modification. Molecular Cell 31, pp. 294-301, Jul. 25, 2008.

Jeffrey C Miller et al. A Tale nuclease architecture for efficient genome editing, Nature Biotechnology, Feb. 2007, vol. 29, No. 2. (8 pages).

Xiaoqiang Wang et al. Modular Recognition of RNA by a Human Pumilio-Homology Domain, Cell, vol. 110, pp. 501-512, Aug. 23, 2002, Plant Biology Division, The Noble Foundation, Ardmore, Oklahoma 73402.

(Continued)

*Primary Examiner* — Jeanette M Lieb
(74) *Attorney, Agent, or Firm* — Westerman, Hattori, Daniels & Adrian, LLP

(57) ABSTRACT

A method for designing a protein capable of binding in an RNA base selective manner or RNA base sequence specific manner is provided. The protein of the present invention is a protein containing one or more of PPR motifs (preferably 2 to 14 PPR motifs) each consisting of a polypeptide of 30- to 38-amino acid length represented by the formula 1 (wherein Helix A is a moiety of 12-amino acid length capable of forming an α-helix structure, and is represented by the formula 2, wherein, in the formula 2, $A_1$ to $A_{12}$ independently represent an amino acid; X does not exist, or is a moiety of 1- to 9-amino acid length; Helix B is a moiety of 11- to 13-amino acid length capable of forming an α-helix structure; and L is a moiety of 2- to 7-amino acid length represented by the formula 3, wherein, in the formula 3, the amino acids are numbered "i" (−1), "ii" (−2), and so on from the C-terminus side, provided that $L_{iii}$ to $L_{vii}$ may not exist), and combination of three amino acids $A_1$, $A_4$ and $L_{ii}$, or combination of two amino acids $A_4$, and $L_{ii}$ is a combination corresponding to a target RNA base or base sequence.

20 Claims, 35 Drawing Sheets

Specification includes a Sequence Listing.

(56) References Cited

OTHER PUBLICATIONS

Jason D. Gillman et al., The petunia restorer of fertility protein is part of a large mitochondrial complex that interacts with transcripts of the CMS-associated locus, Plant J., 2007, vol. 49 No. 2, pp. 217-227.
Sota Fukii et al., Selection patterns on restorer-like genes reveal a conflict between nuclear and mitochondrial genomes throughout angiosperm evolution, Proc. Natl. Acad. Sci. USA, Jan. 25, 2011, vol. 108, No. 4, pp. 1723-1723.
Shuyun Dong et al., Specific and modular binding code for cytosine recognition in Pumilio/FBF (PUF) Rna-binding domains, J. Biol. Cem., Jul. 29, 2011, vol. 286, No. 30, pp. 26732-26742.
Nobuya Koizuka et al., Genetic characterization of a pentatricopeptide repeat protein gene, orf687, that restores fertilit in the cytoplasmic male-sterile kosena radish, Plant j., 2003, vol. 34 No. 4, pp. 407-415.
Alice Barkan et al., A combinatorial amino acid code for RNA recognition by pentatricopeptide repeat proteins, PloS Genet., Aug. 16, 2012, vol. 8 No. 8, e1002910.
Keiko Kobayashi et al., Identification and caracterizaiton of the RNA binding surface of the pentaricopeptide repeat protein, Nucleic Acids REs., Mar. 2012., vol. 40, No. 6, pp. 2712-2723, Epub. Nov. 29, 2011.
Takahiro Nakamura et., Mechanistic insight into pentatricopeptide repeat proteins as sequence-specific RNA-Binding proteins for organellar RNAs in plants, Plant Cell Physiol., Jul. 2012, vol. 53, No. 7, pp. 1171-1179, Epub. Sep. 5, 2012.
International Preliminary Report on Patentability (Chapter II of the Patent Coperation Treaty) (Form PCT/IPEA/416) of the International Application No. PCT/JP2012/077274 dated Feb. 25, 2014 with form PCT/IPEA/409. (24 pages).
Cheom-Gil Ceong et al., Engineering RNA sequence specificity of Pumilio repeats, PNAS, Sep. 12, 2006, vol. 103, No. 37 pp. 13635-13639.
Ian D. Small et al., The PPR motif—a TPR-related motif prevalent in plant organellar proteins, TIBS Feb. 25, 2000, Station de Genetiquem INRA, Route de st-Cyr.
Jesse D Woodson et al. Coordination of gene expression between organellar and nuclear genomes, Nature Reviews Genetics, vol. 9, May 2008.
Sophie Desloire et al., "Identification of the fertility restoration locus, Rfo, in radish, as a member od the pentatricopeptide-repeat protein family", Jun. 1, 2003, EMBO reports vol. 4, No. 6, pp. 558-594, cited in Extended European Search Report dated Jun. 2, 2015.
Extended European Search Report dated Jun. 2, 2015, issued in corresponding Patent Application No. 12841435.6 (7 pages).
Office Action dated Mar. 21, 2017, issued in counterpart European Application No. 12 841 435.6. (5 pages).
Office Action dated Mar. 31, 2017, issued in counterpart Australian Application No. 2012326971. (4 pages).
Office Action dated Aug. 1, 2017, issued in counterpart Japanese Application No. 2017-112765, with English translation (6 pages).
Office Action dated Aug. 1, 2017, issued in counterpart Japanese Application No. 2017-112764, with English translation (9 pages).
Office Action dated Nov. 30, 2017, issued in counterpart European Application No. 12 841 435.6 (5 pages).
English machine translation of WO2011/111289, cited in specification and international search report, previously filed with English abstract only on Oct. 26, 2016.
International Search Report dated Jan. 22, 2013, issued in corresponding International Application No. PCT/JP2012/077274, with forms PCT/ISA/210, PCT/ISA/237 and English translation, (13 pages).
Examination Report date Jan. 3, 2019, issued in counterpart Australian application No. 2017254874. (3 pages).
Office Action dated Jan. 8, 2019, issued in counterpart Japanese application No. 2017-244766, with English translation. (12 pages).

FIG. 1A
```
                    10 12 14 16 18 20 22 24 26 28 vii v iii  i
          1 2 3 4 5 6 7 8 9 11 13 15 17 19 21 23 25 27 29 vi iv ii
    P  vtYntlIsglckaGrleeAlelfeeMkek-GiaPdv
    S  vvynaLidmYaKcGdleeArkvFdeMper-----dv
    L1 fTlasvLkACaslgaLslGkqiHgyviKs-Gfdsde
    L2 vTFlgVLsACSHsGLVeeGLeyFesMkekYGIePde
       *  *                                *
```
FIG. 1B   FIG. 1C
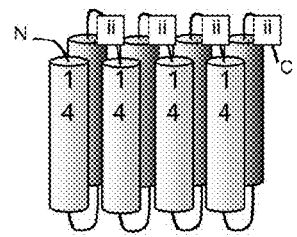 

FIG. 2

| Name | AGI number | Localization | PPR code | Target RNA sequence | Editing site | (ref)* |
|---|---|---|---|---|---|---|
| AHG11 | At2g44880 | - | FND-FTD-YTS-VTD-VNT-ITN-VND-VLK-KTD-AND-ILK-EGN | - | Unknown* | - |
| CLB19 | At1g05750 | Chl | VTN-IH-MTN-VNW-AND-VIN-FNT-VND-VTR-EGI | acuagugcaa | rpoA(78691) | [1] |
| | | | | aguagcccaa | clpP(69942) | |
| CRR21 | At5g55740 | Chl | EGN-YTN-FAD-FPC-FSN-VNT-VSD-ITD-VND-VAD-VSD-INN-INN-ITN-FTL-STE-PND-ITC-EGD | augaacagcagucaaauag | ndhD(118785) | [2] |
| CRR22 | At1g11290 | Chl | FTL-VHV-YTD-FTD-VNS-IVL-NTN-VNT-VMN-SNT-VND-FVN-FTH-TNN-VLS-DGA | aagcuuaccuuagcca | ndhB(96419) | [3] |
| | | | | uaugcagcuucaaacau | ndhD(116281) | |
| | | | | uaacuuaauccuagauca | rpoB(25779) | |
| CRR28 | At1g59720 | Chl | FGS-FND-HPD-YNS-VND-YQD-LND-ANN-VVA-EGD | aucuuugcag | ndhB(96698) | [3] |
| | | | | aauaaugcag | ndhD(116290) | |
| CRR4 | At2g45350 | Chl | FND-FSD-FND-VNN-IND-INW-TDD-VND-TVG-KVS-DND-IVR-OGN | uaucuugucuuua | ndhD(117166) | [4] |
| LOI1 | At4g14850 | Mt | DGP-FNN-VTN-FPD-FCN-ENN-ICD-SNW-SAS-FST-FSN-VNN-MVG-EST | ugauacgauuaauu | nad4(161816) | [5] |
| | | | | uaauaaccuuauuc | cox3(218701) | |
| | | | | uaauauugugacuu | ccb203(257133) | |
| LPA66 | At5g48910 | Chl | LAN-FNN-FPD-FSE-VNS-VNN-VVD-VSN-ISS-VIR-EGD | uguaccuaacg | psbF(63985) | [6] |
| MEF1 | At5g52630 | Mt | NCI-LNS-TSD-HPD-FSN-VSN-YSS-FSN-GNN-ILT-KAW | accuacuucaau | rps4(82101) | [7] |
| | | | | acagaagucuu | nad7(137931) | |
| | | | | aacgaaucccua | nad2(329886) | |
| MEF9 | At1g62260 | Mt | VNW-TSD-FNW-ATA-VLL-YNN-VND-INW-MSH-VND-HTD-PNE-INS-IVC-ESD | uucaagcuuuaccau | nad7(133233) | [8] |
| MEF14 | At3g26780 | Mt | FNT-SPD-FSI-SSD-MVG-SND-VNN-ISD-ITN-FITN-VG-EGG | aguaccuccaagcu | matR(144418) | [9] |
| MEF18 | At5g19020 | Mt | RVN-YND-ANS-VTN-VAR-FTN-VND-VGS-VVY-FAH-AND-FND-IVN-NAT-SNN-IVD-KGD | uccauaaauucuacg | nad4(167599) | [10] |
| MEF19 | At3g05240 | Mt | ISS-YND-FPN-YTN-VGN-TVN-ITT-VND-VLD-ACD-ITD-ILT-EGN | uuauugauuggua | ccb206(239125) | [10] |
| MEF20 | At3g19970 | Mt | RVS-LTW-AGT-TVG-FTN-FTN-ITV-EGD | caacgaaag | rps4(82891) | [10] |
| MEF21 | At2g20540 | Mt | FTN-FND-FPH-VND-INW-ASD-IIQ-GND-ISN-ILK-EGD | acuccgauucg | cox3(218536) | [10] |
| MEF22 | At3g12770 | Mt | FTQ-FND-FPD-FNT-VTD-VVE-DIN-IND-ITD-FSD-VSN-VLQ-QAG | ugcgcuucaauc | nad5(260858) | [10] |
| otp80 | At5g39200 | Chl | FPN-YTN-VSS-SLD-VTD-VTN-FVS-FND-INN-VVG-EGD | ugucgaaucag | rpl23(86055) | [11] |
| otp81 | At2g29760 | Chl | FNN-YPD-FNC-VNS-VVN-TND-VTW-ASN-IVN-HSD-FSN-VTE-KAS | auucuuuugaaa | rps12(69553) | [11] |
| otp82 | At1g08070 | Chl | LNN-YPD-YTY-AKD-VND-SVN-KND-INN-VLA-STS-SND-IVK-EGD | uuaguuucuugg | ndhG(118858) | [11] |
| | | | | guagcugcuucag | ndhB(95644) | [11] |
| otp84 | At3g57430 | Chl | EID-YP5-TNN-VNS-FVN-FND-VND-FSN-FSW-AAN-TAD-FNW-TTN-IMD-ASN-INN-VIS-DAN | auccacuuacuucuauua | ndhF(112349) | [11] |
| | | | | ugcauuaauuauuacua | psbZ(35860) | [11] |
| | | | | gugugauagcauuacua | ndhB(94999) | [11] |
| otp85 | At2g02980 | Chl | VND-YND-YPC-VNN-ILY-KTD-QSD-ILS-KGL | augcguca | ndhD(116494) | [11] |
| otp86 | At3g63370 | Chl | FGT-FNG-SPT-FND-VNN-YVE-YND-VND-VTN-QND-ITD-MGD-VND-VTD-VLE-SVG-LTD-ILW-EVT | uaucauuugauucgau | rps14(37161) | [11] |
| otp87 | At1g74600 | Mt | FKD-VNN-IGY-VSN-YND-YSD-FTS-VTN-CTD-SAR-NND-FCD-TSD-AAD-SAG-DSD-VSD-FSE-SSD-ITD-VVE-RVW | ccaagacgacuagaaagcca | nad7(132094) | [12] |
| | | | | acuuccgauaacgcgaagua | atp1(82180) | |
| SLO1 | At2g22410 | Mt | FND-FPV-IND-VND-VIT-PNT-VTW-AGD-IIN-ATN-LTD-IIQ-KSD | uouccgaaggcg | nad4(162141) | [13] |
| | | | | auucccacuccagcc | nad9(23908) | |
| YS1 | At3g22690 | Chl | FND-YPD-FNW-SCN-VVN-LSN-DND-ILW-NNT-VNW-TSD-VMD-RTD-STD-VVE-VGN | aagaauucccuuggaa | rpoB(25779) | [14] |
| PpPPR_56 | - | Mt | FVN-HNS-ANN-GMD-RTD-ITN-IVD-RTD-VND-ILD-RTN-VND-VVD-SND | uuuggaagucacca | nad3eU230S | [15] |
| | | | | uauagacggaucc | nad4eU272S | [15] |
| PpPPR_71 | - | Mt | RVN-YNT-VNS-ILD-RTD-SNN-ILD-RTD-VTD-IMD-LTD-VSD-VIH-PND-INN-VVT-KGD | uuccacagugcuccuu | ccmFCeU122SF | [16] |
| PpPPR_77 | - | Mt | AVD-FND-INN-IID-RND-VND-VID-RTD-VNN-TLD-QND-ING-VLN-HND-IND-IAD-NND-MTV-SSD-GND-VNN-FVD-RAN-VND-STT-EGN | caauuacuaucaaagcuauuggacau | cox2eU270RW | [15] |
| | | | | acuuuggccuugaagcagcugcuagg | cox3eU733RW | |
| PpPPR_78 | - | Mt | SMD-YNT-HND-TMD-KNS-VTN-IID-ATD-INN-IVD-GND-ITN-VTD-HND-VND-VID-SNN-IND-VVT-EGN | uccugaaugcuaauucaa | cox1eU755SL | [17] |
| | | | | acgauaugacuauauuuaaa | rps14eU137SL | |
| PpPPR_79 | - | Mt | YVN-YNS-VND-FVD-TND-VTS-IMD-RTD-IND-ATD-RND-VTN-IMD-AND-VNN-AVT-KAN | acuuucgacuacuuuu | nad5eU598RC | [17] |
| PpPPR_91 | - | Mt | SGN-NGD-YND-VSN-ILD-ATN-VTN-VVD-INS-MGN-VMD-STN-VTN-VND-VID-VTD-VNN-ITR-QGD | ugcacaauaggauugcau | nad5eU730RW | [15] |

*[References]
1. Chateigner-Boutin, A.L., et al., Plant J., 2008. 56:590-602
2. Okuda, K., et al., Proc. Natl. Acad. Sci. USA, 2007. 104:8178-8183.
3. Okuda, K., et al., Plant Cell, 2009. 21:146-156.
4. Kotera, E., M. Tasaka, and T. Shikanai, Nature, 2005. 433: p. 326-330.
5. Tang, J., et al., Plant J., 2010. 61:456-466.
6. Cai, W., et al., Plant Physiol., 2009. 150:1260-1271.
7. Zehrmann, A., et al., Plant Cell, 2009. 21:558-567.
8. Takenaka, M., Plant Physiol., 2009. 152:939-947.
9. Verbitskiy, D., et al., FEBS Lett., 2011. 585:700-704.
10. Takenaka, M., et al., J. Biol. Chem., 2010. 285:27122-27129.
11. Hammani, K., et al., Plant Cell, 2009. 21:3686-3699.
12. Hammani, K., et al., J. Biol. Chem., 2011. 286:21361-21371.
13. Sung, T.-Y., et al., Plant J., 2010. 63:499-511.
14. Zhou, W., et al., Plant J., 2009. 58: 82-96.
15. Ohtani, S., et al., Plant Cell Physiol., 2010. 51:1942-1949.
16. Tasaki, E., et al., Plant J, 2010. 62:560-570.
17. Uchida, M., et al., FEBS Lett., 2011. 585:2367-2371.

Alignment P4, Amino acid 4  
Measured value

| | 計 | A | U | G | C |
|---|---|---|---|---|---|
| A | 16.00 | 4.33 | 5.50 | 3.00 | 3.17 |
| C | 5.99 | 4.00 | 0.33 | 1.33 | 0.33 |
| D | 1.00 | 0.00 | 0.00 | 1.00 | 0.00 |
| F | 1.00 | 0.00 | 1.00 | 0.00 | 0.00 |
| G | 25.00 | 8.00 | 6.83 | 8.00 | 2.17 |
| H | 1.00 | 0.67 | 0.33 | 0.00 | 0.00 |
| I | 10.00 | 1.83 | 2.83 | 0.83 | 4.50 |
| K | 2.00 | 0.50 | 0.00 | 1.00 | 0.50 |
| L | 15.00 | 2.33 | 8.33 | 0.00 | 4.33 |
| N | 98.96 | 10.66 | 41.66 | 11.33 | 35.32 |
| M | 3.00 | 0.00 | 2.67 | 0.00 | 0.33 |
| P | 17.00 | 1.00 | 13.83 | 1.67 | 0.50 |
| Q | 1.00 | 0.00 | 1.00 | 0.00 | 0.00 |
| R | 1.00 | 1.00 | 0.00 | 0.00 | 0.00 |
| S | 41.99 | 15.83 | 12.33 | 8.83 | 5.00 |
| T | 53.99 | 26.67 | 7.17 | 16.17 | 4.00 |
| V | 33.00 | 9.50 | 13.17 | 2.83 | 7.50 |
| 計 | 326.92 | 86.32 | 116.98 | 55.98 | 67.64 |

P values  5.126E-07  
Theoretical values (Medians)

| | 計 | A | U | G | C |
|---|---|---|---|---|---|
| | 16.00 | 4.22 | 5.72 | 2.74 | 3.31 |
| | 5.99 | 1.58 | 2.14 | 1.03 | 1.24 |
| | 1.00 | 0.26 | 0.36 | 0.17 | 0.21 |
| | 1.00 | 0.26 | 0.36 | 0.17 | 0.21 |
| | 25.00 | 6.60 | 8.94 | 4.28 | 5.17 |
| | 1.00 | 0.26 | 0.36 | 0.17 | 0.21 |
| | 10.00 | 2.64 | 3.58 | 1.71 | 2.07 |
| | 2.00 | 0.53 | 0.72 | 0.34 | 0.41 |
| | 15.00 | 3.96 | 5.37 | 2.57 | 3.10 |
| | 98.96 | 26.12 | 35.40 | 16.94 | 20.47 |
| | 3.00 | 0.79 | 1.07 | 0.51 | 0.62 |
| | 17.00 | 4.49 | 6.08 | 2.91 | 3.52 |
| | 1.00 | 0.26 | 0.36 | 0.17 | 0.21 |
| | 1.00 | 0.26 | 0.36 | 0.17 | 0.21 |
| | 41.99 | 11.08 | 15.02 | 7.19 | 8.69 |
| | 53.99 | 14.25 | 19.32 | 9.24 | 11.17 |
| | 33.00 | 8.71 | 11.80 | 5.65 | 6.83 |
| | 326.92 | 86.30 | 116.95 | 55.97 | 67.63 |

Alignment P4, Amino acid 5  
Measured value

| | 計 | A | U | G | C |
|---|---|---|---|---|---|
| A | 73.979 | 13.165 | 28.658 | 15.662 | 16.494 |
| C | 26.995 | 7.666 | 9.499 | 8 | 1.83 |
| D | 3.999 | 2.333 | 0.333 | 1.333 | 0 |
| E | 4 | 1 | 2 | 0 | 1 |
| F | 6 | 0 | 4.5 | 0 | 1.5 |
| G | 34.984 | 8.329 | 12.331 | 6.163 | 8.161 |
| H | 2 | 0.5 | 1 | 0 | 0.5 |
| I | 5 | 1 | 1 | 0.5 | 2.5 |
| K | 6.999 | 2.666 | 3.333 | 0 | 1 |
| L | 5 | 1 | 1 | 1 | 2 |
| N | 7.999 | 4.333 | 2 | 0 | 1.666 |
| S | 94.974 | 28.494 | 34.992 | 10.995 | 20.493 |
| T | 40.995 | 11.332 | 11.665 | 9.166 | 8.832 |
| V | 10.999 | 2.5 | 4.333 | 2.5 | 1.666 |
| Y | 2.995 | 1.999 | 0.333 | 0.663 | 0 |
| 計 | 326.92 | 86.317 | 116.98 | 55.982 | 67.642 |

P values  0.739419764  
Theoretical values (Medians)

| | 計 | A | U | G | C |
|---|---|---|---|---|---|
| | 73.979 | 19.528 | 26.464 | 12.665 | 15.303 |
| | 26.995 | 7.1258 | 9.6569 | 4.6215 | 5.5841 |
| | 3.999 | 1.0556 | 1.4306 | 0.6846 | 0.8272 |
| | 4 | 1.0559 | 1.4309 | 0.6848 | 0.8274 |
| | 6 | 1.5838 | 2.1464 | 1.0272 | 1.2411 |
| | 34.984 | 9.2346 | 12.515 | 5.9892 | 7.2367 |
| | 2 | 0.5279 | 0.7155 | 0.3424 | 0.4137 |
| | 5 | 1.3198 | 1.7886 | 0.856 | 1.0343 |
| | 6.999 | 1.8475 | 2.5037 | 1.1982 | 1.4478 |
| | 5 | 1.3198 | 1.7886 | 0.856 | 1.0343 |
| | 7.999 | 2.1115 | 2.8615 | 1.3694 | 1.6546 |
| | 94.974 | 25.07 | 33.975 | 16.259 | 19.646 |
| | 40.995 | 10.821 | 14.665 | 7.0183 | 8.4801 |
| | 10.999 | 2.9034 | 3.9346 | 1.883 | 2.2752 |
| | 2.995 | 0.7906 | 1.0714 | 0.5127 | 0.6195 |
| | 326.92 | 86.30 | 116.95 | 55.97 | 67.63 |

FIG. 8

| PPR code | occurrence of the code | Nucleotide occurrence frequency | | | | ²Scoring matrix | | | | ³Probability matrix (for MEME) | | | |
|---|---|---|---|---|---|---|---|---|---|---|---|---|---|
| | | A | G | U | C | A | G | U | C | A | G | U | C |
| VND | 16 | 0.50 | 0.00 | 10.17 | 5.33 | -3.74 | -2.75 | 4.42 | 2.01 | 0.03 | 0.00 | 0.64 | 0.33 |
| FND | 12 | 1.83 | 1.00 | 6.83 | 2.33 | -1.34 | -1.06 | 2.53 | -0.16 | 0.15 | 0.08 | 0.57 | 0.19 |
| EGD | 7 | 0.00 | 7.00 | 0.00 | 0.00 | -1.85 | 5.80 | -2.51 | -1.45 | 0.00 | 1.00 | 0.00 | 0.00 |
| VNN | 7 | 1.33 | 0.00 | 0.33 | 5.33 | -0.52 | -1.20 | -2.18 | 3.88 | 0.19 | 0.00 | 0.05 | 0.76 |
| FSN | 6 | 4.67 | 0.33 | 0.33 | 0.67 | 3.06 | -0.70 | -1.82 | -0.58 | 0.78 | 0.06 | 0.06 | 0.11 |
| VTN | 6 | 3.50 | 1.50 | 0.00 | 1.00 | 1.91 | 0.47 | -2.15 | -0.24 | 0.58 | 0.25 | 0.00 | 0.17 |
| INN | 5 | 0.00 | 0.00 | 1.83 | 3.17 | -1.32 | -0.86 | 0.04 | 2.13 | 0.00 | 0.00 | 0.37 | 0.63 |
| ITD | 5 | 0.00 | 3.00 | 1.00 | 1.00 | -1.32 | 2.14 | -0.79 | -0.04 | 0.00 | 0.60 | 0.20 | 0.20 |
| FTN | 4 | 4.00 | 0.00 | 0.00 | 0.00 | 2.94 | -0.69 | -1.44 | -0.83 | 1.00 | 0.00 | 0.00 | 0.00 |
| TSD | 4 | 0.33 | 0.50 | 2.50 | 0.67 | -0.73 | -0.19 | 1.06 | -0.16 | 0.08 | 0.13 | 0.63 | 0.17 |
| VNS | 4 | 0.00 | 0.00 | 0.67 | 3.33 | -1.06 | -0.69 | -0.77 | 2.50 | 0.00 | 0.00 | 0.17 | 0.83 |
| VSN | 4 | 2.67 | 0.00 | 1.00 | 0.33 | 1.61 | -0.69 | -0.44 | -0.50 | 0.67 | 0.00 | 0.25 | 0.08 |
| YND | 4 | 0.00 | 0.50 | 3.00 | 0.50 | -1.06 | -0.19 | 1.56 | -0.33 | 0.00 | 0.13 | 0.75 | 0.13 |
| FNN | 3 | 1.67 | 1.33 | 0.00 | 0.00 | 0.87 | 0.81 | -1.08 | -0.62 | 0.56 | 0.44 | 0.00 | 0.00 |
| FNW | 3 | 0.33 | 1.00 | 0.67 | 1.00 | -0.46 | 0.48 | -0.41 | 0.38 | 0.11 | 0.33 | 0.22 | 0.33 |
| FPD | 3 | 0.00 | 0.00 | 3.00 | 0.00 | -0.79 | -0.52 | 1.92 | -0.62 | 0.00 | 0.00 | 1.00 | 0.00 |
| INW | 3 | 0.00 | 0.00 | 2.00 | 1.00 | -0.79 | -0.52 | 0.92 | 0.38 | 0.00 | 0.00 | 0.67 | 0.33 |
| VNW | 3 | 0.50 | 0.00 | 1.00 | 1.50 | -0.29 | -0.52 | -0.08 | 0.88 | 0.17 | 0.00 | 0.33 | 0.50 |
| VSD | 3 | 1.50 | 1.00 | 0.50 | 0.00 | 0.71 | 0.48 | -0.58 | -0.62 | 0.50 | 0.33 | 0.17 | 0.00 |
| VTD | 3 | 0.00 | 3.00 | 0.00 | 0.00 | -0.79 | 2.48 | -1.08 | -0.62 | 0.00 | 1.00 | 0.00 | 0.00 |
| VVE | 3 | 1.00 | 0.00 | 1.50 | 0.50 | 0.21 | -0.52 | 0.42 | -0.12 | 0.33 | 0.00 | 0.50 | 0.17 |
| YPD | 3 | 0.00 | 0.00 | 3.00 | 0.00 | -0.79 | -0.52 | 1.92 | -0.62 | 0.00 | 0.00 | 1.00 | 0.00 |
| YTN | 3 | 0.00 | 1.00 | 2.00 | 0.00 | -0.79 | 0.48 | 0.92 | -0.62 | 0.00 | 0.33 | 0.67 | 0.00 |
| ND | 48 | 3.83 | 5.00 | 30.50 | 8.67 | -8.84 | -3.22 | 13.32 | -1.27 | 0.08 | 0.10 | 0.64 | 0.18 |
| NN | 23 | 3.33 | 3.50 | 4.16 | 11.99 | -2.74 | -0.44 | -4.07 | 7.24 | 0.14 | 0.15 | 0.18 | 0.52 |
| TN | 20 | 12.83 | 2.83 | 2.67 | 1.67 | 7.55 | -0.59 | -4.49 | -2.47 | 0.64 | 0.14 | 0.13 | 0.08 |
| SD | 19 | 4.83 | 6.50 | 5.00 | 2.67 | -0.18 | 3.25 | -1.80 | -1.27 | 0.25 | 0.34 | 0.26 | 0.14 |
| TD | 17 | 2.33 | 11.67 | 1.67 | 1.33 | -2.16 | 8.75 | -4.42 | -2.18 | 0.14 | 0.69 | 0.10 | 0.08 |
| SN | 14 | 9.33 | 0.33 | 3.33 | 1.00 | 5.64 | -2.06 | -1.68 | -1.90 | 0.67 | 0.02 | 0.24 | 0.07 |
| GD | 10 | 0.50 | 8.00 | 1.50 | 0.00 | -2.14 | 6.29 | -2.06 | -2.07 | 0.05 | 0.80 | 0.15 | 0.00 |
| NW | 10 | 1.16 | 1.33 | 3.67 | 3.83 | -1.48 | -0.38 | 0.09 | 1.76 | 0.12 | 0.13 | 0.37 | 0.38 |
| PD | 9 | 0.00 | 0.67 | 7.83 | 0.50 | -2.38 | -0.88 | 4.61 | -1.36 | 0.00 | 0.07 | 0.87 | 0.06 |
| VN | 9 | 2.67 | 1.33 | 3.00 | 2.00 | 0.29 | -0.21 | -0.22 | 0.14 | 0.30 | 0.15 | 0.33 | 0.22 |
| NS | 8 | 0.33 | 0.00 | 2.67 | 5.00 | -1.78 | -1.37 | -0.20 | 3.34 | 0.04 | 0.00 | 0.33 | 0.62 |
| NT | 8 | 1.00 | 1.50 | 0.67 | 4.83 | -1.11 | 0.13 | -2.20 | 3.18 | 0.13 | 0.19 | 0.08 | 0.60 |
| GN | 5 | 3.00 | 0.00 | 2.00 | 0.00 | 1.68 | -0.86 | 0.21 | -1.03 | 0.60 | 0.00 | 0.40 | 0.00 |
| VG | 5 | 1.00 | 0.00 | 1.00 | 3.00 | -0.32 | -0.86 | -0.79 | 1.97 | 0.20 | 0.00 | 0.20 | 0.60 |
| AD | 4 | 0.33 | 3.00 | 0.67 | 0.00 | -0.72 | 2.32 | -0.77 | -0.83 | 0.08 | 0.75 | 0.17 | 0.00 |
| SS | 4 | 0.00 | 0.33 | 2.67 | 1.00 | -1.06 | -0.35 | 1.23 | 0.17 | 0.00 | 0.08 | 0.67 | 0.25 |
| VE | 4 | 1.00 | 0.00 | 2.50 | 0.50 | -0.06 | -0.68 | 1.07 | -0.33 | 0.25 | 0.00 | 0.63 | 0.13 |
| AN | 3 | 0.67 | 0.00 | 1.67 | 0.67 | -0.13 | -0.51 | 0.59 | 0.05 | 0.22 | 0.00 | 0.56 | 0.22 |
| CD | 3 | 1.00 | 1.33 | 0.33 | 0.33 | 0.21 | 0.82 | -0.74 | -0.29 | 0.33 | 0.44 | 0.11 | 0.11 |
| IN | 3 | 0.50 | 0.00 | 1.50 | 1.00 | -0.29 | -0.51 | 0.43 | 0.38 | 0.17 | 0.00 | 0.50 | 0.33 |
| TW | 3 | 1.50 | 0.50 | 1.00 | 0.00 | 0.71 | -0.01 | -0.07 | -0.62 | 0.50 | 0.17 | 0.33 | 0.00 |
| VD | 3 | 0.00 | 1.00 | 1.00 | 1.00 | -0.79 | 0.49 | -0.07 | 0.38 | 0.00 | 0.33 | 0.33 | 0.33 |
| VS | 3 | 1.00 | 0.00 | 1.00 | 1.00 | 0.21 | -0.51 | -0.07 | 0.38 | 0.33 | 0.00 | 0.33 | 0.33 |
| ¹Background frequency | | 0.26 | 0.17 | 0.36 | 0.21 | 0.00 | 0.00 | 0.00 | 0.00 | 0.26 | 0.17 | 0.36 | 0.21 |

¹ The value indicates a probability of nucleotide occurrence for all RNA sequences surrounding the RNA editing sites used to construct the PPR code.
² The scoring matrix is estimated by a subtraction of the background frequency from the nucleotide occurrence frequency of the PPR code.
³ The probability matrix is obtained from the nucleotide occurrence frequency.

FIG. 14

| Protein | At code | | At + Pp code* | |
|---|---|---|---|---|
| | P-value | Rank | P-value | Rank |
| CRR21 | 5.0e-8 | 1 | 1.0e-7 | 1 |
| CRR4 | 6.0e-6 | 1 | 6.0e-6 | 1 |
| LPA66 | 9.0e-5 | 21 | 4.0e-5 | 11 |
| OTP80 | >1.0e-5 | ND | 2.0e-5 | 8 |
| OTP81 | 9.0e-5 | 74 | 5.0e-5 | 45 |
| YS1 | 4.0e-5 | 21 | 3.0e-6 | 2 |

ND, not determined

FIG. 15

Table S5. List of scoring matrix for PPR code extracted from 414 PPR motifs in 24 *Arabidopsis* PPR proteins and 5 *Physcomitrella* PPR proteins

| PPR code | occurrence of the code | Nucleotide occurrence frequency | | | | ² Scoring matrix | | | | ³ Probability matrix (for MEME) | | | | P (nt) | P (RY) | P (WS) |
|---|---|---|---|---|---|---|---|---|---|---|---|---|---|---|---|---|
| | | A | G | U | C | A | G | U | C | A | G | U | C | | | |
| VND | 21 | 0.50 | 0.50 | 14.17 | 5.83 | 0.24 | 0.33 | 13.80 | 5.63 | 0.02 | 0.02 | 0.67 | 0.28 | | | 6.9.E-02 |
| FND | 12 | 1.83 | 1.00 | 6.83 | 2.33 | -3.85 | -2.53 | -0.84 | -1.97 | 0.15 | 0.08 | 0.57 | 0.19 | 7.7.E-02 | 8.8.E-02 | 1.2.E-01 |
| VTN | 10 | 7.50 | 1.50 | 0.00 | 1.00 | 4.37 | -0.52 | -4.39 | -1.46 | 0.75 | 0.15 | 0.00 | 0.10 | | | 1.1.E-01 |
| VNN | 9 | 1.33 | 0.00 | 1.33 | 6.33 | -1.28 | -1.68 | -2.33 | 4.28 | 0.15 | 0.00 | 0.15 | 0.70 | | | 2.2.E-01 |
| EGD | 7 | 0.00 | 7.00 | 0.00 | 0.00 | -2.35 | 5.49 | -3.29 | -1.84 | 0.00 | 1.00 | 0.00 | 0.00 | | | |
| INN | 7 | 0.50 | 0.00 | 2.33 | 4.17 | -1.33 | -1.18 | -0.23 | 2.73 | 0.07 | 0.00 | 0.33 | 0.60 | 1.0.E-01 | | 6.1.E-01 |
| VTD | 6 | 0.00 | 5.00 | 1.00 | 0.00 | -1.83 | 3.82 | -1.56 | -1.43 | 0.00 | 0.83 | 0.17 | 0.00 | | 1.0.E-01 | 1.0.E-01 |
| RTD | 6 | 1.00 | 5.00 | 0.00 | 0.00 | -0.57 | 3.99 | -2.19 | -1.23 | 0.17 | 0.83 | 0.00 | 0.00 | | | 1.0.E-01 |
| FSN | 6 | 4.67 | 0.33 | 0.33 | 0.67 | 3.10 | -0.68 | -1.86 | -0.56 | 0.78 | 0.06 | 0.06 | 0.11 | | 1.0.E-01 | 1.0.E-01 |
| ITD | 5 | 0.00 | 3.00 | 1.00 | 1.00 | -1.57 | 1.99 | -1.19 | -0.23 | 0.00 | 0.60 | 0.20 | 0.20 | 2.8.E-01 | 6.5.E-01 | 1.8.E-01 |
| YND | 5 | 0.00 | 0.50 | 3.00 | 1.50 | -1.31 | -0.34 | 1.17 | 0.48 | 0.00 | 0.10 | 0.60 | 0.30 | 2.4.E-01 | 7.4.E-02 | 6.5.E-01 |
| VSN | 5 | 3.67 | 0.00 | 1.00 | 0.33 | 2.36 | -0.84 | -0.83 | -0.69 | 0.73 | 0.00 | 0.20 | 0.07 | 8.4.E-02 | 3.0.E-01 | 5.3.E-02 |
| VNS | 5 | 0.00 | 0.00 | 0.67 | 4.33 | -1.31 | -0.84 | -1.16 | 3.31 | 0.00 | 0.00 | 0.13 | 0.87 | | | 1.0.E-01 |
| FTN | 4 | 4.00 | 0.00 | 0.00 | 0.00 | 2.69 | -0.84 | -1.83 | -1.02 | 1.00 | 0.00 | 0.00 | 0.00 | | | |
| VSD | 4 | 1.50 | 1.00 | 0.50 | 1.00 | 0.46 | 0.33 | -0.96 | 0.18 | 0.38 | 0.25 | 0.13 | 0.25 | 9.2.E-01 | 6.2.E-01 | 1.0.E+00 |
| IND | 4 | 1.00 | 0.00 | 3.00 | 0.00 | -0.04 | -0.67 | 1.54 | -0.82 | 0.25 | 0.00 | 0.75 | 0.00 | 1.1.E-01 | 3.2.E-01 | |
| ITN | 4 | 4.00 | 0.00 | 0.00 | 0.00 | 2.96 | -0.67 | -1.46 | -0.82 | 1.00 | 0.00 | 0.00 | 0.00 | | | |
| IMD | 4 | 0.00 | 0.00 | 3.00 | 1.00 | -1.04 | -0.67 | 1.54 | 0.18 | 0.00 | 0.00 | 0.75 | 0.25 | 1.1.E-01 | | 3.2.E-01 |
| TSD | 4 | 0.33 | 0.50 | 2.50 | 0.67 | -0.71 | -0.17 | 1.04 | -0.15 | 0.08 | 0.13 | 0.63 | 0.17 | 3.8.E-01 | 2.4.E-01 | 4.0.E-01 |
| FPD | 3 | 0.00 | 0.00 | 3.00 | 0.00 | -1.04 | -0.67 | 1.54 | -0.82 | 0.00 | 0.00 | 1.00 | 0.00 | | 8.3.E-02 | 8.3.E-02 |
| INW | 3 | 0.00 | 0.00 | 2.00 | 1.00 | -0.78 | -0.50 | 0.90 | 0.39 | 0.00 | 0.00 | 0.67 | 0.33 | 3.0.E-01 | 8.3.E-02 | 5.6.E-01 |
| VNW | 3 | 0.50 | 0.00 | 1.00 | 1.50 | -0.28 | -0.50 | -0.10 | 0.89 | 0.17 | 0.00 | 0.33 | 0.50 | 6.4.E-01 | 2.5.E-01 | 1.0.E+00 |
| VVE | 3 | 1.00 | 0.00 | 1.50 | 0.50 | 0.22 | -0.50 | 0.40 | -0.11 | 0.33 | 0.00 | 0.50 | 0.17 | 6.4.E-01 | 5.6.E-01 | 2.5.E-01 |
| YPD | 3 | 0.00 | 0.00 | 3.00 | 0.00 | -0.78 | -0.50 | 1.90 | -0.61 | 0.00 | 0.00 | 1.00 | 0.00 | | 8.3.E-02 | 8.3.E-02 |
| YTN | 3 | 0.00 | 1.00 | 2.00 | 0.00 | -0.78 | 0.50 | 0.90 | -0.61 | 0.00 | 0.33 | 0.67 | 0.00 | 3.0.E-01 | 6.6.E-01 | 5.6.E-01 |
| EGN | 3 | 2.00 | 0.00 | 1.00 | 0.00 | 1.22 | -0.50 | -0.10 | -0.61 | 0.67 | 0.00 | 0.33 | 0.00 | 3.0.E-01 | 5.6.E-01 | 8.3.E-02 |
| LTD | 3 | 0.00 | 3.00 | 0.00 | 0.00 | -0.78 | 2.50 | -1.10 | -0.61 | 0.00 | 1.00 | 0.00 | 0.00 | | 8.3.E-02 | 8.3.E-02 |
| SND | 3 | 0.00 | 1.00 | 1.50 | 0.50 | -0.78 | 0.50 | 0.40 | -0.11 | 0.00 | 0.33 | 0.50 | 0.17 | 6.4.E-01 | 5.6.E-01 | 1.0.E+00 |
| HND | 3 | 0.50 | 0.50 | 1.50 | 0.50 | -0.28 | 0.00 | 0.40 | -0.11 | 0.17 | 0.17 | 0.50 | 0.17 | 8.0.E-01 | 5.6.E-01 | 5.6.E-01 |
| IVD | 3 | 1.00 | 0.00 | 0.00 | 2.00 | 0.22 | -0.50 | -1.10 | 1.39 | 0.33 | 0.00 | 0.00 | 0.67 | 3.0.E-01 | 6.6.E-01 | 5.6.E-01 |
| SNN | 3 | 0.00 | 0.00 | 0.50 | 2.50 | -0.78 | -0.50 | -0.60 | 1.89 | 0.00 | 0.00 | 0.17 | 0.83 | 1.3.E-01 | 8.3.E-02 | 2.5.E-01 |
| VVD | 3 | 1.00 | 0.00 | 1.00 | 1.00 | 0.22 | -0.50 | -0.10 | 0.39 | 0.33 | 0.00 | 0.33 | 0.33 | 6.0.E-01 | 5.6.E-01 | 5.6.E-01 |
| FNW | 3 | 0.33 | 1.00 | 0.67 | 1.00 | -0.45 | 0.50 | -0.43 | 0.39 | 0.11 | 0.33 | 0.22 | 0.33 | 9.4.E-01 | 8.5.E-01 | 5.6.E-01 |
| FVN | 3 | 1.67 | 0.33 | 1.00 | 0.00 | 0.88 | -0.17 | -0.10 | -0.61 | 0.56 | 0.11 | 0.33 | 0.00 | 5.3.E-01 | 5.6.E-01 | 1.8.E-01 |
| FNN | 3 | 1.67 | 1.33 | 0.00 | 0.00 | 0.88 | 0.83 | -1.10 | -0.61 | 0.56 | 0.44 | 0.00 | 0.00 | 3.8.E-01 | 8.3.E-02 | 8.5.E-01 |
| ND | 57 | 5.33 | 6.00 | 40.00 | 11.67 | -9.55 | -3.59 | 19.16 | -0.02 | 0.09 | 0.11 | 0.70 | 0.20 | | | |
| NN | 27 | 3.83 | 3.50 | 7.16 | 15.49 | -3.22 | -1.05 | -2.71 | 9.96 | 0.14 | 0.13 | 0.27 | 0.57 | | | 1.0.E-01 |
| TN | 25 | 20.83 | 3.83 | 2.67 | 1.67 | 14.31 | -0.37 | -6.47 | -3.46 | 0.83 | 0.15 | 0.11 | 0.07 | | | |
| TD | 21 | 3.33 | 19.67 | 2.67 | 2.33 | -2.15 | 16.13 | -5.01 | -1.97 | 0.16 | 0.94 | 0.13 | 0.11 | | | |
| SD | 20 | 4.83 | 6.50 | 5.00 | 3.67 | -0.39 | 3.13 | -2.31 | -0.43 | 0.24 | 0.33 | 0.25 | 0.18 | 8.5.E-01 | 5.5.E-01 | 9.4.E-01 |
| SN | 15 | 10.33 | 0.33 | 3.33 | 1.00 | 6.42 | -2.19 | -2.15 | -2.08 | 0.69 | 0.02 | 0.22 | 0.07 | | 1.0.E-01 | |
| GD | 13 | 0.50 | 9.00 | 3.50 | 0.00 | -2.89 | 6.81 | -1.25 | -2.66 | 0.04 | 0.69 | 0.27 | 0.00 | | 9.6.E-02 | 1.7.E-01 |
| NS | 13 | 0.83 | 0.50 | 4.67 | 7.00 | -2.56 | -1.69 | -0.09 | 4.33 | 0.06 | 0.04 | 0.36 | 0.54 | | | 5.8.E-01 |
| VN | 12 | 3.67 | 1.33 | 5.00 | 2.00 | 0.53 | -0.69 | 0.61 | -0.46 | 0.31 | 0.11 | 0.42 | 0.17 | 4.3.E-01 | 6.6.E-01 | 1.2.E-01 |
| NW | 10 | 1.16 | 1.33 | 3.67 | 3.83 | -1.45 | -0.35 | 0.01 | 1.78 | 0.12 | 0.13 | 0.37 | 0.38 | 4.7.E-01 | 1.1.E-01 | 9.2.E-01 |
| PD | 9 | 0.00 | 0.67 | 7.83 | 0.50 | -2.35 | -0.85 | 4.54 | -1.34 | 0.00 | 0.07 | 0.87 | 0.06 | | | |
| NT | 9 | 1.00 | 1.50 | 1.67 | 5.83 | -1.35 | -0.01 | -1.62 | 3.99 | 0.11 | 0.17 | 0.19 | 0.65 | 7.9.E-02 | 8.8.E-02 | 1.1.E-01 |
| GN | 8 | 5.00 | 0.00 | 3.00 | 0.00 | 2.91 | -1.35 | 0.07 | -1.64 | 0.63 | 0.00 | 0.38 | 0.00 | | 4.8.E-01 | |
| MD | 7 | 1.00 | 1.50 | 5.50 | 1.00 | -0.83 | 0.32 | 2.94 | -0.43 | 0.14 | 0.21 | 0.79 | 0.14 | | 9.1.E-02 | 9.1.E-02 |
| VD | 6 | 2.00 | 1.00 | 2.00 | 3.00 | 0.43 | -0.01 | -0.19 | 1.77 | 0.33 | 0.17 | 0.33 | 0.50 | 5.7.E-01 | 2.5.E-01 | 4.1.E-01 |
| VG | 5 | 1.00 | 0.00 | 1.00 | 3.00 | -0.31 | -0.84 | -0.83 | 1.98 | 0.20 | 0.00 | 0.20 | 0.60 | 2.8.E-01 | 1.8.E-01 | 6.5.E-01 |
| AD | 4 | 0.33 | 3.00 | 0.67 | 0.00 | -0.71 | 2.33 | -0.80 | -0.82 | 0.08 | 0.75 | 0.17 | 0.00 | 1.4.E-01 | 1.8.E-01 | 3.2.E-01 |
| SS | 4 | 0.00 | 0.33 | 2.67 | 1.00 | -1.04 | -0.34 | 1.20 | 0.18 | 0.00 | 0.08 | 0.67 | 0.25 | 2.4.E-01 | 9.6.E-02 | 5.1.E-01 |
| VE | 4 | 1.00 | 0.00 | 2.50 | 0.50 | -0.04 | -0.67 | 1.04 | -0.32 | 0.25 | 0.00 | 0.63 | 0.13 | 3.2.E-01 | 3.2.E-01 | 1.3.E-01 |
| AN | 4 | 0.67 | 0.00 | 2.67 | 0.67 | -0.38 | -0.67 | 1.20 | -0.15 | 0.17 | 0.00 | 0.67 | 0.17 | 2.6.E-01 | 1.8.E-01 | 1.8.E-01 |
| CD | 3 | 1.00 | 1.33 | 0.33 | 0.33 | 0.22 | 0.83 | -0.77 | -0.28 | 0.33 | 0.44 | 0.11 | 0.11 | 8.0.E-01 | 3.3.E-01 | 8.5.E-01 |
| IN | 3 | 0.50 | 0.00 | 1.50 | 1.00 | -0.28 | -0.50 | 0.40 | 0.39 | 0.17 | 0.00 | 0.50 | 0.33 | 6.4.E-01 | 2.5.E-01 | 5.6.E-01 |
| TW | 3 | 1.50 | 0.50 | 1.00 | 0.00 | 0.72 | 0.00 | -0.10 | -0.61 | 0.50 | 0.17 | 0.33 | 0.00 | 6.4.E-01 | 5.6.E-01 | 2.5.E-01 |
| VS | 3 | 1.00 | 0.00 | 1.00 | 1.00 | 0.22 | -0.50 | -0.10 | 0.39 | 0.33 | 0.00 | 0.33 | 0.33 | 8.0.E-01 | 5.6.E-01 | 5.6.E-01 |
| LD | 3 | 1.00 | 0.00 | 1.50 | 3.50 | 0.22 | -0.50 | 0.40 | 2.89 | 0.33 | 0.00 | 0.50 | 1.17 | | | 6.8.E-02 |
| TS | 3 | 0.00 | 0.50 | 1.50 | 1.00 | -0.78 | 0.00 | 0.40 | 0.39 | 0.00 | 0.17 | 0.50 | 0.33 | 6.4.E-01 | 2.5.E-01 | 1.0.E+00 |
| ID | 3 | 0.33 | 0.83 | 2.83 | 0.00 | -0.45 | 0.33 | 1.74 | -0.61 | 0.11 | 0.28 | 0.94 | 0.00 | 7.9.E-02 | 2.6.E-01 | 1.4.E-01 |
| VT | 3 | 1.00 | 0.00 | 3.00 | 0.00 | 0.22 | -0.50 | 1.90 | -0.61 | 0.33 | 0.00 | 1.00 | 0.00 | | 2.0.E-01 | |
| ¹ Background frequency | | 0.26 | 0.17 | 0.37 | 0.20 | 0.00 | 0.00 | 0.00 | 0.00 | 0.26 | 0.17 | 0.37 | 0.20 | | | |

¹ The value indicates a probability of nucleotide occurrence for all RNA sequences surrounding the RNA editing sites used to construct the PPR code.
² The scoring matrix is estimated by a subtraction of the background frequency from the nucleotide occurrence frequency of the PPR code.
³ The probability matrix is obtained from the nucleotide occurrence frequency.

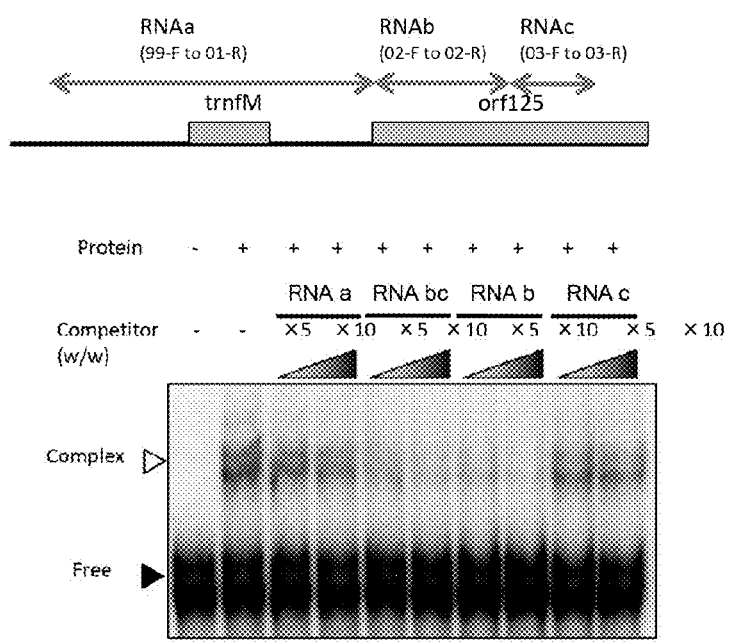

FIG. 18A
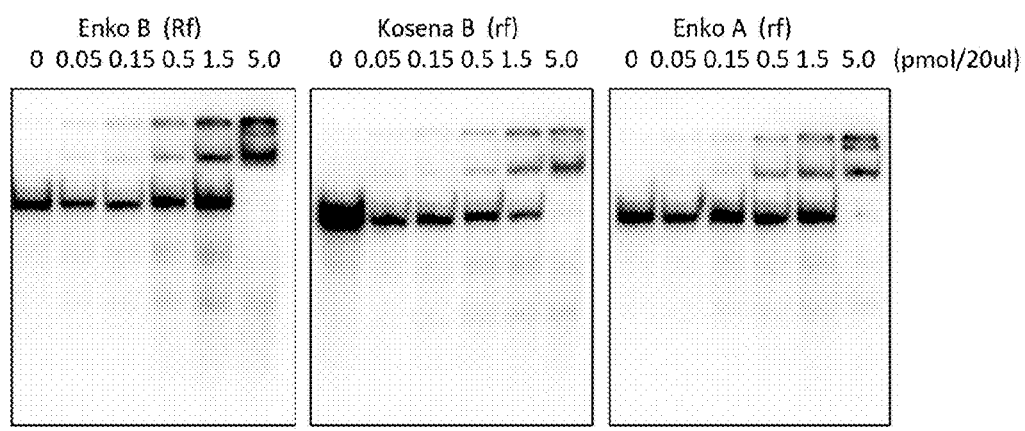
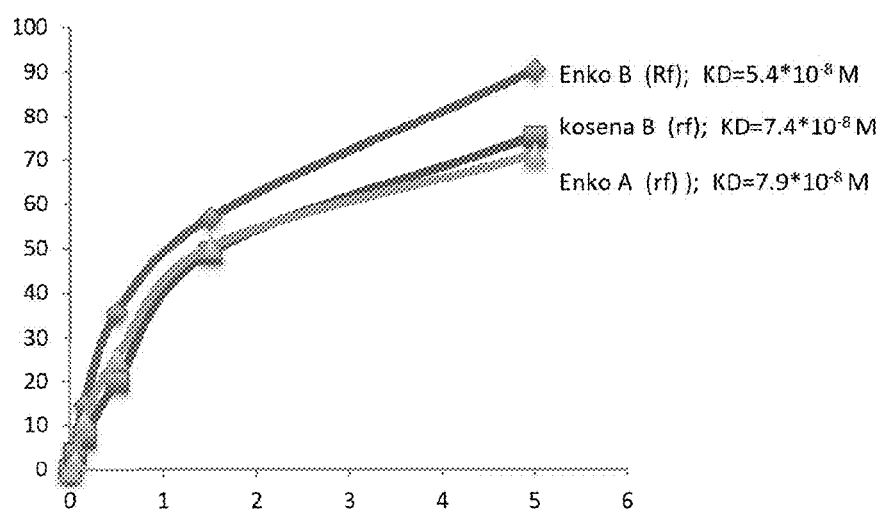
FIG. 18B
Enko B (Rf); KD=5.4*10$^{-8}$ M
kosena B (rf); KD=7.4*10$^{-8}$ M
Enko A (rf) ); KD=7.9*10$^{-8}$ M
|   | EnkoB | kosenaB | EnkoA |
|---|---|---|---|
| 208 | 8.399.E−06 | 4.620.E−04 | 6.299.E−02 |
| 316 | 2.702.E−04 | 2.667.E−04 | 2.630.E−04 |
| 352 | 1.372.E−04 | 7.168.E−03 | 3.535.E−01 |
| 373 | 2.711.E−04 | 5.013.E−03 | 4.007.E−01 |
FIG. 18C

208: GUAGUUCAUUCUGCA
316: UGAUUACCUUUUUCGA
352: AUAAUCUCACUCCUAC
373: GUAAGUUAGUGUAAU

FIG. 20A
FIG. 20B
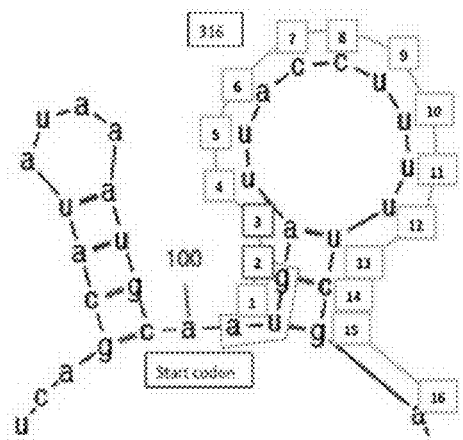
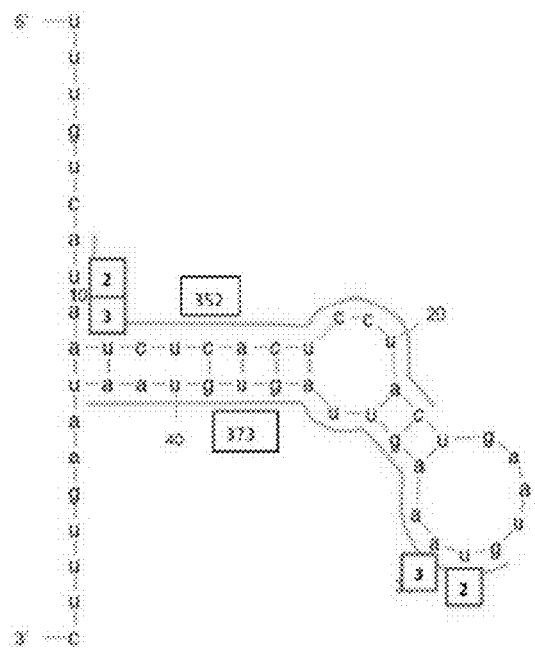
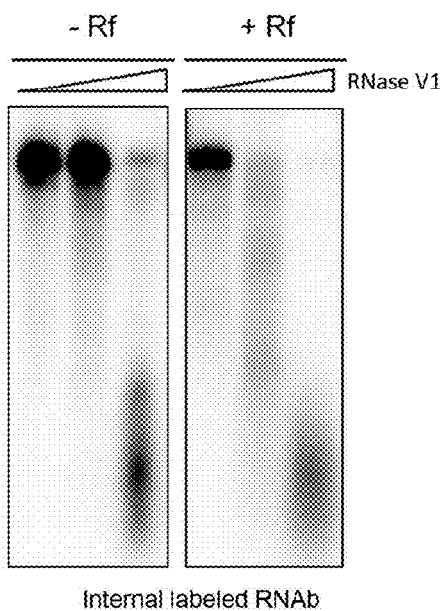
Internal labeled RNAb
FIG. 20C

FIG. 21A

```
Enko_B       MLARVCGFKCSSSPAESAARLFCTRSIRDTLAKAS--GESCEAGFGGESLKLQSGFHEIK
Kosena_B     MLARVCGFKCSSSPAESAARLFCTRSIRDTLAKAS--GESCEAGFGGESLKLQSGFHEIK
Comet_B      MLARVCGFKCSSSPAESAARLFCTRSIRDTLAKAS--GESCEAGFGGESLKLQSGFHEIK
rrORF690-1   MLARVCRFESSSSSVSAARMFCTGSIRHALAKKGRDGESGEAGFGGESLKLRSGFHEIK
rrORF690-2   MLARVCRFESSSSSVSAARMFCTGSIRHALAKKGRDGESGEAGFGGESLKLRSGFHEIK
PC_PPR-A     MLARVCRFESSSSSVSAARFFCTGSIRHALAEKSRDGESGEAGFRGESLKLRSGSYEIK
Enko_A       MLARVCRFESSSSSVSAARFFCTGSIRHALAEKSRDGESGEAGFRGESLKLRSGSYEIK
Comet_A      MLARVCRFESSSSSVSAARLLCTRSIHLPLAEKSRDGENGEAGSGGESLKLQSGSYEIK
Icicle_CA    MLARVYRSCSSSSPAVSAARLFCTRSIRHALAKKSRDGESC----FGCESLKLRSGFHEIK
PC_PPR-BL    MLARVCRFESSSS---VPAARLFCTRSIRHTLAKKS----SGKAGGFSGERLKLQSGFHEIK
                                                        PPR 1                                          PPR 2
Enko_B       GLEDAIDLFSDMLRSRPLPSVVDFCKLMGVVVRMERPDLVISLYQKMERKQIRCDIYSFN
Kosena_B     GLEDAIDLFSDMLRSRPLPSVVDFCKLMGVVVRMERPDLVISLYQKMERKQIRCDIYSFT
Comet_B      GLEDAIDLFSDMLRSRPLPSVVDFCKLMGVVVRMKRPDVVISLHKKVEMRRIPCDAYSFN
rrORF690-1   GLEDAIDLFSDMLRSRPLPSVIDFNKLMGVVVRMERPDLVISLYQKMERKQIPCDVYSFN
rrORF690-2   GLEDAIDLFSDMLRSRPLPSVIDFNKLMGVVVRMERPDLVISLYQKMERKQIPCDVYSFN
PC_PPR-A     GLEDAIDLFSDMLRSRPLPSVIDFNKLMGAVVRMERPDLVISLYQKMERKQIRCDIYSFT
Enko_A       GLEDAIDLFSDMLRSRPLPSVIDFNKLMGAVVRMERPDLVISLYQKMFRKQIRCDIYSFT
Comet_A      GLEDAIDLFSDMLRSRPLPSVIDFNKLMGAVVRMERPDLVISLYQKMERKQIRCDIYSFT
Icicle_CA    GLEDAIDLFGDMVRSRFLPGVIDFCKLMGVVVRMGRLDVVIQLHRRMEMGRVPCNAYQFT
PC_PPR-BL    GLDDAIDLFGYMVKSRPLPCVIDFCKLLGVVVRMERPDVVISLHRKMEMRRIPCNIYSFT
                                                              PPR 3
Enko_B       ILIKCFCSCSKLPFALSTFGKITKLGLHPDVVTFTTLLHGLCVEDRVSEALDFFHQMFET
Kosena_B     ILIKCFCSCSKLPFALSTFGKITKLGLHPDVVTFNTLLHGLCVEDRVSEALNLFHQMFET
Comet_B      ILIKCFCSCSKLPFALSTFGKITKLGLHPDVVTFTTLLHGLCVEDRVSEALNLFHQMFET
rrORF690-1   ILIKCFCSCSKLPFALSTFGKITKLGLHPDVATFNTLLHGLCLDKRVSEALDLFHQMFET
rrORF690-2   ILIKCFCSCSKLPFALSTFGKITKLGLHPDVATFNTLLHGLCLDKRVSEALDLFHQMFET
PC_PPR-A     ILIKCFCSCSKLPFALSTFGKLTKLGLHPDVVTFTTLLHGLCLDHRVSEALDLFHQICR-
Enko_A       ILIKCFCSCSKLPFALSTFGKLTKLGLHPDVVTFTTLLHGLCLDHRVSEALDLFHQICR--
Comet_A      ILIKCFCSCSKLPVALSTFGKLTKLGLHPDVVTFTTLLHGLCVEDRVSEALDLFHQMCK-
Icicle_CA    ILMKCFCSCSKLPFALSTFGKITKLGLHPDVVTFNTLLHGLCVEDRVSEALDLFHQMCK-
PC_PPR-BL    ILIKCFCSCSKLPFALSTFGKITKLGFHPSIVTFSTLLHGLCVEDRVSEALHFFHQICK-
                PPR 4                                              PPR 5
Enko_B       TCRPNVVTFTTLMNGLCREGRIVEAYALLDRMMEDGLQPTQITYGTIVDGMCKKGDTVSA
Kosena_B     TCRPNVVTFTTLMNGLCREGRIVEAVALLDRMMEDGLQPTQITYGTIVDGMCKKGDTVSA
Comet_B      TCRPNVVTFTTLMNGLCREGRIVEAVALLDRMMEDGLQPTQITYGTIVDGMCKKGDTVSA
rrORF690-1   TCRPNIITFTTLMNGLCYEGRVVEAVALLDRMLEDGLQPDQITYGTIVDGMCKMGDTVSA
rrORF690-2   TCRPNIITFTTLMNGLCYEGRVVEAVALLDRMLEDGLQPDQITYGTIVDGMCKMGDTVSA
PC_PPR-A     ---PDVLTFTTLMNGLCREGRVVEAYALLDRMVENGLQPDQITYGTFVDGMCKMGDTVSA
Enko_A       ---PDVLTFTTLMNGLCREGRVVEAVALLDRMVENGLQPDQITYGTIVDGMCKMGDTVSA
Comet_A      ---PNVVTFNTLMNGLCREGRVVEAVALLDQMVENGLQPDQITYGTIVDGMCKMGDTVSA
Icicle_CA    ---PNVVTFTTLMKGLCREGRVVEAVALLDRMVEDGLQPNQITYGTIVDGMCKMGDSVSA
PC_PPR-BL    ---PNVIAFTTLMNGLCREGRVVEAVALLDRMVEDGLQPNQITYGTIVDGMCKMGDTVSA
                PPR 6                                              PPR 7
Enko_B       LNLLRKMEEVSHIIPNVVIYSAIIDSLCKDGRHSDAQNLFTEMQEKGIFPDIFTYNSMIV
Kosena_B     LNLLRKMEEVSHIIPNVVIYSAIIDSLCKDGRHSDAQNLFTEMQEKGIFPDIFTYNSMIV
Comet_B      LNLLRKMEEVSHIIPNVVIYSAIIDSLCKDGRHSDAQNLFTEMQEKGIFPDIFTYNSMIV
rrORF690-1   LNLLRKMEELSHIKPNVVIYSAIIDGLWKDGRHTDAQNLFSEMQEKGIFPNIFTYTCMIN
rrORF690-2   LNLLRKMEELSHIKPNVVIYSAIIDGLWKDGRHTDAQNLFSEMQEKGIFPNIFTYTCMIN
PC_PPR-A     LNLLRKMEEISHIKPNVVIYSAIIDGLCKDGRHSDSHNLFIEMQDKGIFPNIVTYNCMIG
Enko_A       LNLLRKMEEISHIKPNVVIYSAIIDGLCKDGRHSDSHNLFIEMQDKGIFPNIVTYNCMIG
Comet_A      LNLLRKMEEVSHIKPNVVIYSAIIDGLCKDGRHSDAHNLFIEMQDKGIFPNIVTYNCMIG
Icicle_CA    LDLLRKMEEVSHIKPDVVIYSAIIDGLWKDGRHTDAQNLFSEMQDKRIFPDIFTYSCMID
PC_PPR-BL    LNLLRKMEEVSRIKPNVVIYSAIIDGLWKDGRQTDAQNLFSEMQEKGISPNIFTYNCMIN
                                             PPR 8
Enko_B       GFCSSGRWSDAEQLLQEMLERKISPDVVTYNALINAFVKEGKFFEAEELYDEMLPRGIIP
Kosena_B     GFCSSGRWSDAEQLLQEMLERKISPDVVTYNALINAFVKEGKFFEAEELYDEMLPRGIIP
Comet_B      GFCSSGRWSDAEQLLQEMLERKISPDVVTYNALINAFVKEGKFFEAEELYDEMLPRGIIP
rrORF690-1   GFCDSGRWSEAQQLLQEMLVRKISPNVVTYSALINAFVKEGKFFEAEELYDEMLPRGIIP
rrORF690-2   GFCDSGRWSEAQQLLQEMLVRKISPNVVTYSALINAFVKEGKFFEAEELYDEMLPRGIIP
PC_PPR-A     GFCISGRWSAAQRLLQEMLERKISPNVVTYNALINAFVKEGKFFEAEELYDEMLPRGIIP
Enko_A       GFCISGRWSAAQRLLQEMLERKISPNVVTYNALINAFVKEGKFFEAEELYDEMLPRGIIP
Comet_A      GFCISGRWSAAQRLLQEMLVRKISPNVVTYNALINAFVKEGKFFEAEELYDEMLPRGIIP
Icicle_CA    GFCSSGRWSEAQRLLREMLERKISPDVVTYNALVKEGKFFEAEELYDEMLPRGIIP
PC_PPR-BL    GFCSSGRWSEAQRLLREMFERKMSPDVVTFSVLINALVKEGKFFEAEELYNEMLPRGIIP
```

FIG. 21B

```
              PPR 9                              PPR 10
           NIITYSSMIDGFCKQNRLDAAEHMFYLMATKGCSPNL ITFNTLIDGYCGAKRIDDGMELL
Enko_B     NIITYSSMIDGFCKQNPLDAAEHMFYLMATKGCSPNL ITFNTLIDGYCGAKRIDDGMELL
Kosena_B   NIITYSSMIDGFCKQNRLDAAEHMFYLMATKGCSPNL ITFNTLIDGYCGAKRIDDGMELL
Comet_B    SIVTYSSMIDGFCKQNRLDAAEHMFYLMPTKGCSPNL ITFNTLIAGYCRAKRVDDGMELL
rrORF690-1 SIVTYSSMIDGFCKQNRLAAAEHMFYLMPTKGCSPNL ITFNTLIAGYCRAKRVDDGMELL
rrORF690-2 NIIFYNSMIDGFCKQDRLDAAAEDMFYLMATKGCPDV FTFTTLIDGYCGAKRIDDGMELL
PC_PPR-A   NIITYNSMIDGFCKQNRLDAAEHMFYLMATKGCSPDV FTFTTLIDGYCGAKRIDDGMELL
Enko_A     NIITYNSMIDSFCKQNRLDAAEHMFYVMATKGCSPDV FTFNTLIDGYCGAKRIDDGMELL
Comet_A    NIITYSSMIDGFCKQNRLDAAEHMFYLMATKGCSPDV FTFNTLIDGYCGAKRIDDGMELL
Icicle_CA  NIIFYNSMIDGFSKQNRLDAAAERMFYLMATKGCSPDV ITFSILIDGYCGAKRVDDGMKLL
PC_PPR-BL
                     PPR 11                        PPR 12
           HEMTETGLVADT TTYNTLIHGFYLVGDLNAALDLLQEMISSGLCPDI VTCDTLLDGLCDN
Enko_B     HEMTETGLVADT TTYNTLIHGFYLVGDLNAALDLLQEMISSGLCPDI VTCDTLLDGLCDN
Kosena_B   HEMTETGLVADT TTYNTLIHGFCLVGDLNAALDLLQEMISSGLCPDI VTCDTLLDGLCDN
Comet_B    HEMTETGLVADT TTYNTLIHGFCLVEDLNAALDLSQQMISSGVCPDI VTCNTLLDGLCDN
rrORF690-1 HEMTETGLVADT TTYNTLIHGFCLVGDLNAALDLSQQMISSGVCPDI VTCNTLLDGLCDN
rrORF690-2 HEMPRRGLVANT VTYNTLIHGFCLVGDLNAALDLSQQMISSGVCPDI VTCNTLLDGLCDN
PC_PPR-A   HEMPRRGLVANT VTYNTLIHGFCLVGDLNAALDLSQQMISSGVCPDI VTCNTLLDGLCDN
Enko_A     HEMTETGLVADT TTYNTLIHGFCLVGDLNAALDLLQEMVSSGVCPDI VTCNTLLDGLCDN
Comet_A    HEMPEAGLVANT VTYTTLIHCFCGVCDLNSAQDLLQEMISSGVCPNV VTCNTLLDCLCLN
Icicle_CA  HEMSRRGLVANT ITYTTLIHGFCQLCNLNAALDLLQEMISSGVCPNV VTCNTLLDGLCNN
PC_PPR-BL
                                    PPR 13
           GKLKDALEMFKVMQKSKKDLDASHPFNGVEPDV QTYNILISGLINEGKFLEAEELYEEMP
Enko_B     GKLKDALEMFKVMQKSKKDLDASHPFNGVEPDV QTYNILISGLINEGKFLEAEELYEEMP
Kosena_B   GKLKDALEMFKVMQKSKKDLDASHPFNGVEPDV QTYNILISGLINEGKFLEAEELYEEMP
Comet_B    GKLKDALEMFKAMQKSKMDFDASHPFNGVEPDV LTYNILISGLINDGKFLGAEELYEEMP
rrORF690-1 GKLKDALEMFKAMQKSKMDFDASHPFNDVEPDV LTYNILISGLINDGKFLGAEELYEEMP
rrORF690-2 GKLKDALEMFKAMQKSKMDLDASHPFNGVEPDV LTYNILICGLINEGKFLEAEELYEEMP
PC_PPR-A   GKLKDALEMFKAMQKSKMDLDASHPFNGVEPDV LTYNILICGLINEGKFLEAEELYEEMP
Enko_A     GKLKDALEMFKAMQKSKMYIDASHPFNGVEPDV LTYNILICGLINEGKFLEAEELYEEMP
Comet_A    GKLKDALEMFKVMQKSKKNFDASHPFNGVEPDV LTYNILTCGLTNEGKFLEAEELYEEMP
Icicle_CA  GKLKDALEMFKVMQKSKMDLDASHPFNDVEPDV QTYNILICGLINEGKFSEAEELYEEMP
PC_PPR-BL
                   PPR 14                        PPR 15
           HRGIVPDT ITYSSMIDGLCKQSRLDEATQMFDSMGSKSFSPNV VTFTTLINGYCKAGRVD
Enko_B     HRGIVPDT ITYSSMIDGLCKQSRLDEATQMFDSMGSKSFSPNV VTFTTLINGYCKAGRVD
Kosena_B   HRGIVPDT ITYSSMIDGLCKQSRLDEATQMFDSMGSKSFSPNV VTFTTLINGYCKAGRVD
Comet_B    HRGIVPDT FTYNSMICGLCKQNRLDEAKQMSDSMGSKSFSPNV VTFNTLINGYCKAGRVD
rrORF690-1 HRGIVPDT VTYNSVINGLCKQNRLNEAKQMSDSMGSRSFSPNV VTFNTLINGYCKAGRVD
rrORF690-2 HRGIVPDT ITYSSMIDGLCKQSRLDEATQMFVSMGSKSFSPNV VTFNTLINGYCKAGRVD
PC_PPR-A   HRGIVPDT ITYSSMIDGLCKQSRLDEATQMFVSMGSKSFSPNV VTFNTLINGYCKAGRVD
Enko_A     HRGIVPDT ITYSSMIDGLCKQSRLDEATQMSDSMGSKSFSPNV VTFNTLINGYCKAGRVD
Comet_A    HRGIVPDT ITYSSMIDGLCKQSRLDEATQMSDSMGSKSFSPNV VTFNTLINGYCKAGRVD
Icicle_CA  HRGLVPDT ITYNSVIDGLCKQSRLDEATQMFDSMGSKGFSPDV VTFTTLINGYCKVGRVG
PC_PPR-BL
                             PPR 16
           DGLELFCEMGRRGIVANA ITYITLICGFRKVGNINGALDIFQEMISSGVYPDT ITIRNML
Enko_B     DGLELFCEMGRRGIVANA ITYITLICGFRKVGNINGALDIFQEMISSGVYPDT ITIRNML
Kosena_B   DGLELFCEMGRRGIVANA ITYITLICGFRKVGNINGALDIFQEMISSGVYPDT ITIRNML
Comet_B    DGLELFCGMGQRGIVANA ITYITLIHGFRKVDNINGALDIFQEMISSGVYPDT ITIRNML
rrORF690-1 DGLELFCEMGRGVVANA ITYITLIHGFSKVGNINGALDIFQEMMASGVYPDT ITIRNML
rrORF690-2 DGLELFCEMGRRGIVADA IIYITLIYGFRKVGNINGALDIFQEMISSGVYPDT ITIRNML
PC_PPR-A   DGLELFCEMGRRGIVADA ITYITLIYGFRKVGNINGALDIFQEMISSGVYPDT ITIRNML
Enko_A     DGLELFCEMGRRGIVADA ITYITLIYGFRKVGNINGALDIFQEMMASGVYPDT ITIRNML
Comet_A    DGLELFCEMGRRGIVADA ITYITLIYGSRKVGNINGALDIFQEMISSGVYPDT ITIRNML
Icicle_CA  DGLEVFCEMGRRGIVANA ITYKTLIHGFCQVGNINGALDIFQEMISSGVYPDT ITIRNML
PC_PPR-BL Enko_B     TGLWSKEELKRAVAMLEKLQMSMDLSFGG-
Kosena_B   TGLWSKEELKRAVAMLEKLQMSMDLSFGG-
Comet_B    TGLWSKEELKRAVAMLEKLQMSMDLSFGG-
rrORF690-1 TGLWSKEELKRAVAMLEDLQMSVGYCLEDE
rrORF690-2 TGLWSKEEVKRAVAMLEDLQMSVGYCLEDE
PC_PPR-A   TGFWSKEELERAVAMLEDLQR---YCLEDE
Enko_A     TGFWSKEELERAVAMLEDLQMSVGYCLEDE
Comet_A    TGLWSKEELKRAVAMLEDLQMSVGYCLEDE
Icicle_CA  TGLWSKEELERAVAMLEVLQMSVGYCLEDE
PC_PPR-BL  TGLWSKEELKRAVQCL--------------
```

FIG. 22

METHOD FOR DESIGNING RNA BINDING PROTEIN UTILIZING PPR MOTIF, AND USE THEREOF

CROSS-REFERENCE TO RELATED APPLICATION

This application is a Divisional of U.S. patent application Ser. No. 15/962,127, filed on Apr. 25, 2018, which is a Divisional of U.S. patent application Ser. No. 15/335,243, filed on Oct. 26, 2016 (issued as U.S. Pat. No. 9,984,202), which is a Divisional of U.S. patent application Ser. No. 14/352,697, filed on Jul. 22, 2014 (issued as U.S. Pat. No. 9,513,283), which is a U.S. National Stage entry of International Application No. PCT/JP2012/077274, filed on Oct. 22, 2012, which claims priority to Japanese Patent Application No. 2011-231346, filed on Oct. 21, 2011, the entirety of all of which is incorporated herein by reference.

TECHNICAL FIELD

The present invention relates to a protein capable of selectively or specifically binding to an intended RNA base or RNA sequence. According to the present invention, a pentatricopeptide repeat (PPR) motif is used. The present invention can be used for identification and design of an RNA binding protein, identification of a target RNA of a PPR protein, as well as functional control of RNA. The present invention is useful in the medical field, agricultural field, and so forth.

BACKGROUND ART

In recent years, techniques of binding nucleic acid binding protein factors elucidated by various analyses to an intended sequence have been established and utilized. By using such a sequence-specific binding, it is becoming possible to analyze intracellular localization of a target nucleic acid (DNA or RNA), eliminate a target DNA sequence, or control (activate or inactivate) expression of a gene coding for a protein existing downstream from such a target sequence.

Although there are being conducted research and development utilizing zinc finger proteins (Non-patent document 1) and TAL effectors (Non-patent document 2, Patent document 1), which are protein factors that act on DNA, as protein engineering materials, development of protein factors that specifically act on RNA is still extremely limited. This is because any general correspondence between affinity to RNA of amino acid sequences constituting proteins and bindable RNA sequences has been scarcely elucidated, or there is no such correspondence. Concerning the pumilio protein constituted by repetition of two or more puf motifs each consisting of 38 amino acids, it has been exceptionally demonstrated that one puf motif binds to one RNA base (Non-patent document 3), and it is being attempted to develop a novel protein having an RNA binding property and a technique of modifying RNA binding property by using the pumilio proteins (Non-patent document 4). However, the puf motifs are highly conserved, and exist only in an extremely small number. Therefore, they are used only for creation of a protein factor that interacts with a limited RNA sequence.

The PPR proteins (proteins having the pentatricopeptide repeat (PPR) motif) have been identified on the basis of genome sequence information (Non-patent document 5), which proteins constitute such a large family consisting of about 500 members only for plants. Although the PPR proteins are nuclear-encoded, they chiefly act for control of organelles (chloroplasts and mitochondria) at the RNA level, cleavage, translation, splicing, editing, and stability of RNA in a gene-specific manner. The PPR proteins typically have a structure comprising about 10 contiguous poorly conserved 35-amino acid motifs, i.e., PPR motifs, and it is considered that the combination of the PPR motifs is responsible for the sequence-selective binding with RNA. Almost all the PPR proteins consist of only the repeats of about 10 PPR motifs, and in many cases, any domain required for expression of catalytic action cannot be found in them. Therefore, it is considered that the identity of the PPR proteins is an RNA adapter (Non-patent document 6).

The inventors of the present invention proposed a method for modifying an RNA-binding protein using this PPR motif (Patent document 2).

PRIOR ART REFERENCES

Patent Documents

Patent document 1: WO2011/072246
Patent document 2: WO2011/111829

Non-Patent Documents

Non-patent document 1: Maeder, M. L., Thibodeau-Beganny, S., Osiak, A., Wright, D. A., Anthony, R. M., Eichtinger, M., Jiang, T., Foley, J. E., Winfrey, R. J., Townsend, J. A., et al. (2008), Rapid "open-source" engineering of customized zinc-finger nucleases for highly efficient gene modification, Mol. Cell, 31, 294-301

Non-patent document 2: Miller, J. C., Tan, S., Qiao, G, Barlow, K. A., Wang, J., Xia, D. F., Meng, X, Paschon, D. E., Leung, E., Hinkley, S. J., et al. (2011), A TALE nuclease architecture for efficient genome editing, Nature Biotech., 29, 143-148.

Non-patent document 3: Wang, X., McLachlan, J., Zamore, P. D., and Hall, T. M. (2002), Modular recognition of RNA by a human pumilio-homology domain, Cell, 110, 501-512

Non-patent document 4: Cheong, C. G, and Hall, T. M. (2006), Engineering RNA sequence specificity of Pumilio repeats, Proc. Natl. Acad. Sci. USA, 103, 13635-13639

Non-patent document 5: Small, I. D., and Peeters, N. (2000), The PPR motif—a TPR-related motif prevalent in plant organellar proteins, Trends Biochem. Sci., 25, 46-47

Non-patent document 6: Woodson, J. D., and Chory, J. (2008), Coordination of gene expression between organellar and nuclear genomes, Nature Rev. Genet., 9, 383-395

SUMMARY OF THE INVENTION

Object to be Achieved by the Invention

The properties of the PPR proteins as an RNA adapter are expected to be determined by the properties of the PPR motifs constituting the PPR proteins and combination of a plurality of the PPR motifs. However, correlation of the amino acid constitution and function thereof are scarcely clarified. If amino acids that function when the PPR motifs exhibit the RNA-binding property are identified, and relation between structure of a PPR motif and a target base is elucidated, a protein capable of bringing to an RNA having arbitrary sequence and length may be constructed by artificially manipulating structure of a PPR motif or combination of a plurality of PPR motifs.

Means for Achieving the Object

In order to achieve the aforementioned object, the inventors of the present invention examined genetically analyzed PPR proteins, especially such PPR proteins involved in the RNA editing (modification of genetic information at the RNA level, especially conversion from cytosine (henceforth abbreviated as C) to uracil (henceforth abbreviated as U)), and target RNA sequences thereof, and elucidated that three amino acids in the PPR motifs (amino acids 1, 4, and "ii" (−2)) comprise information responsible for binding to a specific RNA base by using computational scientific techniques. More precisely, the inventors of the present invention found that the binding RNA base selectivity (also referred to as specificity) of the PPR motif is determined by three amino acids, i.e., the first and fourth amino acids contained in the first helix among two of the α-helix structures constituting the motif, as well as the second ("ii" (−2)) amino acid from the end (C-terminus side) in the moiety that can form a loop structure after the second helix, and accomplished the present invention.

The present invention thus provides the followings.

[1] A method for designing a protein that can bind to an RNA molecule in an RNA base-selective or RNA base sequence-specific manner, wherein:

the protein is a protein containing one or more of PPR motifs (preferably 2 to 14 PPR motifs) each consisting of a polypeptide of 30- to 38-amino acid length represented by the formula 1:

[F1]

(HelixA)-X-(HelixB)-L  (Formula 1)

(wherein:

Helix A is a moiety of 12-amino acid length capable of forming an α-helix structure, and is represented by the formula 2:

[F2]

$A_1$-$A_2$-$A_3$-$A_4$-$A_5$-$A_6$-$A_7$-$A_8$-$A_9$-$A_{10}$-$A_{11}$-$A_{12}$  (Formula 2)

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[F3]

$L_{vii}$-$L_{vi}$-$L_v$-$L_{iv}$-$L_{iii}$-$L_{ii}$-$L_i$  (Formula 3)

wherein, in the formula 3, the amino acids are numbered "i" (−1), "ii" (−2), and so on from the C-terminus side, provided that $L_{iii}$ to $L_{vii}$ may not exist), and combination of three amino acids $A_1$, $A_4$ and $L_{ii}$, or combination of two amino acids $A_4$, and $L_{ii}$ is a combination corresponding to a target RNA base or base sequence.

[2] The method according to [1], wherein the combination of the three amino acids $A_1$, $A_4$ and $L_{ii}$ is a combination corresponding to the target RNA base or base sequence, and the combination of the amino acids is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

[3] The method according to [1], wherein the combination of the two amino acids $A_4$ and $L_{ii}$ is a combination corresponding to the target RNA base or base sequence, and the combination of the amino acids is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

[4] A method for identifying a target base or base sequence for an RNA-binding protein comprising one or more (preferably 2 to 14) of the PPR motifs defined in [1], wherein:

the base or base sequence is identified by determining presence or absence of a base corresponding to a combination of the three amino acids $A_1$, $A_4$ and $L_{ii}$ of the PPR motifs, or a combination of the two amino acids $A_4$ and $L_{ii}$ of the PPR motifs on the basis of any of the propositions (3-1) to (3-16) mentioned in [2], or any of the propositions (2-1) to (2-12) mentioned in [3].

[5] A method for identifying a PPR protein that comprises one or more (preferably 2 to 14) of the PPR motifs defined in [1], and can bind to a target RNA base or a target RNA having a specific base sequence, wherein:

the PPR protein is identified by determining presence or absence of a combination of the three amino acids $A_1$, $A_4$ and $L_{ii}$ of the PPR motifs corresponding to the target RNA base or a specific base constituting the target RNA on the basis of any of the propositions (3-1) to (3-16) mentioned in [2], or any of the propositions (2-1) to (2-12) mentioned in [3].

[6] A method for controlling a function of RNA, comprising using a protein designed by the method according to [1].

[7] A complex comprising a region consisting of a protein designed by the method according to [1] and a functional region, which have been linked together.

[8] A method for modifying a cellular genetic material, which comprises the following steps:

preparing a cell containing an RNA having a target sequence; and introducing the complex according to [7] into the cell, so that the protein region of the complex binds to the RNA having the target sequence, and therefore the functional region modifies the target sequence.

[9] A method for judging fertility of a gene of a PPR protein, which comprises:

the step of detecting amino acid polymorphism observed among various varieties for a gene of a PPR protein that functions as a fertility restoration factor for cytoplasmic male sterility;

the step of specifying relation of the polymorphism and the fertility for the gene; and the step of specifying a base sequence of a gene of a PPR protein obtained from a test sample, and determining fertility of the test sample.

[10] The method according to [9], wherein the PPR protein is a protein comprising one or more (preferably 2 to 16) of PPR motifs each consisting of a polypeptide of 30- to 38-amino acid length represented by the formula 1 defined in [1].

[11] The method according to [9] or [10], wherein the amino acid polymorphism is specified as polymorphism observed in units of the PPR motifs.

[12] The method according to any one of [9] to [11], wherein the polymorphism observed in the PPR motifs is identified by a combination of the three amino acids $A_1$, $A_4$ and $L_{ii}$, or a combination of the two amino acids $A_4$ and $L_{ii}$ of the motif of the formula 1.

[13] The method according to [12], wherein the polymorphism observed in the PPR motifs is identified as polymorphism of amino acid 4 ($A_4$) in the motifs of the formula 1.

[14] The method according to [13], wherein the fertility is indicated by the fact that amino acids 4 in all of the PPR motifs in the PPR protein are the same as amino acids 4 in all of the corresponding PPR motifs of Enko B, or the fact that the amino acids "ii" in all of the PPR motifs in the PPR protein are the same as the amino acids "ii" in all of the corresponding PPR motifs of Enko B.

[15] The method according to any one of [9] to [14], wherein the gene of the PPR protein is a family gene carried at the same locus as that of the "ORF687 gene" coding for Enko B, a gene coding for a protein showing an amino acid identity of 90% or higher to Enko B, or a gene showing a nucleotide sequence identity of 90% or higher to the "ORF687 gene" coding for Enko B.

[16] The method according to any one of [9] to [15], wherein the proteins encoded by the orf687-like genes of various varieties are any of the proteins of SEQ ID NOS: 576 to 578 and 585 to 591.

Effect of the Invention

According to the present invention, a PPR motif capable of binding to a target RNA base and a protein containing it can be provided. By using a plurality of PPR motifs, a protein capable of binding to a target RNA having an arbitrary sequence or length can be provided.

According to the present invention, a target RNA of an arbitrary PPR protein can be predicted and identified, and conversely, a PPR protein capable of binding to an arbitrary RNA can be predicted and identified. Prediction of such a target RNA sequence enhances the possibility of elucidating the genetic identity thereof and using it. For example, in the case of considering fertility as a function of the PPR protein according to the present invention, for an industrially useful gene of PPR protein such as those capable of functioning as a restoration factor for cytoplasmic male sterility, functionalities of various homologous genes thereof providing proteins that show amino acid polymorphism can be determined on the basis of the difference of the target RNA sequences thereof.

Further, a functional region can be bound to a PPR motif or PPR protein provided by the present invention to prepare a complex.

The present invention can further be utilized for a method of delivering the aforementioned complex to a living body and allowing it to function, preparation of a transformant using a nucleic acid sequence (DNA or RNA) coding for a protein obtained by the present invention, as well as specific modification, control, and impartation of a function in various scenes in organisms (cells, tissues, and individuals).

BRIEF DESCRIPTION OF THE DRAWINGS

FIGS. 1A-1C show the conserved sequences and amino acid numbers of the PPR motif. FIG. 1A shows the amino acids constituting the PPR motif defined in the present invention, and the amino acid numbers thereof. FIG. 1B shows the positions of the three amino acids (1, 4, and "ii" (−2)) that control the binding base selecting property on the putative structure. FIG. 1C shows the positions of the amino acids on the putative structure. By using the total amino acid sequences of *Arabidopsis thaliana* CRR4 (SEQ ID NO: 6)

and CRR21 (SEQ ID NO: 3) as the query sequences for the program PHYRE (http://www.sbg.bio.ic.ac.uk/phyre/), the putative structures were analyzed. As a result, the structures were predicted with high scores using O-GlucNAc transferase (1w3b) as the template (4.3e-17 and 4.7e-16, for CRR4 and CRR21). Among the structures, the 5th PPR motif of CRR4 (left figure), and the 8th PPR motif of CRR21 (right figure) are shown. The positions 1, 4, and "ii" (−2) are shown as sticks in magenta color (dark gray in monochromatic indication).

FIG. 2 shows the RNA-editing PPR proteins analyzed so far and the RNA-editing sites as targets thereof.

Figure 3A:
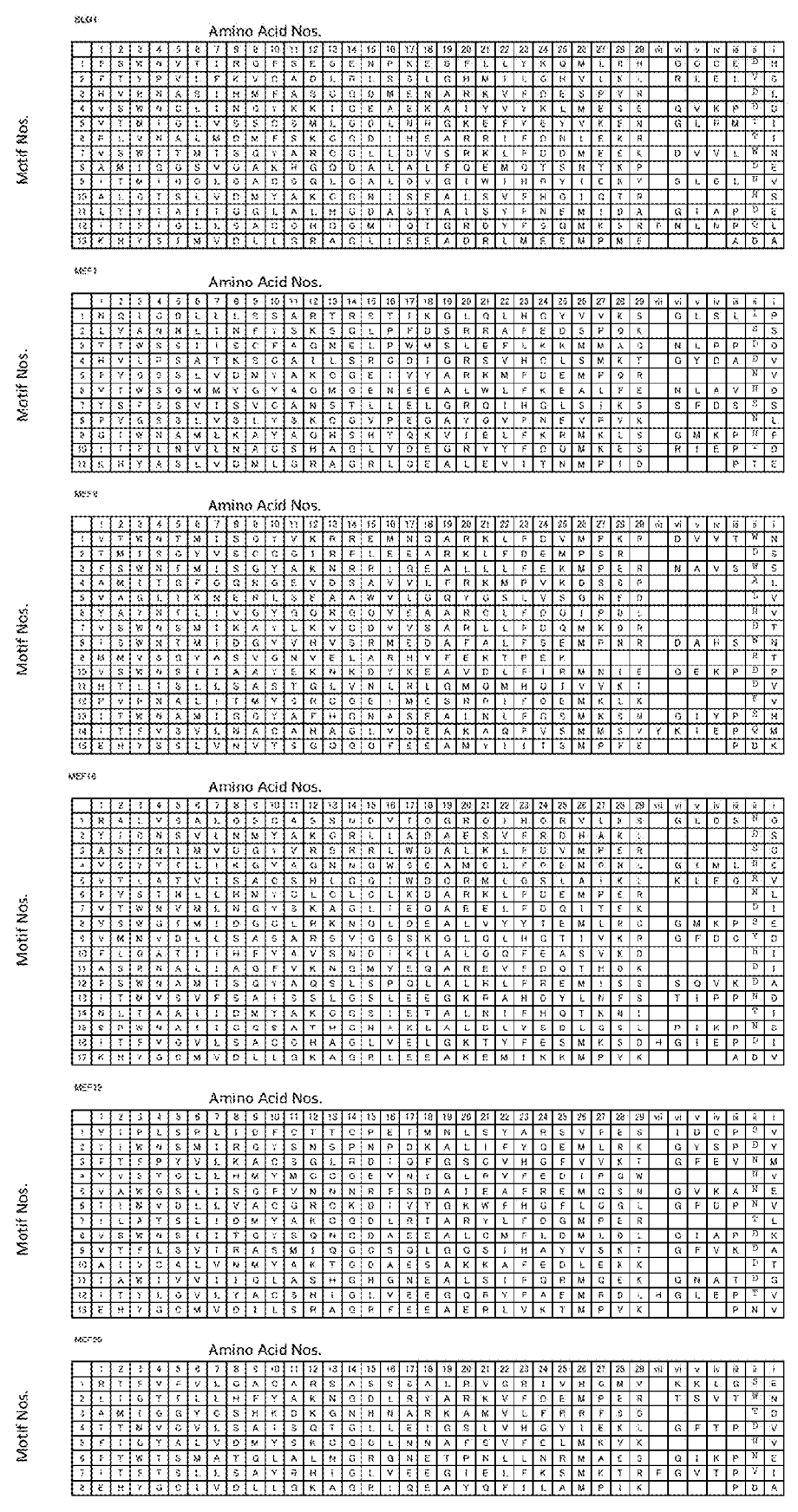

FIG. 3A shows the PPR motif sequences and amino acid numbers of *Arabidopsis thaliana* RNA-editing PPR proteins.

Figure 3B:
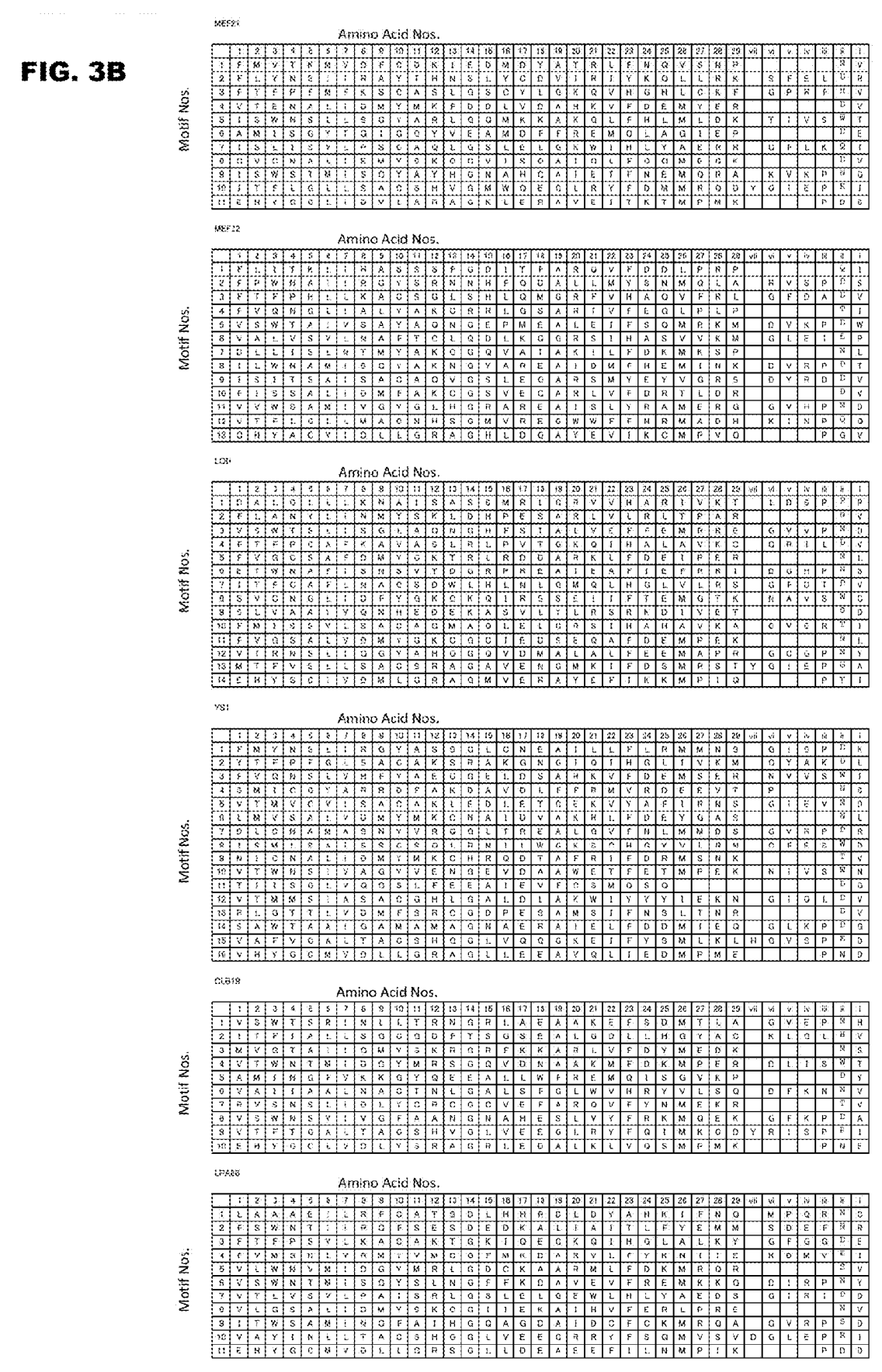

FIG. 3B shows continuation of FIG. 3A.

Figure 3C:
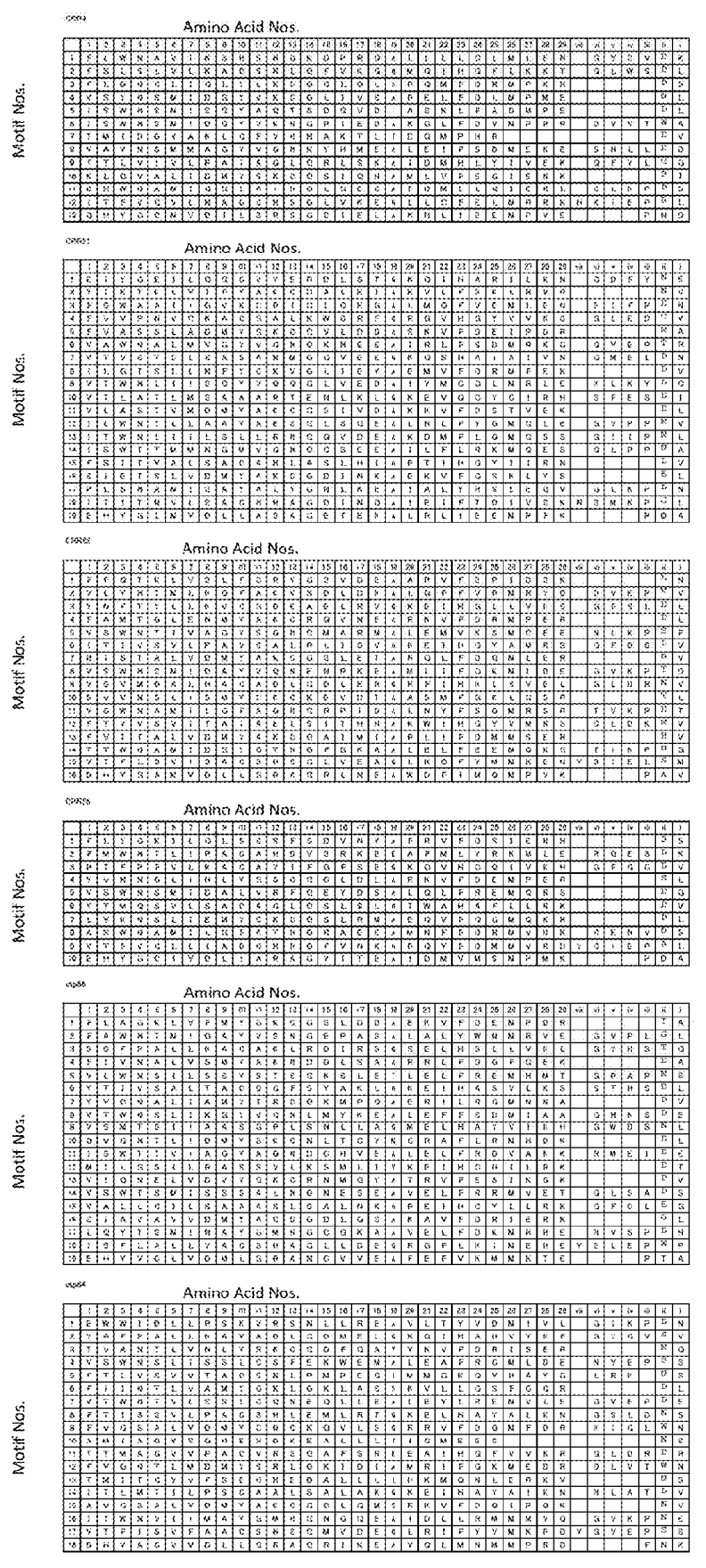

FIG. 3C shows continuation of FIG. 3B.

Figure 3D:
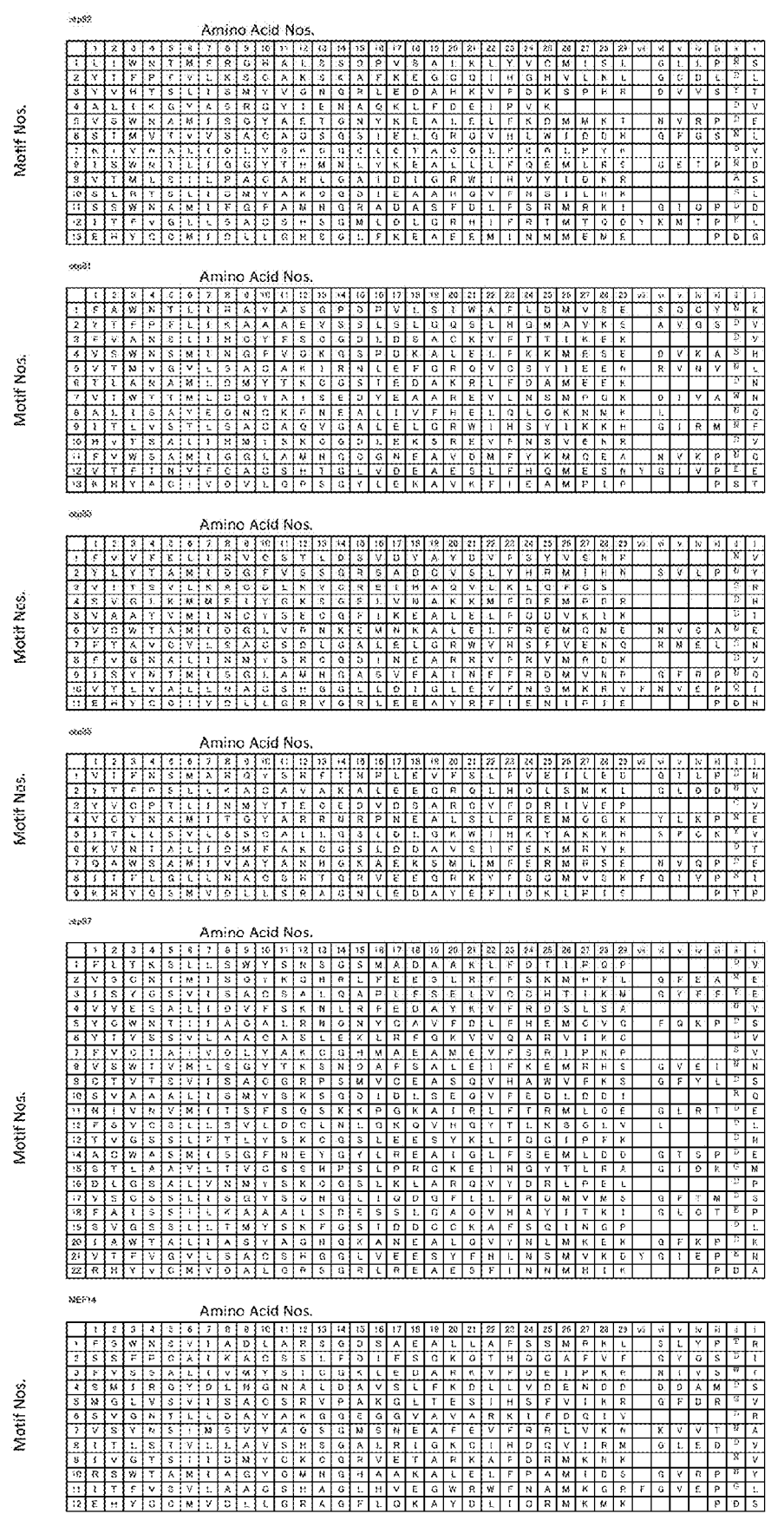

FIG. 3D shows continuation of FIG. 3C.

Figure 4A:
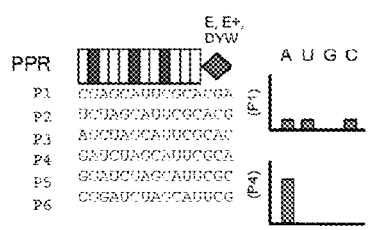
Figure 4B:
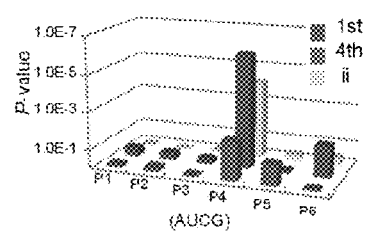
Figure 4C:
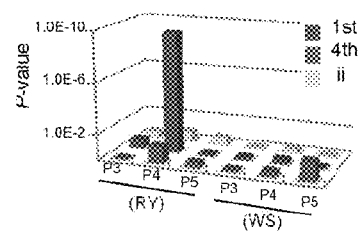
Figure 4D:
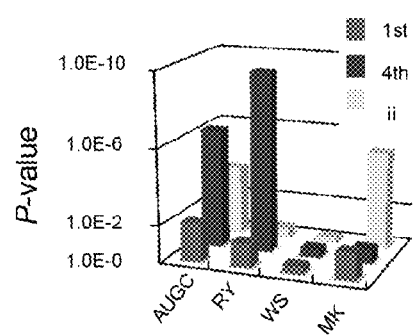
Figure 4E:
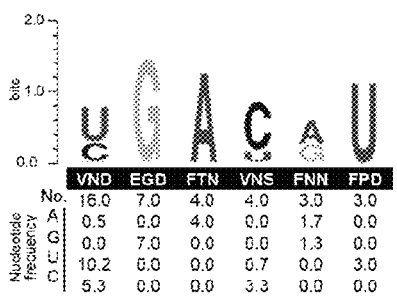

FIGS. 4A-4E show the amino acids in the PPR motifs involved in the RNA recognition. FIG. 4A shows identification of amino acids having a binding nucleotide specifying capacity in the PPR motif. The PPR motifs of RNA-editing PPR protein are aligned with an RNA-editing site upstream sequence in various positions. The alignment was performed by arranging the sequences at a 1-motif to 1-nucleotide correspondence, in a contiguous linear manner. The alignment P1 was obtained by fitting the last PPR motif of the protein to the base 1 nucleotide before the editable C. The base sequence was then moved toward the right, 1 base at a time, to obtain the alignments P2 to P6. The squares represent PPR motifs, and the diamond represents additional motifs (E, E+, DYW) on the C terminus side. If amino acids at specific sites in the motif (for example, amino acids of the motifs indicated in green (dark gray in monochromatic indication)) are responsible for the RNA base recognition, low randomness can be expected for corresponding nucleotides in a specific alignment (lower figure on the right). Otherwise, high randomness is expected (upper figure on the right). FIG. 4B shows binding RNA base specifying capacities of amino acids 1, 4, and "ii" (−2). Low randomness between the amino acid and the base in each alignment is shown in terms of a P value. FIG. 4C shows binding RNA base specifying capacities of amino acids 1, 4, and "ii" (−2) for various classifications of nucleic acids. They are indicated in a similar manner to that of FIG. 4B. The nucleic acids are classified according to type of nucleobase, purine or pyrimidine (RY, A & G or U & C), and presence or absence of hydrogen bond groups (WS, A & U or G & C). FIG. 4D shows results of further detailed analysis of the binding base specifying capacities of the RNA recognition amino acids in the PPR motifs shown in FIG. 4C mentioned above. It was demonstrated that, in addition to that amino acid 4 mainly determines the type of the binding base, purine or pyrimidine (RY), the amino acid "ii" (−2) functions to determine the form of the nucleotide, amino form (A and C) or keto form (G and U) (MK) (FIG. 4D). FIG. 4E shows examples of RNA recognition codes (PPR codes) of several PPR motifs. The white letters indicates types of amino acids 1, 4, and "ii" (−2). The occurrence frequencies of the codes are indicated in the row of "No.", and the occurrence frequencies of the corresponding nucleic acids are indicated in the rows of "Nucleotide frequency".

FIG. 5 shows identification (examples) of the amino acids in the PPR motifs involved in the RNA recognition. The amino acids involved in the RNA recognition were searched for by using data sets of RNA bases corresponding the PPR motifs in each alignment. For example, by using data of RNA bases corresponding the PPR motifs in alignment P4, the binding RNA base specifying capacities of amino acids 4 and 5 were analyzed. For each alignment, data were first sorted according to the types of the amino acids, and the numbers of the RNA bases contained were calculated (upper left table). Then, theoretical values of the numbers were prepared on the basis of the medians of the occurrence frequencies of all the RNA bases contained in the data sets (upper right table). By the chi square test using these two kinds of data, P values were calculated. The upper tables show the analysis results for amino acid 4 in alignment P4, for which significant P values were obtained, and the lower tables show the analysis results for the amino acid 5 in alignment P4, for which significant P values were not obtained.

Figure 6A:
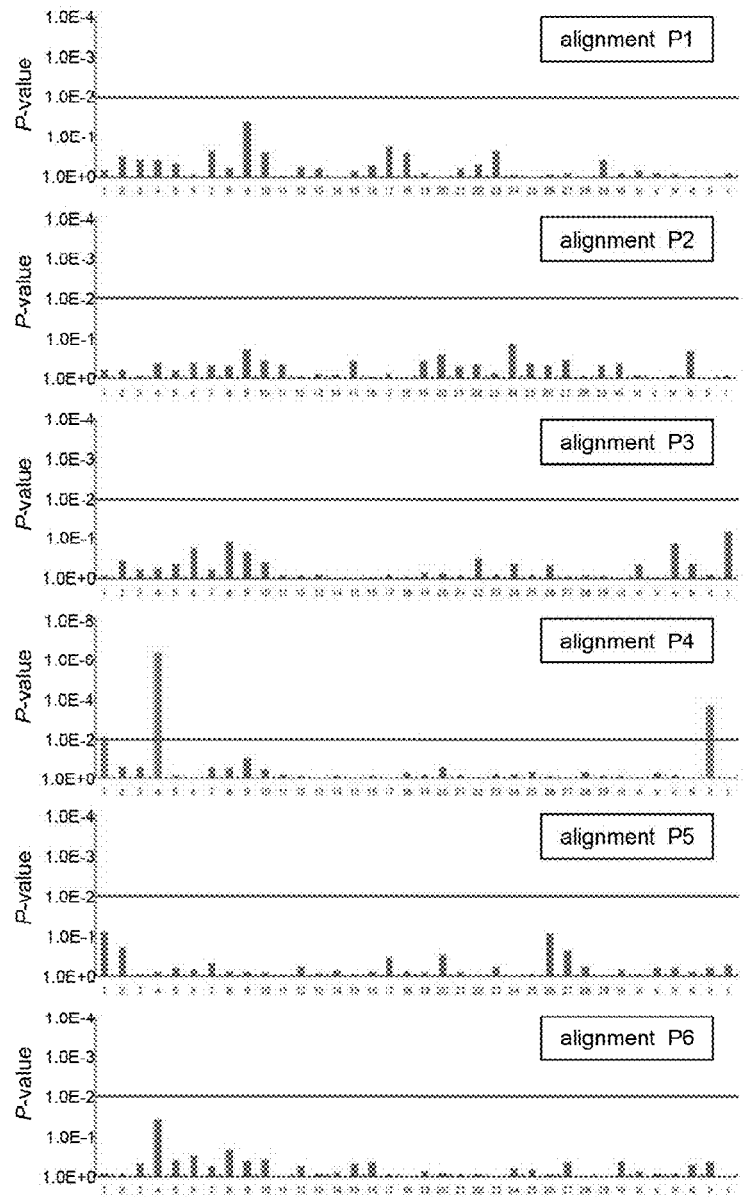
Figure 6B:
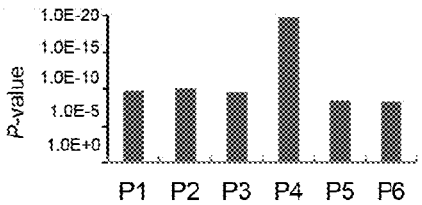

FIGS. 6A and 6B show results of search for the amino acids responsible for the RNA base specifying capacity. FIG. 6A shows P values for low randomness between the type of amino acid and the occurrence frequency of base calculated for the amino acids of all the positions in the alignments P1 to P6. The amino acids that showed significant P values ($P<0.01$) are indicated in magenta color (dark gray in monochromatic indication). The lines (horizontal lines in the graphs) in cyan color (dark gray in monochromatic indication) indicate P value of 0.01. FIG. 6B shows the summary of the low randomness for each alignment. A product of the P values of the amino acids of the positions shown in FIG. 6A for each alignment is shown as a total value of the low randomness for that alignment.

Figure 7:
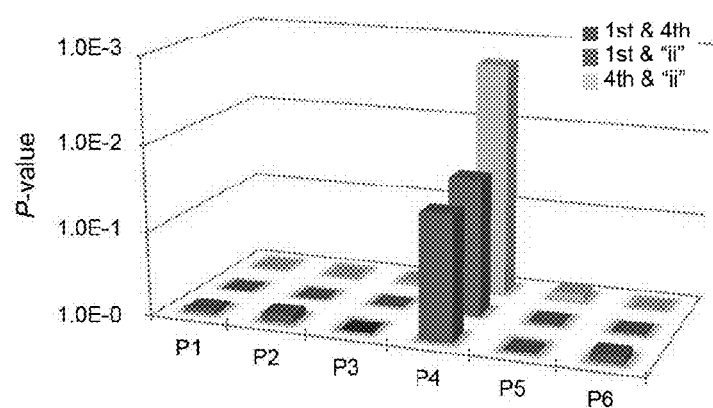

FIG. 7 shows the binding RNA base specifying capacities exerted by two amino acids. The binding RNA base specifying capacities exerted by different combinations of two amino acids (amino acids 1 and 4, 1 and "ii", and 4 and "ii") were analyzed on the basis of low randomness of amino acids and corresponding bases, and the results are shown in the same manner as that used in FIG. 4.

FIG. 8 shows the RNA recognition codes of the PPR motifs extracted from *Arabidopsis thaliana*.

Figure 9:
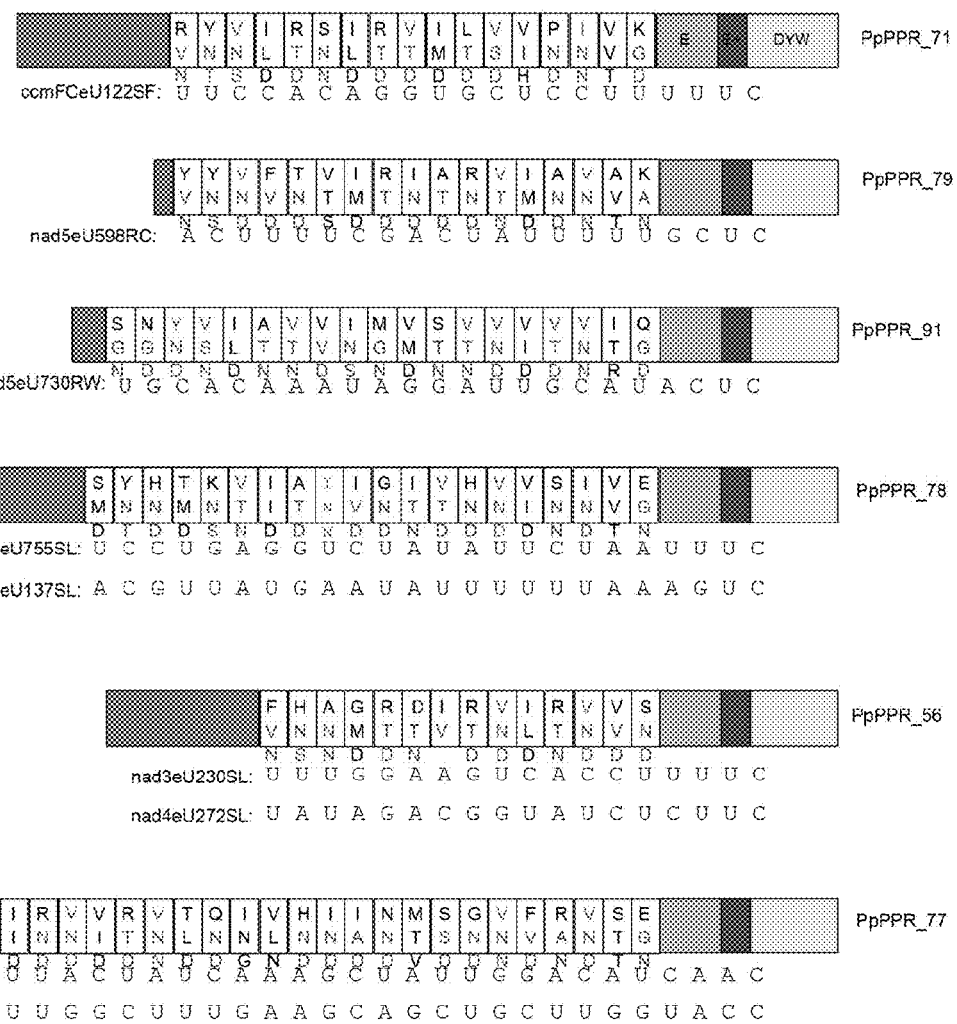

FIG. 9 shows the sequences of *Physcomitrella patens* subsp. *patens* RNA-editing PPR proteins and the RNA-editing sites on which the proteins act. Together with the motif structures of the proteins, the sequences of amino acids 1, 4, and "ii" (−2) in each PPR motif are shown. The letters in magenta and cyan colors (both are in dark gray in monochromatic indication) show the combinations of amino acids homologous to the triPPR or diPPR codes extracted from *Arabidopsis thaliana*. The additional motifs (E, E+, DYW) on the C terminus side are also shown. The sequences of the RNA-editing sites on which the proteins act (upstream sequences containing editable C) are shown in terms of the positions in alignment P4 shown in FIG. 4.

Figure 10:
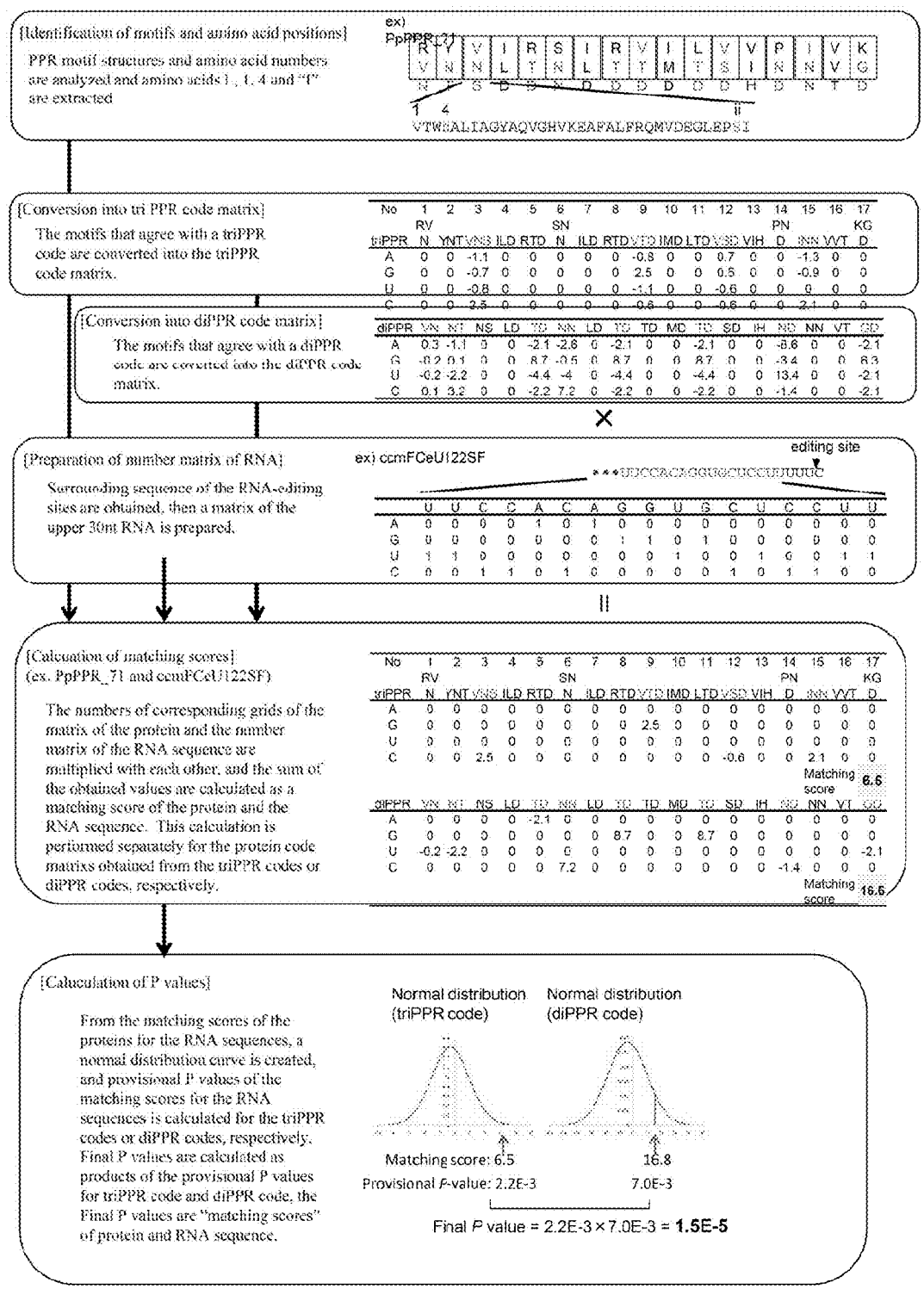

FIG. 10 shows a flowchart of a method for calculating matching score between a PPR protein and an RNA-editing site RNA sequence. From the Uniprot or PROSITE database, PPR models of proteins are obtained, and the amino acid numbers are given according to FIG. 1. Amino acids 1, 4, and "ii" are extracted. As an example, the moss PPR protein, PpPPR71, is shown. Then, the matching combinations of amino acids are converted into a triPPR code matrix. The motifs that could not be converted into the triPPR codes are then converted into a diPPR code matrix. In parallel, the RNA-editing site 30 nt (the last nucleotide is the editable C) are converted into an expression matrix. As an example, there is shown the ccmFCeU122SF sequence, on which the PpPPR71 protein acts. Then, products of numbers of corresponding grids of the protein code matrix and the RNA expression matrix are obtained, and matching scores are calculated from the sum of them. The last line of the protein code matrix should be matched to the line corresponding to the base 4 nucleotide before the editable C. This calculation is performed for protein code matrixes prepared from the triPPR codes and the diPPR codes. A provisional P value for each RNA sequence is calculated with each of the triPPR codes and diPPR codes using a normal distribution curve prepared from matching scores for a plurality of RNA sequences. The final matching score (P value) is calculated as a product of the provisional P values of the triPPR and diPPR codes.

Figures 11A, 11B:
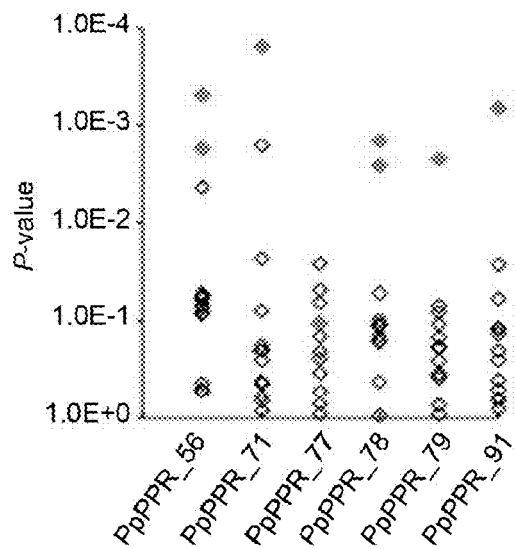

FIGS. 11A and 11B show prediction of the target RNA sequences of the PPR proteins using the PPR codes. FIG. 11A shows the matching scores for the RNA-editing sites of the triPPR or the diPPR codes obtained by conversion of amino acids 1, 4, and "ii" (−2) extracted from the moss PPR proteins as shown in FIG. 10, which values are shown in terms of P values. As the RNA-editing sites, 13 RNA-editing sites of the moss were used, and as reference sequences, 34 RNA-editing sites of Arabidopsis thaliana chloroplast were used. In the drawing, only the matching scores for the 13 RNA-editing sites of the moss are shown. The diamonds indicate matching scores of the proteins for the respective editing sites. The correct editing sites are shown in magenta color (solid gray in monochromatic indication). FIG. 11B shows the P values shown in FIG. 11A in the form of table.

Figure 12A:
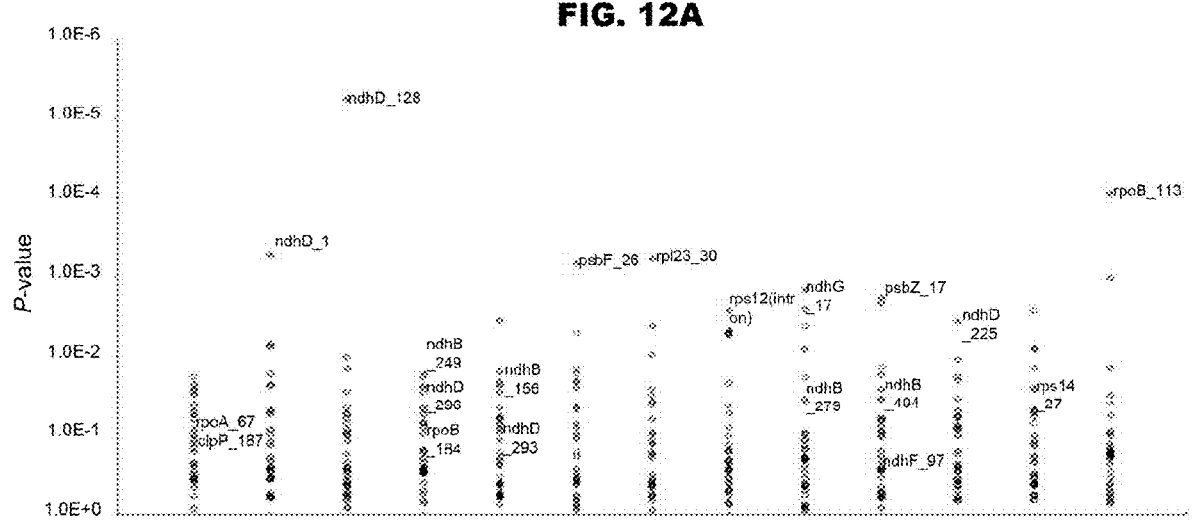
Figure 12B:
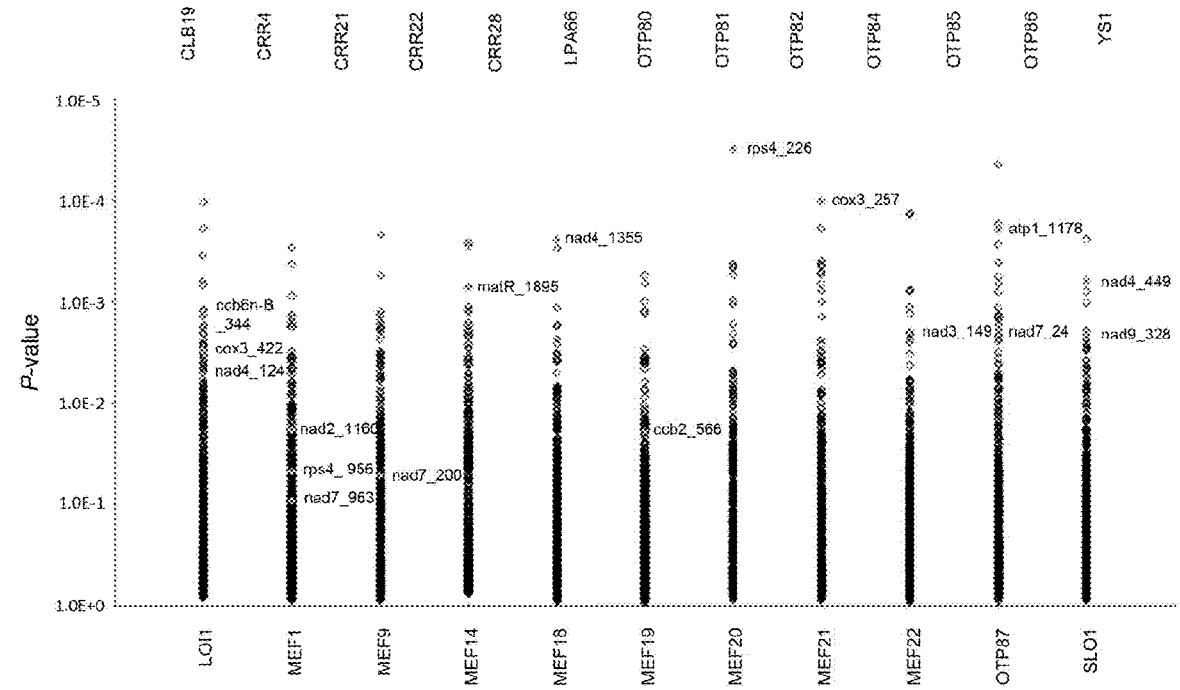

FIGS. 12A and 12B show verification of accuracy for prediction of RNA-editing sites using Arabidopsis thaliana RNA-editing proteins. The prediction accuracy was verified by using the Arabidopsis thaliana PPR proteins used for the code extraction. FIG. 12A shows prediction of RNA-editing sites of 13 known PPR proteins with respect to the total 34 chloroplast RNA-editing sites. The diamonds indicate the matching scores between the proteins and the RNA-editing site sequences. The correct RNA-editing sites are shown in magenta color (solid gray in monochromatic indication). FIG. 12B shows prediction of RNA-editing sites of 11 known PPR proteins with respect to the total 488 mitochondria RNA-editing sites.

Figures 13A, 13B, 13C, 13D:
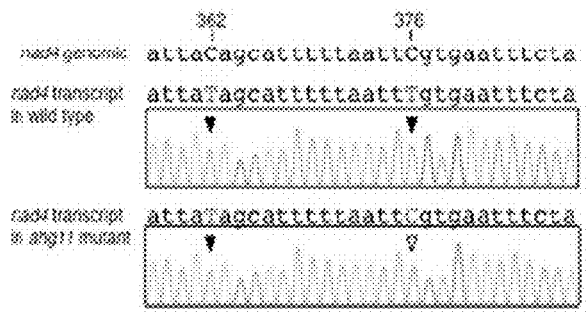

FIGS. 13A-13D show prediction of the target RNA editing sites of Arabidopsis thaliana PPR protein AHG11, and experimental verification thereof. FIG. 13A shows the motif structure of AHG11. It has a typical structure of RNA-editing PPR protein comprising 12 PPR motifs and the additional motifs (E, E+, DYW) on the C terminus side. In Ahg11 mutants, there can be found a new translation stop codon in the coding region generated by the point mutation at the position indicated with the asterisk (295 Trp). FIG. 13B shows prediction of the target RNA-editing sites using all the RNA-editing sites contained in the chloroplasts and mitochondria of Arabidopsis thaliana. The top ten editing sites that showed the highest P values are shown. Presence or absence of the RNA editing in wild strain and mutant strain was experimentally verified, and the results are shown in the column of Editing status. The sites for which RNA editing was detected in both the wild strain and the mutant strain are indicated as E, and the site for which RNA editing could not observed only in the mutant strain is indicated as Un. FIG. 13C shows the results of the prediction in the form of graph. FIG. 13D shows experimental verification of the target RNA-editing sites of AHG11. There are shown the results of the sequence analysis of the region containing the mitochondria nad4. RNAs were extracted from the wild strain and the ahg11 mutant strain, cDNAs were prepared by reverse transcription, and nucleotide sequence analysis of them was conducted. There are two RNA-editing sites (nsd4_362 and _376) in this region. The edited sites are indicated with black arrows, and the non-edited site is indicated with a white arrow.

FIG. 14 shows prediction of the target sites in the chloroplast genome sequence. The target sites were predicted in the Arabidopsis thaliana chloroplast total genome sequence (154,478 bp) by using six PPR proteins. For the prediction, the codes extracted from Arabidopsis thaliana (At codes) or the codes extracted from Arabidopsis thaliana and the moss (At+Pp codes) were used.

FIG. 15 shows the RNA recognition codes of the PPR motifs extracted from Arabidopsis thaliana and Physcomitrella patens subsp. patens.

Figure 16A:
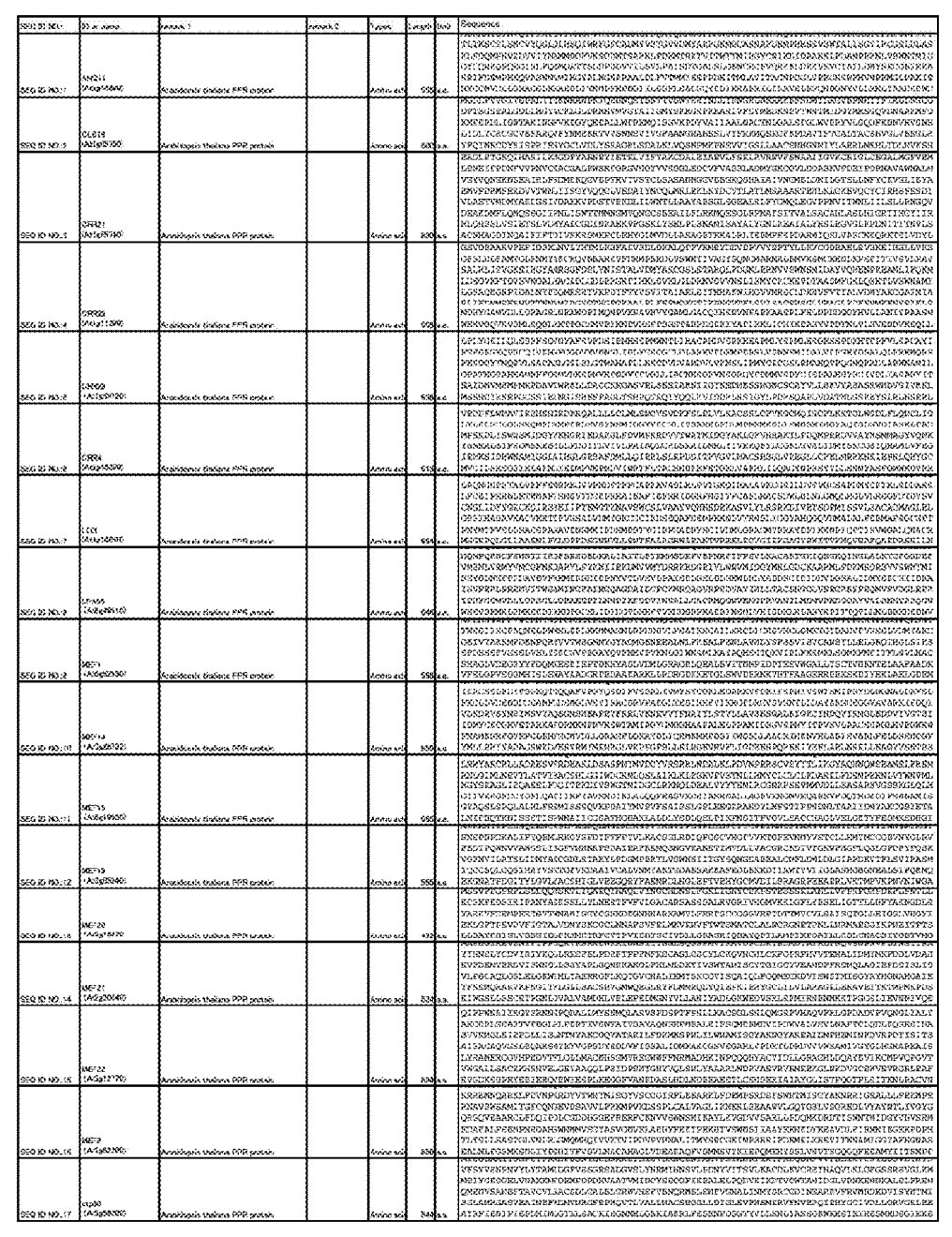

FIG. 16A shows amino acid sequences or nucleotide sequences relevant to the present invention.

Figure 16B:
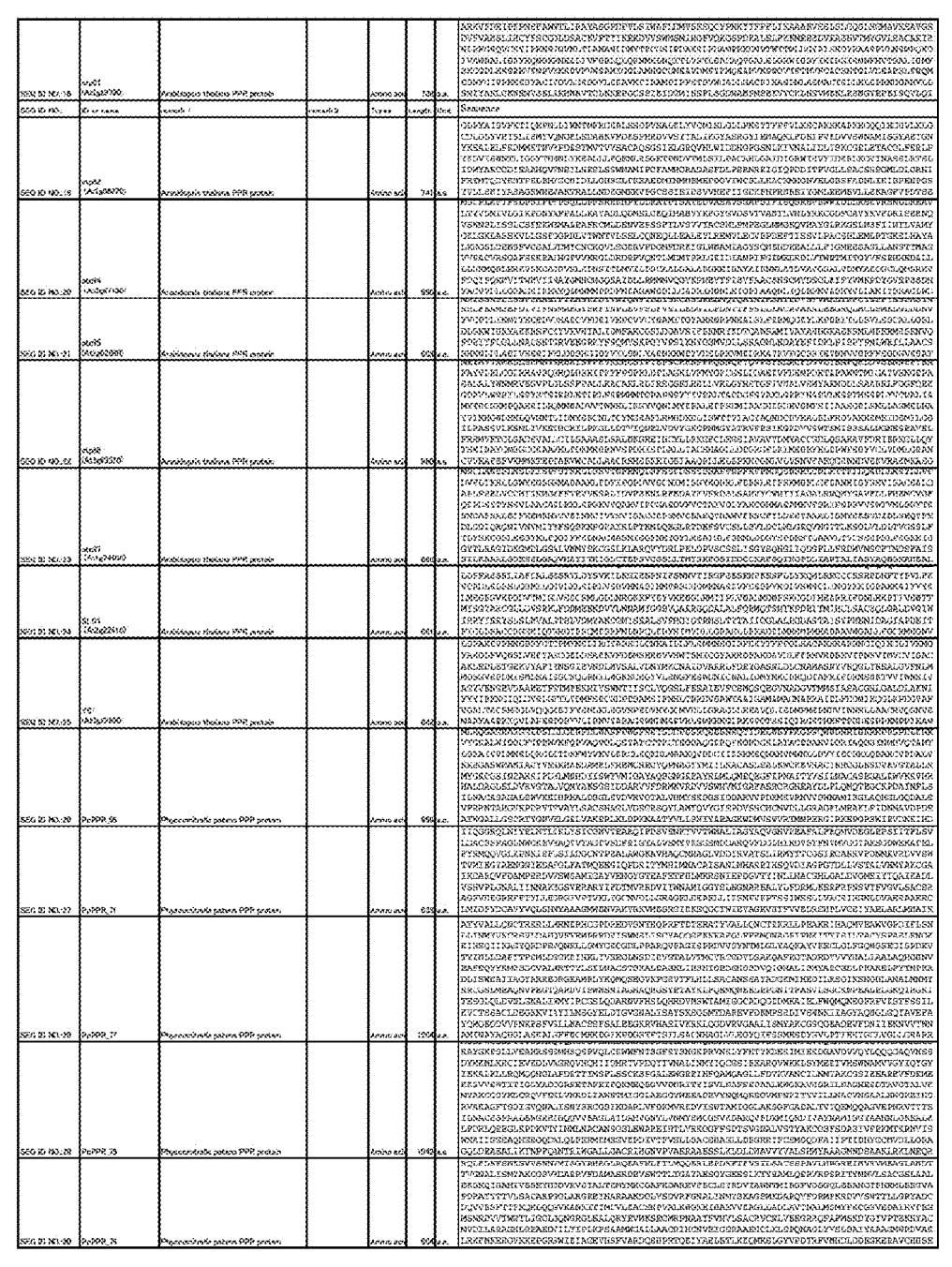

FIG. 16B shows amino acid sequences or nucleotide sequences relevant to the present invention.

Figure 16C:
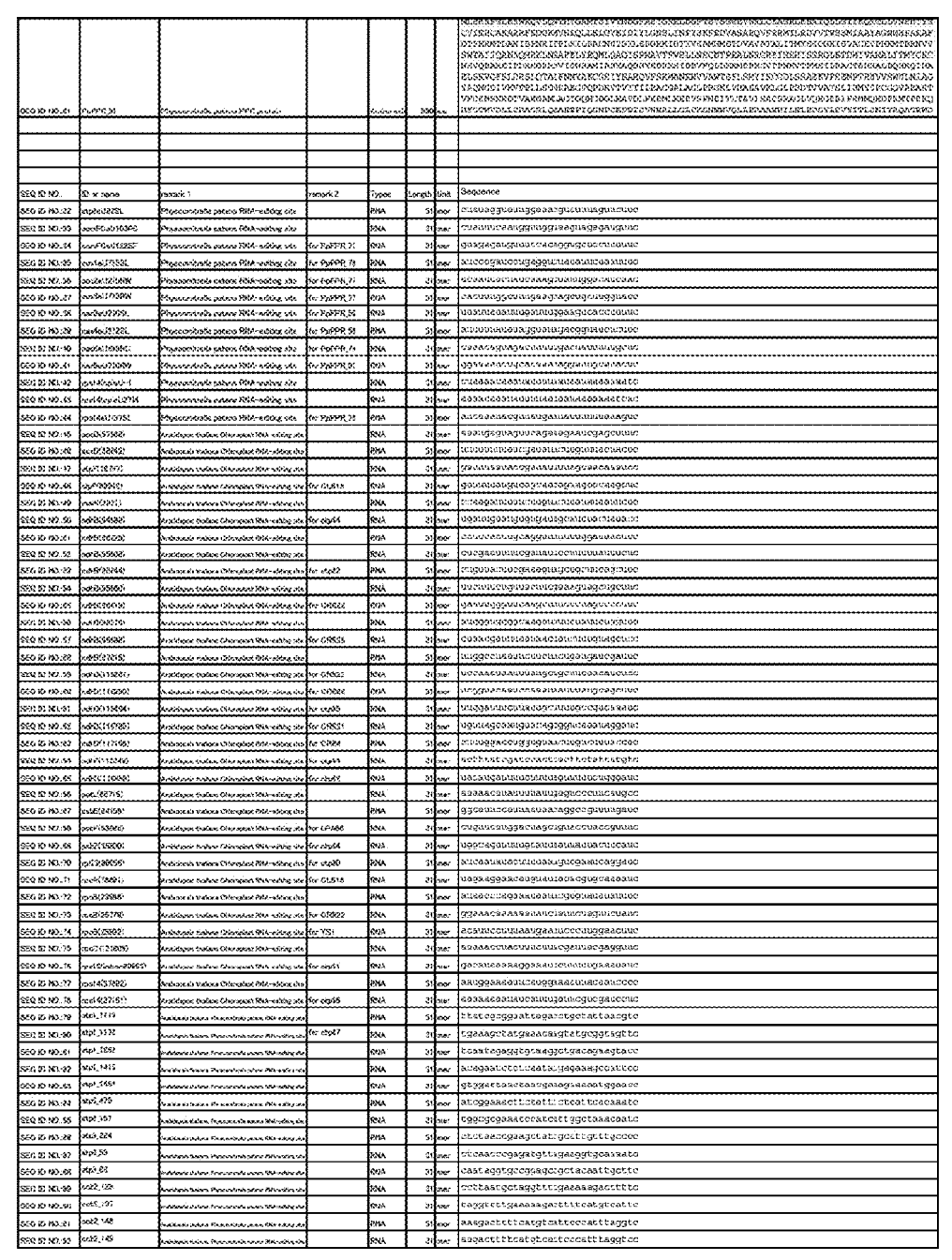

FIG. 16C shows amino acid sequences or nucleotide sequences relevant to the present invention.

Figure 16D:
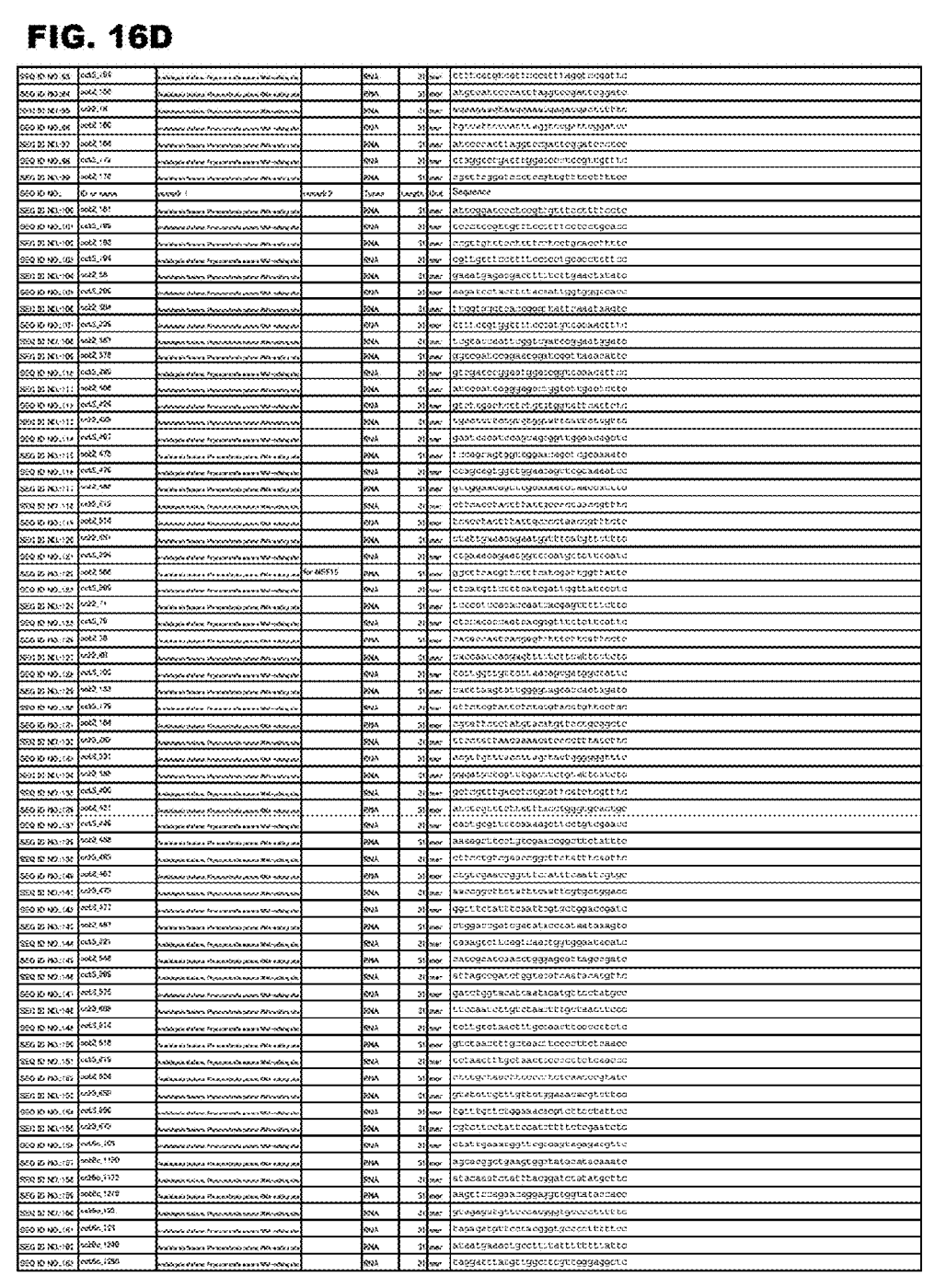

FIG. 16D shows amino acid sequences or nucleotide sequences relevant to the present invention.

Figure 16E:
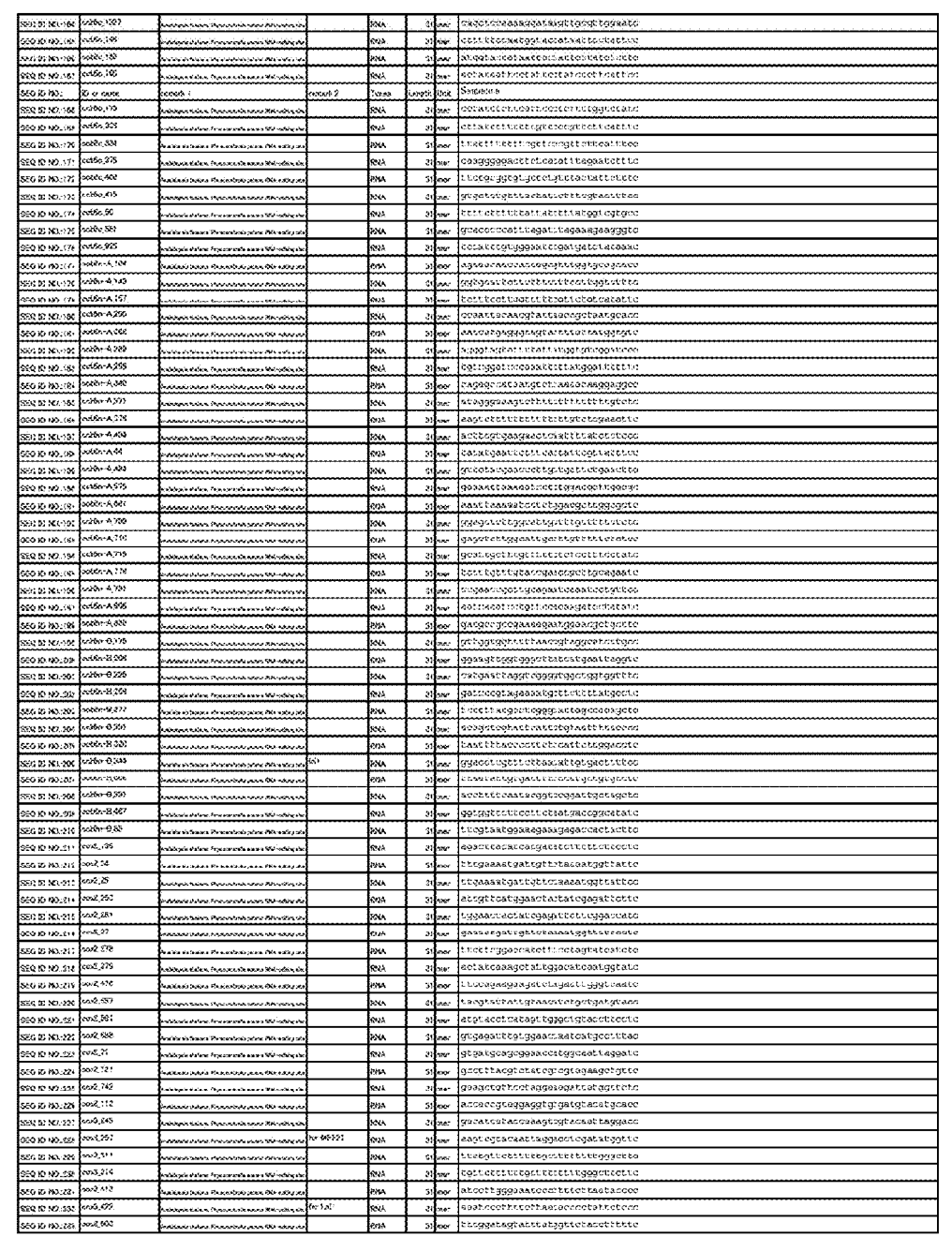

FIG. 16E shows amino acid sequences or nucleotide sequences relevant to the present invention.

Figure 16F:
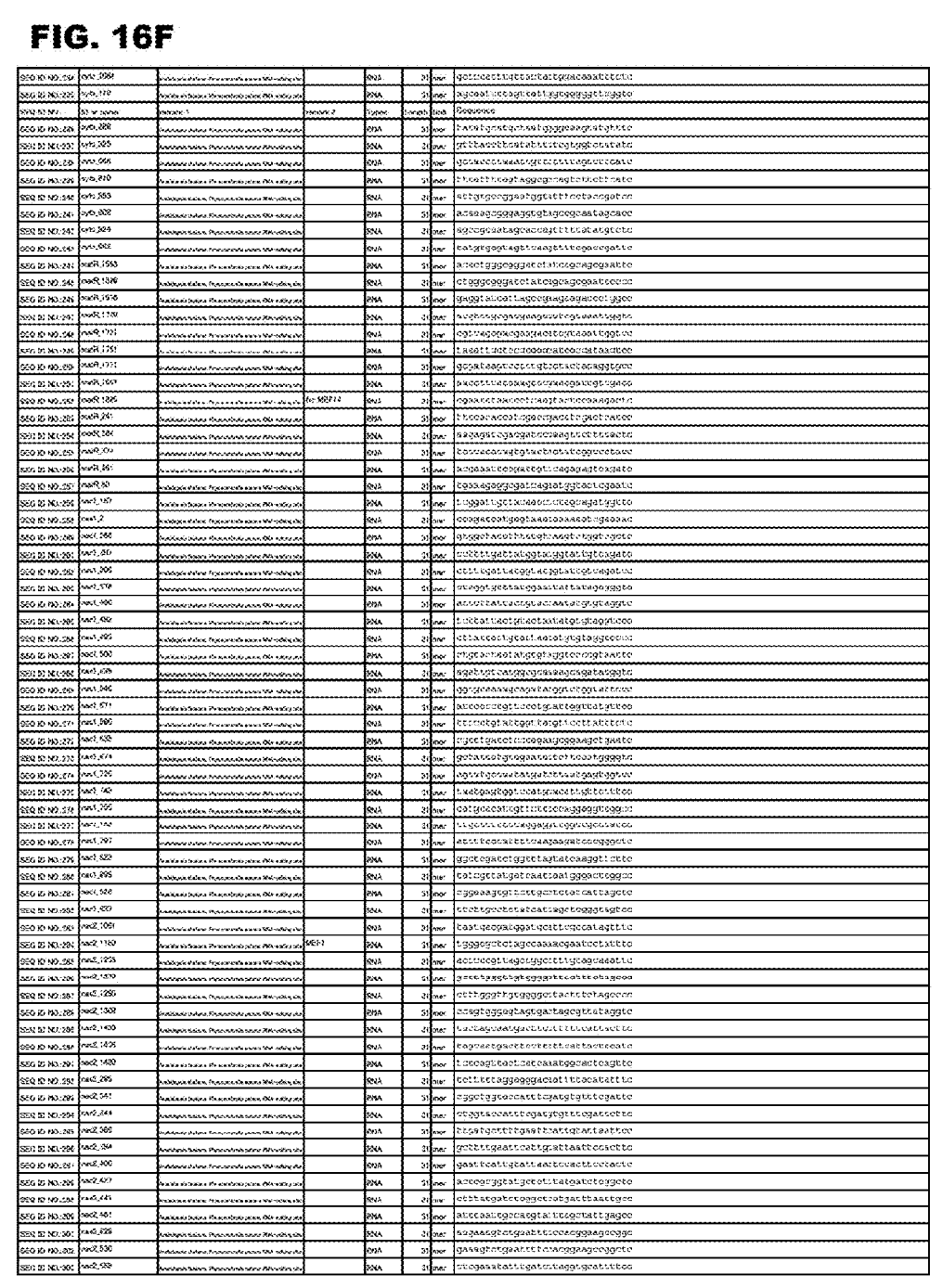

FIG. 16F shows amino acid sequences or nucleotide sequences relevant to the present invention.

Figure 16G:
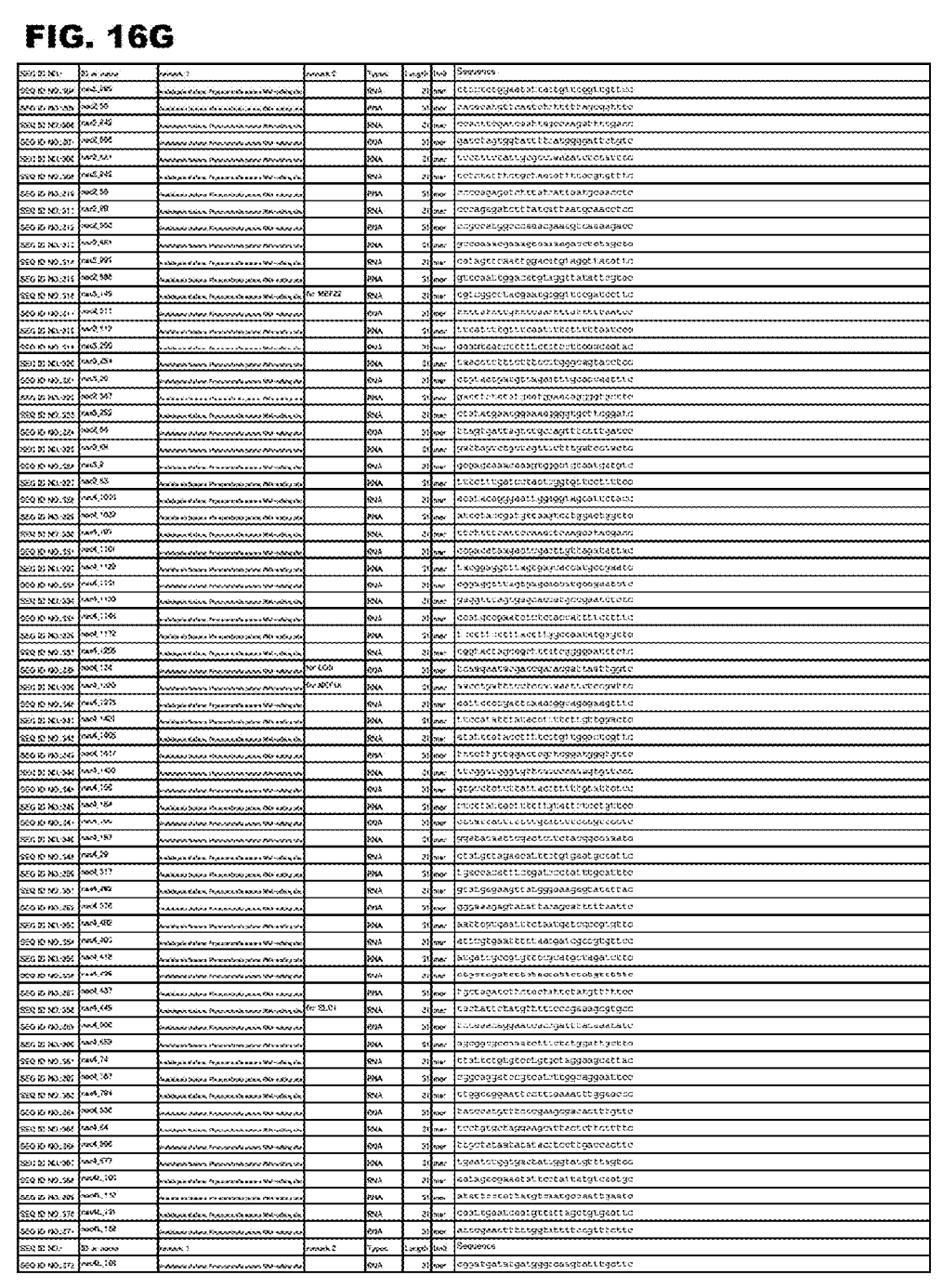

FIG. 16G shows amino acid sequences or nucleotide sequences relevant to the present invention.

Figure 16H:
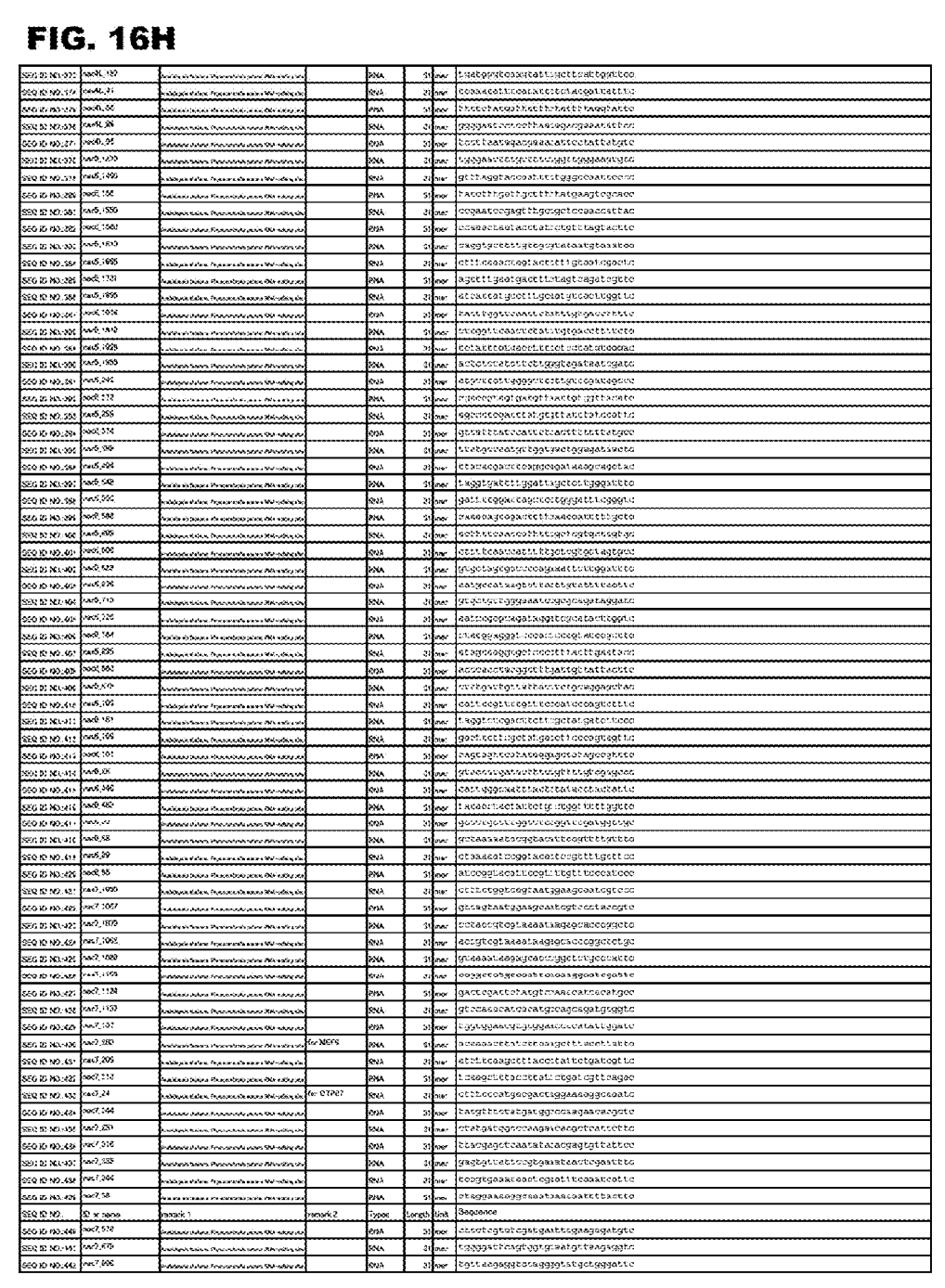

FIG. 16H shows amino acid sequences or nucleotide sequences relevant to the present invention.

Figure 16I:
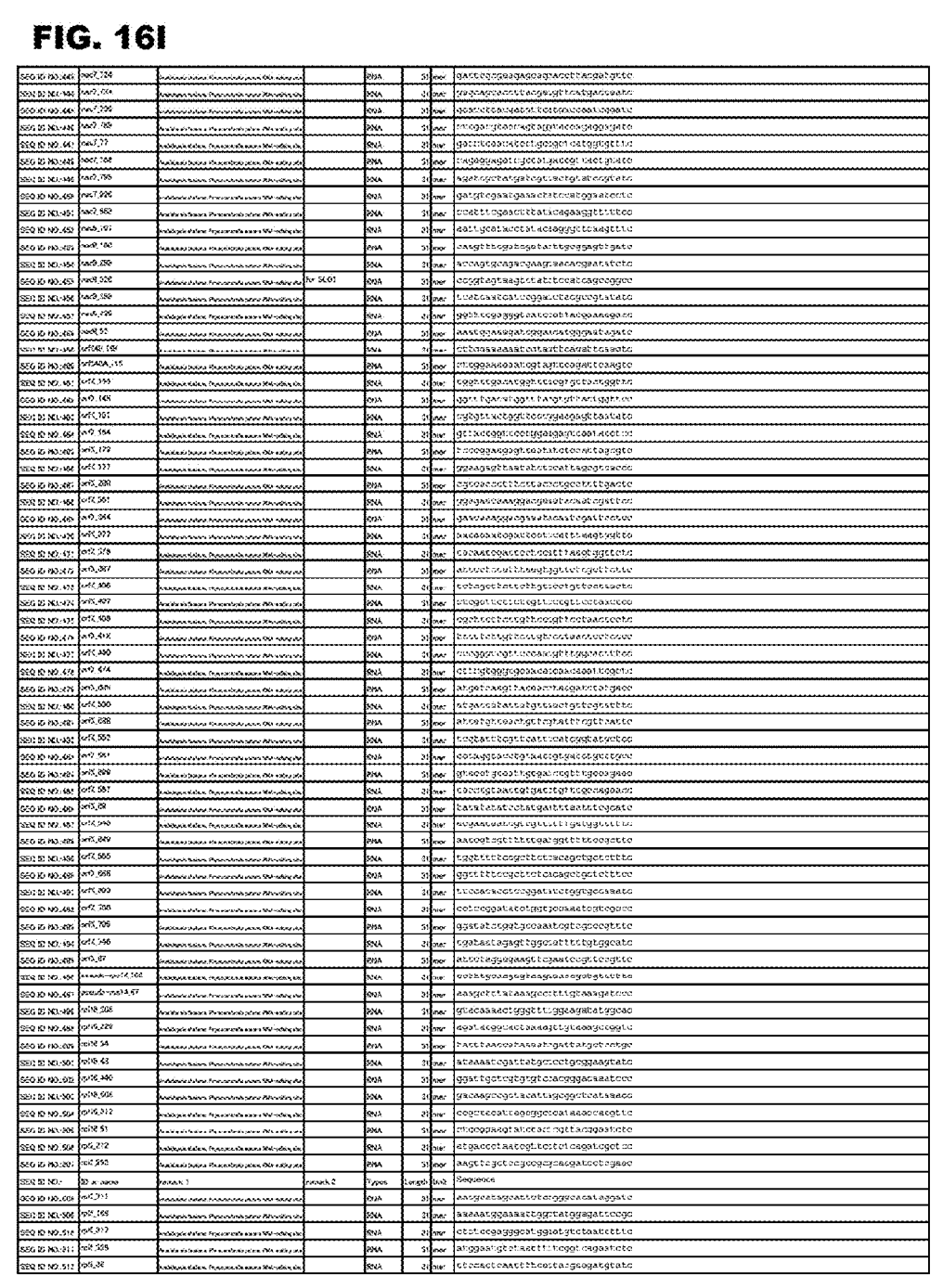

FIG. 16I shows amino acid sequences or nucleotide sequences relevant to the present invention.

Figure 16J:
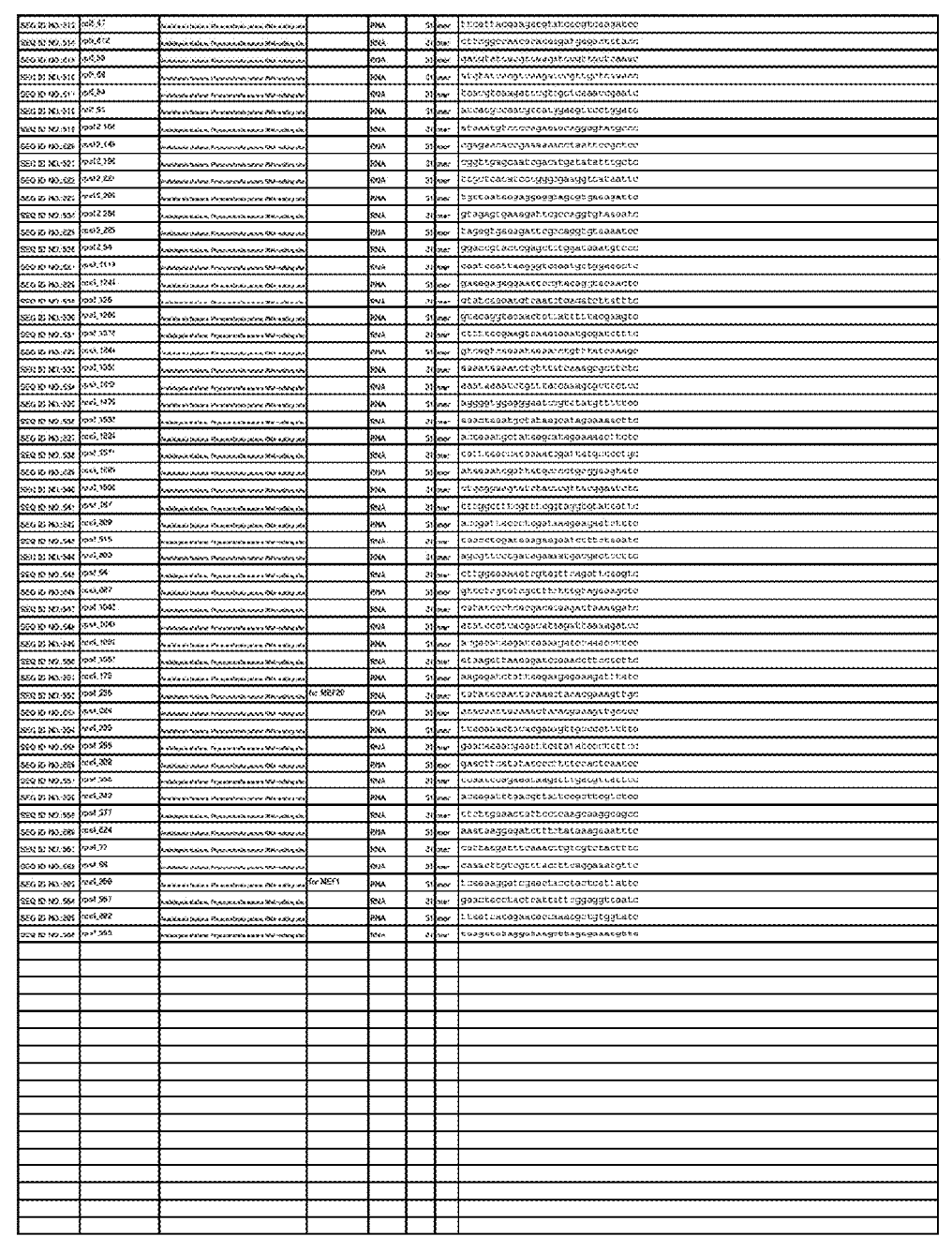

FIG. 16J shows amino acid sequences or nucleotide sequences relevant to the present invention.

FIGS. 17A and 17B show analysis of the binding of the Enko B protein and RNA containing the cytoplasmic male sterility (CMS) gene. FIG. 17A shows a schematic diagram around the mitochondrial orf125, and also schematically shows the regions of RNAa, RNAbc, RNAb, and RNAc used in the binding experiment. FIG. 17B shows binding of the Enko B protein and RNA. Enko B protein (1.4 nmol) and $^{32}$P-labeled RNAbc (0.1 ng) were reacted in the presence of non-labeled RNAa, RNAbc, RNAb, and RNAc (×5 and ×10 w/w with respect to RNAbc, used as a competitive inhibition substance) in 20 L of a reaction mixture to perform the gel shift competition experiment.

FIGS. 18A-18C show binding of the ORF687-like proteins and RNA. FIG. 18A shows the results of analysis of RNA binding characteristics of ORF687-like proteins performed by gel shift assay for binding of Enko B (Rf), Kosena B (rf), and Enko A (rf) with RNAb. FIG. 18B is shows the results of FIG. 18A in the form of graph, and dissociation constants (KD) of the proteins representing the RNA binding capacities thereof were calculated on the basis of this graph. FIG. 18C shows the results of calculation of the matching scores of Enko B (Rf), Kosena B (rf), and Enko A (rf), and potential binding sites thereof performed in the same manner as that used for obtaining the results shown in FIG. 19.

Figure 19A:
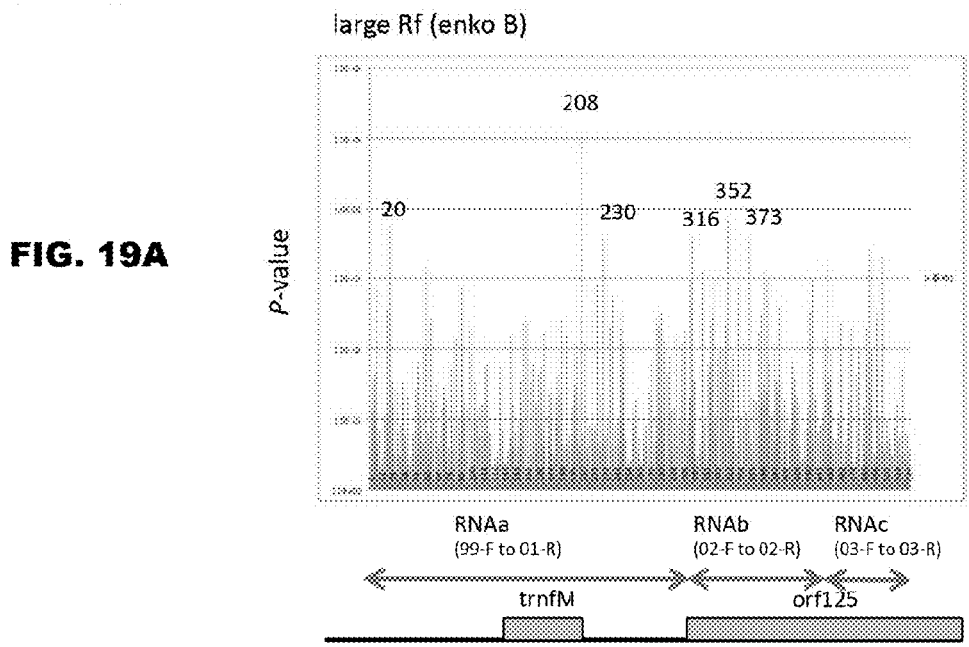
Figure 19B:
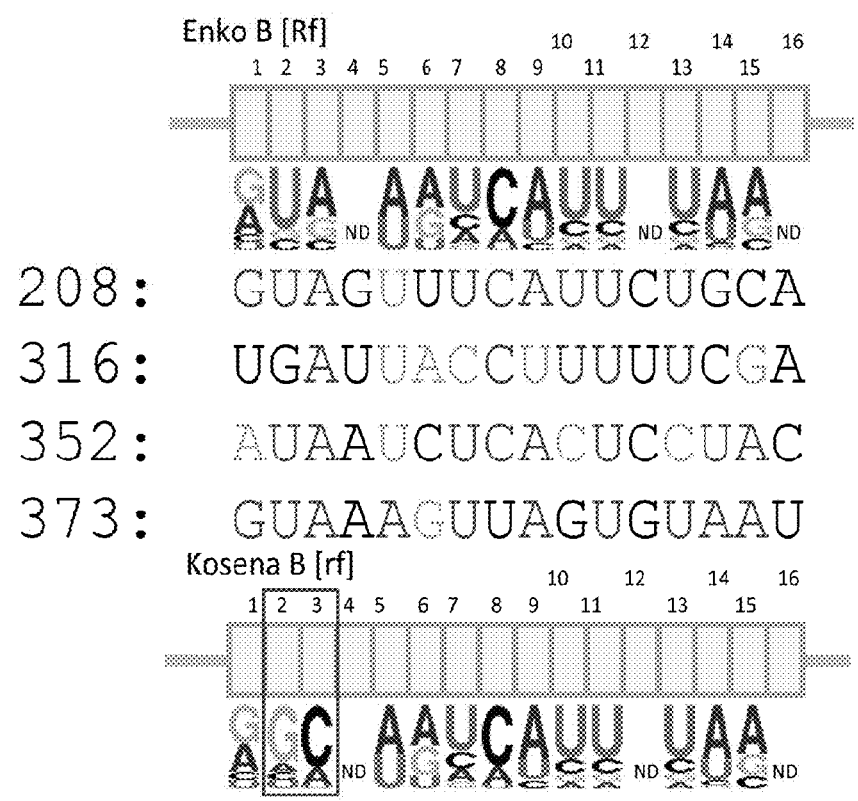

FIGS. 19A and 19B show prediction of binding sequence of the fertility restoration factor that acts on Ogura-type cytoplasm. FIG. 19A shows the results for prediction of binding of the Enko B protein using the PPR codes, and the structure of RNA containing the CMS gene orf125 is shown in the lower diagram of FIG. 19A. As for the regions from RNAa to RNAc shown in FIG. 19A, refer to FIG. 17. In FIG. 19A, the regions of Nos. 208, 230, 316, 352 and 373 are focused on, among the regions that showed a significantly high P value (FIG. 19A).

FIGS. 20A-20C show the secondary structure and structural change of the candidate binding RNA region of ORF687-like protein. FIG. 20A shows the secondary structure of the region including the region of No. 306 and the predicted binding sites for the ORF687-like protein, and shows PPR motifs with boxes together with the corresponding bases. The 2nd and 3rd PPR motifs for which Enko B (Rf) and Kosena B (rf) show a remarkable difference are emphasized.

FIG. 20B shows the secondary structure of the region including the regions of Nos. 352 and 373 and the predicted binding sites for the ORF687-like protein. FIG. 20C shows results indicating structural change of RNAb induced by Enko B, which were obtained by mixing RNAb and Enko B protein, and then adding a double-strand selective RNase (RNase V1).

Figure 22:
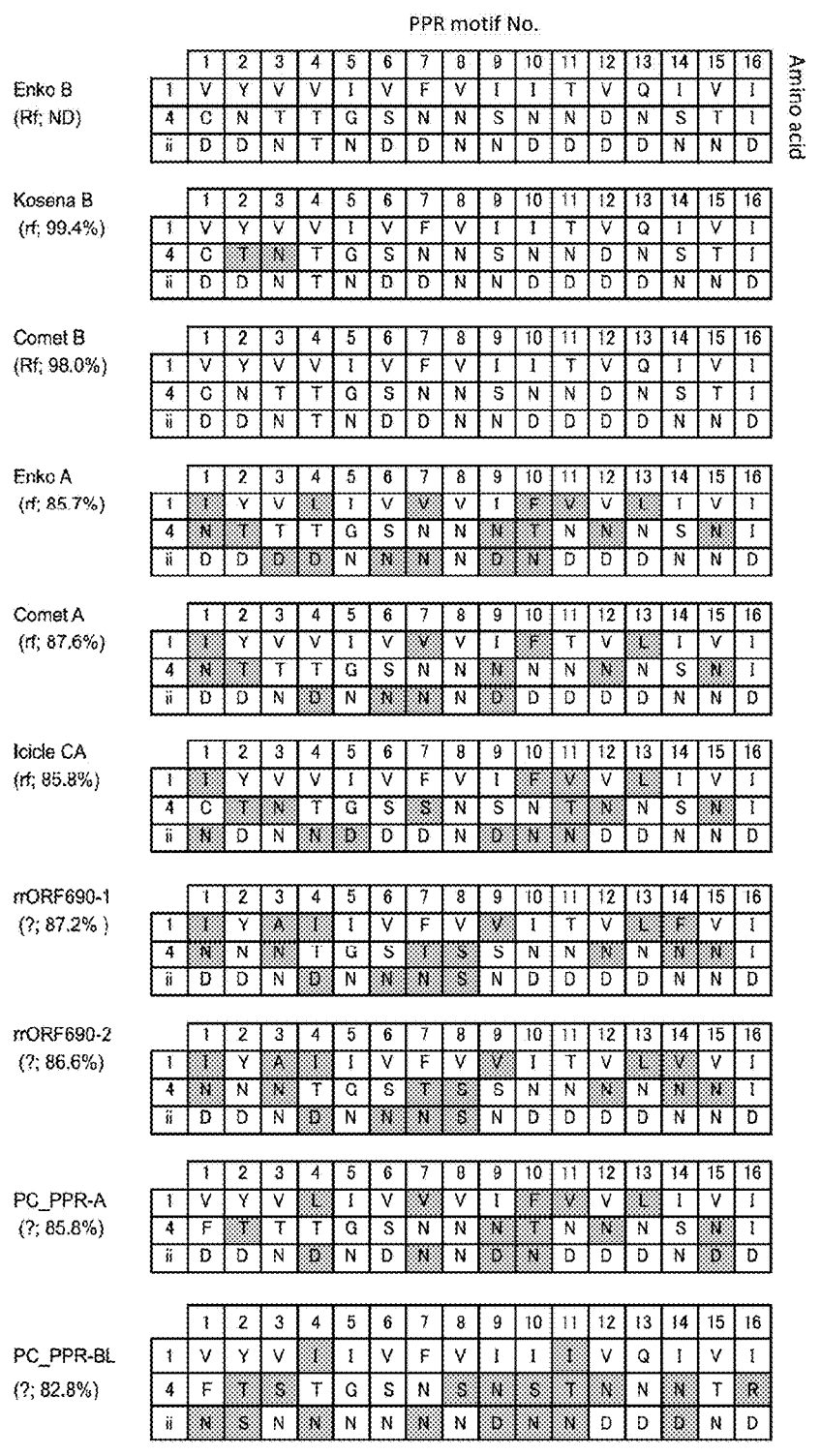

FIG. 21A shows alignment of ORF687-like proteins.
FIG. 21B shows alignment of ORF687-like proteins.
FIG. 22 shows a list of the base specifying amino acids of ORF687-like proteins contained in various radish varieties.

DESCRIPTION OF EMBODIMENTS

[PPR Motif and PPR Protein]

The term "PPR motif" used in the present invention refers to a polypeptide consisting of 30 to 38 amino acids and having an amino acid sequence showing an E value determined by amino acid sequence analysis using a protein domain search program on the Web, i.e., an E value obtained by using Pfam, PF01535, or Prosite, PS51375, not larger than a predetermined value (desirably E-03), unless especially indicated. The position numbers of amino acids constituting the PPR motif defined in the present invention are substantially synonymous with those obtainable with PF01535, but they correspond to those obtained by subtracting 2 from the numbers of the amino acid positions obtained with PS51375 (for example, the position 1 referred to in the present invention is the position 3 obtained with PS51375). Further, the amino acid "ii" (−2) is the second amino acid from the end (C-terminus side) of the amino acids constituting the PPR motif, or the second amino acid towards the N-terminus side from the first amino acid of the following PPR motif, i.e., −2nd amino acid (FIG. 1). When the following PPR motif is not definitely identified, the amino acid 2 amino acids before the first amino acid of the following helical structure is the amino acid "ii". For Pfam, http://pfam.sanger.ac.uk/ can be referred to, and for Prosite, http://www.expasy.org/prosite/ can be referred to.

Although the conservativeness of the conserved amino acid sequence of the PPR motif is low at the amino acid level, two of the α-helixes as the secondary structure are well conserved. Although a typical PPR motif is constituted by 35 amino acids, the length thereof is as variable as 30 to 38 amino acids.

More specifically, the PPR motif referred to in the present invention consists of a polypeptide of a 30- to 38-amino acid length represented by the formula 1.

[F 4]

$$(HelixA)-X-(HelixB)-L \qquad \text{(Formula 1)}$$

In the formula:

Helix A is a moiety of 12-amino acid length capable of forming an α-helix structure, and is represented by the formula 2;

[F 5]

$$A_1-A_2-A_3-A_4-A_5-A_6-A_7-A_8-A_9-A_{10}-A_{11}-A_{12} \qquad \text{(Formula 2)}$$

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[F 6]

$$L_{vii}-L_{vi}-L_v-L_{iv}-L_{iii}-L_{ii}-L_i \qquad \text{(Formula 3)}$$

wherein, in the formula 3, the amino acids are numbered "i" (−1), "ii" (−2), and so on from the C-terminus side, provided that $L_{iii}$ to $L_{vii}$ may not exist.

The term "PPR protein" used in the present invention refers to a PPR protein comprising one or more, preferably two or more, of the above-mentioned PPR motifs, unless especially indicated. The term "protein" used in this specification refers to any substance consisting of a polypeptide (chain consisting of a plurality of amino acids bound via peptide bonds), unless especially indicated, and includes those consisting of a polypeptide of a comparatively low molecular weight. The term "amino acid" used in the present invention refers to a usual amino acid molecule, and also refers to an amino acid residue constituting a peptide chain. Which one is referred to shall be clear to those skilled in the art from the context.

Many kinds of PPR proteins exist in plants, and in the case of *Arabidopsis thaliana*, about 500 kinds of proteins and about 5000 kinds of the motifs can be found. Also in many land plants, such as rice plant, poplar, and selaginella, PPR motifs and PPR proteins of various amino acid sequences exist. It is known that some PPR proteins are important factors for obtaining F1 seeds for hybrid vigor as a fertility restoration factor that works for pollen (male gamete) formation. As an action analogous to the fertility restoration, it has been clarified that some PPR proteins work for speciation. It has also been clarified that most of PPR proteins act on RNA in mitochondria or chloroplasts.

For animals, it is known that anomaly of the PPR protein identified as LRPPRC causes Leigh syndrome French Canadian type (LSFC, Leigh's syndrome, subacute necrotizing encephalomyelopathy).

The term "selectively" used in the present invention concerning the binding property of the PPR motif with RNA base means that the binding activity for one base among the RNA bases is higher than the binding activities for the other bases, unless otherwise indicated. Concerning this selectivity, those skilled in the art can plan and conduct an experiment for confirming it, and it can also be obtained by calculation as disclosed in the examples described in this specification. The term RNA base used in the present invention refers to a base of a ribonucleotide constituting RNA, specifically, any one of adenine (A), guanine (G), cytosine (C), and uracil (U). The PPR protein may have selectivity for a base in RNA, but it does not bind to a nucleic acid monomer. Although the sequence searching method for the conserved amino acids as the PPR motif had been established before the present invention was accomplished, the correspondence between the amino acid and the selective binding with RNA base was not discovered at all.

The present invention provides the following findings.

(I) Information Concerning Positions of Amino Acids Important for the Selective Binding:

Specifically, combination of the three amino acids, amino acids 1, 4, and "ii" (−1) ($A_1$, $A_4$, $L_{ii}$), or combination of the two amino acids, amino acids 4 and "ii" (−1) ($A_4$, $L_{ii}$), is important for the selective binding with an RNA base, and to which RNA base the motif binds is determined by such a combination.

The present invention is based on the findings concerning combination of the three amino acids $A_1$, $A_4$, and $L_{ii}$, and/or combination of the two amino acids $A_4$, and $L_{ii}$ found by the inventors of the present invention.

(II) Information Concerning the Correspondence of Combination of the Three Amino Acids of a, $A_4$, and $L_{ii}$ and RNA Base:

Specifically, the followings are mentioned.

(3-1) When the combination of the three amino acids of $A_1$, $A_4$, and $L_{ii}$ is a combination of valine, asparagine, and aspartic acid as $A_1$, $A_4$, and $L_{ii}$, respectively, the PPR motif has a selective RNA base binding capacity that it strongly binds to U, less strongly binds to C, and still less strongly binds to A or G.

(3-2) When the combination of the three amino acids of $A_1$, $A_4$, and $L_{ii}$ is a combination of valine, threonine, and asparagine as $A_1$, $A_4$, and $L_{ii}$, respectively, the PPR motif has a selective RNA base binding capacity that it strongly binds to A, less strongly binds to G and still less strongly binds to C, but dose not binds to U.

(3-3) When the combination of the three amino acids of $A_1$, $A_4$, and $L_{ii}$ is a combination of valine, asparagine, and asparagine as $A_1$, $A_4$, and $L_{ii}$, respectively, the PPR motif has a selective RNA base binding capacity that it strongly binds to C, and less strongly binds to A or U, but does not bind to G.

(3-4) When the combination of the three amino acids of $A_1$, $A_4$, and $L_{ii}$ is a combination of glutamic acid, glycine, and aspartic acid as $A_1$, $A_4$, and $L_{ii}$, respectively, the PPR motif has a selective RNA base binding capacity that it strongly binds to Q but does not bind to A, U, and C.

(3-5) When the combination of the three amino acids of $A_1$, $A_4$, and $L_{ii}$ is a combination of isoleucine, asparagine, and asparagine as $A_1$, $A_4$, and $L_{ii}$, respectively, the PPR motif has a selective RNA base binding capacity that it strongly binds to C, less strongly binds to U, and still less strongly binds to A, but does not bind to G.

(3-6) When the combination of the three amino acids of $A_1$, $A_4$, and $L_{ii}$ is a combination of valine, threonine, and aspartic acid as $A_1$, $A_4$, and $L_{ii}$, respectively, the PPR motif has a selective RNA base binding capacity that it strongly binds to Q and less strongly binds to U, but does not bind to A and C.

(3-7) When the combination of the three amino acids of $A_1$, $A_4$, and $L_{ii}$ is a combination of lysine, threonine, and aspartic acid as $A_1$, $A_4$, and $L_{ii}$, respectively, the PPR motif has a selective RNA base binding capacity that it strongly binds to Q and less strongly binds to A, but does not bind to U and C.

(3-8) When the combination of the three amino acids of $A_1$, $A_4$, and $L_{ii}$ is a combination of phenylalanine, serine, and asparagine as $A_1$, $A_4$, and $L_{ii}$, respectively, the PPR motif has a selective RNA base binding capacity that it strongly binds to A, less strongly binds to C, and still less strongly binds to G and U.

(3-9) When the combination of the three amino acids of $A_1$, $A_4$, and $L_{ii}$ is a combination of valine, asparagine, and serine as $A_1$, $A_4$, and $L_{ii}$, respectively, the PPR motif has a selective RNA base binding capacity that it strongly binds to C, and less strongly binds to U, but does not bind to A and G.

(3-10) When the combination of the three amino acids of $A_1$, $A_4$, and $L_{ii}$ is a combination of phenylalanine, threonine, and asparagine as $A_1$, $A_4$, and $L_{ii}$, respectively, the PPR motif has a selective RNA base binding capacity that it strongly binds to A, but does not bind to Q U, and C.

(3-11) When the combination of the three amino acids of $A_1$, $A_4$, and $L_{ii}$ is a combination of isoleucine, asparagine, and aspartic acid as $A_1$, $A_4$, and $L_{ii}$, respectively, the PPR motif has a selective RNA base binding capacity that it strongly binds to U, and less strongly binds to A, but does not bind to G and C.

(3-12) When the combination of the three amino acids of $A_1$, $A_4$, and $L_{ii}$ is a combination of threonine, threonine, and asparagine as $A_1$, $A_4$, and $L_{ii}$, respectively, the PPR motif has a selective RNA base binding capacity that it strongly binds to A, but does not bind to Q U, and C.

(3-13) When the combination of the three amino acids of $A_1$, $A_4$, and $L_{ii}$ is a combination of isoleucine, methionine, and aspartic acid as $A_1$, $A_4$, and $L_{ii}$, respectively, the PPR motif has a selective RNA base binding capacity that it strongly binds to U, and less strongly binds to C, but does not bind to A and G.

(3-14) When the combination of the three amino acids of $A_1$, $A_4$, and $L_{ii}$ is a combination of phenylalanine, proline, and aspartic acid as $A_1$, $A_4$, and $L_{ii}$, respectively, the PPR motif has a selective RNA base binding capacity that it strongly binds to U, and less strongly binds to C, but does not bind to A and G.

(3-15) When the combination of the three amino acids of $A_1$, $A_4$, and $L_{ii}$ is a combination of tyrosine, proline, and aspartic acid as $A_1$, $A_4$, and $L_{ii}$, respectively, the PPR motif has a selective RNA base binding capacity that it strongly binds to U, but does not bind to A, G and C.

(3-16) When the combination of the three amino acids of $A_1$, $A_4$, and $L_{ii}$ is a combination of leucine, threonine, and aspartic acid as $A_1$, $A_4$, and $L_{ii}$, respectively, the PPR motif has a selective RNA base binding capacity that it strongly binds to Q but does not bind to A, U, and C.

(II) Information Concerning the Correspondence of Combination of the Two Amino Acids of $A_4$, and $L_{ii}$ and RNA Base:

Specifically, the followings are mentioned.

(2-1) When $A_4$ and $L_{ii}$ are asparagine and aspartic acid, respectively, the PPR motif has a selective RNA base binding capacity that it strongly binds to U, less strongly binds to C, and still less strongly binds to A and G.

(2-2) When $A_4$ and $L_{ii}$ are asparagine and asparagine, respectively, the PPR motif has a selective RNA base binding capacity that it strongly binds to C, less strongly binds to U, and still less strongly binds to A and G.

(2-3) When $A_4$ and $L_{ii}$ are threonine and asparagine, respectively, the PPR motif has a selective RNA base binding capacity that it strongly binds to A, and weakly binds to Q U, and C.

(2-4) When $A_4$ and $L_{ii}$ are threonine and aspartic acid, respectively, the PPR motif has a selective RNA base binding capacity that it strongly binds to Q and weakly binds to A, U, and C.

(2-5) When $A_4$ and $L_{ii}$ are serine and asparagine, respectively, the PPR motif has a selective RNA base binding capacity that it strongly binds to A, and less strongly binds to Q U, and C.

(2-6) When $A_4$ and $L_{ii}$ are glycine and aspartic acid, respectively, the PPR motif has a selective RNA base binding capacity that it strongly binds to Q less strongly binds to U, and still less strongly binds to A, but does not bind to C.

(2-7) When $A_4$ and $L_{ii}$ are asparagine and serine, respectively, the PPR motif has a selective RNA base binding capacity that it strongly binds to C, less strongly binds to U, and still less strongly binds to A and G.

(2-8) When $A_4$ and $L_{ii}$ are proline and aspartic acid, respectively, the PPR motif has a selective RNA base binding capacity that it strongly binds to U, and less strongly binds to G and C, but does not bind to A.

(2-9) When $A_4$ and $L_{ii}$ are glycine and asparagine, respectively, the PPR motif has a selective RNA base binding capacity that it strongly binds to A, and less strongly binds to Q but does not bind to C and U.

(2-10) When $A_4$ and $L_{ii}$ are methionine and aspartic acid, respectively, the PPR motif has a selective RNA base binding capacity that it strongly binds to U, and weakly binds to A, Q and C.

(2-11) When $A_4$ and $L_{ii}$ are leucine and aspartic acid, respectively, the PPR motif has a selective RNA base binding capacity that it strongly binds to C, and less strongly binds to U, but does not bind to A and G.

(2-12) When $A_4$ and $L_{ii}$ are valine and threonine, respectively, the PPR motif has a selective RNA base binding capacity that it strongly binds to U, and less strongly binds to A, but does not bind to G and C.

In the examples described in this specification, binding of proteins partially analyzed genetically or molecular biologically and potential RNA target sequences thereof are further analyzed by computational science techniques to obtain the aforementioned findings. More precisely, binding or selective binding of the proteins and RNA is analyzed on the basis of P value (probability) as an index. According to the present invention, when the P value is 0.05 or smaller (contingency of 5% or less), which means a generally significant level, preferably when the P value is 0.01 or smaller (contingency of 1% or less), more preferably when a more significant P value compared with the foregoing levels is calculated, it is evaluated that the probability for binding of the protein and RNA is sufficiently high. Such judgment based on the P value can fully be understood by those skilled in the art.

Binding property of a specific combination of amino acids at specific positions for an RNA base can be experimentally confirmed. Experiments for such a purpose include preparation of a PPR motif or a protein containing a plurality of PPR motifs, preparation of a substrate RNA, and test for the binding property (for example, gel shift assay). These experiments are well known to those skilled in the art, and for specific procedures and conditions for them, Patent document 2, for example, can be referred to.

[Use of PPR Motif and PPR Protein]

Identification and Design:

One PPR motif can recognize a specific base of RNA. Further, according to the present invention, by choosing amino acids of specific positions, PPR motifs that selectively recognize each of A, U, G and C can be selected or designed, and a protein containing an appropriate series of such PPR motifs can recognize a corresponding specific sequence. Therefore, according to the present invention, a natural PPR protein that selectively binds to RNA having a specific base sequence can be predicted and identified, and conversely, RNA that serves as a target of binding of a PPR protein can be predicted and identified. The prediction and identification of such a target is useful for elucidating genetic identity thereof, and expands availability of the target. Further, according to the present invention, a PPR motif that can selectively bind to a desired RNA base, and a protein comprising a plurality of PPR motifs that can sequence-specifically bind to a desired RNA can be designed. For designing moieties other than the amino acids of the important positions in the PPR motif, sequence information of natural PPR motifs can be referred to. Further, such a PPR motif or protein as mentioned above can also be designed by replacing only the amino acids of the positions of interest in the whole sequence of a natural PPR motif or protein. Although the number of repetition times of the PPR motif can be appropriately chosen depending on the target sequence, it may be, for example, 2 or more, or 2 to 20.

At the time of the designing, types of amino acids other than those of the combination of amino acids 1, 4, and "ii" or amino acids 4, and "ii" may be taken into consideration. For example, types of the 8th and 12th amino acids described in Patent document 2 mentioned above may be important for expression of the RNA binding activity. According to the study of the inventors of the present invention, $A_8$ of a certain PPR motif and $A_{12}$ of the same PPR motif may cooperate for binding to RNA. $A_8$ may be a basic amino acid, preferably lysine, or an acidic amino acid, preferably aspartic acid, and $A_{12}$ may be a basic amino acid, a neutral amino acid, or a hydrophobic amino acid.

The designed motif or protein can be prepared by the methods well known to those skilled in the art. That is, the present invention provides a PPR motif that selectively binds to a specific RNA base, and a PPR protein that specifically binds to RNA having a specific sequence, which are designed by paying attention to the combination of amino acids 1, 4, and "ii" or the combination of amino acids 4 and "ii". In particular, it was found that, for the action on fertility as a function of the PPR protein, amino acid 4 ($A_4$) and the amino acid "ii" are effective for both the cases of the aforementioned combination of three amino acids and combination of two amino acids. Such a motif and protein can be prepared by the methods well known to those skilled in the art, even in a relatively large amount, and such methods may comprise determining a nucleic acid sequence coding for an amino acid sequence of an objective motif or protein from that amino acid sequence, cloning it, and preparing a transformant that produces the objective motif or protein.

Preparation of Complex and Use Thereof:

The PPR motif or PPR protein provided by the present invention can be made into a complex by binding a functional region. The functional region means a moiety having a specific biological function such as enzymatic function, catalytic function, inhibition function, and promotion function exerted in living bodies or cells, or a moiety having a function as a marker. Such a region consists of, for example, a protein, peptide, nucleic acid, physiologically active substance, or drug. Examples of protein as the functional region include ribonuclease (RNase). Examples of RNase include RNase A (for example, bovine pancreatic ribonuclease A, PDB 2AAS) and RNase H. Such a complex does not exist in the nature, and it is a novel substance. Further, the complex provided by the present invention may be able to deliver the functional region to a living body or cell in an RNA sequence-specific manner, and allow it to function. It may be therefore able to modify or disrupt RNA, or impart a novel function to RNA, in a living body or cell in an RNA sequence-specific manner, like the zinc finger proteins (Non-patent document 1 mentioned above) or TAL effector (Non-patent document 2 and Patent document 1 mentioned above). Furthermore, it may be able to deliver a drug to RNA in an RNA sequence-specific manner. Therefore, the present invention provides a method for delivering a functional material in an RNA sequence-specific manner.

It is known that some PPR proteins are important for obtaining F1 seeds for hybrid vigor as a fertility restoration factor that works for pollen (male gamete) formation. It is expected that a fertility restoration factor not identified yet can be identified, and a technique for highly utilize such a factor can be developed by the present invention. For example, as elucidated in the examples described in this specification, if amino acid polymorphism is detected for a gene for a specific PPR motif in a PPR protein that works as a fertility restoration factor for cytoplasmic male sterility, and relation of the polymorphism and fertility is established for the gene, it can be judged whether the gene of the PPR protein in a test sample has a genotype relating to fertility or a genotype relating to sterility. Examples of the gene of the PPR protein in which the polymorphism is detected in such a case as mentioned above include, for example, in the case of radish, a family gene locating at the same locus as that of the "OFR687 gene" coding for the OFR687 protein of Enko (named Enko B), a gene coding for a protein showing an amino acid identity of 90% or higher to Enko B, and a gene showing a nucleotide sequence identity of 90% or higher to the "ORF687 gene" coding for Enko B. The family gene locating at the same locus as that of the "OFR687 gene" coding for the OFR687 protein of Enko (named Enko B) includes all the genes shown in FIGS. 21 and 22 (Kosena B, Comet B, Enko A, Comet A, Icicle CA, rrORF690-1, rrORF690-2, PC_PPR-A, PC_PPR-BL), but it does not limited to these. The gene coding for a protein showing an amino acid identity of 90% or higher to Enko B, and the gene showing a nucleotide sequence identity of 90% or higher to the "ORF687 gene" coding for Enko B can be obtained by searching gene databases, and the species as the origin thereof is not limited to those of radish. The PPR motif is a PPR motif consisting of a polypeptide of 30- to 38-amino acid length represented by the formula 1 mentioned above, and the PPR protein may comprise one or more of such PPR motifs (preferably 2 to 16 motifs). As the polymorphism in the PPR motif, there can be used polymorphism of the combination of amino acids 1, 4, and "ii" or the combination of amino acids 4 and "ii", which was elucidated to be responsible for the binding of PPR motif to RNA by the present invention. As seen from the P values shown in FIG. 4B or 4D, among the amino acids of the combinations responsible for the binding of the PPR motif to RNA, amino acid 4 plays the most important role, and the amino acid "ii" plays the secondarily important role. It was further elucidated that, in comparison with the PPR protein of Enko B, the fact that amino acids 4 of all the PPR motifs in a protein encoded by a gene as a test subject are the same as those of Enko B, or the fact that the amino acids "ii" in all the corresponding PPR motifs are the same as those of Enko B is important for the function as a fertility restoration factor. Further, it was also elucidated that, similarly to the fertility restoration, some PPR proteins act on speciation. It is expected that identification and modification of a target RNA of the PPR protein enable mating of species, of which mating has so far been impossible. Further, since most of the PPR proteins act on RNA in mitochondria and chloroplasts, the novel PPR proteins provided by the present invention will contribute to modification and improvement of the functions concerning photosynthesis, respiration, and synthesis of useful metabolites.

Further, for animals, it is known that anomaly of the PPR protein identified as LRPPRC causes Leigh syndrome French Canadian type (LSFC, Leigh's syndrome, subacute necrotizing encephalomyelopathy). The present invention can contribute to the treatment (prophylactic treatment, therapeutic treatment, suppression of advance) of LSFC.

Further, the PPR proteins are involved in all the steps of RNA processing seen in organelles, digestion, RNA editing, translation, splicing, and RNA stability. According to the present invention, it can be expected that, by modifying the binding base selectivity of a PPR motif, expression of a desired RNA can be modified.

The PPR proteins used in the present invention as materials mainly function for specification of the editing site of RNA editing (conversion of genetic information on RNA, C to U in many cases) (refer to References 2 and 3 mentioned later). The PPR proteins of this type have an additional motif suggested to interact with an RNA editing enzyme existing on the C-terminus side. It can be expected that, by using a PPR protein having such a structure, nucleotide polymorphism can be introduced, and a disease or condition induced by nucleotide polymorphism can be treated.

Further, a part of PPR proteins have an RNA cleavage enzyme on the C-terminus side. By modifying the binding RNA base selectivity of the PPR motif on the N terminus side of such a PPR protein, an RNA sequence-specific RNA cleaving enzyme can be constituted. Furthermore, a complex having a marker moiety such as GFP bound to a PPR protein can be used for visualizing a desired RNA in a living body.

Further, the existing PPR proteins include those that act on DNA. It has been reported that one of them is the transcription activator of a mitochondrial gene, and another one is a transcription activator localizing in the nucleus. Therefore, it may also be possible to design a protein factor that binds to a desired DNA sequence on the basis of the findings obtained by the present invention.

EXAMPLES

Example 1: Collection of PPR Proteins Involved in RNA Editing and Target Sequences Thereof With reference to the information shown in FIG. 2, the PPR proteins of *Arabidopsis thaliana* involved in RNA editing so far analyzed (SEQ ID NOS: 2 to 24) were collected from the *Arabidopsis thaliana* genome information database (MATDB: http://mips.gsf.de/proj/thal/db/index.html), and sequences around RNA-editing sites that serve as a target (SEQ ID NOS: 48, 50, 53, 55, 57, 59, 60, 61, 62, 63, 64, 65, 68, 69, 70, 71, 73, 74, 76, 78, 80, 122, 206, 228, 232, 252, 284, 316, 338, 339, 358, 430, 433, 455, 552 and 563) were collected from the RNA-editing database (http://biologia.unical.it/py_script/overview.html). As the RNA sequences, those of 31 nucleotides upstream from the editable C (cytosine) residue including that C were collected. All the collected proteins and RNA-editing sites corresponding to the proteins are shown in FIG. 2.

To the PPR motif structures in the proteins, the amino acid numbers defined in the present invention, as well as the information of the Uniprot database (http://www.uniprot.org/) are imparted. The PPR motifs contained in 24 of the *Arabidopsis thalianas* PPR proteins (SEQ ID NOS: 2 to 25) used for the experiments and amino acid numbers thereof are shown in FIG. 3.

Example 2: Identification of Amino Acids that Impart Binding Base Selectivity

The researches so far elucidated that the PPR proteins involved in RNA editing have a motif having a specific conserved amino acid sequence on the C-terminus side (E, E+ and DYW motifs, provided that DYW motif often does not exist). It has been suggested that more than ten amino acids in the E+ motif are required for the conversion from C (cytosine) to U (uracil), not for the selective binding to RNA (Reference 3). Further, it has also suggested in the past non-patent paper that the information required for recognition of the editable C is included in the 20 upstream nucleotides and 5 downstream nucleotides thereof. That is, it can be predicted that a plurality of PPR motifs in the PPR protein recognize "somewhere" of the upstream sequence of the editable C, and the E+ motif locates near the editable C. Furthermore, there is considered a possibility that specific amino acids in the PPR motif may recognize the RNA residue of the upstream sequence to which they bind (FIG. 4A).

This possibility was verified by using the 24 RNA-editing PPR proteins of *Arabidopsis thaliana* and target RNA sequences thereof described in Example 1. First, all the PPR motifs of the PPR protein were aligned with the corresponding RNA residues by arranging the last PPR motif in the protein at the first nucleotide from the editable C with 1-motif to 1-nucleotide correspondence in linear contiguity (FIG. 4A, alignment P1). Then, the RNA sequence was moved toward the right, 1 nucleotide at a time, to obtain the alignments P2 to P6. In the data set for each of these alignments P1 to P6, the information on the RNA residues corresponding to the PPR motifs was collected.

For a PPR protein that works for a single editing site, a score of 1 was given to each occurrence of the RNA nucleotide (A, U, G or C). For PPR proteins that work for 2 and 3 editing sites, scores of 0.5 and 0.3 were given to each occurrence of the RNA nucleotide, respectively. Then, the sets of PPR motifs and nucleotides were sorted according to types of amino acids for each of the amino acid numbers in the PPR motifs. It can generally be predicted that amino acids and RNA residues randomly appear for the types thereof (high-randomness or high-entropy) (an example is shown in the upper graph on the right side in FIG. 4A). However, if an amino acid of a specific position has binding RNA base selecting capacity, it is predicted that the corresponding RNA base is converged to one kind or limited kinds of them in correct alignments (P1 to P6 mentioned above) (low randomness or low entropy, an example is shown in the lower graph on the right side in FIG. 4A).

The aforementioned low randomness was calculated for all the amino acid numbers of the PPR motifs for the data sets of the alignments P1 to P6 created above. The low randomness was calculated by the chi square test based on a theoretical value (average of occurrence frequencies of all the nucleotides) (examples are shown in FIG. 5).

As a result, for amino acids 1, 4 and "ii" (−2) in alignment P4, it was determined that the significance value P is smaller than 0.01 (probability lower than 1%) (FIG. 4B). That is, it was revealed that the last PPR motif in the RNA-editing PPR protein is arranged at the base 4 nucleotides before the editable C, and the three amino acids (1, 4, and "ii") are responsible for the binding RNA base selection. Further, because any significant P value was not calculated for the alignments P3 and P5, it was revealed that there is no interference from the PPR motifs of both sides, i.e., one PPR motif recognizes one RNA residue, and the binding does not depends on the constitution of the motifs. For the other amino acids in alignment P4, and all the amino acids of the other alignments, any significant P value was not obtained (FIG. 6). Further, the RNA bases were classified into those of purine (A and G) or pyrimidine (C and U) (RY), and the same calculation was performed. As a result, an extremely significant P value (P<0.01) was obtained only for amino acid 4 (FIG. 4C). This indicates that amino acid 4 mainly determines which one of purine and pyrimidine is the RNA base to be bound. The binding base specifying capacity of the RNA recognition amino acids in the PPR motif shown in FIG. 4C was analyzed in more detail. As a result, in addition to that amino acid 4 mainly distinguishes the type of the base to which it binds, purine or pyrimidine (RY), it was found that the amino acid "ii" (−2) works to distinguish the form of the base, amino form (A and C) or keto form (G and U) (MK, FIG. 4D).

Combinations of the three amino acids (1, 4, and "ii") used 3 times or more were defined as triPPR codes among the RNA recognition codes of the PPR motifs, and P value was calculated for each of them to calculate the binding RNA base specifying capacity thereof. A part of the identified triPPR codes are shown in FIG. 4E.

Since the amino acids of the three positions were extremely diverse, the binding RNA base specifying capacity was calculated for two amino acids (1 and 4, 1 and "ii", or 4 and "ii"). As a result, a remarkable P value was calculated for the combination of amino acids 4 and "ii" (FIG. 7). Therefore, combinations of amino acids 4 and "ii" used 3 times or more were defined as diPPR codes among the RNA recognition codes of the PPR motifs. The identified triPPR codes and diPPR codes are shown in FIG. 8.

Example 3: Verification of Identified RNA Recognition Codes

The RNA recognition codes for the PPR motifs identified by using the RNA-editing PPR proteins of *Arabidopsis thaliana* were verified. For the verification, the RNA-editing PPR proteins of *Physcomitrella patens* subsp. *patens* were used. It has already been elucidated that, in *Physcomitrella patens* subsp. *patens* (henceforth referred to as moss), RNA editing occurs at 13 sites in total (11 site in mitochondria, 2 sites in chloroplasts, SEQ ID NOS: 32 to 44). Further, it has also been elucidated that 6 PPR proteins (PpPPR_56, 71, 77, 78, 79, and 91) work for RNA editing at 9 sites, respectively. The proteins and corresponding RNA-editing sites are shown in FIG. 9.

The verification was performed as shown in FIG. 10. First, the amino acid sequence information of the moss PPR proteins was obtained from a non-patent paper (SEQ ID NOS: 26 to 31, FIGS. 2 and 9), and the three amino acids (1, 4, and "ii") were extracted from each PPR motif according to the PPR motif model defined as shown in FIG. 1. When the combination of the extracted three amino acids agreed with any one of the triPPR codes identified from *Arabidopsis thaliana*, it was converted into a binding base scoring matrix represented by that code. Then, a PPR motif that could not converted with any of the triPPR codes, but agreed with any one of the diPPR codes was converted into the binding nucleotide scoring matrix of diPPR code. In parallel, surrounding sequences of the RNA-editing sites (31-mer sequences having the editable C at the 3' end) were obtained from a non-patent paper (SEQ ID NOS: 32 to 44, FIGS. 2, 9 and 16), and converted into such a number matrix of the RNA sequence as shown in FIG. 10. The numbers of corresponding grids of the binding base scoring matrix of the protein and the number matrix of the RNA sequence were multiplied with each other, so as not to contradict to the above-mentioned alignment P4 (the last PPR motif corresponds to the base 4 nucleotides before the editable C), and the sum of the obtained values was calculated as a matching score of the protein and the RNA sequence. This calculation was performed for the triPPR codes, diPPR codes, and the PPR binding base scoring matrixes (PPR scoring matrixes) thereof.

For one kind of protein, this calculation was performed for all the RNA-editing sites of the moss (13 sites). Further, the same calculation was also performed for 34 RNA sequences of the RNA-editing sites of *Arabidopsis thaliana* chloroplast (FIG. 16, SEQ ID NOS: 45 to 78) as reference sequences of RNA-editing site surrounding sequences.

Then, from the matching scores of the proteins for the RNA sequences, a normal distribution curve was created, and provisional P values of the matching scores for the RNA sequences were calculated for the triPPR codes and diPPR codes, respectively.

Final P values (matching scores of protein and RNA sequence) were calculated as products of the provisional P values for triPPR code and diPPR code.

The matching scores of the moss PPR proteins and 13 moss RNA-editing sites are shown in FIG. 11. As a result of the analysis, 6 kinds of the proteins were computationally specified for the correct RNA-editing sites out of the 7 kinds of the proteins. That is, this analysis revealed that all the information for the binding RNA base specification performed by the PPR motif is contained in the three amino acids (1, 4, and "ii"). In other words, it was revealed that a PPR protein that binds to an intended RNA sequence can be searched for by referring to the information on the combinations of the two or three amino acids shown in FIG. 8 (triPPR and diPPR codes). At the same time, it was also shown that an artificial protein that binds to an intended RNA sequence can be synthesized by using or binding a PPR motif having such amino acid information.

Example 4: Identification of Target Molecules of Unanalyzed RNA-Editing PPR Proteins Then, analysis was performed by using *Arabidopsis thaliana*, which has a larger number of RNA-editing sites compared with the moss (34 sites in chloroplastic genome (SEQ ID NOS: 45 to 78), and 488 sites in mitochondrial genome (SEQ ID NOS: 79 to 566), see FIG. 6). In order to verify prediction accuracy, RNA-editing sites of 24 kinds of PPR proteins used for the code extraction were predicted. As a result, for the chloroplast-localized PPR proteins, at least one correct RNA-editing site was predicted with the highest P value for 10 kinds of proteins out of 13 kinds of the proteins. For mitochondria-localized PPR proteins, a correct RNA-editing site was predicted with a value within top 20 thereof for 8 kinds of proteins out of 11 kinds of the proteins (FIG. 12). On the basis of the results of this verification of prediction accuracy, target RNA-editing sites of the PPR proteins of which function was unknown were predicted. An AHG11 mutant is a mutant having anomaly in the abscisic acid pathway, and the proteins encoded by the genes thereof (ahg11, at2g44880) have a typical RNA-editing PPR protein-like motif structure (FIG. 13, SEQ ID NO: 1). RNA-editing sites were predicted, and 405 sites for mitochondria and 30 sites for chloroplasts including those of values within the top 20 thereof were experimentally verified. As a result, it was revealed that only the RNA editing of mitochondria nad4_376 predicted with the 7th highest P value had anomaly in the mutant (FIG. 13).

Then, it was attempted to identify target RNA sequences in the total genomes of the organelles i.e., a data set of about $3 \times 10^5$ RNA sequences. For this analysis, the probability matrix of PPR codes shown in FIG. 8 was used. Further, for the motifs having a combination of amino acids not agreeing with any of the diPPR and triPPR codes, background frequency was applied. The probability matrices of the produced proteins were subjected to the FIMO analysis in MEME suite (http://meme.nbcr.net/meme4_6_1/fimo-intro.html) together with the chloroplast total nucleotide sequence of *Arabidopsis thaliana* (AP000423).

As a result, for CRR4 and CRR21, target RNA sequences thereof could be correctly predicted. Further, the codes were improved by extracting the PPR codes also from the moss PPR proteins (FIG. 15). As a result, the prediction accuracy was markedly improved for several proteins. These results indicate that one correct target sequence can be identified from RNA sequences of several hundreds of thousands patterns by using the identified PPR codes. Conversely, by searching for a PPR motif having amino acids matching the code at the positions (1, 4, and "ii"), a protein that binds to the intended useful RNA sequence can be identified. Alternatively, it was shown that, by binding a PPR motif, an artificial RNA binding protein showing high sequence selectivity can be created. It will also be understood by those skilled in the art that, by obtaining a combination of amino acids at the concerned positions matching any of the PPR codes through introduction of mutation, intended RNA binding selectivity can be imparted. FIG. 15 shows evaluation of the binding RNA base selecting capacity of triPPR codes and diPPR codes based on the P values. It can be estimated that PPR codes that showed a significant P value ($P<0.05$) have high binding RNA base selecting capacity.

Example 5: Prediction of Target RNA Sequence of Radish Rf

Then, on the basis of the findings obtained by the present invention, functions of the PPR proteins that work as a fertility restoration factor for cytoplasmic male sterility were determined (Examples 5 to 9).

The cytoplasmic male sterility (CMS) is a characteristic that the male gamete comes to no longer normally function due to a mutation in a cytoplasmic genome, especially a mitochondrial genome. It is known that this characteristic is compensated by a fertility restoration gene (restorer of fertility, Rf), which often exists in the nucleus, and the male gamete is thereby made normal. This characteristic is used for the first filial hybrid breeding method, and is one of the agriculturally important characteristics. It is known that, in such a CMS-Rf system, the Rf gene codes for a PPR protein in many cases.

Sterility of the Ogura-type (synonym, Kosena-type) cytoplasm used in the first filial hybrid breeding method for radish or rapeseed originates in expression of the orf125 gene in a mitochondrial genome, and canceled by the presence of the nuclear-encoded orf687 gene, and the cytoplasm acquires fertility. The orf687 gene product is a PPR protein, and it is considered that it acts on RNA containing orf125 to inactivate the expression thereof, and the sterility is canceled as a result.

However, it has become clear from the past thremmatological analyses that amino acid polymorphism is observed for the orf687-like genes of various radish pedigrees, and that this amino acid polymorphism affects the function of the gene as a fertility restoration factor. However, any method for estimating functionality of a gene from the amino acid sequence encoded thereby has not been established.

Therefore, a PPR motif was first specified in the amino acid sequence of the ORF687 protein of the radish variety Enko (named Enko B), which is known to function as a dominant Rf, amino acids responsible for the base specifying capacity (1, 4, and ii) were extracted from it, and converted into a PPR code, and then the target RNA sequence thereof was predicted for a transcription product containing the mitochondrial orf125 (FIG. 19) In parallel, three kinds of ORF687-like proteins, the ORF687 protein of the radish variety Enko (named Enko B), which is known to function as a dominant Rf, an ORF687-like protein that is similarly contained in Enko and well resembles the ORF687, but acts as a recessive gene (named Enko A), and a gene homologous to the Enko ORF687 existing in the genome of Kosena, which is a different radish variety (named Kosena B, recessive gene), are used as experimental materials, and the characteristics of them were biochemically analyzed.

(5-1) Preparation of the Genomic DNA from Radish

Radish was cultured on the Murashige and Skoog medium (containing 2% sucrose and 0.5% Gellangam) for three weeks. The green leaves (0.5 g) of the cultured plant were extracted with phenol/chloroform, and then ethanol was added to insolubilize DNA. The collected DNA was dissolved in 100 μl of the TE solution (10 mM Tris-HCl (pH 8.0), 1 mM EDTA), 10 units of RNase A (DNase-free, Takara Bio) was added to the mixture, and the reaction was allowed at 37° C. for 30 minutes. Then, the reaction mixture was extracted again with phenol/chloroform, and DNA was collected by ethanol precipitation. DNA was obtained in an amount of 10 Gg.

(5-2) Cloning of Genes Coding for ORF687-Like Proteins

By performing PCR using radish genomic DNA as the template, oligonucleotide primers, Enko_B-F primer and Enko_B-R primer (SEQ ID NOS: 567 and 568, respectively), for Enko B, oligonucleotide primers, kosena_B-F primer and kosena_B-R primer (SEQ ID NOS: 569 and 570, respectively), for Kosena B, or oligonucleotide primers, Enko_A-F primer and Enko_A-R primer (SEQ ID NOS: 571 and 572, respectively), for Enko A, and KOD-FX (TOYOBO) as a DNA extension enzyme in 50 l of a reaction mixture with 25 cycles of 95° C. for 30 seconds, 60° C. for 30 seconds, and 72° C. for 30 seconds, the genes were amplified, respectively.

The obtained DNA fragments were cloned by using the pBAD/Thio-TOPO vector (Invitrogen) according to the attached protocol. The DNA sequences were determined to confirm that the sequences were those homologous to the intended corresponding DNA sequences (Enko B (SEQ ID NO:573), Kosena B (SEQ ID NO: 574), Enko A (SEQ ID NO: 575)).

(5-3) Preparation of Recombinant ORF687-Like Proteins

The *Escherichia coli* TOP10 strain (Invitrogen) was transformed with the plasmids obtained above. The *Escherichia coli* strain was cultured at 37° C. in 300 ml of the LB medium containing ampicillin at a concentration of 100 μg/ml (300 mL of the medium contained in a 1-L conical flask). When the turbidity of the culture medium in terms of the absorbance at a wavelength of 600 nm reached 0.5, L-arabinose as an inducer was added at a final concentration of 0.2%, and culture was further continued for 4 hours.

The cells were collected by centrifugation, then suspended in 200 ml of Buffer A (50 mM Tris-HCl (pH 8.0), 500 mM KCl, 2 mM imidazole, 10 mM MgCl$_2$, 0.5% Triton X100, 10% glycerol) containing 1 mg/ml of lysozyme, and disrupted by ultrasonication and freezing/thawing. The cell suspension was centrifuged at 15,000×g for 20 minutes, and then the supernatant was collected as a crude extract.

This crude extract was applied to a column filled with a nickel column resin (ProBond A, Invitrogen) equilibrated with Buffer A.

After the column was sufficiently washed with Buffer A containing 20 mM imidazole, column chromatography was performed with two-step concentration gradient, in which the objective protein was eluted with Buffer A containing 200 mM imidazole. The obtained proteins were fusion proteins comprising the amino acid sequence of SEQ ID NO: 576 (Enko B), SEQ ID NO: 577 (Kosena B), or SEQ ID NO: 578 (Enko A), the amino acid sequence of thioredoxin for enhancing solubility on the N terminus side, and a histidine tag sequence on the C-terminus side. Each purified fraction in a volume of 100 μl was dialyzed against 500 mL of Buffer E (20 mM Tris-HCl (pH 7.9), 60 mM KCl, 12.5 mM MgCl$_2$, 0.1 mM EDTA, 17% glycerol, 2 mM DTT), and then used as a purified sample.

(5-4) Preparation of Substrate RNA

As the substrate RNA, three kinds of RNAs containing the sequence of a mitochondrial DNA of Ogura-type radish cytoplasm, RNAa, RNAb, and RNAc, were used.

The DNAs were amplified by PCR using oligonucleotide primers, A-F primer and A-R primer (SEQ ID NOS: 579 and 580, respectively), for RNAa, oligonucleotide primers, B-F primer and B-R primer (SEQ ID NOS: 581 and 582 respectively), for RNAb, or oligonucleotide primers, C-F primer and C-R primer (SEQ ID NOS: 583 and 584, respectively), for RNAc, and KODFX (TOYOBO) as a DNA extension enzyme, in 50 μl of a reaction mixture containing 10 ng of the aforementioned Ogura-type radish cytoplasm DNA as the template, with 25 cycles of 95° C. for 30 seconds, 60° C. for 30 seconds, and 72° C. for 30 seconds. To each of the forward primers (–F), the T7 promoter sequence for synthesizing the substrate RNA in vitro was added.

Each of the obtained DNA fragments was purified by developing it on agarose gel, and then excising a gel section containing it. By allowing a reaction using the purified DNA fragment as the template at 37° C. for 60 minutes in 20 μl of a reaction mixture containing NTP mix (10 nmol GTP, CPT, ATP, and 0.5 nmol UTP), 4 μl [$32^P$]α-UTP (GE Healthcare, 3000 Ci/mmol), and T7 RNA polymerase (Takara Bio), a substrate RNA was synthesized.

The substrate RNA was subjected to phenol/chloroform extraction and ethanol precipitation, and then the total amount thereof was developed by electrophoresis on denatured 6% polyacrylamide gel containing 6 M urea, and the $^{32}$P-labeled RNA was detected by exposing the gel to an X-ray film for 60 seconds.

Then, the section of the $^{32}$P-labeled RNA was excised from the gel, and immersed in 200 l of a gel elution solution (0.3 M sodium acetate, 2.5 mM EDTA, 0.01% SDS) at 4° C. for 12 hours to elute the RNA from the gel. The radioactivity of 1 l of the RNA fraction was measured, and the total amount of the synthesized RNA was calculated. The RNA solution was subjected to ethanol precipitation, and then the RNA was dissolved in ultrapure water at 2500 cpm/μl (1 fmol/μl). By this preparation method, about 100 μl of RNA of 2500 cpm/μl was usually obtained.

(5-5) Binding Experiment of Protein and RNA

Recombinant proteins of Enko B (Rf), Kosena B (rf), and Enko A (rf, ORF687-like protein existing in the Enko variety) were prepared, and the RNA binding activities thereof were verified. The RNA binding activities of the prepared recombinant proteins (Enko B (SEQ ID NO: 576), Kosena B (SEQ ID NO: 577), and Enko A (SEQ ID NO: 578)) were analyzed by the gel shift assay. The aforementioned substrate RNA (BD120, 375 pM, 7.5 fmol/20 μL) and 0 to 2500 nM of each recombinant protein were mixed in 20 μl of a reaction mixture (10 mM Tris-HCl (pH 7.9), 30 mM KCl, 6 mM MgCl$_2$, 2 mM DTT, 8% glycerol, 0.0067% Triton X-100), and the reaction was allowed at 25° C. for 15 minutes. Then, 4 μl of a 80% glycerol solution was added to the reaction mixture, 10 μL of the mixture was developed on 10% non-denatured polyacrylamide gel containing 1×TBE (89 mM Tris-HCl, 89 mM boric acid, 2 mM EDTA), and after the electrophoresis, the gel was dried. The radioactivity of RNA in the gel was measured with Bioimaging Analyzer BAS2000 (Fuji Photo Film).

Example 6: RNA Binding Experiment Using Recombinant Proteins

FIG. 17 shows the analysis of binding of the Enko B protein and RNA containing the cytoplasmic male sterility (CMS) gene. FIG. 17A shows a schematic diagram around the mitochondrial orf125, and also schematically shows the regions of RNAa, RNAbc, RNAb, and RNAc used in the binding experiment. FIG. 17B shows binding of the Enko B protein and RNA. Enko B protein (1.4 nmol) and $^{32}$P-labeled RNAbc (0.1 ng) were reacted in the presence of non-labeled RNAa, RNAbc, RNAb, and RNAc (×5 and ×10 w/w with respect to RNAbc, used as a competitive inhibition substance) in 20 μL of a reaction mixture to perform the gel shift competition experiment. Complex Δ mentioned on the left side of the diagram indicates the complex of the protein and RNA, and Free ▲ indicates RNA itself.

As shown in the drawings, the binding of the protein and RNA is visualized as a difference in the migration degree of the $^{32}$P-labeled RNA. This is because the molecular weight of the complex of the $^{32}$P-labeled RNA and the protein is larger than the molecular weight of the $^{32}$P-labeled RNA alone, and therefore the migration degree thereof in the electrophoresis becomes smaller.

In this experiment, a recombinant protein of Enko B was prepared, and binding thereof with a mitochondrial RNA containing orf125 was verified by competition gel shift assay. RI-labeled RNAb and the protein were mixed, and then non-labeled RNA was added. That is, a more reduced signal intensity of the band at the position indicated as Complex means that RNA at that position added as a competitor and the protein binds, i.e., the position corresponds to an RNA region to which Enko B binds with higher affinity. As a result, it was revealed that Enko B strongly binds to the region of RNAb.

The candidate sequence of No. 208 shows the most significant P value in the binding sequence prediction shown in FIG. 19, and correctly locates at the 3' end of tRNA methionine. However, the analyses so far revealed that there is no difference in amount of tRNA and configuration of RNA containing orf125 (presence or absence of cleavage) between sterile and fertility-restored pedigrees, and the in vitro binding experiment (FIG. 17B) revealed that the RNAa sequence containing the sequence of No. 208 and Enko B do not bind. Therefore, it was judged that this region is not involved in fertility and sterility of Ogura-type cytoplasm.

Accordingly, further analysis was focused on the regions of Nos. 316, 352 and 373 contained in RNAb. RNAb consists of 125 b. Although it was attempted to narrow down the binding region to a 20 b order by using scanning mutation, it could not be limited to a single site (data are now shown). Therefore, it was considered that a plurality of binding sites for Enko B might exist in RNAb.

Example 7: RNA Binding Activity of Rf-Like Proteins

FIG. 18 shows binding of ORF687-like proteins and RNA. FIG. 18A shows the results of analysis of RNA binding characteristics of ORF687-like proteins performed by gel shift assay for binding of Enko B (Rf), Kosena B (rf), and Enko A (rf) with RNAb. FIG. 18B is shows the results of FIG. 18A in the form of graph, and dissociation constants (KD) of the proteins representing the RNA binding capacities thereof were calculated on the basis of this graph. FIG. 18C shows the results of calculation of the matching scores of Enko B (Rf), Kosena B (rf), and Enko A (rf), and potential binding sites thereof performed in the same manner as that used for obtaining the results shown in FIG. 19.

As a result, in the non-competing state, all of the three kinds of proteins (Enko B, Kosena B, and Enko A) bound to RNAb with high affinity. As for Kosena B, the RNA binding activity was analyzed in the competing state, but definite difference of the activity was not observed compared with that observed for Enko B (FIGS. 18A and 18B).

Kosena B often shows an RNA binding activity slightly lower than that of Enko B (lower by about 2 times in terms of KD). However, 10 times or more of difference of the activity is detected in many cases for general RNA binding, and the above difference cannot be regarded as a significant difference.

The proteins do not show definite difference of matching scores for the corresponding regions also in the prediction based on the PPR codes (FIG. 18C). Therefore, it was decided to examine a possibility that the difference of Enko B and Kosena B might originate in difference of actions exerted after binding, not in simple difference in RNA binding affinity.

Further, prediction of binding sequences of a fertility restoration factor that acts on the Ogura-type cytoplasm are shown in FIG. 19. FIG. 19A shows the results for prediction of binding of the Enko B protein using the PPR codes, and the structure of RNA containing the CMS gene orf125 is shown in the lower diagram of FIG. 19A. As for the regions from RNAa to RNAc shown in FIG. 19A, refer to FIG. 17. In FIG. 19A, the regions of Nos. 208, 230, 316, 352 and 373 are focused on, among the regions that showed a significantly high P value (FIG. 19A).

Further, sequence logos of the target RNA sequences predicted from the ORF687 protein sequence (sequences of the regions that showed a significant P value (Nos. 208, 316, 352, 373)), candidate binding RNA sequences, and sequence logos of the target RNA sequences predicted from the sequence of the ORF687-like protein of the radish variety having a recessive rf, Kosena (Kosena B) are shown in FIG. 19B. Further, the predicted binding base of Kosena B, which is a recessive rf, is also shown.

It was revealed that the bases specified by EnkoB and Kosena B are different (UA in the case of Rf, and GC in the case of rf), because of the amino acid polymorphism in the 2nd and 3rd PPR motifs. It could be predicted that this difference is directly linked with the functional difference between Rf and rf.

Example 8: Prediction and Analysis of RNA Structure

On the basis of computerized prediction and in vitro RNA binding experiment, there was contemplated a possibility that Rf binds the region of RNAb, especially the regions of Nos. 316, 352 and 373. On the basis of the in vitro analysis, there was also contemplated a possibility that RNAb has a plurality of binding sites. Therefore, the secondary structure of the RNAb sequence was predicted, and attention was paid to the regions.

The results are shown in FIG. 20. FIG. 20 shows the secondary structure and structural change of the candidate binding RNA regions of ORF687-like protein. FIG. 20A shows the secondary structure of the region including the region of No. 306 and the predicted binding sites for the ORF687-like protein, and shows PPR motifs with boxes together with the corresponding bases. The 2nd and 3rd PPR motifs for which Enko B (Rf) and Kosena B (rf) show a remarkable difference are emphasized. FIG. 20B shows the secondary structure of the region including the regions of Nos. 352 and 373 and the predicted binding sites for the ORF687-like protein. FIG. 20C shows results indicating structural change of RNAb induced by Enko B, which were obtained by mixing RNAb and Enko B protein, and then adding a double-strand selective RNase (RNase V1).

As a result, it was revealed that the No. 316 region corresponds to the stem loop structure immediately downstream from the start codon of orf125 (FIG. 20A). Further, the 2nd and 3rd PPR motifs showing polymorphism between Enko B and Kosena B located in the double-strand at the root of the stem loop. In particular, the base corresponding the 3rd PPR motif is A in Enko B, whereas it is C in Kosena B (refer to FIG. 19B). On the basis of these results, there was contemplated a working hypothesis that Enko B binds to the region concerned to promote formation of the stem loop structure, and thereby inhibit translation of orf125.

A double-strand structure is also predicted for the Nos. 352 and 373 regions, and it was contemplated that the Rf protein binds on the both sides (FIG. 20B). However, in such a case, it is expected that the structure will be destroyed by the binding of Rf (formation of single strand is promoted). Further, differences in corresponding base and structure were not contemplated for the 2nd and 3rd PPR motifs, for which Rf and rf show difference, and any specific molecular mechanism could not be predicted.

Therefore, internally-labeled RNA was mixed with the proteins, and RNase V1 was added to the mixture to decompose only the labeled RNA. RNase V1 is an RNase that selectively cleaves only double-strand regions of RNA. As a result, it was demonstrated that the substrate RNA is more quickly decomposed in the presence of the protein, namely, formation of double-stranded RNA is promoted in the presence of Rf (Enko B) (FIG. 20C). That is, it was considered that the translation inhibition based on the formation of double-stranded RNA in orf125 mRNA by Rf is the major cause of the fertility restoration in Ogura-type cytoplasmic male sterility.

Example 9: Determination of Function for Fertility Restoration Capacity of ORF687-Like Gene ORF687-like genes have so far been isolated from various radish varieties, and the functionality thereof as Rf is estimated on the basis of mating experiments. However, the encoded amino acid sequences are very alike, and therefore it is impossible to determine the functionality as Rf from the conservation characteristics of the whole amino acid sequences.

In this example, sequences of the ORF687-like proteins were first analyzed. Specifically, the protein sequences shown in SEQ ID NOS: 576 to 578 and 585 to 591 were used as materials, and the sequences of them as the PPR proteins were analyzed. By using all the sequences as query sequences for CLUSTALW (http://www.genome.jp/tools/clustalw/), sequence alignment was obtained. By using the domain analysis software usable on the Web:
Pfam (http://pfam.sanger.ac.uk/),
InterProScan (http://www.ebi.ac.uk/Tools/InterProScan/), and
Prosite (http://www.expasy.org/prosite/),
alignment of the ORF687-like proteins was created, and the PPR motif structures of the proteins were analyzed. The results are shown in FIG. 21. All the ORF687-like proteins each consist of 16 PPR motifs (FIG. 21).

From the obtained PPR motif models, amino acids 1, 2, and "ii" (−2) according to the amino acid numbers shown in Non-patent document 5 were extracted, and used for determination of the function for the fertility restoration ability of the ORF-like proteins.

Thus, functions of the 9 kinds of Rf-like genes were determined by using the PPR codes. The amino acids responsible for the base specifying capacity (1, 4, and ii) were extracted in the same manner as that used for Enko B mentioned above, converted into PPR codes, and used for determination of the functionality thereof by using the amino acid species as RNA binding windows (FIG. 22). Although Enko B and Kosena B show a homology of 99.4% for the whole sequences, two of RNA binding windows show amino acid polymorphism, and it was considered that they were deeply involved in dominance and recessiveness for the fertility restoration by the ORF687-like genes (Non-patent reference 4). Further, the gene Comet B locating on the same locus as that of Enko B in the variety Comet shows a homology of 98.0% with respect to Enko B, and the RNA binding windows of them are completely the same. The finding that Comet B is a dominant gene obtained by the past mating tests could be verified. Further, Enko A is an overlapping gene locating near Enko B, and it was suggested also from the viewpoint of RNA recognition that it is a recessive gene. These data suggest that, for the dominance and recessiveness for the fertility restoration of the ORF687-like genes, it is important that the amino acids responsible for the base specifying capacity (1, 4, ii) are the same in all the corresponding PPR motifs in the ORF687-like genes, in particular, they have the same amino acids 4 ($A_4$), or the same amino acids "ii". Inter alia, it is considered that it is especially important that they have the same amino acids 4 ($A_4$). From this point of view, it was considered that the genes locating on the same locus as that of Enko B in various pedigrees of radish, of which information concerning fertility is unknown, rrORF690-1, rrORF690-2, icicle_pprCA, PC_PPR-A, and PC_PPR-BL, have RNA binding windows different from those of Enko B, which is a dominant gene, and these genes are also recessive rf.

The results described above suggest that the PPR codes used in the present invention can accelerate the determination of functions of industrially useful PPR proteins, which act as a fertility restoration factor. When a new pedigree is used for the first filial hybrid breeding method using the CMS-Rf system, whether candidate Rf gene sequences have fertility restoration ability can be determined from the sequences thereof by the above technique. The inventors of the present invention determined functions of the ORF687-like genes of 21 kinds of novel radish varieties, and successfully determined whether the fertility restoration ability of the ORF-like gene is dominant or recessive for 19 varieties (data are not shown). This technique can be applied not only to radish of the Ogura-type cytoplasm, but also to various cytoplasms and plant varieties containing a PPR protein as Rf.

REFERENCES CITED IN EXAMPLES

Reference 1: Small, I. D., and Peeters, N. (2000), The PPR motif—a TPR-related motif prevalent in plant organellar proteins, Trends Biochem. Sci., 25, 46-47

Reference 2: Lurin, C., Andres, C., Aubourg, S., Bellaoui, M., Bitton, F., Bruyere, C., Caboche, M., Debast, C., Gualberto, J., Hoffmann, B., et al. (2004), Genome-wide analysis of *Arabidopsis* pentatricopeptide repeat proteins reveals their essential role in organelle biogenesis, Plant Cell, 16, 2089-2103

Reference 3: Okuda, K., Myouga, F., Motohashi, R., Shinozaki, K., and Shikanai, T. (2007), Conserved domain structure of pentatricopeptide repeat proteins involved in chloroplast RNA editing, Proc. Natl. Acad. Sci. USA, 104, 8178-8183

Reference 4: Koizuka N, Imai R, Fujimoto H, Hayakawa T, Kimura Y, et al. (2003), Genetic characterization of a pentatricopeptide repeat protein gene, orf687, that restores fertility in the cytoplasmic male-sterile Kosena radish, Plant J., 34:407-415

Reference 5: Nakamura T, Yagi Y, Kobayashi K. (2012), Mechanistic insight into pentatricopeptide repeat proteins as sequence-specific RNA-binding proteins for organellar RNAs in plants, Plant & Cell Physiology, 53:1171-1179

---

What is claimed is:

1. A method for controlling a function of a RNA having a target sequence, comprising:
    determining a nucleic acid sequence coding for an amino acid sequence of a protein,
    cloning said nucleic acid sequence, and
    preparing a transformant which produces the protein,
    wherein the protein contains one or more of PPR motifs, each consisting of a polypeptide of 30- to 38-amino acid length represented by the formula 1:

(HelixA)-X-(HelixB)-L             (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$    (Formula 2)

wherein, in the formula 2, $A_1$ to $A_{12}$ independently represent an amino acid;
    wherein, in the formula 1, X is a moiety of 1- to 9-amino acid length and is optional;
    wherein, in the formula 1, Helix B is a moiety of 11- to 13-amino acid length capable of forming an α-helix structure; and
    wherein, in the formula 1, L is a moiety of 2- to 7-amino acid length represented by the formula 3;

$L_{vii}$-$L_{vi}$-$L_v$-$L_{iv}$-$L_{iii}$-$L_{ii}$-$L_i$    (Formula 3)

wherein, in the formula 3, $L_i$ to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$ corresponds to the target sequence;
    preparing a cell containing the RNA having the target sequence; and
    introducing the protein into the cell, whereby the protein binds to the RNA having the target sequence.

2. The method according to claim 1, wherein the method is conducted to modify an expression of the RNA having the target sequence.

3. The method according to claim 1, wherein the combination of the three amino acids $A_1$, $A_4$ and $L_{ii}$ is determined according to any one of the following propositions:
    (3-1) when the three amino acids $A_1$, $A_4$, and $L_{ii}$ are valine, asparagine, and aspartic acid, respectively, the PPR motif can selectively bind to U (uracil);
    (3-2) when the three amino acids $A_1$, $A_4$, and $L_{ii}$ are valine, threonine, and asparagine, respectively, the PPR motif can selectively bind to A (adenine);
    (3-3) when the three amino acids $A_1$, $A_4$, and $L_{ii}$ are valine, asparagine, and asparagine, respectively, the PPR motif can selectively bind to C (cytosine);
    (3-4) when the three amino acids $A_1$, $A_4$, and $L_{ii}$ are glutamic acid, glycine, and aspartic acid, respectively, the PPR motif can selectively bind to G (guanine);
    (3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

4. The method according to claim 1, wherein the combination of the two amino acids $A_4$ and $L_{ii}$ is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

5. The method according to claim 2, wherein the protein is involved in digestion, editing, translation, splicing, or stability of the RNA having the target sequence.

6. A method for controlling a function of an RNA having a target sequence, comprising:

preparing a protein which contains one or more of PPR motifs, each consisting of a polypeptide of 30- to 38-amino acid length represented by the formula 1:

$$\text{(HelixA)-X-(HelixB)-L} \quad \text{(Formula 1)}$$

wherein, in formula 1, Helix A is a moiety of 12-amino acid length capable of forming an α-helix structure, and is represented by the formula 2:

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \quad \text{(Formula 2)}$$

wherein, in the formula 2, $A_1$ to $A_{12}$ independently represent an amino acid;

wherein, in the formula 1, X is a moiety of 1- to 9-amino acid length and is optional;

wherein, in the formula 1, Helix B is a moiety of 11- to 13-amino acid length capable of forming an α-helix structure; and wherein, in the formula 1, L is a moiety of 2- to 7-amino acid length represented by the formula 3;

$$L_{vii}\text{-}L_{vi}\text{-}L_{v}\text{-}L_{iv}\text{-}L_{iii}\text{-}L_{ii}\text{-}L_{i} \quad \text{(Formula 3)}$$

wherein, in the formula 3, $L_i$ to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$, corresponds to the target sequence;

preparing a cell containing the RNA having the target sequence; and introducing the protein into the cell, whereby the protein binds to the RNA having the target sequence.

7. The method according to claim 6, wherein the method is conducted to modify an expression of the RNA having the target sequence.

8. The method according to claim 6, wherein the combination of the three amino acids $A_1$, $A_4$ and $L_{ii}$ is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

9. The method according to claim 6, wherein the combination of the two amino acids $A_4$ and $L_{ii}$ is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

10. The method according to claim 7, wherein the protein is involved in digestion, editing, translation, splicing, or stability of the RNA having the target sequence.

11. A method for controlling a function of RNA, comprising:

preparing a complex comprising a protein region consisting of a protein linked to a functional region, the protein containing one or more of PPR motifs, each consisting of a polypeptide of 30- to 38-amino acid length represented by the formula 1:

(HelixA)-X-(HelixB)-L  (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$  (Formula 2)

wherein, in the formula 2, $A_1$ to $A_{12}$ independently represent an amino acid;

wherein, in the formula 1, X is a moiety of 1- to 9-amino acid length and is optional;

wherein, in the formula 1, Helix B is a moiety of 11- to 13-amino acid length capable of forming an α-helix structure; and wherein, in the formula 1, L is a moiety of 2- to 7-amino acid length represented by the formula 3;

$L_{vii}$-$L_{vi}$-$L_v$-$L_{iv}$-$L_{ii}$-$L_i$  (Formula 3)

wherein, in the formula 3, $L_i$ to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$ corresponds to the target sequence;

preparing a cell containing an RNA having a target sequence; and introducing the complex into the cell, whereby the protein region of the complex binds to the RNA having the target sequence and the functional region modifies the function of the RNA.

12. The method according to claim 11, wherein the combination of the three amino acids $A_1$, $A_4$ and $L_{ii}$ is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

13. The method according to claim 11, wherein the combination of the two amino acids $A_4$ and $L_{ii}$ is determined according to any one of the following propositions:
   (2-1) when $A_4$ and $L_{ii}$ are asparagine and aspartic acid, respectively, the motif can selectively bind to U;
   (2-2) when $A_4$ and $L_{ii}$ are asparagine and asparagine, respectively, the motif can selectively bind to C;
   (2-3) when $A_4$ and $L_{ii}$ are threonine and asparagine, respectively, the motif can selectively bind to A;
   (2-4) when $A_4$ and $L_{ii}$ are threonine and aspartic acid, respectively, the motif can selectively bind to G;
   (2-5) when $A_4$ and $L_{ii}$ are serine and asparagine, respectively, the motif can selectively bind to A;
   (2-6) when $A_4$ and $L_{ii}$ are glycine and aspartic acid, respectively, the motif can selectively bind to G;
   (2-7) when $A_4$ and $L_{ii}$ are asparagine and serine, respectively, the motif can selectively bind to C;
   (2-8) when $A_4$ and $L_{ii}$ are proline and aspartic acid, respectively, the motif can selectively bind to U;
   (2-9) when $A_4$ and $L_{ii}$ are glycine and asparagine, respectively, the motif can selectively bind to A;
   (2-10) when $A_4$ and $L_{ii}$ are methionine and aspartic acid, respectively, the motif can selectively bind to U;
   (2-11) when $A_4$ and $L_{ii}$ are leucine and aspartic acid, respectively, the motif can selectively bind to C; and
   (2-12) when $A_4$ and $L_{ii}$ are valine and threonine, respectively, the motif can selectively bind to U.

14. A method for modifying a cellular genetic material, comprising:
   preparing a cell containing an RNA having a target sequence; and
   introducing a complex into the cell, the complex comprising a protein region consisting of a protein linked to a functional region, the protein containing one or more of PPR motifs, each consisting of a polypeptide of 30- to 38-amino acid length represented by the formula 1:

(HelixA)-X-(HelixB)-L    (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$    (Formula 2)

wherein, in the formula 2, $A_1$ to $A_{11}$ independently represent an amino acid;
   wherein, in the formula 1, X is a moiety of 1- to 9-amino acid length and is optional;
   wherein, in the formula 1, Helix B is a moiety of 11- to 13-amino acid length capable of forming an α-helix structure; and
   wherein, in the formula 1, L is a moiety of 2- to 7-amino acid length represented by the formula 3;

$L_{vii}$-$L_{vi}$-$L_v$-$L_{iv}$-$L_{iii}$-$L_{ii}$-$L_i$    (Formula 3)

wherein, in the formula 3, $L_i$ to $L_{vii}$ independently represent an amino acid, and $L_{iii}$ to $L_{vii}$ are optional, and
   wherein a combination of three amino acids $A_1$, $A_4$ and $L_{ii}$, or a combination of two amino acids $A_4$ and $L_{ii}$ corresponds to the target sequence;
   whereby the protein region of the complex binds to the RNA having the target sequence and the functional region modifies the target sequence.

15. The method according to claim 14, wherein the combination of the three amino acids $A_1$, $A_4$ and $L_{ii}$ is determined according to any one of the following propositions:
   (3-1) when the three amino acids $A_1$, $A_4$, and $L_{ii}$ are valine, asparagine, and aspartic acid, respectively, the PPR motif can selectively bind to U (uracil);
   (3-2) when the three amino acids $A_1$, $A_4$, and $L_{ii}$ are valine, threonine, and asparagine, respectively, the PPR motif can selectively bind to A (adenine);
   (3-3) when the three amino acids $A_1$, $A_4$, and $L_{ii}$ are valine, asparagine, and asparagine, respectively, the PPR motif can selectively bind to C (cytosine);
   (3-4) when the three amino acids $A_1$, $A_4$, and $L_{ii}$ are glutamic acid, glycine, and aspartic acid, respectively, the PPR motif can selectively bind to G (guanine);
   (3-5) when the three amino acids $A_1$, $A_4$, and $L_{ii}$ are isoleucine, asparagine, and asparagine, respectively, the PPR motif can selectively bind to C or U;
   (3-6) when the three amino acids $A_1$, $A_4$, and $L_{ii}$ are valine, threonine, and aspartic acid, respectively, the PPR motif can selectively bind to G;
   (3-7) when the three amino acids $A_1$, $A_4$, and $L_{ii}$ are lysine, threonine, and aspartic acid, respectively, the PPR motif can selectively bind to G;
   (3-8) when the three amino acids $A_1$, $A_4$, and $L_{ii}$ are phenylalanine, serine, and asparagine, respectively, the PPR motif can selectively bind to A;
   (3-9) when the three amino acids $A_1$, $A_4$, and $L_{ii}$ are valine, asparagine, and serine, respectively, the PPR motif can selectively bind to C;
   (3-10) when the three amino acids $A_1$, $A_4$, and $L_{ii}$ are phenylalanine, threonine, and asparagine, respectively, the PPR motif can selectively bind to A;
   (3-11) when the three amino acids $A_1$, $A_4$, and $L_{ii}$ are isoleucine, asparagine, and aspartic acid, respectively, the PPR motif can selectively bind to U or A;
   (3-12) when the three amino acids $A_1$, $A_4$, and $L_{ii}$ are threonine, threonine, and asparagine, respectively, the PPR motif can selectively bind to A;
   (3-13) when the three amino acids $A_1$, $A_4$, and $L_{ii}$ are isoleucine, methionine, and aspartic acid, respectively, the PPR motif can selectively bind to U or C;
   (3-14) when the three amino acids $A_1$, $A_4$, and $L_{ii}$ are phenylalanine, proline, and aspartic acid, respectively, the PPR motif can selectively bind to U;
   (3-15) when the three amino acids $A_1$, $A_4$, and $L_{ii}$ are tyrosine, proline, and aspartic acid, respectively, the PPR motif can selectively bind to U; and
   (3-16) when the three amino acids $A_1$, $A_4$, and $L_{ii}$ are leucine, threonine, and aspartic acid, respectively, the PPR motif can selectively bind to G.

16. The method according to claim 14, wherein the combination of the two amino acids $A_4$ and $L_{ii}$ is determined according to any one of the following propositions:
   (2-1) when $A_4$ and $L_{ii}$ are asparagine and aspartic acid, respectively, the motif can selectively bind to U;
   (2-2) when $A_4$ and $L_{ii}$ are asparagine and asparagine, respectively, the motif can selectively bind to C;
   (2-3) when $A_4$ and $L_{ii}$ are threonine and asparagine, respectively, the motif can selectively bind to A;
   (2-4) when $A_4$ and $L_{ii}$ are threonine and aspartic acid, respectively, the motif can selectively bind to G;
   (2-5) when $A_4$ and $L_{ii}$ are serine and asparagine, respectively, the motif can selectively bind to A;
   (2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;
(2-8) when $A_4$ and $L_{ii}$ are proline and aspartic acid, respectively, the motif can selectively bind to U;
(2-9) when $A_4$ and $L_{ii}$ are glycine and asparagine, respectively, the motif can selectively bind to A;
(2-10) when $A_4$ and $L_{ii}$ are methionine and aspartic acid, respectively, the motif can selectively bind to U;
(2-11) when $A_4$ and $L_{ii}$ are leucine and aspartic acid, respectively, the motif can selectively bind to C; and
(2-12) when $A_4$ and $L_{ii}$ are valine and threonine, respectively, the motif can selectively bind to U.

17. A method for visualizing a target sequence, comprising:
preparing a complex comprising a protein region consisting of a protein, linked to a functional region,
determining a nucleic acid sequence coding for an amino acid sequence of a protein,
cloning said nucleic acid sequence, and
preparing a transformant which produces the protein,
wherein the protein contains one or more of PPR motifs, each consisting of a polypeptide of 30- to 38-amino acid length represented by the formula 1:

(HelixA)-X-(HelixB)-L  (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$  (Formula 2)

wherein, in the formula 2, $A_1$ to $A_{12}$ independently represent an amino acid;
wherein, in the formula 1, X is a moiety of 1- to 9-amino acid length and is optional;
wherein, in the formula 1, Helix B is a moiety of 11- to 13-amino acid length capable of forming an α-helix structure; and
wherein, in the formula 1, L is a moiety of 2- to 7-amino acid length represented by the formula 3;

$L_{vii}$-$L_{vi}$-$L_v$-$L_{iv}$-$L_{ii}$-$L_i$  (Formula 3)

wherein, in the formula 3, $L_i$ to $L_{vii}$ independently represent an amino acid, and $L_{iii}$ to $L_{vii}$ are optional, and
wherein a combination of three amino acids $A_1$, $A_4$ and $L_{ii}$, or a combination of two amino acids $A_4$ and $L_{ii}$ corresponds to the target sequence;
preparing a cell containing an RNA having the target sequence; and
introducing the complex into the cell, wherein the functional region is a marker moiety, whereby the protein region of the complex binds to the RNA having the target sequence, and the marker moiety visualizes the target sequence.

18. A method for delivering a functional region to a cell, comprising:
preparing a complex comprising a protein region consisting of a protein, linked to a functional region,
determining a nucleic acid sequence coding for an amino acid sequence of a protein,
cloning said nucleic acid sequence, and
preparing a transformant which produces the protein,
wherein the protein contains one or more of PPR motifs, each consisting of a polypeptide of 30- to 38-amino acid length represented by the formula 1:

(HelixA)-X-(HelixB)-L  (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$  (Formula 2)

wherein, in the formula 2, $A_1$ to $A_{12}$ independently represent an amino acid;
wherein, in the formula 1, X is a moiety of 1- to 9-amino acid length and is optional;
wherein, in the formula 1, Helix B is a moiety of 11- to 13-amino acid length capable of forming an α-helix structure; and
wherein, in the formula 1, L is a moiety of 2- to 7-amino acid length represented by the formula 3;

$L_{vii}$-$L_{vi}$-$L_v$-$L_{iv}$-$L_{ii}$-$L_i$  (Formula 3)

wherein, in the formula 3, $L_i$ to $L_{vii}$ independently represent an amino acid, and $L_{iii}$ to $L_{vii}$ are optional, and
wherein a combination of three amino acids $A_1$, $A_4$ and $L_{ii}$, or a combination of two amino acids $A_4$ and $L_{ii}$ corresponds to the target sequence
preparing a cell containing an RNA having a target sequence; and
introducing the complex into the cell, whereby the protein region of the complex binds to the RNA having the target sequence, and the functional region is delivered to the target sequence.

19. A method for visualizing a target sequence, which comprises the following steps:
preparing a cell containing an RNA having a target sequence; and
introducing a complex into the cell, the complex comprising a protein region consisting of a protein linked to a functional region, the protein containing one or more of PPR motifs, each consisting of a polypeptide of 30- to 38-amino acid length represented by the formula 1:

(HelixA)-X-(HelixB)-L  (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$  (Formula 2)

wherein, in the formula 2, $A_1$ to $A_{12}$ independently represent an amino acid;
wherein, in the formula 1, X is a moiety of 1- to 9-amino acid length and is optional;
wherein, in the formula 1, Helix B is a moiety of 11- to 13-amino acid length capable of forming an α-helix structure; and
wherein, in the formula 1, L is a moiety of 2- to 7-amino acid length represented by the formula 3;

$L_{vii}$-$L_{vi}$-$L_v$-$L_{iv}$-$L_{ii}$-$L_i$  (Formula 3)

wherein, in the formula 3, $L_i$ to $L_{vii}$ independently represent an amino acid, and $L_{iii}$ to $L_{vii}$ are optional, and
wherein a combination of three amino acids $A_1$, $A_4$ and $L_{ii}$, or a combination of two amino acids $A_4$ and $L_{ii}$ corresponds to the target sequence;
wherein the functional region is a marker moiety, whereby the protein region of the complex binds to the RNA having the target sequence, and the marker moiety visualizes the target sequence.

20. A method for delivering a functional region, which comprises the following steps:
preparing a cell containing an RNA having a target sequence; and introducing a complex into the cell, the complex comprising a protein region consisting of a protein linked to a functional region, the protein containing one or more of PPR motifs, each consisting of a polypeptide of 30- to 38-amino acid length represented by the formula 1:

(HelixA)-X-(HelixB)-L     (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$     (Formula 2)

wherein, in the formula 2, $A_1$ to $A_{12}$ independently represent an amino acid;
wherein, in the formula 1, X is a moiety of 1- to 9-amino acid length and is optional;
wherein, in the formula 1, Helix B is a moiety of 11- to 13-amino acid length capable of forming an α-helix structure; and
wherein, in the formula 1, L is a moiety of 2- to 7-amino acid length represented by the formula 3;

$L_{vii}$-$L_{vi}$-$L_v$-$L_{iv}$-$L_{ii}$-$L_i$     (Formula 3)

wherein, in the formula 3, $L_i$ to $L_{vii}$ independently represent an amino acid, and $L_{iii}$ to $L_{vii}$ are optional, and
wherein a combination of three amino acids $A_1$, $A_4$ and $L_{ii}$, or a combination of two amino acids $A_4$ and $L_{ii}$ corresponds to the target sequence;
whereby the protein region of the complex binds to the RNA having the target sequence, and the functional region is delivered to the target sequence.

* * * * *

SEQUENCE LISTING

<160> NUMBER OF SEQ ID NOS: 591

<210> SEQ ID NO 1
<211> LENGTH: 555
<212> TYPE: PRT
<213> ORGANISM: Arabidopsis thaliana

<400> SEQUENCE: 1

```
Met Leu Arg His Ala Ile Glu Thr Asn Val Gln Ile Phe Thr Lys Phe
1               5                   10                  15

Leu Val Ile Ser Ala Ser Ala Val Gly Ile Gly Tyr Ala Arg Lys Leu
            20                  25                  30

Phe Asp Gln Arg Pro Gln Arg Asp Asp Ser Phe Leu Ser Asn Ser Met
        35                  40                  45

Ile Lys Ala Tyr Leu Glu Thr Arg Gln Tyr Pro Asp Ser Phe Ala Leu
    50                  55                  60

Tyr Arg Asp Leu Arg Lys Glu Thr Cys Phe Ala Pro Asp Asn Phe Thr
65                  70                  75                  80

Phe Thr Thr Leu Thr Lys Ser Cys Ser Leu Ser Met Cys Val Tyr Gln
            85                  90                  95

Gly Leu Gln Leu His Ser Gln Ile Trp Arg Phe Gly Phe Cys Ala Asp
            100                 105                 110

Met Tyr Val Ser Thr Gly Val Val Asp Met Tyr Ala Lys Phe Gly Lys
        115                 120                 125

Met Gly Cys Ala Arg Asn Ala Phe Asp Glu Met Pro His Arg Ser Glu
    130                 135                 140

Val Ser Trp Thr Ala Leu Ile Ser Gly Tyr Ile Arg Cys Gly Glu Leu
145                 150                 155                 160

Asp Leu Ala Ser Lys Leu Phe Asp Gln Met Pro His Val Lys Asp Val
            165                 170                 175

Val Ile Tyr Asn Ala Met Met Asp Gly Phe Val Lys Ser Gly Asp Met
            180                 185                 190

Thr Ser Ala Arg Arg Leu Phe Asp Glu Met Thr His Lys Thr Val Ile
        195                 200                 205

Thr Trp Thr Thr Met Ile His Gly Tyr Cys Asn Ile Lys Asp Ile Asp
    210                 215                 220

Ala Ala Arg Lys Leu Phe Asp Ala Met Pro Glu Arg Asn Leu Val Ser
225                 230                 235                 240

Trp Asn Thr Met Ile Gly Gly Tyr Cys Gln Asn Lys Gln Pro Gln Glu
            245                 250                 255

Gly Ile Arg Leu Phe Gln Glu Met Gln Ala Thr Thr Ser Leu Asp Pro
            260                 265                 270

Asp Asp Val Thr Ile Leu Ser Val Leu Pro Ala Ile Ser Asp Thr Gly
```

```
            275                 280                 285
Ala Leu Ser Leu Gly Glu Trp Cys His Cys Phe Val Gln Arg Lys Lys
        290                 295                 300
Leu Asp Lys Lys Val Lys Val Cys Thr Ala Ile Leu Asp Met Tyr Ser
305                 310                 315                 320
Lys Cys Gly Glu Ile Glu Lys Ala Lys Arg Ile Phe Asp Glu Met Pro
            325                 330                 335
Glu Lys Gln Val Ala Ser Trp Asn Ala Met Ile His Gly Tyr Ala Leu
        340                 345                 350
Asn Gly Asn Ala Arg Ala Leu Asp Leu Phe Val Thr Met Met Ile
        355                 360                 365
Glu Glu Lys Pro Asp Glu Ile Thr Met Leu Ala Val Ile Thr Ala Cys
        370                 375                 380
Asn His Gly Gly Leu Val Glu Glu Gly Arg Lys Trp Phe His Val Met
385                 390                 395                 400
Arg Glu Met Gly Leu Asn Ala Lys Ile Glu His Tyr Gly Cys Met Val
            405                 410                 415
Asp Leu Leu Gly Arg Ala Gly Ser Leu Lys Glu Ala Glu Asp Leu Ile
        420                 425                 430
Thr Asn Met Pro Phe Glu Pro Asn Gly Ile Ile Leu Ser Ser Phe Leu
        435                 440                 445
Ser Ala Cys Gly Gln Tyr Lys Asp Ile Glu Arg Ala Glu Arg Ile Leu
        450                 455                 460
Lys Lys Ala Val Glu Leu Glu Pro Gln Asn Asp Gly Asn Tyr Val Leu
465                 470                 475                 480
Leu Arg Asn Leu Tyr Ala Ala Asp Lys Arg Trp Asp Asp Phe Gly Met
            485                 490                 495
Val Lys Asn Val Met Arg Lys Asn Gln Ala Lys Lys Glu Val Gly Cys
        500                 505                 510
Ser Leu Ile Glu Ile Asn Tyr Ile Val Ser Glu Phe Ile Ser Gly Asp
        515                 520                 525
Thr Thr His Pro His Arg Arg Ser Ile His Leu Val Leu Gly Asp Leu
        530                 535                 540
Leu Met His Met Asn Glu Glu Lys Tyr Asn Trp
545                 550                 555

<210> SEQ ID NO 2
<211> LENGTH: 500
<212> TYPE: PRT
<213> ORGANISM: Arabidopsis thaliana

<400> SEQUENCE: 2

Met Gly Leu Leu Pro Val Val Gly Ile Thr Ser Pro Ala Leu Ile Thr
1               5                   10                  15
His Lys Asn His Ala Asn Pro Lys Ile Gln Arg His Asn Gln Ser Thr
            20                  25                  30
Ser Glu Thr Thr Val Ser Trp Thr Ser Arg Ile Asn Leu Leu Thr Arg
        35                  40                  45
Asn Gly Arg Leu Ala Glu Ala Ala Lys Glu Phe Ser Asp Met Thr Leu
    50                  55                  60
Ala Gly Val Glu Pro Asn His Ile Thr Phe Ile Ala Leu Leu Ser Gly
65                  70                  75                  80
Cys Gly Asp Phe Thr Ser Gly Ser Glu Ala Leu Gly Asp Leu Leu His
                85                  90                  95
```

```
Gly Tyr Ala Cys Lys Leu Gly Leu Asp Arg Asn His Val Met Val Gly
                100                 105                 110

Thr Ala Ile Ile Gly Met Tyr Ser Lys Arg Gly Arg Phe Lys Lys Ala
            115                 120                 125

Arg Leu Val Phe Asp Tyr Met Glu Asp Lys Asn Ser Val Thr Trp Asn
        130                 135                 140

Thr Met Ile Asp Gly Tyr Met Arg Ser Gly Gln Val Asp Asn Ala Ala
145                 150                 155                 160

Lys Met Phe Asp Lys Met Pro Glu Arg Asp Leu Ile Ser Trp Thr Ala
                165                 170                 175

Met Ile Asn Gly Phe Val Lys Lys Gly Tyr Gln Glu Glu Ala Leu Leu
            180                 185                 190

Trp Phe Arg Glu Met Gln Ile Ser Gly Val Lys Pro Asp Tyr Val Ala
        195                 200                 205

Ile Ile Ala Ala Leu Asn Ala Cys Thr Asn Leu Gly Ala Leu Ser Phe
    210                 215                 220

Gly Leu Trp Val His Arg Tyr Val Leu Ser Gln Asp Phe Lys Asn Asn
225                 230                 235                 240

Val Arg Val Ser Asn Ser Leu Ile Asp Leu Tyr Cys Arg Cys Gly Cys
                245                 250                 255

Val Glu Phe Ala Arg Gln Val Phe Tyr Asn Met Glu Lys Arg Thr Val
            260                 265                 270

Val Ser Trp Asn Ser Val Ile Val Gly Phe Ala Ala Asn Gly Asn Ala
        275                 280                 285

His Glu Ser Leu Val Tyr Phe Arg Lys Met Gln Glu Lys Gly Phe Lys
    290                 295                 300

Pro Asp Ala Val Thr Phe Thr Gly Ala Leu Thr Ala Cys Ser His Val
305                 310                 315                 320

Gly Leu Val Glu Glu Gly Leu Arg Tyr Phe Gln Ile Met Lys Cys Asp
                325                 330                 335

Tyr Arg Ile Ser Pro Arg Ile Glu His Tyr Gly Cys Leu Val Asp Leu
            340                 345                 350

Tyr Ser Arg Ala Gly Arg Leu Glu Asp Ala Leu Lys Leu Val Gln Ser
        355                 360                 365

Met Pro Met Lys Pro Asn Glu Val Val Ile Gly Ser Leu Leu Ala Ala
    370                 375                 380

Cys Ser Asn His Gly Asn Asn Ile Val Leu Ala Glu Arg Leu Met Lys
385                 390                 395                 400

His Leu Thr Asp Leu Asn Val Lys Ser His Ser Asn Tyr Val Ile Leu
                405                 410                 415

Ser Asn Met Tyr Ala Ala Asp Gly Lys Trp Glu Gly Ala Ser Lys Met
            420                 425                 430

Arg Arg Lys Met Lys Gly Leu Gly Leu Lys Lys Gln Pro Gly Phe Ser
        435                 440                 445

Ser Ile Glu Ile Asp Asp Cys Met His Val Phe Met Ala Gly Asp Asn
    450                 455                 460

Ala His Val Glu Thr Thr Tyr Ile Arg Glu Val Leu Glu Leu Ile Ser
465                 470                 475                 480

Ser Asp Leu Arg Leu Gln Gly Cys Val Val Glu Thr Leu Ala Gly Asp
                485                 490                 495

Leu Leu Asn Ala
            500
```

-continued

```
<210> SEQ ID NO 3
<211> LENGTH: 830
<212> TYPE: PRT
<213> ORGANISM: Arabidopsis thaliana

<400> SEQUENCE: 3

Met Ala Ser Leu Pro Phe Asn Thr Ile Pro Asn Lys Val Pro Phe Ser
1               5                   10                  15

Val Ser Ser Lys Pro Ser Lys His His Asp Glu Gln Ala His Ser
            20                  25                  30

Pro Ser Ser Thr Ser Tyr Phe His Arg Val Ser Ser Leu Cys Lys Asn
            35                  40                  45

Gly Glu Ile Lys Glu Ala Leu Ser Leu Val Thr Glu Met Asp Phe Arg
50                  55                  60

Asn Leu Arg Ile Gly Pro Glu Ile Tyr Gly Glu Ile Leu Gln Gly Cys
65                  70                  75                  80

Val Tyr Glu Arg Asp Leu Ser Thr Gly Lys Gln Ile His Ala Arg Ile
                85                  90                  95

Leu Lys Asn Gly Asp Phe Tyr Ala Arg Asn Glu Tyr Ile Glu Thr Lys
                100                 105                 110

Leu Val Ile Phe Tyr Ala Lys Cys Asp Ala Leu Glu Ile Ala Glu Val
            115                 120                 125

Leu Phe Ser Lys Leu Arg Val Arg Asn Val Phe Ser Trp Ala Ala Ile
130                 135                 140

Ile Gly Val Lys Cys Arg Ile Gly Leu Cys Glu Gly Ala Leu Met Gly
145                 150                 155                 160

Phe Val Glu Met Leu Glu Asn Glu Ile Phe Pro Asp Asn Phe Val Val
                165                 170                 175

Pro Asn Val Cys Lys Ala Cys Gly Ala Leu Lys Trp Ser Arg Phe Gly
            180                 185                 190

Arg Gly Val His Gly Tyr Val Val Lys Ser Gly Leu Glu Asp Cys Val
            195                 200                 205

Phe Val Ala Ser Ser Leu Ala Asp Met Tyr Gly Lys Cys Gly Val Leu
210                 215                 220

Asp Asp Ala Ser Lys Val Phe Asp Glu Ile Pro Asp Arg Asn Ala Val
225                 230                 235                 240

Ala Trp Asn Ala Leu Met Val Gly Tyr Val Gln Asn Gly Lys Asn Glu
                245                 250                 255

Glu Ala Ile Arg Leu Phe Ser Asp Met Arg Lys Gln Gly Val Glu Pro
            260                 265                 270

Thr Arg Val Thr Val Ser Thr Cys Leu Ser Ala Ser Ala Asn Met Gly
            275                 280                 285

Gly Val Glu Glu Gly Lys Gln Ser His Ala Ile Ala Ile Val Asn Gly
290                 295                 300

Met Glu Leu Asp Asn Ile Leu Gly Thr Ser Leu Leu Asn Phe Tyr Cys
305                 310                 315                 320

Lys Val Gly Leu Ile Glu Tyr Ala Glu Met Val Phe Asp Arg Met Phe
                325                 330                 335

Glu Lys Asp Val Val Thr Trp Asn Leu Ile Ile Ser Gly Tyr Val Gln
            340                 345                 350

Gln Gly Leu Val Glu Asp Ala Ile Tyr Met Cys Gln Leu Met Arg Leu
            355                 360                 365

Glu Lys Leu Lys Tyr Asp Cys Val Thr Leu Ala Thr Leu Met Ser Ala
370                 375                 380
```

```
Ala Ala Arg Thr Glu Asn Leu Lys Leu Gly Lys Glu Val Gln Cys Tyr
385                 390                 395                 400

Cys Ile Arg His Ser Phe Glu Ser Asp Ile Val Leu Ala Ser Thr Val
            405                 410                 415

Met Asp Met Tyr Ala Lys Cys Gly Ser Ile Val Asp Ala Lys Lys Val
        420                 425                 430

Phe Asp Ser Thr Val Glu Lys Asp Leu Ile Leu Trp Asn Thr Leu Leu
    435                 440                 445

Ala Ala Tyr Ala Glu Ser Gly Leu Ser Gly Glu Ala Leu Arg Leu Phe
450                 455                 460

Tyr Gly Met Gln Leu Glu Gly Val Pro Pro Asn Val Ile Thr Trp Asn
465                 470                 475                 480

Leu Ile Ile Leu Ser Leu Leu Arg Asn Gly Gln Val Asp Glu Ala Lys
            485                 490                 495

Asp Met Phe Leu Gln Met Gln Ser Ser Gly Ile Ile Pro Asn Leu Ile
        500                 505                 510

Ser Trp Thr Thr Met Met Asn Gly Met Val Gln Asn Gly Cys Ser Glu
    515                 520                 525

Glu Ala Ile Leu Phe Leu Arg Lys Met Gln Glu Ser Gly Leu Arg Pro
530                 535                 540

Asn Ala Phe Ser Ile Thr Val Ala Leu Ser Ala Cys Ala His Leu Ala
545                 550                 555                 560

Ser Leu His Ile Gly Arg Thr Ile His Gly Tyr Ile Ile Arg Asn Leu
            565                 570                 575

Gln His Ser Ser Leu Val Ser Ile Glu Thr Ser Leu Val Asp Met Tyr
        580                 585                 590

Ala Lys Cys Gly Asp Ile Asn Lys Ala Glu Lys Val Phe Gly Ser Lys
    595                 600                 605

Leu Tyr Ser Glu Leu Pro Leu Ser Asn Ala Met Ile Ser Ala Tyr Ala
610                 615                 620

Leu Tyr Gly Asn Leu Lys Glu Ala Ile Ala Leu Tyr Arg Ser Leu Glu
625                 630                 635                 640

Gly Val Gly Leu Lys Pro Asp Asn Ile Thr Ile Thr Asn Val Leu Ser
            645                 650                 655

Ala Cys Asn His Ala Gly Asp Ile Asn Gln Ala Ile Glu Ile Phe Thr
        660                 665                 670

Asp Ile Val Ser Lys Arg Ser Met Lys Pro Cys Leu Glu His Tyr Gly
    675                 680                 685

Leu Met Val Asp Leu Leu Ala Ser Ala Gly Glu Thr Glu Lys Ala Leu
690                 695                 700

Arg Leu Ile Glu Glu Met Pro Phe Lys Pro Asp Ala Arg Met Ile Gln
705                 710                 715                 720

Ser Leu Val Ala Ser Cys Asn Lys Gln Arg Lys Thr Glu Leu Val Asp
            725                 730                 735

Tyr Leu Ser Arg Lys Leu Leu Glu Ser Glu Pro Glu Asn Ser Gly Asn
        740                 745                 750

Tyr Val Thr Ile Ser Asn Ala Tyr Ala Val Glu Gly Ser Trp Asp Glu
    755                 760                 765

Val Val Lys Met Arg Glu Met Lys Ala Lys Gly Leu Lys Lys Lys
770                 775                 780

Pro Gly Cys Ser Trp Ile Gln Ile Thr Gly Glu Glu Gly Val His Val
785                 790                 795                 800

Phe Val Ala Asn Asp Lys Thr His Thr Arg Ile Asn Glu Ile Gln Met
```

805                 810                 815
Met Leu Ala Leu Leu Tyr Asp Met Gly Thr Gly Ser Lys
            820                 825                 830

<210> SEQ ID NO 4
<211> LENGTH: 809
<212> TYPE: PRT
<213> ORGANISM: Arabidopsis thaliana

<400> SEQUENCE: 4

Met Ser Ser Gln Leu Val Gln Phe Ser Thr Val Pro Gln Ile Pro Asn
1               5                   10                  15

Pro Pro Ser Arg His Arg His Phe Leu Ser Glu Arg Asn Tyr Ile Pro
            20                  25                  30

Ala Asn Val Tyr Glu His Pro Ala Ala Leu Leu Leu Glu Arg Cys Ser
        35                  40                  45

Ser Leu Lys Glu Leu Arg Gln Ile Leu Pro Leu Val Phe Lys Asn Gly
    50                  55                  60

Leu Tyr Gln Glu His Phe Phe Gln Thr Lys Leu Val Ser Leu Phe Cys
65                  70                  75                  80

Arg Tyr Gly Ser Val Asp Glu Ala Ala Arg Val Phe Glu Pro Ile Asp
                85                  90                  95

Ser Lys Leu Asn Val Leu Tyr His Thr Met Leu Lys Gly Phe Ala Lys
            100                 105                 110

Val Ser Asp Leu Asp Lys Ala Leu Gln Phe Phe Val Arg Met Arg Tyr
        115                 120                 125

Asp Asp Val Glu Pro Val Val Tyr Asn Phe Thr Tyr Leu Leu Lys Val
    130                 135                 140

Cys Gly Asp Glu Ala Glu Leu Arg Val Gly Lys Glu Ile His Gly Leu
145                 150                 155                 160

Leu Val Lys Ser Gly Phe Ser Leu Asp Leu Phe Ala Met Thr Gly Leu
                165                 170                 175

Glu Asn Met Tyr Ala Lys Cys Arg Gln Val Asn Glu Ala Arg Lys Val
            180                 185                 190

Phe Asp Arg Met Pro Glu Arg Asp Leu Val Ser Trp Asn Thr Ile Val
        195                 200                 205

Ala Gly Tyr Ser Gln Asn Gly Met Ala Arg Met Ala Leu Glu Met Val
    210                 215                 220

Lys Ser Met Cys Glu Glu Asn Leu Lys Pro Ser Phe Ile Thr Ile Val
225                 230                 235                 240

Ser Val Leu Pro Ala Val Ser Ala Leu Arg Leu Ile Ser Val Gly Lys
                245                 250                 255

Glu Ile His Gly Tyr Ala Met Arg Ser Gly Phe Asp Ser Leu Val Asn
            260                 265                 270

Ile Ser Thr Ala Leu Val Asp Met Tyr Ala Lys Cys Gly Ser Leu Glu
        275                 280                 285

Thr Ala Arg Gln Leu Phe Asp Gly Met Leu Glu Arg Asn Val Val Ser
    290                 295                 300

Trp Asn Ser Met Ile Asp Ala Tyr Val Gln Asn Glu Asn Pro Lys Glu
305                 310                 315                 320

Ala Met Leu Ile Phe Gln Lys Met Leu Asp Glu Gly Val Lys Pro Thr
                325                 330                 335

Asp Val Ser Val Met Gly Ala Leu His Ala Cys Ala Asp Leu Gly Asp
            340                 345                 350

```
Leu Glu Arg Gly Arg Phe Ile His Lys Leu Ser Val Glu Leu Gly Leu
            355                 360                 365
Asp Arg Asn Val Ser Val Val Asn Ser Leu Ile Ser Met Tyr Cys Lys
        370                 375                 380
Cys Lys Glu Val Asp Thr Ala Ala Ser Met Phe Gly Lys Leu Gln Ser
385                 390                 395                 400
Arg Thr Leu Val Ser Trp Asn Ala Met Ile Leu Gly Phe Ala Gln Asn
                405                 410                 415
Gly Arg Pro Ile Asp Ala Leu Asn Tyr Phe Ser Gln Met Arg Ser Arg
            420                 425                 430
Thr Val Lys Pro Asp Thr Phe Thr Tyr Val Ser Val Ile Thr Ala Ile
        435                 440                 445
Ala Glu Leu Ser Ile Thr His His Ala Lys Trp Ile His Gly Val Val
    450                 455                 460
Met Arg Ser Cys Leu Asp Lys Asn Val Phe Val Thr Thr Ala Leu Val
465                 470                 475                 480
Asp Met Tyr Ala Lys Cys Gly Ala Ile Met Ile Ala Arg Leu Ile Phe
                485                 490                 495
Asp Met Met Ser Glu Arg His Val Thr Thr Trp Asn Ala Met Ile Asp
            500                 505                 510
Gly Tyr Gly Thr His Gly Phe Gly Lys Ala Ala Leu Glu Leu Phe Glu
        515                 520                 525
Glu Met Gln Lys Gly Thr Ile Lys Pro Asn Gly Val Thr Phe Leu Ser
    530                 535                 540
Val Ile Ser Ala Cys Ser His Ser Gly Leu Val Glu Ala Gly Leu Lys
545                 550                 555                 560
Cys Phe Tyr Met Met Lys Glu Asn Tyr Ser Ile Glu Leu Ser Met Asp
                565                 570                 575
His Tyr Gly Ala Met Val Asp Leu Leu Gly Arg Ala Gly Arg Leu Asn
            580                 585                 590
Glu Ala Trp Asp Phe Ile Met Gln Met Pro Val Lys Pro Ala Val Asn
        595                 600                 605
Val Tyr Gly Ala Met Leu Gly Ala Cys Gln Ile His Lys Asn Val Asn
    610                 615                 620
Phe Ala Glu Lys Ala Ala Glu Arg Leu Phe Glu Leu Asn Pro Asp Asp
625                 630                 635                 640
Gly Gly Tyr His Val Leu Leu Ala Asn Ile Tyr Arg Ala Ala Ser Met
                645                 650                 655
Trp Glu Lys Val Gly Gln Val Arg Val Ser Met Leu Arg Gln Gly Leu
            660                 665                 670
Arg Lys Thr Pro Gly Cys Ser Met Val Glu Ile Lys Asn Glu Val His
        675                 680                 685
Ser Phe Phe Ser Gly Ser Thr Ala His Pro Asp Ser Lys Lys Ile Tyr
    690                 695                 700
Ala Phe Leu Glu Lys Leu Ile Cys His Ile Lys Glu Ala Gly Tyr Val
705                 710                 715                 720
Pro Asp Thr Asn Leu Val Leu Gly Val Glu Asn Asp Val Lys Glu Gln
                725                 730                 735
Leu Leu Ser Thr His Ser Glu Lys Leu Ala Ile Ser Phe Gly Leu Leu
            740                 745                 750
Asn Thr Thr Ala Gly Thr Thr Ile His Val Arg Lys Asn Leu Arg Val
        755                 760                 765
Cys Ala Asp Cys His Asn Ala Thr Lys Tyr Ile Ser Leu Val Thr Gly
```

```
                770             775             780
Arg Glu Ile Val Val Arg Asp Met Gln Arg Phe His His Phe Lys Asn
785                 790                 795                 800

Gly Ala Cys Ser Cys Gly Asp Tyr Trp
                805

<210> SEQ ID NO 5
<211> LENGTH: 638
<212> TYPE: PRT
<213> ORGANISM: Arabidopsis thaliana

<400> SEQUENCE: 5

Met Val Val Arg Ser Ile Ile Val Ser Pro Thr Thr Ile Thr Tyr
1               5                   10                  15

Tyr His Pro Met Ser Ile Gly Leu Leu Val His Pro Leu Ser Pro His
                20                  25                  30

Ile Pro Pro Ala Ser Ser Pro Ser Ala Ser Thr Ala Gly Asn His His
            35                  40                  45

Gln Arg Ile Phe Ser Leu Ala Glu Thr Cys Ser Asp Met Ser Gln Leu
    50                  55                  60

Lys Gln Leu His Ala Phe Thr Leu Arg Thr Thr Tyr Pro Glu Glu Pro
65                  70                  75                  80

Ala Thr Leu Phe Leu Tyr Gly Lys Ile Leu Gln Leu Ser Ser Ser Phe
                85                  90                  95

Ser Asp Val Asn Tyr Ala Phe Arg Val Phe Asp Ser Ile Glu Asn His
                100                 105                 110

Ser Ser Phe Met Trp Asn Thr Leu Ile Arg Ala Cys Ala His Asp Val
            115                 120                 125

Ser Arg Lys Glu Glu Ala Phe Met Leu Tyr Arg Lys Met Leu Glu Arg
130                 135                 140

Gly Glu Ser Ser Pro Asp Lys His Thr Phe Pro Phe Val Leu Lys Ala
145                 150                 155                 160

Cys Ala Tyr Ile Phe Gly Phe Ser Glu Gly Lys Gln Val His Cys Gln
                165                 170                 175

Ile Val Lys His Gly Phe Gly Gly Asp Val Tyr Val Asn Asn Gly Leu
                180                 185                 190

Ile His Leu Tyr Gly Ser Cys Gly Cys Leu Asp Leu Ala Arg Lys Val
            195                 200                 205

Phe Asp Glu Met Pro Glu Arg Ser Leu Val Ser Trp Asn Ser Met Ile
    210                 215                 220

Asp Ala Leu Val Arg Phe Gly Glu Tyr Asp Ser Ala Leu Gln Leu Phe
225                 230                 235                 240

Arg Glu Met Gln Arg Ser Phe Glu Pro Asp Gly Tyr Thr Met Gln Ser
                245                 250                 255

Val Leu Ser Ala Cys Ala Gly Leu Gly Ser Leu Ser Leu Gly Thr Trp
                260                 265                 270

Ala His Ala Phe Leu Leu Arg Lys Cys Asp Val Asp Val Ala Met Asp
            275                 280                 285

Val Leu Val Lys Asn Ser Leu Ile Glu Met Tyr Cys Lys Cys Gly Ser
    290                 295                 300

Leu Arg Met Ala Glu Gln Val Phe Gln Gly Met Gln Lys Arg Asp Leu
305                 310                 315                 320

Ala Ser Trp Asn Ala Met Ile Leu Gly Phe Ala Thr His Gly Arg Ala
                325                 330                 335
```

```
Glu Glu Ala Met Asn Phe Phe Asp Arg Met Val Asp Lys Arg Glu Asn
                340                 345                 350

Val Arg Pro Asn Ser Val Thr Phe Val Gly Leu Leu Ile Ala Cys Asn
            355                 360                 365

His Arg Gly Phe Val Asn Lys Gly Arg Gln Tyr Phe Asp Met Met Val
        370                 375                 380

Arg Asp Tyr Cys Ile Glu Pro Ala Leu Glu His Tyr Gly Cys Ile Val
385                 390                 395                 400

Asp Leu Ile Ala Arg Ala Gly Tyr Ile Thr Glu Ala Ile Asp Met Val
                405                 410                 415

Met Ser Met Pro Met Lys Pro Asp Ala Val Ile Trp Arg Ser Leu Leu
            420                 425                 430

Asp Ala Cys Cys Lys Lys Gly Ala Ser Val Glu Leu Ser Glu Glu Ile
        435                 440                 445

Ala Arg Asn Ile Ile Gly Thr Lys Glu Asp Asn Glu Ser Ser Asn Gly
    450                 455                 460

Asn Cys Ser Gly Ala Tyr Val Leu Leu Ser Arg Val Tyr Ala Ser Ala
465                 470                 475                 480

Ser Arg Trp Asn Asp Val Gly Ile Val Arg Lys Leu Met Ser Glu His
                485                 490                 495

Gly Ile Arg Lys Glu Pro Gly Cys Ser Ser Ile Glu Ile Asn Gly Ile
            500                 505                 510

Ser His Glu Phe Phe Ala Gly Asp Thr Ser His Pro Gln Thr Lys Gln
        515                 520                 525

Ile Tyr Gln Gln Leu Lys Val Ile Asp Asp Arg Leu Arg Ser Ile Gly
    530                 535                 540

Tyr Leu Pro Asp Arg Ser Gln Ala Pro Leu Val Asp Ala Thr Asn Asp
545                 550                 555                 560

Gly Ser Lys Glu Tyr Ser Leu Arg Leu His Ser Glu Arg Leu Ala Ile
                565                 570                 575

Ala Phe Gly Leu Ile Asn Leu Pro Pro Gln Thr Pro Ile Arg Ile Phe
            580                 585                 590

Lys Asn Leu Arg Val Cys Asn Asp Cys His Glu Val Thr Lys Leu Ile
        595                 600                 605

Ser Lys Val Phe Asn Thr Glu Ile Ile Val Arg Asp Arg Val Arg Phe
    610                 615                 620

His His Phe Lys Asp Gly Ser Cys Ser Cys Leu Asp Tyr Trp
625                 630                 635

<210> SEQ ID NO 6
<211> LENGTH: 613
<212> TYPE: PRT
<213> ORGANISM: Arabidopsis thaliana

<400> SEQUENCE: 6

Met Leu Val Phe Lys Ser Thr Met Glu Cys Ser Ile Ser Ser Thr Ile
1               5                   10                  15

His Val Leu Gly Ser Cys Lys Thr Ser Asp Asp Val Asn Gln Ile His
                20                  25                  30

Gly Arg Leu Ile Lys Thr Gly Ile Ile Lys Asn Ser Asn Leu Thr Thr
            35                  40                  45

Arg Ile Val Leu Ala Phe Ala Ser Ser Arg Arg Pro Tyr Leu Ala Asp
        50                  55                  60

Phe Ala Arg Cys Val Phe His Glu Tyr His Val Cys Ser Phe Ser Phe
65                  70                  75                  80
```

```
Gly Glu Val Glu Asp Pro Phe Leu Trp Asn Ala Val Ile Lys Ser His
                85                  90                  95

Ser His Gly Lys Asp Pro Arg Gln Ala Leu Leu Leu Cys Leu Met
            100                 105                 110

Leu Glu Asn Gly Val Ser Val Asp Lys Phe Ser Leu Ser Leu Val Leu
            115                 120                 125

Lys Ala Cys Ser Arg Leu Gly Phe Val Lys Gly Met Gln Ile His
130                 135                 140

Gly Phe Leu Lys Lys Thr Gly Leu Trp Ser Asp Leu Phe Leu Gln Asn
145                 150                 155                 160

Cys Leu Ile Gly Leu Tyr Leu Lys Cys Gly Cys Leu Gly Leu Ser Arg
                165                 170                 175

Gln Met Phe Asp Arg Met Pro Lys Arg Asp Ser Val Ser Tyr Asn Ser
            180                 185                 190

Met Ile Asp Gly Tyr Val Lys Cys Gly Leu Ile Val Ser Ala Arg Glu
            195                 200                 205

Leu Phe Asp Leu Met Pro Met Glu Met Lys Asn Leu Ile Ser Trp Asn
210                 215                 220

Ser Met Ile Ser Gly Tyr Ala Gln Thr Ser Asp Gly Val Asp Ile Ala
225                 230                 235                 240

Ser Lys Leu Phe Ala Asp Met Pro Glu Lys Asp Leu Ile Ser Trp Asn
                245                 250                 255

Ser Met Ile Asp Gly Tyr Val Lys His Gly Arg Ile Glu Asp Ala Lys
            260                 265                 270

Gly Leu Phe Asp Val Met Pro Arg Arg Asp Val Val Thr Trp Ala Thr
            275                 280                 285

Met Ile Asp Gly Tyr Ala Lys Leu Gly Phe Val His His Ala Lys Thr
            290                 295                 300

Leu Phe Asp Gln Met Pro His Arg Asp Val Val Ala Tyr Asn Ser Met
305                 310                 315                 320

Met Ala Gly Tyr Val Gln Asn Lys Tyr His Met Glu Ala Leu Glu Ile
                325                 330                 335

Phe Ser Asp Met Glu Lys Glu Ser His Leu Leu Pro Asp Thr Thr
            340                 345                 350

Leu Val Ile Val Leu Pro Ala Ile Ala Gln Leu Gly Arg Leu Ser Lys
            355                 360                 365

Ala Ile Asp Met His Leu Tyr Ile Val Glu Lys Gln Phe Tyr Leu Gly
370                 375                 380

Gly Lys Leu Gly Val Ala Leu Ile Asp Met Tyr Ser Lys Cys Gly Ser
385                 390                 395                 400

Ile Gln His Ala Met Leu Val Phe Glu Gly Ile Glu Asn Lys Ser Ile
                405                 410                 415

Asp His Trp Asn Ala Met Ile Gly Gly Leu Ala Ile His Gly Leu Gly
            420                 425                 430

Glu Ser Ala Phe Asp Met Leu Leu Gln Ile Glu Arg Leu Ser Leu Lys
            435                 440                 445

Pro Asp Asp Ile Thr Phe Val Gly Val Leu Asn Ala Cys Ser His Ser
450                 455                 460

Gly Leu Val Lys Glu Gly Leu Leu Cys Phe Glu Leu Met Arg Arg Lys
465                 470                 475                 480

His Lys Ile Glu Pro Arg Leu Gln His Tyr Gly Cys Met Val Asp Ile
                485                 490                 495
```

```
Leu Ser Arg Ser Gly Ser Ile Glu Leu Ala Lys Asn Leu Ile Glu Glu
            500                 505                 510

Met Pro Val Glu Pro Asn Asp Val Ile Trp Arg Thr Phe Leu Thr Ala
            515                 520                 525

Cys Ser His His Lys Glu Phe Glu Thr Gly Glu Leu Val Ala Lys His
            530                 535                 540

Leu Ile Leu Gln Ala Gly Tyr Asn Pro Ser Ser Tyr Val Leu Leu Ser
545                 550                 555                 560

Asn Met Tyr Ala Ser Phe Gly Met Trp Lys Asp Val Arg Val Arg
            565                 570                 575

Thr Met Met Lys Glu Arg Lys Ile Glu Lys Ile Pro Gly Cys Ser Trp
            580                 585                 590

Ile Glu Leu Asp Gly Arg Val His Glu Phe Phe Val Asp Ser Ile Glu
            595                 600                 605

Val Ser Ser Thr Leu
            610

<210> SEQ ID NO 7
<211> LENGTH: 684
<212> TYPE: PRT
<213> ORGANISM: Arabidopsis thaliana

<400> SEQUENCE: 7

Met Ser Leu Leu Ser Ala Asp Ala Leu Gly Leu Leu Leu Lys Asn Ala
1               5                   10                  15

Ile Ser Ala Ser Ser Met Arg Leu Gly Arg Val Val His Ala Arg Ile
            20                  25                  30

Val Lys Thr Leu Asp Ser Pro Pro Pro Phe Leu Ala Asn Tyr Leu
            35                  40                  45

Ile Asn Met Tyr Ser Lys Leu Asp His Pro Glu Ser Ala Arg Leu Val
        50                  55                  60

Leu Arg Leu Thr Pro Ala Arg Asn Val Val Ser Trp Thr Ser Leu Ile
65                  70                  75                  80

Ser Gly Leu Ala Gln Asn Gly His Phe Ser Thr Ala Leu Val Glu Phe
                85                  90                  95

Phe Glu Met Arg Arg Glu Gly Val Val Pro Asn Asp Phe Thr Phe Pro
            100                 105                 110

Cys Ala Phe Lys Ala Val Ala Ser Leu Arg Leu Pro Val Thr Gly Lys
            115                 120                 125

Gln Ile His Ala Leu Ala Val Lys Cys Gly Arg Ile Leu Asp Val Phe
        130                 135                 140

Val Gly Cys Ser Ala Phe Asp Met Tyr Cys Lys Thr Arg Leu Arg Asp
145                 150                 155                 160

Asp Ala Arg Lys Leu Phe Asp Glu Ile Pro Glu Arg Asn Leu Glu Thr
                165                 170                 175

Trp Asn Ala Phe Ile Ser Asn Ser Val Thr Asp Gly Arg Pro Arg Glu
            180                 185                 190

Ala Ile Glu Ala Phe Ile Glu Phe Arg Arg Ile Asp Gly His Pro Asn
        195                 200                 205

Ser Ile Thr Phe Cys Ala Phe Leu Asn Ala Cys Ser Asp Trp Leu His
        210                 215                 220

Leu Asn Leu Gly Met Gln Leu His Gly Leu Val Leu Arg Ser Gly Phe
225                 230                 235                 240

Asp Thr Asp Val Ser Val Cys Asn Gly Leu Ile Asp Phe Tyr Gly Lys
                245                 250                 255
```

-continued

Cys Lys Gln Ile Arg Ser Ser Glu Ile Ile Phe Thr Glu Met Gly Thr
            260                 265                 270

Lys Asn Ala Val Ser Trp Cys Ser Leu Val Ala Ala Tyr Val Gln Asn
            275                 280                 285

His Glu Asp Glu Lys Ala Ser Val Leu Tyr Leu Arg Ser Arg Lys Asp
            290                 295                 300

Ile Val Glu Thr Ser Asp Phe Met Ile Ser Ser Val Leu Ser Ala Cys
305                 310                 315                 320

Ala Gly Met Ala Gly Leu Glu Leu Gly Arg Ser Ile His Ala His Ala
                325                 330                 335

Val Lys Ala Cys Val Glu Arg Thr Ile Phe Val Gly Ser Ala Leu Val
            340                 345                 350

Asp Met Tyr Gly Lys Cys Gly Cys Ile Glu Asp Ser Glu Gln Ala Phe
            355                 360                 365

Asp Glu Met Pro Glu Lys Asn Leu Val Thr Arg Asn Ser Leu Ile Gly
            370                 375                 380

Gly Tyr Ala His Gln Gly Gln Val Asp Met Ala Leu Ala Leu Phe Glu
385                 390                 395                 400

Glu Met Ala Pro Arg Gly Cys Gly Pro Thr Pro Asn Tyr Met Thr Phe
                405                 410                 415

Val Ser Leu Leu Ser Ala Cys Ser Arg Ala Gly Ala Val Glu Asn Gly
            420                 425                 430

Met Lys Ile Phe Asp Ser Met Arg Ser Thr Tyr Gly Ile Glu Pro Gly
            435                 440                 445

Ala Glu His Tyr Ser Cys Ile Val Asp Met Leu Gly Arg Ala Gly Met
    450                 455                 460

Val Glu Arg Ala Tyr Glu Phe Ile Lys Lys Met Pro Ile Gln Pro Thr
465                 470                 475                 480

Ile Ser Val Trp Gly Ala Leu Gln Asn Ala Cys Arg Met His Gly Lys
                485                 490                 495

Pro Gln Leu Gly Leu Leu Ala Ala Glu Asn Leu Phe Lys Leu Asp Pro
            500                 505                 510

Lys Asp Ser Gly Asn His Val Leu Leu Ser Asn Thr Phe Ala Ala Ala
            515                 520                 525

Gly Arg Trp Ala Glu Ala Asn Thr Val Arg Glu Glu Leu Lys Gly Val
            530                 535                 540

Gly Ile Lys Lys Gly Ala Gly Tyr Ser Trp Ile Thr Val Lys Asn Gln
545                 550                 555                 560

Val His Ala Phe Gln Ala Lys Asp Arg Ser His Ile Leu Asn Lys Glu
                565                 570                 575

Ile Gln Thr Thr Leu Ala Lys Leu Arg Asn Glu Met Glu Ala Ala Gly
            580                 585                 590

Tyr Lys Pro Asp Leu Lys Leu Ser Leu Tyr Asp Leu Glu Glu Glu Glu
            595                 600                 605

Lys Ala Ala Glu Val Ser His Ser Glu Lys Leu Ala Leu Ala Phe
            610                 615                 620

Gly Leu Leu Ser Leu Pro Leu Ser Val Pro Ile Arg Ile Thr Lys Asn
625                 630                 635                 640

Leu Arg Ile Cys Gly Asp Cys His Ser Phe Phe Lys Phe Val Ser Gly
                645                 650                 655

Ser Val Lys Arg Glu Ile Ile Val Arg Asp Asn Asn Arg Phe His Arg
            660                 665                 670

```
Phe Lys Asp Gly Ile Cys Ser Cys Lys Asp Tyr Trp
            675                 680

<210> SEQ ID NO 8
<211> LENGTH: 646
<212> TYPE: PRT
<213> ORGANISM: Arabidopsis thaliana

<400> SEQUENCE: 8

Met Asn Pro Thr Gln Thr Leu Phe Ser Pro Gly Gly Asn Ser Pro Ala
1               5                   10                  15

Ser Ser Pro Ala Ser His Pro Ser Ser Leu Phe Pro Gln Ile Asn Asn
                20                  25                  30

Cys Arg Thr Ile Arg Asp Leu Ser Gln Ile His Ala Val Phe Ile Lys
            35                  40                  45

Ser Gly Gln Met Arg Asp Thr Leu Ala Ala Glu Ile Leu Arg Phe
    50                  55                  60

Cys Ala Thr Ser Asp Leu His His Arg Asp Leu Asp Tyr Ala His Lys
65                  70                  75                  80

Ile Phe Asn Gln Met Pro Gln Arg Asn Cys Phe Ser Trp Asn Thr Ile
                85                  90                  95

Ile Arg Gly Phe Ser Glu Ser Asp Glu Asp Lys Ala Leu Ile Ala Ile
            100                 105                 110

Thr Leu Phe Tyr Glu Met Met Ser Asp Glu Phe Val Glu Pro Asn Arg
        115                 120                 125

Phe Thr Phe Pro Ser Val Leu Lys Ala Cys Ala Lys Thr Gly Lys Ile
    130                 135                 140

Gln Glu Gly Lys Gln Ile His Gly Leu Ala Leu Lys Tyr Gly Phe Gly
145                 150                 155                 160

Gly Asp Glu Phe Val Met Ser Asn Leu Val Arg Met Tyr Val Met Cys
                165                 170                 175

Gly Phe Met Lys Asp Ala Arg Val Leu Phe Tyr Lys Asn Ile Ile Glu
            180                 185                 190

Lys Asp Met Val Val Met Thr Asp Arg Arg Lys Arg Asp Gly Glu Ile
        195                 200                 205

Val Leu Trp Asn Val Met Ile Asp Gly Tyr Met Arg Leu Gly Asp Cys
    210                 215                 220

Lys Ala Ala Arg Met Leu Phe Asp Lys Met Arg Gln Arg Ser Val Val
225                 230                 235                 240

Ser Trp Asn Thr Met Ile Ser Gly Tyr Ser Leu Asn Gly Phe Phe Lys
                245                 250                 255

Asp Ala Val Glu Val Phe Arg Glu Met Lys Lys Gly Asp Ile Arg Pro
            260                 265                 270

Asn Tyr Val Thr Leu Val Ser Val Leu Pro Ala Ile Ser Arg Leu Gly
        275                 280                 285

Ser Leu Glu Leu Gly Glu Trp Leu His Leu Tyr Ala Glu Asp Ser Gly
    290                 295                 300

Ile Arg Ile Asp Asp Val Leu Gly Ser Ala Leu Ile Asp Met Tyr Ser
305                 310                 315                 320

Lys Cys Gly Ile Ile Glu Lys Ala Ile His Val Phe Gly Arg Leu Pro
                325                 330                 335

Arg Glu Asn Val Ile Thr Trp Ser Ala Met Ile Asn Gly Phe Ala Ile
            340                 345                 350

His Gly Gln Ala Gly Asp Ala Ile Asp Cys Phe Cys Lys Met Arg Gln
        355                 360                 365
```

Ala Gly Val Arg Pro Ser Asp Val Ala Tyr Ile Asn Leu Leu Thr Ala
    370                 375                 380

Cys Ser His Gly Gly Leu Val Glu Glu Gly Arg Arg Tyr Phe Ser Gln
385                 390                 395                 400

Met Val Ser Val Asp Gly Leu Glu Pro Arg Ile Glu His Tyr Gly Cys
            405                 410                 415

Met Val Asp Leu Leu Gly Arg Ser Gly Leu Leu Asp Glu Ala Glu Glu
            420                 425                 430

Phe Ile Leu Asn Met Pro Ile Lys Pro Asp Asp Val Ile Trp Lys Ala
            435                 440                 445

Leu Leu Gly Ala Cys Arg Met Gln Gly Asn Val Glu Met Gly Lys Arg
    450                 455                 460

Val Ala Asn Ile Leu Met Asp Met Val Pro His Asp Ser Gly Ala Tyr
465                 470                 475                 480

Val Ala Leu Ser Asn Met Tyr Ala Ser Gln Gly Asn Trp Ser Glu Val
            485                 490                 495

Ser Glu Met Arg Leu Arg Met Lys Glu Lys Asp Ile Arg Lys Asp Pro
            500                 505                 510

Gly Cys Ser Leu Ile Asp Ile Asp Gly Val Leu His Glu Phe Val Val
            515                 520                 525

Glu Asp Asp Ser His Pro Lys Ala Lys Glu Ile Asn Ser Met Leu Val
530                 535                 540

Glu Ile Ser Asp Lys Leu Arg Leu Ala Gly Tyr Arg Pro Ile Thr Thr
545                 550                 555                 560

Gln Val Leu Leu Asn Leu Glu Glu Glu Asp Lys Glu Asn Val Leu His
            565                 570                 575

Tyr His Ser Glu Lys Ile Ala Thr Ala Phe Gly Leu Ile Ser Thr Ser
            580                 585                 590

Pro Gly Lys Pro Ile Arg Ile Val Lys Asn Leu Arg Ile Cys Glu Asp
            595                 600                 605

Cys His Ser Ser Ile Lys Leu Ile Ser Lys Val Tyr Lys Arg Lys Ile
    610                 615                 620

Thr Val Arg Asp Arg Lys Arg Phe His His Phe Gln Asp Gly Ser Cys
625                 630                 635                 640

Ser Cys Met Asp Tyr Trp
            645

<210> SEQ ID NO 9
<211> LENGTH: 588
<212> TYPE: PRT
<213> ORGANISM: Arabidopsis thaliana

<400> SEQUENCE: 9

Met Ala Leu Asn Ser Ser Ala Phe Phe Val Pro Cys His Asn Tyr Asn
1               5                   10                  15

Gln Ile Cys Asp Leu Leu Leu Ser Ala Arg Thr Arg Ser Thr Ile
            20                  25                  30

Lys Gly Leu Gln Leu His Gly Tyr Val Val Lys Ser Gly Leu Ser Leu
        35                  40                  45

Ile Pro Leu Val Ala Asn Leu Ile Asn Phe Tyr Ser Lys Ser Gln
        50                  55                  60

Leu Pro Phe Asp Ser Arg Arg Ala Phe Glu Asp Ser Pro Gln Lys Ser
65                  70                  75                  80

Ser Thr Thr Trp Ser Ser Ile Ile Ser Cys Phe Ala Gln Asn Glu Leu

```
                    85                 90                  95
Pro Trp Met Ser Leu Glu Phe Leu Lys Lys Met Met Ala Gly Asn Leu
                100                 105                110
Arg Pro Asp Asp His Val Leu Pro Ser Ala Thr Lys Ser Cys Ala Ile
                115                 120                125
Leu Ser Arg Cys Asp Ile Gly Arg Ser Val His Cys Leu Ser Met Lys
                130                 135                140
Thr Gly Tyr Asp Ala Asp Val Phe Val Gly Ser Ser Leu Val Asp Met
145                 150                 155                160
Tyr Ala Lys Cys Gly Glu Ile Val Tyr Ala Arg Lys Met Phe Asp Glu
                165                 170                175
Met Pro Gln Arg Asn Val Val Thr Trp Ser Gly Met Met Tyr Gly Tyr
                180                 185                190
Ala Gln Met Gly Glu Asn Glu Glu Ala Leu Trp Leu Phe Lys Glu Ala
                195                 200                205
Leu Phe Glu Asn Leu Ala Val Asn Asp Tyr Ser Phe Ser Ser Val Ile
                210                 215                220
Ser Val Cys Ala Asn Ser Thr Leu Leu Glu Leu Gly Arg Gln Ile His
225                 230                 235                240
Gly Leu Ser Ile Lys Ser Ser Phe Asp Ser Ser Phe Val Gly Ser
                245                 250                255
Ser Leu Val Ser Leu Tyr Ser Lys Cys Gly Val Pro Glu Gly Ala Tyr
                260                 265                270
Gln Val Phe Asn Glu Val Pro Val Lys Asn Leu Gly Ile Trp Asn Ala
                275                 280                285
Met Leu Lys Ala Tyr Ala Gln His Ser His Thr Gln Lys Val Ile Glu
                290                 295                300
Leu Phe Lys Arg Met Lys Leu Ser Gly Met Lys Pro Asn Phe Ile Thr
305                 310                 315                320
Phe Leu Asn Val Leu Asn Ala Cys Ser His Ala Gly Leu Val Asp Glu
                325                 330                335
Gly Arg Tyr Tyr Phe Asp Gln Met Lys Glu Ser Arg Ile Glu Pro Thr
                340                 345                350
Asp Lys His Tyr Ala Ser Leu Val Asp Met Leu Gly Arg Ala Gly Arg
                355                 360                365
Leu Gln Glu Ala Leu Glu Val Ile Thr Asn Met Pro Ile Asp Pro Thr
                370                 375                380
Glu Ser Val Trp Gly Ala Leu Leu Thr Ser Cys Thr Val His Lys Asn
385                 390                 395                400
Thr Glu Leu Ala Ala Phe Ala Ala Asp Lys Val Phe Glu Leu Gly Pro
                405                 410                415
Val Ser Ser Gly Met His Ile Ser Leu Ser Asn Ala Tyr Ala Ala Asp
                420                 425                430
Gly Arg Phe Glu Asp Ala Ala Lys Ala Arg Lys Leu Leu Arg Asp Arg
                435                 440                445
Gly Glu Lys Lys Glu Thr Gly Leu Ser Trp Val Glu Arg Asn Lys
                450                 455                460
Val His Thr Phe Ala Ala Gly Glu Arg His Glu Lys Ser Lys Glu
465                 470                 475                480
Ile Tyr Glu Lys Leu Ala Glu Leu Gly Glu Glu Met Glu Lys Ala Gly
                485                 490                495
Tyr Ile Ala Asp Thr Ser Tyr Val Leu Arg Glu Val Asp Gly Asp Glu
                500                 505                510
```

```
Lys Asn Gln Thr Ile Arg Tyr His Ser Glu Arg Leu Ala Ile Ala Phe
            515                 520                 525

Gly Leu Ile Thr Phe Pro Ala Asp Arg Pro Ile Arg Val Met Lys Asn
        530                 535                 540

Leu Arg Val Cys Gly Asp Cys His Asn Ala Ile Lys Phe Met Ser Val
545                 550                 555                 560

Cys Thr Arg Arg Val Ile Ile Val Arg Asp Asn Asn Arg Phe His Arg
                565                 570                 575

Phe Glu Asp Gly Lys Cys Ser Cys Asn Asp Tyr Trp
            580                 585

<210> SEQ ID NO 10
<211> LENGTH: 659
<212> TYPE: PRT
<213> ORGANISM: Arabidopsis thaliana

<400> SEQUENCE: 10

Met Lys Val Arg Ser Lys Lys Ala Leu Phe Cys Ser Val Ser Arg Leu
1               5                   10                  15

Leu His Thr Glu Arg His Thr Glu Arg Gln Asn Leu Thr Thr Leu Phe
            20                  25                  30

Asn Arg Tyr Val Asp Lys Thr Asp Val Phe Ser Trp Asn Ser Val Ile
        35                  40                  45

Ala Asp Leu Ala Arg Ser Gly Asp Ser Ala Glu Ala Leu Leu Ala Phe
    50                  55                  60

Ser Ser Met Arg Lys Leu Ser Leu Tyr Pro Thr Arg Ser Ser Phe Pro
65                  70                  75                  80

Cys Ala Ile Lys Ala Cys Ser Ser Leu Phe Asp Ile Phe Ser Gly Lys
                85                  90                  95

Gln Thr His Gln Gln Ala Phe Val Phe Gly Tyr Gln Ser Asp Ile Phe
            100                 105                 110

Val Ser Ser Ala Leu Ile Val Met Tyr Ser Thr Cys Gly Lys Leu Glu
        115                 120                 125

Asp Ala Arg Lys Val Phe Asp Glu Ile Pro Lys Arg Asn Ile Val Ser
    130                 135                 140

Trp Thr Ser Met Ile Arg Gly Tyr Asp Leu Asn Gly Asn Ala Leu Asp
145                 150                 155                 160

Ala Val Ser Leu Phe Lys Asp Leu Leu Val Asp Glu Asn Asp Asp Asp
                165                 170                 175

Asp Ala Met Phe Leu Asp Ser Met Gly Leu Val Ser Val Ile Ser Ala
            180                 185                 190

Cys Ser Arg Val Pro Ala Lys Gly Leu Thr Glu Ser Ile His Ser Phe
        195                 200                 205

Val Ile Lys Arg Gly Phe Asp Arg Gly Val Ser Val Gly Asn Thr Leu
    210                 215                 220

Leu Asp Ala Tyr Ala Lys Gly Gly Glu Gly Val Ala Val Ala Arg
225                 230                 235                 240

Lys Ile Phe Asp Gln Ile Val Asp Lys Asp Arg Val Ser Tyr Asn Ser
                245                 250                 255

Ile Met Ser Val Tyr Ala Gln Ser Gly Met Ser Asn Glu Ala Phe Glu
            260                 265                 270

Val Phe Arg Arg Leu Val Lys Asn Lys Val Val Thr Phe Asn Ala Ile
        275                 280                 285

Thr Leu Ser Thr Val Leu Leu Ala Val Ser His Ser Gly Ala Leu Arg
```

290                 295                 300
Ile Gly Lys Cys Ile His Asp Gln Val Ile Arg Met Gly Leu Glu Asp
305                 310                 315                 320

Asp Val Ile Val Gly Thr Ser Ile Ile Asp Met Tyr Cys Lys Cys Gly
                325                 330                 335

Arg Val Glu Thr Ala Arg Lys Ala Phe Asp Arg Met Lys Asn Lys Asn
            340                 345                 350

Val Arg Ser Trp Thr Ala Met Ile Ala Gly Tyr Gly Met His Gly His
        355                 360                 365

Ala Ala Lys Ala Leu Glu Leu Phe Pro Ala Met Ile Asp Ser Gly Val
370                 375                 380

Arg Pro Asn Tyr Ile Thr Phe Val Ser Val Leu Ala Ala Cys Ser His
385                 390                 395                 400

Ala Gly Leu His Val Glu Gly Trp Arg Trp Phe Asn Ala Met Lys Gly
                405                 410                 415

Arg Phe Gly Val Glu Pro Gly Leu Glu His Tyr Gly Cys Met Val Asp
            420                 425                 430

Leu Leu Gly Arg Ala Gly Phe Leu Gln Lys Ala Tyr Asp Leu Ile Gln
        435                 440                 445

Arg Met Lys Met Lys Pro Asp Ser Ile Ile Trp Ser Ser Leu Leu Ala
450                 455                 460

Ala Cys Arg Ile His Lys Asn Val Glu Leu Ala Glu Ile Ser Val Ala
465                 470                 475                 480

Arg Leu Phe Glu Leu Asp Ser Ser Asn Cys Gly Tyr Tyr Met Leu Leu
                485                 490                 495

Ser His Ile Tyr Ala Asp Ala Gly Arg Trp Lys Asp Val Glu Arg Val
            500                 505                 510

Arg Met Ile Met Lys Asn Arg Gly Leu Val Lys Pro Pro Gly Phe Ser
        515                 520                 525

Leu Leu Glu Leu Asn Gly Glu Val His Val Phe Leu Ile Gly Asp Glu
530                 535                 540

Glu His Pro Gln Arg Glu Lys Ile Tyr Glu Phe Leu Ala Glu Leu Asn
545                 550                 555                 560

Arg Lys Leu Leu Glu Ala Gly Tyr Val Ser Asn Thr Ser Ser Val Cys
                565                 570                 575

His Asp Val Asp Glu Glu Lys Glu Met Thr Leu Arg Val His Ser
            580                 585                 590

Glu Lys Leu Ala Ile Ala Phe Gly Ile Met Asn Thr Val Pro Gly Ser
        595                 600                 605

Thr Val Asn Val Val Lys Asn Leu Arg Val Cys Ser Asp Cys His Asn
610                 615                 620

Val Ile Lys Leu Ile Ser Lys Ile Val Asp Arg Glu Phe Val Val Arg
625                 630                 635                 640

Asp Ala Lys Arg Phe His His Phe Lys Asp Gly Gly Cys Ser Cys Gly
                645                 650                 655

Asp Tyr Trp

<210> SEQ ID NO 11
<211> LENGTH: 685
<212> TYPE: PRT
<213> ORGANISM: Arabidopsis thaliana

<400> SEQUENCE: 11

Met Ile Lys Leu Ile Arg Phe Phe Arg Ser Arg Arg Cys Trp Val Ile

```
  1               5                   10                  15
Ser Leu Gln Ala Arg Cys Phe Ser Ala Pro Ser Arg Thr His Phe Asp
                 20                  25                  30
Phe Ser Gly Glu Ser Ser Asp Thr Glu Arg Ala Leu Val Ser Ala Leu
                 35                  40                  45
Gly Ser Cys Ala Ser Ser Asn Asp Val Thr Cys Gly Arg Gln Ile His
                 50                  55                  60
Cys Arg Val Leu Lys Ser Gly Leu Asp Ser Asn Gly Tyr Ile Cys Asn
 65                  70                  75                  80
Ser Val Leu Asn Met Tyr Ala Lys Cys Arg Leu Leu Ala Asp Ala Glu
                 85                  90                  95
Ser Val Phe Arg Asp His Ala Lys Leu Asp Ser Ala Ser Phe Asn Ile
                100                 105                 110
Met Val Asp Gly Tyr Val Arg Ser Arg Leu Trp Asp Ala Leu Lys
                115                 120                 125
Leu Phe Asp Val Met Pro Glu Arg Ser Cys Val Ser Tyr Thr Thr Leu
130                 135                 140
Ile Lys Gly Tyr Ala Gln Asn Asn Gln Trp Ser Glu Ala Met Glu Leu
145                 150                 155                 160
Phe Arg Glu Met Arg Asn Leu Gly Ile Met Leu Asn Glu Val Thr Leu
                165                 170                 175
Ala Thr Val Ile Ser Ala Cys Ser His Leu Gly Gly Ile Trp Asp Cys
                180                 185                 190
Arg Met Leu Gln Ser Leu Ala Ile Lys Leu Lys Leu Glu Gly Arg Val
                195                 200                 205
Phe Val Ser Thr Asn Leu Leu His Met Tyr Cys Leu Cys Leu
210                 215                 220
Lys Asp Ala Arg Lys Leu Phe Asp Glu Met Pro Glu Arg Asn Leu Val
225                 230                 235                 240
Thr Trp Asn Val Met Leu Asn Gly Tyr Ser Lys Ala Gly Leu Ile Glu
                245                 250                 255
Gln Ala Glu Glu Leu Phe Asp Gln Ile Thr Glu Lys Asp Ile Val Ser
                260                 265                 270
Trp Gly Thr Met Ile Asp Gly Cys Leu Arg Lys Asn Gln Leu Asp Glu
                275                 280                 285
Ala Leu Val Tyr Tyr Thr Glu Met Leu Arg Cys Gly Met Lys Pro Ser
                290                 295                 300
Glu Val Met Met Val Asp Leu Leu Ser Ala Ser Ala Arg Ser Val Gly
305                 310                 315                 320
Ser Ser Lys Gly Leu Gln Leu His Gly Thr Ile Val Lys Arg Gly Phe
                325                 330                 335
Asp Cys Tyr Asp Phe Leu Gln Ala Thr Ile Ile His Phe Tyr Ala Val
                340                 345                 350
Ser Asn Asp Ile Lys Leu Ala Leu Gln Gln Phe Glu Ala Ser Val Lys
                355                 360                 365
Asp His Ile Ala Ser Arg Asn Ala Leu Ile Ala Gly Phe Val Lys Asn
                370                 375                 380
Gly Met Val Glu Gln Ala Arg Glu Val Phe Asp Gln Thr His Asp Lys
385                 390                 395                 400
Asp Ile Phe Ser Trp Asn Ala Met Ile Ser Gly Tyr Ala Gln Ser Leu
                405                 410                 415
Ser Pro Gln Leu Ala Leu His Leu Phe Arg Glu Met Ile Ser Ser Ser
                420                 425                 430
```

```
Gln Val Lys Pro Asp Ala Ile Thr Met Val Ser Val Phe Ser Ala Ile
            435                 440                 445

Ser Ser Leu Gly Ser Leu Glu Glu Gly Lys Arg Ala His Asp Tyr Leu
450                 455                 460

Asn Phe Ser Thr Ile Pro Pro Asn Asp Asn Leu Thr Ala Ala Ile Ile
465                 470                 475                 480

Asp Met Tyr Ala Lys Cys Gly Ser Ile Glu Thr Ala Leu Asn Ile Phe
            485                 490                 495

His Gln Thr Lys Asn Ile Ser Ser Thr Ile Ser Pro Trp Asn Ala
            500                 505                 510

Ile Ile Cys Gly Ser Ala Thr His Gly His Ala Lys Leu Ala Leu Asp
            515                 520                 525

Leu Tyr Ser Asp Leu Gln Ser Leu Pro Ile Lys Pro Asn Ser Ile Thr
530                 535                 540

Phe Val Gly Val Leu Ser Ala Cys Cys His Ala Gly Leu Val Glu Leu
545                 550                 555                 560

Gly Lys Thr Tyr Phe Glu Ser Met Lys Ser Asp His Gly Ile Glu Pro
                565                 570                 575

Asp Ile Lys His Tyr Gly Cys Met Val Asp Leu Leu Gly Lys Ala Gly
            580                 585                 590

Arg Leu Glu Glu Ala Lys Glu Met Ile Lys Met Pro Val Lys Ala
595                 600                 605

Asp Val Met Ile Trp Gly Met Leu Leu Ser Ala Ser Arg Thr His Gly
            610                 615                 620

Asn Val Glu Ile Ala Glu Leu Ala Ala Thr Glu Leu Ala Ala Ile Asp
625                 630                 635                 640

Pro Ser His Gly Gly Cys Lys Val Met Leu Ser Asn Val Tyr Ala Asp
                645                 650                 655

Ala Gly Arg Trp Glu Asp Val Ala Leu Val Arg Glu Glu Met Arg Thr
            660                 665                 670

Arg Asp Val Glu Trp Ser Arg Ala Phe Ser Gly Val Val
            675                 680                 685

<210> SEQ ID NO 12
<211> LENGTH: 565
<212> TYPE: PRT
<213> ORGANISM: Arabidopsis thaliana

<400> SEQUENCE: 12

Met Met Lys Lys His Tyr Lys Pro Ile Leu Ser Gln Leu Glu Asn Cys
1               5                   10                  15

Arg Ser Leu Val Glu Leu Asn Gln Leu His Gly Leu Met Ile Lys Ser
            20                  25                  30

Ser Val Ile Arg Asn Val Ile Pro Leu Ser Arg Leu Ile Asp Phe Cys
        35                  40                  45

Thr Thr Cys Pro Glu Thr Met Asn Leu Ser Tyr Ala Arg Ser Val Phe
    50                  55                  60

Glu Ser Ile Asp Cys Pro Ser Val Tyr Ile Trp Asn Ser Met Ile Arg
65                  70                  75                  80

Gly Tyr Ser Asn Ser Pro Asn Pro Asp Lys Ala Leu Ile Phe Tyr Gln
                85                  90                  95

Glu Met Leu Arg Lys Gly Tyr Ser Pro Asp Tyr Phe Thr Phe Pro Tyr
            100                 105                 110

Val Leu Lys Ala Cys Ser Gly Leu Arg Asp Ile Gln Phe Gly Ser Cys
```

-continued

```
            115                 120                 125
Val His Gly Phe Val Lys Thr Gly Phe Glu Val Asn Met Tyr Val
            130                 135                 140

Ser Thr Cys Leu Leu His Met Tyr Met Cys Cys Gly Glu Val Asn Tyr
145                 150                 155                 160

Gly Leu Arg Val Phe Glu Asp Ile Pro Gln Trp Asn Val Val Ala Trp
                    165                 170                 175

Gly Ser Leu Ile Ser Gly Phe Val Asn Asn Asn Arg Phe Ser Asp Ala
                    180                 185                 190

Ile Glu Ala Phe Arg Glu Met Gln Ser Asn Gly Val Lys Ala Asn Glu
                    195                 200                 205

Thr Ile Met Val Asp Leu Leu Val Ala Cys Gly Arg Cys Lys Asp Ile
            210                 215                 220

Val Thr Gly Lys Trp Phe His Gly Phe Leu Gln Gly Leu Gly Phe Asp
225                 230                 235                 240

Pro Tyr Phe Gln Ser Lys Val Gly Phe Asn Val Ile Leu Ala Thr Ser
                    245                 250                 255

Leu Ile Asp Met Tyr Ala Lys Cys Gly Asp Leu Arg Thr Ala Arg Tyr
                    260                 265                 270

Leu Phe Asp Gly Met Pro Glu Arg Thr Leu Val Ser Trp Asn Ser Ile
                    275                 280                 285

Ile Thr Gly Tyr Ser Gln Asn Gly Asp Ala Glu Glu Ala Leu Cys Met
            290                 295                 300

Phe Leu Asp Met Leu Asp Leu Gly Ile Ala Pro Asp Lys Val Thr Phe
305                 310                 315                 320

Leu Ser Val Ile Arg Ala Ser Met Ile Gln Gly Cys Ser Gln Leu Gly
                    325                 330                 335

Gln Ser Ile His Ala Tyr Val Ser Lys Thr Gly Phe Val Lys Asp Ala
                    340                 345                 350

Ala Ile Val Cys Ala Leu Val Asn Met Tyr Ala Lys Thr Gly Asp Ala
                    355                 360                 365

Glu Ser Ala Lys Lys Ala Phe Glu Asp Leu Glu Lys Lys Asp Thr Ile
            370                 375                 380

Ala Trp Thr Val Val Ile Ile Gly Leu Ala Ser His Gly His Gly Asn
385                 390                 395                 400

Glu Ala Leu Ser Ile Phe Gln Arg Met Gln Lys Gly Asn Ala Thr
                    405                 410                 415

Pro Asp Gly Ile Thr Tyr Leu Gly Val Leu Tyr Ala Cys Ser His Ile
                    420                 425                 430

Gly Leu Val Glu Glu Gly Gln Arg Tyr Phe Ala Glu Met Arg Asp Leu
                    435                 440                 445

His Gly Leu Glu Pro Thr Val Glu His Tyr Gly Cys Met Val Asp Ile
            450                 455                 460

Leu Ser Arg Ala Gly Arg Phe Glu Glu Ala Glu Arg Leu Val Lys Thr
465                 470                 475                 480

Met Pro Val Lys Pro Asn Val Asn Ile Trp Gly Ala Leu Leu Asn Gly
                    485                 490                 495

Cys Asp Ile His Glu Asn Leu Glu Leu Thr Asp Arg Ile Arg Ser Met
                    500                 505                 510

Val Ala Glu Pro Glu Glu Leu Gly Ser Gly Ile Tyr Val Leu Leu Ser
                    515                 520                 525

Asn Ile Tyr Ala Lys Ala Gly Arg Trp Ala Asp Val Lys Leu Ile Arg
            530                 535                 540
```

Glu Ser Met Lys Ser Lys Arg Val Asp Lys Val Leu Gly His Ser Ser
545                 550                 555                 560

Val Glu Thr Met Phe
                565

<210> SEQ ID NO 13
<211> LENGTH: 472
<212> TYPE: PRT
<213> ORGANISM: Arabidopsis thaliana

<400> SEQUENCE: 13

Met Ser Ser Val Phe Pro Gly Pro Arg Phe Leu Ser Leu Leu Gln Gln
1               5                   10                  15

Asn Ser Lys Thr Leu Ile Gln Ala Lys Gln Ile His Ala Gln Leu Val
            20                  25                  30

Ile Asn Gly Cys His Asp Asn Ser Leu Phe Gly Lys Leu Ile Gly His
        35                  40                  45

Tyr Cys Ser Lys Pro Ser Thr Glu Ser Ser Lys Leu Ala His Leu
    50                  55                  60

Leu Val Phe Pro Arg Phe Gly His Pro Asp Lys Phe Leu Phe Asn Thr
65                  70                  75                  80

Leu Leu Lys Cys Ser Lys Pro Glu Asp Ser Ile Arg Ile Phe Ala Asn
                85                  90                  95

Tyr Ala Ser Lys Ser Ser Leu Leu Tyr Leu Asn Glu Arg Thr Phe Val
            100                 105                 110

Phe Val Leu Gly Ala Cys Ala Arg Ser Ala Ser Ser Ala Leu Arg
            115                 120                 125

Val Gly Arg Ile Val His Gly Met Val Lys Lys Leu Gly Phe Leu Tyr
130                 135                 140

Glu Ser Glu Leu Ile Gly Thr Thr Leu Leu His Phe Tyr Ala Lys Asn
145                 150                 155                 160

Gly Asp Leu Arg Tyr Ala Arg Lys Val Phe Asp Glu Met Pro Glu Arg
                165                 170                 175

Thr Ser Val Thr Trp Asn Ala Met Ile Gly Gly Tyr Cys Ser His Lys
            180                 185                 190

Asp Lys Gly Asn His Asn Ala Arg Lys Ala Met Val Leu Phe Arg Arg
        195                 200                 205

Phe Ser Cys Cys Gly Ser Gly Val Arg Pro Thr Asp Thr Thr Met Val
210                 215                 220

Cys Val Leu Ser Ala Ile Ser Gln Thr Gly Leu Leu Glu Ile Gly Ser
225                 230                 235                 240

Leu Val His Gly Tyr Ile Glu Lys Leu Gly Phe Thr Pro Glu Val Asp
                245                 250                 255

Val Phe Ile Gly Thr Ala Leu Val Asp Met Tyr Ser Lys Cys Gly Cys
            260                 265                 270

Leu Asn Asn Ala Phe Ser Val Phe Glu Leu Met Lys Val Lys Asn Val
        275                 280                 285

Phe Thr Trp Thr Ser Met Ala Thr Gly Leu Ala Leu Asn Gly Arg Gly
    290                 295                 300

Asn Glu Thr Pro Asn Leu Leu Asn Arg Met Ala Glu Ser Gly Ile Lys
305                 310                 315                 320

Pro Asn Glu Ile Thr Phe Thr Ser Leu Leu Ser Ala Tyr Arg His Ile
                325                 330                 335

Gly Leu Val Glu Glu Gly Ile Glu Leu Phe Lys Ser Met Lys Thr Arg

```
                340             345             350
Phe Gly Val Thr Pro Val Ile Glu His Tyr Gly Cys Ile Val Asp Leu
            355                 360                 365
Leu Gly Lys Ala Gly Arg Ile Gln Glu Ala Tyr Gln Phe Ile Leu Ala
        370                 375                 380
Met Pro Ile Lys Pro Asp Ala Ile Leu Leu Arg Ser Leu Cys Asn Ala
385                 390                 395                 400
Cys Ser Ile Tyr Gly Glu Thr Val Met Gly Glu Ile Gly Lys Ala
                405                 410                 415
Leu Leu Glu Ile Glu Arg Glu Asp Glu Lys Leu Ser Gly Ser Glu Cys
            420                 425                 430
Glu Asp Tyr Val Ala Leu Ser Asn Val Leu Ala His Lys Gly Lys Trp
        435                 440                 445
Val Glu Val Glu Lys Leu Arg Lys Glu Met Lys Glu Arg Arg Ile Lys
            450                 455                 460
Thr Arg Pro Gly Tyr Ser Phe Val
465                 470

<210> SEQ ID NO 14
<211> LENGTH: 534
<212> TYPE: PRT
<213> ORGANISM: Arabidopsis thaliana

<400> SEQUENCE: 14

Met Ala Phe His Gly Ile Arg Glu Val Glu Asn Tyr Phe Ile Pro Phe
1               5                   10                  15
Leu Gln Arg Val Lys Ser Arg Asn Glu Trp Lys Lys Ile Asn Ala Ser
            20                  25                  30
Ile Ile Ile His Gly Leu Ser Gln Ser Ser Phe Met Val Thr Lys Met
        35                  40                  45
Val Asp Phe Cys Asp Lys Ile Glu Asp Met Asp Tyr Ala Thr Arg Leu
50                  55                  60
Phe Asn Gln Val Ser Asn Pro Asn Val Phe Leu Tyr Asn Ser Ile Ile
65                  70                  75                  80
Arg Ala Tyr Thr His Asn Ser Leu Tyr Cys Asp Val Ile Arg Ile Tyr
                85                  90                  95
Lys Gln Leu Leu Arg Lys Ser Phe Glu Leu Pro Asp Arg Phe Thr Phe
            100                 105                 110
Pro Phe Met Phe Lys Ser Cys Ala Ser Leu Gly Ser Cys Tyr Leu Gly
        115                 120                 125
Lys Gln Val His Gly His Leu Cys Lys Phe Gly Pro Arg Phe His Val
    130                 135                 140
Val Thr Glu Asn Ala Leu Ile Asp Met Tyr Met Lys Phe Asp Asp Leu
145                 150                 155                 160
Val Asp Ala His Lys Val Phe Asp Glu Met Tyr Glu Arg Asp Val Ile
                165                 170                 175
Ser Trp Asn Ser Leu Leu Ser Gly Tyr Ala Arg Leu Gly Gln Met Lys
            180                 185                 190
Lys Ala Lys Gly Leu Phe His Leu Met Leu Asp Lys Thr Ile Val Ser
        195                 200                 205
Trp Thr Ala Met Ile Ser Gly Tyr Thr Gly Ile Gly Cys Tyr Val Glu
    210                 215                 220
Ala Met Asp Phe Phe Arg Glu Met Gln Leu Ala Gly Ile Glu Pro Asp
225                 230                 235                 240
```

-continued

```
Glu Ile Ser Leu Ile Ser Val Leu Pro Ser Cys Ala Gln Leu Gly Ser
            245                 250                 255

Leu Glu Leu Gly Lys Trp Ile His Leu Tyr Ala Glu Arg Arg Gly Phe
        260                 265                 270

Leu Lys Gln Thr Gly Val Cys Asn Ala Leu Ile Glu Met Tyr Ser Lys
    275                 280                 285

Cys Gly Val Ile Ser Gln Ala Ile Gln Leu Phe Gly Gln Met Glu Gly
290                 295                 300

Lys Asp Val Ile Ser Trp Ser Thr Met Ile Ser Gly Tyr Ala Tyr His
305                 310                 315                 320

Gly Asn Ala His Gly Ala Ile Glu Thr Phe Asn Glu Met Gln Arg Ala
                325                 330                 335

Lys Val Lys Pro Asn Gly Ile Thr Phe Leu Gly Leu Leu Ser Ala Cys
            340                 345                 350

Ser His Val Gly Met Trp Gln Glu Gly Leu Arg Tyr Phe Asp Met Met
        355                 360                 365

Arg Gln Asp Tyr Gln Ile Glu Pro Lys Ile Glu His Tyr Gly Cys Leu
    370                 375                 380

Ile Asp Val Leu Ala Arg Ala Gly Lys Leu Glu Arg Ala Val Glu Ile
385                 390                 395                 400

Thr Lys Thr Met Pro Met Lys Pro Asp Ser Lys Ile Trp Gly Ser Leu
                405                 410                 415

Leu Ser Ser Cys Arg Thr Pro Gly Asn Leu Asp Val Ala Leu Val Ala
            420                 425                 430

Met Asp His Leu Val Glu Leu Glu Pro Glu Asp Met Gly Asn Tyr Val
        435                 440                 445

Leu Leu Ala Asn Ile Tyr Ala Asp Leu Gly Lys Trp Glu Asp Val Ser
    450                 455                 460

Arg Leu Arg Lys Met Ile Arg Asn Glu Asn Met Lys Lys Thr Pro Gly
465                 470                 475                 480

Gly Ser Leu Ile Glu Val Asn Asn Ile Val Gln Glu Phe Val Ser Gly
                485                 490                 495

Asp Asn Ser Lys Pro Phe Trp Thr Glu Ile Ser Ile Val Leu Gln Leu
            500                 505                 510

Phe Thr Ser His Gln Asp Gln Asp Val Ile Thr Asn Asn Asn Ala Leu
        515                 520                 525

Ala Phe Ile Gly Ile Val
    530
```

<210> SEQ ID NO 15
<211> LENGTH: 694
<212> TYPE: PRT
<213> ORGANISM: Arabidopsis thaliana

<400> SEQUENCE: 15

```
Met Ser Glu Ala Ser Cys Leu Ala Ser Pro Leu Leu Tyr Thr Asn Ser
1               5                   10                  15

Gly Ile His Ser Asp Ser Phe Tyr Ala Ser Leu Ile Asp Ser Ala Thr
            20                  25                  30

His Lys Ala Gln Leu Lys Gln Ile His Ala Arg Leu Leu Val Leu Gly
        35                  40                  45

Leu Gln Phe Ser Gly Phe Leu Ile Thr Lys Leu Ile His Ala Ser Ser
    50                  55                  60

Ser Phe Gly Asp Ile Thr Phe Ala Arg Gln Val Phe Asp Leu Pro
65                  70                  75                  80
```

```
Arg Pro Gln Ile Phe Pro Trp Asn Ala Ile Ile Arg Gly Tyr Ser Arg
            85                  90                  95

Asn Asn His Phe Gln Asp Ala Leu Leu Met Tyr Ser Asn Met Gln Leu
            100                 105                 110

Ala Arg Val Ser Pro Asp Ser Phe Thr Phe Pro His Leu Leu Lys Ala
            115                 120                 125

Cys Ser Gly Leu Ser His Leu Gln Met Gly Arg Phe Val His Ala Gln
            130                 135                 140

Val Phe Arg Leu Gly Phe Asp Ala Asp Val Phe Val Gln Asn Gly Leu
145                 150                 155                 160

Ile Ala Leu Tyr Ala Lys Cys Arg Arg Leu Gly Ser Ala Arg Thr Val
            165                 170                 175

Phe Glu Gly Leu Pro Leu Pro Glu Arg Thr Ile Val Ser Trp Thr Ala
            180                 185                 190

Ile Val Ser Ala Tyr Ala Gln Asn Gly Glu Pro Met Glu Ala Leu Glu
            195                 200                 205

Ile Phe Ser Gln Met Arg Lys Met Asp Val Lys Pro Asp Trp Val Ala
            210                 215                 220

Leu Val Ser Val Leu Asn Ala Phe Thr Cys Leu Gln Asp Leu Lys Gln
225                 230                 235                 240

Gly Arg Ser Ile His Ala Ser Val Val Lys Met Gly Leu Glu Ile Glu
            245                 250                 255

Pro Asp Leu Leu Ile Ser Leu Asn Thr Met Tyr Ala Lys Cys Gly Gln
            260                 265                 270

Val Ala Thr Ala Lys Ile Leu Phe Asp Lys Met Lys Ser Pro Asn Leu
            275                 280                 285

Ile Leu Trp Asn Ala Met Ile Ser Gly Tyr Ala Lys Asn Gly Tyr Ala
            290                 295                 300

Arg Glu Ala Ile Asp Met Phe His Glu Met Ile Asn Lys Asp Val Arg
305                 310                 315                 320

Pro Asp Thr Ile Ser Ile Thr Ser Ala Ile Ser Ala Cys Ala Gln Val
            325                 330                 335

Gly Ser Leu Glu Gln Ala Arg Ser Met Tyr Glu Tyr Val Gly Arg Ser
            340                 345                 350

Asp Tyr Arg Asp Asp Val Phe Ile Ser Ser Ala Leu Ile Asp Met Phe
            355                 360                 365

Ala Lys Cys Gly Ser Val Glu Gly Ala Arg Leu Val Phe Asp Arg Thr
            370                 375                 380

Leu Asp Arg Asp Val Val Val Trp Ser Ala Met Ile Val Gly Tyr Gly
385                 390                 395                 400

Leu His Gly Arg Ala Arg Glu Ala Ile Ser Leu Tyr Arg Ala Met Glu
            405                 410                 415

Arg Gly Gly Val His Pro Asn Asp Val Thr Phe Leu Gly Leu Leu Met
            420                 425                 430

Ala Cys Asn His Ser Gly Met Val Arg Glu Gly Trp Trp Phe Phe Asn
            435                 440                 445

Arg Met Ala Asp His Lys Ile Asn Pro Gln Gln His Tyr Ala Cys
            450                 455                 460

Val Ile Asp Leu Leu Gly Arg Ala Gly His Leu Asp Gln Ala Tyr Glu
465                 470                 475                 480

Val Ile Lys Cys Met Pro Val Gln Pro Gly Val Thr Val Trp Gly Ala
            485                 490                 495
```

```
Leu Leu Ser Ala Cys Lys Lys His Arg His Val Glu Leu Gly Glu Tyr
            500                 505                 510

Ala Ala Gln Gln Leu Phe Ser Ile Asp Pro Ser Asn Thr Gly His Tyr
        515                 520                 525

Val Gln Leu Ser Asn Leu Tyr Ala Ala Ala Arg Leu Trp Asp Arg Val
    530                 535                 540

Ala Glu Val Arg Val Arg Met Lys Glu Lys Gly Leu Asn Lys Asp Val
545                 550                 555                 560

Gly Cys Ser Trp Val Glu Val Arg Gly Arg Leu Glu Ala Phe Arg Val
                565                 570                 575

Gly Asp Lys Ser His Pro Arg Tyr Glu Glu Ile Glu Arg Gln Val Glu
            580                 585                 590

Trp Ile Glu Ser Arg Leu Lys Glu Gly Gly Phe Val Ala Asn Lys Asp
        595                 600                 605

Ala Ser Leu His Asp Leu Asn Asp Glu Glu Ala Glu Glu Thr Leu Cys
    610                 615                 620

Ser His Ser Glu Arg Ile Ala Ile Ala Tyr Gly Leu Ile Ser Thr Pro
625                 630                 635                 640

Gln Gly Thr Pro Leu Arg Ile Thr Lys Asn Leu Arg Ala Cys Val Asn
                645                 650                 655

Cys His Ala Ala Thr Lys Leu Ile Ser Lys Leu Val Asp Arg Glu Ile
            660                 665                 670

Val Val Arg Asp Thr Asn Arg Phe His His Phe Lys Asp Gly Val Cys
        675                 680                 685

Ser Cys Gly Asp Tyr Trp
    690

<210> SEQ ID NO 16
<211> LENGTH: 656
<212> TYPE: PRT
<213> ORGANISM: Arabidopsis thaliana

<400> SEQUENCE: 16

Met Ile Arg Ser Arg Ser Val Leu Leu Ile Phe Arg Lys Val Leu Tyr
1               5                   10                  15

Gln Ser Ser Cys Leu Lys Cys Leu Leu Cys Ala Asn Ser Phe Ser Thr
            20                  25                  30

Ser Val Ser Ser Leu Gly Phe Arg Ala Thr Asn Lys Glu Leu Asn
        35                  40                  45

Gln Met Ile Arg Ser Gly Tyr Ile Ala Glu Ala Arg Asp Ile Phe Glu
    50                  55                  60

Lys Leu Glu Ala Arg Asn Thr Val Thr Trp Asn Thr Met Ile Ser Gly
65                  70                  75                  80

Tyr Val Lys Arg Arg Glu Met Asn Gln Ala Arg Lys Leu Phe Asp Val
                85                  90                  95

Met Pro Lys Arg Asp Val Val Thr Trp Asn Thr Met Ile Ser Gly Tyr
            100                 105                 110

Val Ser Cys Gly Gly Ile Arg Phe Leu Glu Glu Ala Arg Lys Leu Phe
        115                 120                 125

Asp Glu Met Pro Ser Arg Asp Ser Phe Ser Trp Asn Thr Met Ile Ser
    130                 135                 140

Gly Tyr Ala Lys Asn Arg Arg Ile Gly Glu Ala Leu Leu Leu Phe Glu
145                 150                 155                 160

Lys Met Pro Glu Arg Asn Ala Val Ser Trp Ser Ala Met Ile Thr Gly
                165                 170                 175
```

-continued

Phe Cys Gln Asn Gly Glu Val Asp Ser Ala Val Val Leu Phe Arg Lys
            180                 185                 190

Met Pro Val Lys Asp Ser Ser Pro Leu Cys Ala Leu Val Ala Gly Leu
            195                 200                 205

Ile Lys Asn Glu Arg Leu Ser Glu Ala Ala Trp Val Leu Gly Gln Tyr
210                 215                 220

Gly Ser Leu Val Ser Gly Arg Glu Asp Leu Val Tyr Ala Tyr Asn Thr
225                 230                 235                 240

Leu Ile Val Gly Tyr Gly Gln Arg Gly Gln Val Glu Ala Ala Arg Cys
                245                 250                 255

Leu Phe Asp Gln Ile Pro Asp Leu Cys Gly Asp His Gly Gly Glu
            260                 265                 270

Phe Arg Glu Arg Phe Cys Lys Asn Val Val Ser Trp Asn Ser Met Ile
            275                 280                 285

Lys Ala Tyr Leu Lys Val Gly Asp Val Val Ser Ala Arg Leu Leu Phe
290                 295                 300

Asp Gln Met Lys Asp Arg Asp Thr Ile Ser Trp Asn Thr Met Ile Asp
305                 310                 315                 320

Gly Tyr Val His Val Ser Arg Met Glu Asp Ala Phe Ala Leu Phe Ser
                325                 330                 335

Glu Met Pro Asn Arg Asp Ala His Ser Trp Asn Met Met Val Ser Gly
            340                 345                 350

Tyr Ala Ser Val Gly Asn Val Glu Leu Ala Arg His Tyr Phe Glu Lys
            355                 360                 365

Thr Pro Glu Lys His Thr Val Ser Trp Asn Ser Ile Ile Ala Ala Tyr
            370                 375                 380

Glu Lys Asn Lys Asp Tyr Lys Glu Ala Val Asp Leu Phe Ile Arg Met
385                 390                 395                 400

Asn Ile Glu Gly Glu Lys Pro Asp Pro His Thr Leu Thr Ser Leu Leu
                405                 410                 415

Ser Ala Ser Thr Gly Leu Val Asn Leu Arg Leu Gly Met Gln Met His
            420                 425                 430

Gln Ile Val Val Lys Thr Val Ile Pro Asp Val Pro Val His Asn Ala
            435                 440                 445

Leu Ile Thr Met Tyr Ser Arg Cys Gly Glu Ile Met Glu Ser Arg Arg
450                 455                 460

Ile Phe Asp Glu Met Lys Leu Lys Arg Glu Val Ile Thr Trp Asn Ala
465                 470                 475                 480

Met Ile Gly Gly Tyr Ala Phe His Gly Asn Ala Ser Glu Ala Leu Asn
                485                 490                 495

Leu Phe Gly Ser Met Lys Ser Asn Gly Ile Tyr Pro Ser His Ile Thr
            500                 505                 510

Phe Val Ser Val Leu Asn Ala Cys Ala His Ala Gly Leu Val Asp Glu
            515                 520                 525

Ala Lys Ala Gln Phe Val Ser Met Met Ser Val Tyr Lys Ile Glu Pro
            530                 535                 540

Gln Met Glu His Tyr Ser Ser Leu Val Asn Val Thr Ser Gly Gln Gly
545                 550                 555                 560

Gln Phe Glu Glu Ala Met Tyr Ile Ile Thr Ser Met Pro Phe Glu Pro
                565                 570                 575

Asp Lys Thr Val Trp Gly Ala Leu Leu Asp Ala Cys Arg Ile Tyr Asn
            580                 585                 590

```
Asn Val Gly Leu Ala His Val Ala Glu Ala Met Ser Arg Leu Glu
            595                 600                 605

Pro Glu Ser Ser Thr Pro Tyr Val Leu Tyr Asn Met Tyr Ala Asp
        610                 615                 620

Met Gly Leu Trp Asp Glu Ala Ser Gln Val Arg Met Asn Met Glu Ser
625                 630                 635                 640

Lys Arg Ile Lys Lys Glu Arg Gly Ser Ser Trp Val Asp Ser Thr
                645                 650                 655

<210> SEQ ID NO 17
<211> LENGTH: 544
<212> TYPE: PRT
<213> ORGANISM: Arabidopsis thaliana

<400> SEQUENCE: 17

Met Ile Ser Ser Leu Ala Ala Ile Thr Gly Gly Pro Ser Thr Phe Arg
1               5                   10                  15

Arg Asp Pro Asp Ser Asn Thr Leu Arg Leu Ser Arg Arg Lys Thr Leu
                20                  25                  30

Ile Ser Val Leu Arg Ser Cys Lys Asn Ile Ala His Val Pro Ser Ile
            35                  40                  45

His Ala Lys Ile Ile Arg Thr Phe His Asp Gln Asp Ala Phe Val Val
        50                  55                  60

Phe Glu Leu Ile Arg Val Cys Ser Thr Leu Asp Ser Val Asp Tyr Ala
65                  70                  75                  80

Tyr Asp Val Phe Ser Tyr Val Ser Asn Pro Asn Val Tyr Leu Tyr Thr
                85                  90                  95

Ala Met Ile Asp Gly Phe Val Ser Ser Gly Arg Ser Ala Asp Gly Val
            100                 105                 110

Ser Leu Tyr His Arg Met Ile His Asn Ser Val Leu Pro Asp Asn Tyr
        115                 120                 125

Val Ile Thr Ser Val Leu Lys Ala Cys Asp Leu Lys Val Cys Arg Glu
130                 135                 140

Ile His Ala Gln Val Leu Lys Leu Gly Phe Gly Ser Ser Arg Ser Val
145                 150                 155                 160

Gly Leu Lys Met Met Glu Ile Tyr Gly Lys Ser Gly Glu Leu Val Asn
                165                 170                 175

Ala Lys Lys Met Phe Asp Glu Met Pro Asp Arg Asp His Val Ala Ala
            180                 185                 190

Thr Val Met Ile Asn Cys Tyr Ser Glu Cys Gly Phe Ile Lys Glu Ala
        195                 200                 205

Leu Glu Leu Phe Gln Asp Val Lys Ile Lys Asp Thr Val Cys Trp Thr
    210                 215                 220

Ala Met Ile Asp Gly Leu Val Arg Asn Lys Met Asn Lys Ala Leu
225                 230                 235                 240

Glu Leu Phe Arg Glu Met Gln Met Glu Asn Val Ser Ala Asn Glu Phe
                245                 250                 255

Thr Ala Val Cys Val Leu Ser Ala Cys Ser Asp Leu Gly Ala Leu Glu
            260                 265                 270

Leu Gly Arg Trp Val His Ser Phe Val Glu Asn Gln Arg Met Glu Leu
        275                 280                 285

Ser Asn Phe Val Gly Asn Ala Leu Ile Asn Met Tyr Ser Arg Cys Gly
    290                 295                 300

Asp Ile Asn Glu Ala Arg Arg Val Phe Arg Val Met Arg Asp Lys Asp
305                 310                 315                 320
```

```
Val Ile Ser Tyr Asn Thr Met Ile Ser Gly Leu Ala Met His Gly Ala
                325                 330                 335

Ser Val Glu Ala Ile Asn Glu Phe Arg Asp Met Val Asn Arg Gly Phe
            340                 345                 350

Arg Pro Asn Gln Val Thr Leu Val Ala Leu Leu Asn Ala Cys Ser His
        355                 360                 365

Gly Gly Leu Leu Asp Ile Gly Leu Glu Val Phe Asn Ser Met Lys Arg
    370                 375                 380

Val Phe Asn Val Glu Pro Gln Ile Glu His Tyr Gly Cys Ile Val Asp
385                 390                 395                 400

Leu Leu Gly Arg Val Gly Arg Leu Glu Glu Ala Tyr Arg Phe Ile Glu
                405                 410                 415

Asn Ile Pro Ile Glu Pro Asp His Ile Met Leu Gly Thr Leu Leu Ser
            420                 425                 430

Ala Cys Lys Ile His Gly Asn Met Glu Leu Gly Glu Lys Ile Ala Lys
        435                 440                 445

Arg Leu Phe Glu Ser Glu Asn Pro Asp Ser Gly Thr Tyr Val Leu Leu
    450                 455                 460

Ser Asn Leu Tyr Ala Ser Ser Gly Lys Trp Lys Glu Ser Thr Glu Ile
465                 470                 475                 480

Arg Glu Ser Met Arg Asp Ser Gly Ile Glu Lys Glu Pro Gly Cys Ser
                485                 490                 495

Thr Ile Glu Val Asp Asn Gln Ile His Glu Phe Leu Val Gly Asp Ile
            500                 505                 510

Ala His Pro His Lys Glu Ala Ile Tyr Gln Arg Leu Gln Glu Leu Asn
        515                 520                 525

Arg Ile Leu Arg Phe Lys Glu Asn Gln Ile Asp Ile Ile Met Gly Phe
    530                 535                 540

<210> SEQ ID NO 18
<211> LENGTH: 738
<212> TYPE: PRT
<213> ORGANISM: Arabidopsis thaliana

<400> SEQUENCE: 18

Met Ala Ile Phe Ser Thr Ala Gln Pro Leu Ser Leu Pro Arg His Pro
1               5                   10                  15

Asn Phe Ser Asn Pro Asn Gln Pro Thr Thr Asn Glu Arg Ser Arg
                20                  25                  30

His Ile Ser Leu Ile Glu Arg Cys Val Ser Leu Arg Gln Leu Lys Gln
            35                  40                  45

Thr His Gly His Met Ile Arg Thr Gly Thr Phe Ser Asp Pro Tyr Ser
        50                  55                  60

Ala Ser Lys Leu Phe Ala Met Ala Ala Leu Ser Ser Phe Ala Ser Leu
65                  70                  75                  80

Glu Tyr Ala Arg Lys Val Phe Asp Glu Ile Pro Lys Pro Asn Ser Phe
                85                  90                  95

Ala Trp Asn Thr Leu Ile Arg Ala Tyr Ala Ser Gly Pro Asp Pro Val
            100                 105                 110

Leu Ser Ile Trp Ala Phe Leu Asp Met Val Ser Glu Ser Gln Cys Tyr
        115                 120                 125

Pro Asn Lys Tyr Thr Phe Pro Phe Leu Ile Lys Ala Ala Ala Glu Val
    130                 135                 140

Ser Ser Leu Ser Leu Gly Gln Ser Leu His Gly Met Ala Val Lys Ser
```

```
            145                 150                 155                 160
Ala Val Gly Ser Asp Val Phe Val Ala Asn Ser Leu Ile His Cys Tyr
                165                 170                 175

Phe Ser Cys Gly Asp Leu Asp Ser Ala Cys Lys Val Phe Thr Thr Ile
                180                 185                 190

Lys Glu Lys Asp Val Val Ser Trp Asn Ser Met Ile Asn Gly Phe Val
                195                 200                 205

Gln Lys Gly Ser Pro Asp Lys Ala Leu Glu Leu Phe Lys Lys Met Glu
            210                 215                 220

Ser Glu Asp Val Lys Ala Ser His Val Thr Met Val Gly Val Leu Ser
225                 230                 235                 240

Ala Cys Ala Lys Ile Arg Asn Leu Glu Phe Gly Arg Gln Val Cys Ser
                245                 250                 255

Tyr Ile Glu Glu Asn Arg Val Asn Val Asn Leu Thr Leu Ala Asn Ala
                260                 265                 270

Met Leu Asp Met Tyr Thr Lys Cys Gly Ser Ile Glu Asp Ala Lys Arg
            275                 280                 285

Leu Phe Asp Ala Met Glu Glu Lys Asp Asn Val Thr Trp Thr Thr Met
        290                 295                 300

Leu Asp Gly Tyr Ala Ile Ser Glu Asp Tyr Glu Ala Ala Arg Glu Val
305                 310                 315                 320

Leu Asn Ser Met Pro Gln Lys Asp Ile Val Ala Trp Asn Ala Leu Ile
                325                 330                 335

Ser Ala Tyr Glu Gln Asn Gly Lys Pro Asn Glu Ala Leu Ile Val Phe
                340                 345                 350

His Glu Leu Gln Leu Gln Lys Asn Met Lys Leu Asn Gln Ile Thr Leu
            355                 360                 365

Val Ser Thr Leu Ser Ala Cys Ala Gln Val Gly Ala Leu Glu Leu Gly
        370                 375                 380

Arg Trp Ile His Ser Tyr Ile Lys Lys His Gly Ile Arg Met Asn Phe
385                 390                 395                 400

His Val Thr Ser Ala Leu Ile His Met Tyr Ser Lys Cys Gly Asp Leu
                405                 410                 415

Glu Lys Ser Arg Glu Val Phe Asn Ser Val Glu Lys Arg Asp Val Phe
            420                 425                 430

Val Trp Ser Ala Met Ile Gly Gly Leu Ala Met His Gly Cys Gly Asn
                435                 440                 445

Glu Ala Val Asp Met Phe Tyr Lys Met Gln Glu Ala Asn Val Lys Pro
450                 455                 460

Asn Gly Val Thr Phe Thr Asn Val Phe Cys Ala Cys Ser His Thr Gly
465                 470                 475                 480

Leu Val Asp Glu Ala Glu Ser Leu Phe His Gln Met Glu Ser Asn Tyr
                485                 490                 495

Gly Ile Val Pro Glu Glu Lys His Tyr Ala Cys Ile Val Asp Val Leu
                500                 505                 510

Gly Arg Ser Gly Tyr Leu Glu Lys Ala Val Lys Phe Ile Glu Ala Met
            515                 520                 525

Pro Ile Pro Pro Ser Thr Ser Val Trp Gly Ala Leu Leu Gly Ala Cys
        530                 535                 540

Lys Ile His Ala Asn Leu Asn Leu Ala Glu Met Ala Cys Thr Arg Leu
545                 550                 555                 560

Leu Glu Leu Glu Pro Arg Asn Asp Gly Ala His Val Leu Leu Ser Asn
                565                 570                 575
```

-continued

```
Ile Tyr Ala Lys Leu Gly Lys Trp Glu Asn Val Ser Glu Leu Arg Lys
            580                 585                 590

His Met Arg Val Thr Gly Leu Lys Lys Glu Pro Gly Cys Ser Ser Ile
        595                 600                 605

Glu Ile Asp Gly Met Ile His Glu Phe Leu Ser Gly Asp Asn Ala His
    610                 615                 620

Pro Met Ser Glu Lys Val Tyr Gly Lys Leu His Glu Val Met Glu Lys
625                 630                 635                 640

Leu Lys Ser Asn Gly Tyr Glu Pro Glu Ile Ser Gln Val Leu Gln Ile
                645                 650                 655

Ile Glu Glu Glu Met Lys Glu Gln Ser Leu Asn Leu His Ser Glu
            660                 665                 670

Lys Leu Ala Ile Cys Tyr Gly Leu Ile Ser Thr Glu Ala Pro Lys Val
        675                 680                 685

Ile Arg Val Ile Lys Asn Leu Arg Val Cys Gly Asp Cys His Ser Val
    690                 695                 700

Ala Lys Leu Ile Ser Gln Leu Tyr Asp Arg Glu Ile Ile Val Arg Asp
705                 710                 715                 720

Arg Tyr Arg Phe His His Phe Arg Asn Gly Gln Cys Ser Cys Asn Asp
                725                 730                 735

Phe Trp

<210> SEQ ID NO 19
<211> LENGTH: 741
<212> TYPE: PRT
<213> ORGANISM: Arabidopsis thaliana

<400> SEQUENCE: 19

Met Met Leu Ser Cys Ser Pro Leu Thr Val Pro Ser Ser Ser Tyr Pro
1               5                   10                  15

Phe His Phe Leu Pro Ser Ser Ser Asp Pro Pro Tyr Asp Ser Ile Arg
            20                  25                  30

Asn His Pro Ser Leu Ser Leu Leu His Asn Cys Lys Thr Leu Gln Ser
        35                  40                  45

Leu Arg Ile Ile His Ala Gln Met Ile Lys Ile Gly Leu His Asn Thr
    50                  55                  60

Asn Tyr Ala Leu Ser Lys Leu Ile Glu Phe Cys Ile Leu Ser Pro His
65                  70                  75                  80

Phe Glu Gly Leu Pro Tyr Ala Ile Ser Val Phe Lys Thr Ile Gln Glu
                85                  90                  95

Pro Asn Leu Leu Ile Trp Asn Thr Met Phe Arg Gly His Ala Leu Ser
            100                 105                 110

Ser Asp Pro Val Ser Ala Leu Lys Leu Tyr Val Cys Met Ile Ser Leu
        115                 120                 125

Gly Leu Leu Pro Asn Ser Tyr Thr Phe Pro Phe Val Leu Lys Ser Cys
    130                 135                 140

Ala Lys Ser Lys Ala Phe Lys Glu Gly Gln Gln Ile His Gly His Val
145                 150                 155                 160

Leu Lys Leu Gly Cys Asp Leu Asp Leu Tyr Val His Thr Ser Leu Ile
                165                 170                 175

Ser Met Tyr Val Gln Asn Gly Arg Leu Glu Asp Ala His Lys Val Phe
            180                 185                 190

Asp Lys Ser Pro His Arg Asp Val Val Ser Tyr Thr Ala Leu Ile Lys
        195                 200                 205
```

```
Gly Tyr Ala Ser Arg Gly Tyr Ile Glu Asn Ala Gln Lys Leu Phe Asp
            210                 215                 220

Glu Ile Pro Val Lys Asp Val Val Ser Trp Asn Ala Met Ile Ser Gly
225                 230                 235                 240

Tyr Ala Glu Thr Gly Asn Tyr Lys Glu Ala Leu Glu Leu Phe Lys Asp
                245                 250                 255

Met Met Lys Thr Asn Val Arg Pro Asp Glu Ser Thr Met Val Thr Val
            260                 265                 270

Val Ser Ala Cys Ala Gln Ser Gly Ser Ile Glu Leu Gly Arg Gln Val
275                 280                 285

His Leu Trp Ile Asp Asp His Gly Phe Gly Ser Asn Leu Lys Ile Val
290                 295                 300

Asn Ala Leu Ile Asp Leu Tyr Ser Lys Cys Gly Glu Leu Glu Thr Ala
305                 310                 315                 320

Cys Gly Leu Phe Glu Arg Leu Pro Tyr Lys Asp Val Ile Ser Trp Asn
                325                 330                 335

Thr Leu Ile Gly Gly Tyr Thr His Met Asn Leu Tyr Lys Glu Ala Leu
                340                 345                 350

Leu Leu Phe Gln Glu Met Leu Arg Ser Gly Glu Thr Pro Asn Asp Val
355                 360                 365

Thr Met Leu Ser Ile Leu Pro Ala Cys Ala His Leu Gly Ala Ile Asp
370                 375                 380

Ile Gly Arg Trp Ile His Val Tyr Ile Asp Lys Arg Leu Lys Gly Val
385                 390                 395                 400

Thr Asn Ala Ser Ser Leu Arg Thr Ser Leu Ile Asp Met Tyr Ala Lys
                405                 410                 415

Cys Gly Asp Ile Glu Ala Ala His Gln Val Phe Asn Ser Ile Leu His
                420                 425                 430

Lys Ser Leu Ser Ser Trp Asn Ala Met Ile Phe Gly Phe Ala Met His
435                 440                 445

Gly Arg Ala Asp Ala Ser Phe Asp Leu Phe Ser Arg Met Arg Lys Ile
450                 455                 460

Gly Ile Gln Pro Asp Asp Ile Thr Phe Val Gly Leu Leu Ser Ala Cys
465                 470                 475                 480

Ser His Ser Gly Met Leu Asp Leu Gly Arg His Ile Phe Arg Thr Met
                485                 490                 495

Thr Gln Asp Tyr Lys Met Thr Pro Lys Leu Glu His Tyr Gly Cys Met
                500                 505                 510

Ile Asp Leu Leu Gly His Ser Gly Leu Phe Lys Glu Ala Glu Glu Met
            515                 520                 525

Ile Asn Met Met Glu Met Glu Pro Asp Gly Val Ile Trp Cys Ser Leu
            530                 535                 540

Leu Lys Ala Cys Lys Met His Gly Asn Val Glu Leu Gly Glu Ser Phe
545                 550                 555                 560

Ala Glu Asn Leu Ile Lys Ile Glu Pro Glu Asn Pro Gly Ser Tyr Val
                565                 570                 575

Leu Leu Ser Asn Ile Tyr Ala Ser Ala Gly Arg Trp Asn Glu Val Ala
                580                 585                 590

Lys Thr Arg Ala Leu Leu Asn Asp Lys Gly Met Lys Lys Val Pro Gly
            595                 600                 605

Cys Ser Ser Ile Glu Ile Asp Ser Val Val His Glu Phe Ile Ile Gly
610                 615                 620
```

```
Asp Lys Phe His Pro Arg Asn Arg Glu Ile Tyr Gly Met Leu Glu Glu
625                 630                 635                 640

Met Glu Val Leu Leu Glu Lys Ala Gly Phe Val Pro Asp Thr Ser Glu
            645                 650                 655

Val Leu Gln Glu Met Glu Glu Trp Lys Glu Gly Ala Leu Arg His
        660                 665                 670

His Ser Glu Lys Leu Ala Ile Ala Phe Gly Leu Ile Ser Thr Lys Pro
        675                 680                 685

Gly Thr Lys Leu Thr Ile Val Lys Asn Leu Arg Val Cys Arg Asn Cys
        690                 695                 700

His Glu Ala Thr Lys Leu Ile Ser Lys Ile Tyr Lys Arg Glu Ile Ile
705                 710                 715                 720

Ala Arg Asp Arg Thr Arg Phe His His Phe Arg Asp Gly Val Cys Ser
                725                 730                 735

Cys Asn Asp Tyr Trp
                740

<210> SEQ ID NO 20
<211> LENGTH: 890
<212> TYPE: PRT
<213> ORGANISM: Arabidopsis thaliana

<400> SEQUENCE: 20

Met Ser Cys Pro Leu Ala Phe Thr Phe Ser Leu Pro Ser Ile Phe Pro
1               5                   10                  15

Phe Pro Ser Gln Leu Leu Pro Phe Ser Arg His Lys His Pro Tyr Leu
            20                  25                  30

Leu Arg Ala Thr Pro Thr Ser Ala Thr Glu Asp Val Ala Ser Ala Val
        35                  40                  45

Ser Gly Ala Pro Ser Ile Phe Ile Ser Gln Ser Arg Ser Pro Glu Trp
    50                  55                  60

Trp Ile Asp Leu Leu Arg Ser Lys Val Arg Ser Asn Leu Leu Arg Glu
65                  70                  75                  80

Ala Val Leu Thr Tyr Val Asp Met Ile Val Leu Gly Ile Lys Pro Asp
                85                  90                  95

Asn Tyr Ala Phe Pro Ala Leu Leu Lys Ala Val Ala Asp Leu Gln Asp
            100                 105                 110

Met Glu Leu Gly Lys Gln Ile His Ala His Val Tyr Lys Phe Gly Tyr
        115                 120                 125

Gly Val Asp Ser Val Thr Val Ala Asn Thr Leu Val Asn Leu Tyr Arg
    130                 135                 140

Lys Cys Gly Asp Phe Gly Ala Val Tyr Lys Val Phe Asp Arg Ile Ser
145                 150                 155                 160

Glu Arg Asn Gln Val Ser Trp Asn Ser Leu Ile Ser Ser Leu Cys Ser
                165                 170                 175

Phe Glu Lys Trp Glu Met Ala Leu Glu Ala Phe Arg Cys Met Leu Asp
            180                 185                 190

Glu Asn Val Glu Pro Ser Ser Phe Thr Leu Val Ser Val Val Thr Ala
        195                 200                 205

Cys Ser Asn Leu Pro Met Pro Glu Gly Leu Met Met Gly Lys Gln Val
    210                 215                 220

His Ala Tyr Gly Leu Arg Lys Gly Glu Leu Asn Ser Phe Ile Ile Asn
225                 230                 235                 240

Thr Leu Val Ala Met Tyr Gly Lys Leu Gly Lys Leu Ala Ser Ser Lys
                245                 250                 255
```

-continued

```
Val Leu Leu Gly Ser Phe Gly Gly Arg Asp Leu Val Thr Trp Asn Thr
            260                 265                 270

Val Leu Ser Ser Leu Cys Gln Asn Glu Gln Leu Leu Glu Ala Leu Glu
            275                 280                 285

Tyr Leu Arg Glu Met Val Leu Glu Gly Val Pro Asp Glu Phe Thr
            290                 295                 300

Ile Ser Ser Val Leu Pro Ala Cys Ser His Leu Glu Met Leu Arg Thr
305                 310                 315                 320

Gly Lys Glu Leu His Ala Tyr Ala Leu Lys Asn Gly Ser Leu Asp Glu
                325                 330                 335

Asn Ser Phe Val Gly Ser Ala Leu Val Asp Met Tyr Cys Asn Cys Lys
            340                 345                 350

Gln Val Leu Ser Gly Arg Arg Val Phe Asp Gly Met Phe Asp Arg Lys
            355                 360                 365

Ile Gly Leu Trp Asn Ala Met Ile Ala Gly Tyr Ser Gln Asn Glu His
            370                 375                 380

Asp Lys Glu Ala Leu Leu Phe Ile Gly Met Glu Glu Ser Ala Gly
385                 390                 395                 400

Leu Leu Ala Asn Ser Thr Thr Met Ala Gly Val Val Pro Ala Cys Val
                405                 410                 415

Arg Ser Gly Ala Phe Ser Arg Lys Glu Ala Ile His Gly Phe Val Val
            420                 425                 430

Lys Arg Gly Leu Asp Arg Asp Arg Phe Val Gln Asn Thr Leu Met Asp
            435                 440                 445

Met Tyr Ser Arg Leu Gly Lys Ile Asp Ile Ala Met Arg Ile Phe Gly
            450                 455                 460

Lys Met Glu Asp Arg Asp Leu Val Thr Trp Asn Thr Met Ile Thr Gly
465                 470                 475                 480

Tyr Val Phe Ser Glu His His Glu Asp Ala Leu Leu Leu His Lys
                485                 490                 495

Met Gln Asn Leu Glu Arg Lys Val Ser Lys Gly Ala Ser Arg Val Ser
            500                 505                 510

Leu Lys Pro Asn Ser Ile Thr Leu Met Thr Ile Leu Pro Ser Cys Ala
            515                 520                 525

Ala Leu Ser Ala Leu Ala Lys Gly Lys Glu Ile His Ala Tyr Ala Ile
            530                 535                 540

Lys Asn Asn Leu Ala Thr Asp Val Ala Val Gly Ser Ala Leu Val Asp
545                 550                 555                 560

Met Tyr Ala Lys Cys Gly Cys Leu Gln Met Ser Arg Lys Val Phe Asp
                565                 570                 575

Gln Ile Pro Gln Lys Asn Val Ile Thr Trp Asn Val Ile Met Ala
            580                 585                 590

Tyr Gly Met His Gly Asn Gly Gln Glu Ala Ile Asp Leu Leu Arg Met
            595                 600                 605

Met Met Val Gln Gly Val Lys Pro Asn Glu Val Thr Phe Ile Ser Val
            610                 615                 620

Phe Ala Ala Cys Ser His Ser Gly Met Val Asp Glu Gly Leu Arg Ile
625                 630                 635                 640

Phe Tyr Val Met Lys Pro Asp Tyr Gly Val Glu Pro Ser Ser Asp His
                645                 650                 655

Tyr Ala Cys Val Val Asp Leu Leu Gly Arg Ala Gly Arg Ile Lys Glu
            660                 665                 670
```

```
Ala Tyr Gln Leu Met Asn Met Met Pro Arg Asp Phe Asn Lys Ala Gly
            675                 680                 685

Ala Trp Ser Ser Leu Leu Gly Ala Ser Arg Ile His Asn Asn Leu Glu
    690                 695                 700

Ile Gly Glu Ile Ala Ala Gln Asn Leu Ile Gln Leu Glu Pro Asn Val
705                 710                 715                 720

Ala Ser His Tyr Val Leu Leu Ala Asn Ile Tyr Ser Ala Gly Leu
                725                 730                 735

Trp Asp Lys Ala Thr Glu Val Arg Arg Asn Met Lys Glu Gln Gly Val
                740                 745                 750

Arg Lys Glu Pro Gly Cys Ser Trp Ile Glu His Gly Asp Glu Val His
            755                 760                 765

Lys Phe Val Ala Gly Asp Ser Ser His Pro Gln Ser Glu Lys Leu Ser
    770                 775                 780

Gly Tyr Leu Glu Thr Leu Trp Glu Arg Met Arg Lys Glu Gly Tyr Val
785                 790                 795                 800

Pro Asp Thr Ser Cys Val Leu His Asn Val Glu Glu Asp Glu Lys Glu
                805                 810                 815

Ile Leu Leu Cys Gly His Ser Glu Lys Leu Ala Ile Ala Phe Gly Ile
                820                 825                 830

Leu Asn Thr Ser Pro Gly Thr Ile Ile Arg Val Ala Lys Asn Leu Arg
            835                 840                 845

Val Cys Asn Asp Cys His Leu Ala Thr Lys Phe Ile Ser Lys Ile Val
    850                 855                 860

Asp Arg Glu Ile Ile Leu Arg Asp Val Arg Arg Phe His Arg Phe Lys
865                 870                 875                 880

Asn Gly Thr Cys Ser Cys Gly Asp Tyr Trp
                885                 890

<210> SEQ ID NO 21
<211> LENGTH: 603
<212> TYPE: PRT
<213> ORGANISM: Arabidopsis thaliana

<400> SEQUENCE: 21

Met Ala Ile Ser Ser Ala Ser Leu Ile Ser Ser Phe Ser His Ala Glu
1               5                   10                  15

Thr Phe Thr Lys His Ser Lys Ile Asp Thr Val Asn Thr Gln Asn Pro
                20                  25                  30

Ile Leu Leu Ile Ser Lys Cys Asn Ser Leu Arg Glu Leu Met Gln Ile
            35                  40                  45

Gln Ala Tyr Ala Ile Lys Ser His Ile Glu Asp Val Ser Phe Val Ala
    50                  55                  60

Lys Leu Ile Asn Phe Cys Thr Glu Ser Pro Thr Glu Ser Ser Met Ser
65                  70                  75                  80

Tyr Ala Arg His Leu Phe Glu Ala Met Ser Glu Pro Asp Ile Val Ile
                85                  90                  95

Phe Asn Ser Met Ala Arg Gly Tyr Ser Arg Phe Thr Asn Pro Leu Glu
                100                 105                 110

Val Phe Ser Leu Phe Val Glu Ile Leu Glu Asp Gly Ile Leu Pro Asp
            115                 120                 125

Asn Tyr Thr Phe Pro Ser Leu Leu Lys Ala Cys Ala Val Ala Lys Ala
    130                 135                 140

Leu Glu Glu Gly Arg Gln Leu His Cys Leu Ser Met Lys Leu Gly Leu
145                 150                 155                 160
```

```
Asp Asp Asn Val Tyr Val Cys Pro Thr Leu Ile Asn Met Tyr Thr Glu
            165                 170                 175

Cys Glu Asp Val Asp Ser Ala Arg Cys Val Phe Asp Arg Ile Val Glu
            180                 185                 190

Pro Cys Val Val Cys Tyr Asn Ala Met Ile Thr Gly Tyr Ala Arg Arg
            195                 200                 205

Asn Arg Pro Asn Glu Ala Leu Ser Leu Phe Arg Glu Met Gln Gly Lys
        210                 215                 220

Tyr Leu Lys Pro Asn Glu Ile Thr Leu Leu Ser Val Leu Ser Ser Cys
225                 230                 235                 240

Ala Leu Leu Gly Ser Leu Asp Leu Gly Lys Trp Ile His Lys Tyr Ala
            245                 250                 255

Lys Lys His Ser Phe Cys Lys Tyr Val Lys Val Asn Thr Ala Leu Ile
            260                 265                 270

Asp Met Phe Ala Lys Cys Gly Ser Leu Asp Asp Ala Val Ser Ile Phe
            275                 280                 285

Glu Lys Met Arg Tyr Lys Asp Thr Gln Ala Trp Ser Ala Met Ile Val
            290                 295                 300

Ala Tyr Ala Asn His Gly Lys Ala Glu Lys Ser Met Leu Met Phe Glu
305                 310                 315                 320

Arg Met Arg Ser Glu Asn Val Gln Pro Asp Glu Ile Thr Phe Leu Gly
            325                 330                 335

Leu Leu Asn Ala Cys Ser His Thr Gly Arg Val Glu Glu Gly Arg Lys
            340                 345                 350

Tyr Phe Ser Gln Met Val Ser Lys Phe Gly Ile Val Pro Ser Ile Lys
            355                 360                 365

His Tyr Gly Ser Met Val Asp Leu Leu Ser Arg Ala Gly Asn Leu Glu
            370                 375                 380

Asp Ala Tyr Glu Phe Ile Asp Lys Leu Pro Ile Ser Pro Thr Pro Met
385                 390                 395                 400

Leu Trp Arg Ile Leu Leu Ala Ala Cys Ser Ser His Asn Asn Leu Asp
            405                 410                 415

Leu Ala Glu Lys Val Ser Glu Arg Ile Phe Glu Leu Asp Ser His
            420                 425                 430

Gly Gly Asp Tyr Val Ile Leu Ser Asn Leu Tyr Ala Arg Asn Lys Lys
            435                 440                 445

Trp Glu Tyr Val Asp Ser Leu Arg Lys Val Met Lys Asp Arg Lys Ala
        450                 455                 460

Val Lys Val Pro Gly Cys Ser Ser Ile Glu Val Asn Asn Val Val His
465                 470                 475                 480

Glu Phe Phe Ser Gly Asp Gly Val Lys Ser Ala Thr Thr Lys Leu His
            485                 490                 495

Arg Ala Leu Asp Glu Met Val Lys Glu Leu Lys Leu Ser Gly Tyr Val
            500                 505                 510

Pro Asp Thr Ser Met Val Val His Ala Asn Met Asn Asp Gln Glu Lys
            515                 520                 525

Glu Ile Thr Leu Arg Tyr His Ser Glu Lys Leu Ala Ile Thr Phe Gly
            530                 535                 540

Leu Leu Asn Thr Pro Pro Gly Thr Thr Ile Arg Val Val Lys Asn Leu
545                 550                 555                 560

Arg Val Cys Arg Asp Cys His Asn Ala Ala Lys Leu Ile Ser Leu Ile
            565                 570                 575
```

```
Phe Gly Arg Lys Val Val Leu Arg Asp Val Gln Arg Phe His His Phe
            580                 585                 590

Glu Asp Gly Lys Cys Ser Cys Gly Asp Phe Trp
        595                 600

<210> SEQ ID NO 22
<211> LENGTH: 960
<212> TYPE: PRT
<213> ORGANISM: Arabidopsis thaliana

<400> SEQUENCE: 22

Met Glu Tyr Ala Val Thr Asn Met Arg Leu Leu Ser Asn Met Met Tyr
1               5                   10                  15

Ser Ala Ser Ala Ile Ser Phe Pro Arg Val Arg Leu His Cys Ser Ile
            20                  25                  30

Pro Thr Glu Pro Ser Cys Arg Arg Asn Pro Phe Arg Gln Ser Asn Gln
        35                  40                  45

Pro Val Gln Val Pro Ser Pro Lys Leu Ala Cys Phe Asp Gly Val Leu
    50                  55                  60

Thr Glu Ala Phe Gln Arg Leu Asp Val Ser Glu Asn Asn Ser Pro Val
65                  70                  75                  80

Glu Ala Phe Ala Tyr Val Leu Glu Leu Cys Gly Lys Arg Arg Ala Val
                85                  90                  95

Ser Gln Gly Arg Gln Leu His Ser Arg Ile Phe Lys Thr Phe Pro Ser
            100                 105                 110

Phe Glu Leu Asp Phe Leu Ala Gly Lys Leu Val Phe Met Tyr Gly Lys
        115                 120                 125

Cys Gly Ser Leu Asp Asp Ala Glu Lys Val Phe Asp Glu Met Pro Asp
    130                 135                 140

Arg Thr Ala Phe Ala Trp Asn Thr Met Ile Gly Ala Tyr Val Ser Asn
145                 150                 155                 160

Gly Glu Pro Ala Ser Ala Leu Ala Leu Tyr Trp Asn Met Arg Val Glu
                165                 170                 175

Gly Val Pro Leu Gly Leu Ser Ser Phe Pro Ala Leu Leu Lys Ala Cys
            180                 185                 190

Ala Lys Leu Arg Asp Ile Arg Ser Gly Ser Glu Leu His Ser Leu Leu
        195                 200                 205

Val Lys Leu Gly Tyr His Ser Thr Gly Phe Ile Val Asn Ala Leu Val
    210                 215                 220

Ser Met Tyr Ala Lys Asn Asp Asp Leu Ser Ala Ala Arg Arg Leu Phe
225                 230                 235                 240

Asp Gly Phe Gln Glu Lys Gly Asp Ala Val Leu Trp Asn Ser Ile Leu
                245                 250                 255

Ser Ser Tyr Ser Thr Ser Gly Lys Ser Leu Glu Thr Leu Glu Leu Phe
            260                 265                 270

Arg Glu Met His Met Thr Gly Pro Ala Pro Asn Ser Tyr Thr Ile Val
        275                 280                 285

Ser Ala Leu Thr Ala Cys Asp Gly Phe Ser Tyr Ala Lys Leu Gly Lys
    290                 295                 300

Glu Ile His Ala Ser Val Leu Lys Ser Ser Thr His Ser Ser Glu Leu
305                 310                 315                 320

Tyr Val Cys Asn Ala Leu Ile Ala Met Tyr Thr Arg Cys Gly Lys Met
                325                 330                 335

Pro Gln Ala Glu Arg Ile Leu Arg Gln Met Asn Asn Ala Asp Val Val
            340                 345                 350
```

-continued

```
Thr Trp Asn Ser Leu Ile Lys Gly Tyr Val Gln Asn Leu Met Tyr Lys
        355                 360                 365
Glu Ala Leu Glu Phe Phe Ser Asp Met Ile Ala Ala Gly His Lys Ser
        370                 375                 380
Asp Glu Val Ser Met Thr Ser Ile Ile Ala Ala Ser Gly Arg Leu Ser
385                 390                 395                 400
Asn Leu Leu Ala Gly Met Glu Leu His Ala Tyr Val Ile Lys His Gly
                    405                 410                 415
Trp Asp Ser Asn Leu Gln Val Gly Asn Thr Leu Ile Asp Met Tyr Ser
                420                 425                 430
Lys Cys Asn Leu Thr Cys Tyr Met Gly Arg Ala Phe Leu Arg Met His
                435                 440                 445
Asp Lys Asp Leu Ile Ser Trp Thr Thr Val Ile Ala Gly Tyr Ala Gln
        450                 455                 460
Asn Asp Cys His Val Glu Ala Leu Glu Leu Phe Arg Asp Val Ala Lys
465                 470                 475                 480
Lys Arg Met Glu Ile Asp Glu Met Ile Leu Gly Ser Ile Leu Arg Ala
                    485                 490                 495
Ser Ser Val Leu Lys Ser Met Leu Ile Val Lys Glu Ile His Cys His
                500                 505                 510
Ile Leu Arg Lys Gly Leu Leu Asp Thr Val Ile Gln Asn Glu Leu Val
        515                 520                 525
Asp Val Tyr Gly Lys Cys Arg Asn Met Gly Tyr Ala Thr Arg Val Phe
        530                 535                 540
Glu Ser Ile Lys Gly Lys Asp Val Val Ser Trp Thr Ser Met Ile Ser
545                 550                 555                 560
Ser Ser Ala Leu Asn Gly Asn Glu Ser Glu Ala Val Glu Leu Phe Arg
                    565                 570                 575
Arg Met Val Glu Thr Gly Leu Ser Ala Asp Ser Val Ala Leu Leu Cys
                580                 585                 590
Ile Leu Ser Ala Ala Ser Leu Ser Ala Leu Asn Lys Gly Arg Glu
                595                 600                 605
Ile His Cys Tyr Leu Leu Arg Lys Gly Phe Cys Leu Glu Gly Ser Ile
        610                 615                 620
Ala Val Ala Val Val Asp Met Tyr Ala Cys Cys Gly Asp Leu Gln Ser
625                 630                 635                 640
Ala Lys Ala Val Phe Asp Arg Ile Glu Arg Lys Gly Leu Leu Gln Tyr
                    645                 650                 655
Thr Ser Met Ile Asn Ala Tyr Gly Met His Gly Cys Gly Lys Ala Ala
                660                 665                 670
Val Glu Leu Phe Asp Lys Met Arg His Glu Asn Val Ser Pro Asp His
                675                 680                 685
Ile Ser Phe Leu Ala Leu Leu Tyr Ala Cys Ser His Ala Gly Leu Leu
        690                 695                 700
Asp Glu Gly Arg Gly Phe Leu Lys Ile Met Glu His Glu Tyr Glu Leu
705                 710                 715                 720
Glu Pro Trp Pro Glu His Tyr Val Cys Leu Val Asp Met Leu Gly Arg
                    725                 730                 735
Ala Asn Cys Val Val Glu Ala Phe Glu Phe Val Lys Met Met Lys Thr
                740                 745                 750
Glu Pro Thr Ala Glu Val Trp Cys Ala Leu Leu Ala Ala Cys Arg Ser
        755                 760                 765
```

-continued

```
His Ser Glu Lys Glu Ile Gly Glu Ile Ala Ala Gln Arg Leu Leu Glu
    770                 775                 780

Leu Glu Pro Lys Asn Pro Gly Asn Leu Val Leu Val Ser Asn Val Phe
785                 790                 795                 800

Ala Glu Gln Gly Arg Trp Asn Asp Val Glu Lys Val Arg Ala Lys Met
                805                 810                 815

Lys Ala Ser Gly Met Glu Lys His Pro Gly Cys Ser Trp Ile Glu Met
                820                 825                 830

Asp Gly Lys Val His Lys Phe Thr Ala Arg Asp Lys Ser His Pro Glu
            835                 840                 845

Ser Lys Glu Ile Tyr Glu Lys Leu Ser Glu Val Thr Arg Lys Leu Glu
850                 855                 860

Arg Glu Val Gly Tyr Val Ala Asp Thr Lys Phe Val Leu His Asn Val
865                 870                 875                 880

Asp Glu Gly Glu Lys Val Gln Met Leu His Gly His Ser Glu Arg Ile
                885                 890                 895

Ala Ile Ala Tyr Gly Leu Leu Arg Thr Pro Asp Arg Ala Cys Leu Arg
                900                 905                 910

Ile Thr Lys Asn Leu Arg Val Cys Arg Asp Cys His Thr Phe Cys Lys
            915                 920                 925

Leu Val Ser Lys Leu Phe Arg Arg Asp Ile Val Met Arg Asp Ala Asn
930                 935                 940

Arg Phe His His Phe Glu Ser Gly Leu Cys Ser Cys Gly Asp Ser Trp
945                 950                 955                 960
```

<210> SEQ ID NO 23
<211> LENGTH: 895
<212> TYPE: PRT
<213> ORGANISM: Arabidopsis thaliana

<400> SEQUENCE: 23

```
Met Asn Cys Leu Ala Asn Glu Ser Leu Asn Ser Leu Lys Ile Ser Pro
1               5                   10                  15

Phe Ser Thr Ser Arg Leu Leu Ser Ser Val Thr Asn Phe Arg Asn Gln
                20                  25                  30

Leu Ser Phe Ser Ser Lys Asp Ser Ser Ser Ser Ala Pro Phe Asn
            35                  40                  45

Pro Phe Arg Phe Phe Asn Asp Gln Ser Asn Ser Arg Leu Cys Asn Leu
50                  55                  60

Arg Thr Thr Lys Ile Leu Gln Ala His Leu Leu Arg Arg Tyr Leu Leu
65                  70                  75                  80

Pro Phe Asp Val Phe Leu Thr Lys Ser Leu Leu Ser Trp Tyr Ser Asn
                85                  90                  95

Ser Gly Ser Met Ala Asp Ala Ala Lys Leu Phe Asp Thr Ile Pro Gln
                100                 105                 110

Pro Asp Val Val Ser Cys Asn Ile Met Ile Ser Gly Tyr Lys Gln His
            115                 120                 125

Arg Leu Phe Glu Glu Ser Leu Arg Phe Phe Ser Lys Met His Phe Leu
130                 135                 140

Gly Phe Glu Ala Asn Glu Ile Ser Tyr Gly Ser Val Ile Ser Ala Cys
145                 150                 155                 160

Ser Ala Leu Gln Ala Pro Leu Phe Ser Glu Leu Val Cys Cys His Thr
                165                 170                 175

Ile Lys Met Gly Tyr Phe Phe Tyr Glu Val Val Glu Ser Ala Leu Ile
                180                 185                 190
```

```
Asp Val Phe Ser Lys Asn Leu Arg Phe Glu Asp Ala Tyr Lys Val Phe
        195                 200                 205

Arg Asp Ser Leu Ser Ala Asn Val Tyr Cys Trp Asn Thr Ile Ile Ala
210                 215                 220

Gly Ala Leu Arg Asn Gln Asn Tyr Gly Ala Val Phe Asp Leu Phe His
225                 230                 235                 240

Glu Met Cys Val Gly Phe Gln Lys Pro Asp Ser Tyr Thr Tyr Ser Ser
                245                 250                 255

Val Leu Ala Ala Cys Ala Ser Leu Glu Lys Leu Arg Phe Gly Lys Val
                260                 265                 270

Val Gln Ala Arg Val Ile Lys Cys Gly Ala Glu Asp Val Phe Val Cys
            275                 280                 285

Thr Ala Ile Val Asp Leu Tyr Ala Lys Cys Gly His Met Ala Glu Ala
        290                 295                 300

Met Glu Val Phe Ser Arg Ile Pro Asn Pro Ser Val Val Ser Trp Thr
305                 310                 315                 320

Val Met Leu Ser Gly Tyr Thr Lys Ser Asn Asp Ala Phe Ser Ala Leu
                325                 330                 335

Glu Ile Phe Lys Glu Met Arg His Ser Gly Val Glu Ile Asn Asn Cys
                340                 345                 350

Thr Val Thr Ser Val Ile Ser Ala Cys Gly Arg Pro Ser Met Val Cys
            355                 360                 365

Glu Ala Ser Gln Val His Ala Trp Val Phe Lys Ser Gly Phe Tyr Leu
        370                 375                 380

Asp Ser Ser Val Ala Ala Leu Ile Ser Met Tyr Ser Lys Ser Gly
385                 390                 395                 400

Asp Ile Asp Leu Ser Glu Gln Val Phe Glu Asp Leu Asp Ile Gln
                405                 410                 415

Arg Gln Asn Ile Val Asn Val Met Ile Thr Ser Phe Ser Gln Ser Lys
                420                 425                 430

Lys Pro Gly Lys Ala Ile Arg Leu Phe Thr Arg Met Leu Gln Glu Gly
            435                 440                 445

Leu Arg Thr Asp Glu Phe Ser Val Cys Ser Leu Leu Ser Val Leu Asp
        450                 455                 460

Cys Leu Asn Leu Gly Lys Gln Val His Gly Tyr Thr Leu Lys Ser Gly
465                 470                 475                 480

Leu Val Leu Asp Leu Thr Val Gly Ser Ser Leu Phe Thr Leu Tyr Ser
                485                 490                 495

Lys Cys Gly Ser Leu Glu Glu Ser Tyr Lys Leu Phe Gln Gly Ile Pro
                500                 505                 510

Phe Lys Asp Asn Ala Cys Trp Ala Ser Met Ile Ser Gly Phe Asn Glu
            515                 520                 525

Tyr Gly Tyr Leu Arg Glu Ala Ile Gly Leu Phe Ser Glu Met Leu Asp
        530                 535                 540

Asp Gly Thr Ser Pro Asp Glu Ser Thr Leu Ala Ala Val Leu Thr Val
545                 550                 555                 560

Cys Ser Ser His Pro Ser Leu Pro Arg Gly Lys Glu Ile His Gly Tyr
                565                 570                 575

Thr Leu Arg Ala Gly Ile Asp Lys Gly Met Asp Leu Gly Ser Ala Leu
                580                 585                 590

Val Asn Met Tyr Ser Lys Cys Gly Ser Leu Lys Leu Ala Arg Gln Val
            595                 600                 605
```

Tyr Asp Arg Leu Pro Glu Leu Asp Pro Val Ser Cys Ser Ser Leu Ile
610 615 620

Ser Gly Tyr Ser Gln His Gly Leu Ile Gln Asp Gly Phe Leu Leu Phe
625 630 635 640

Arg Asp Met Val Met Ser Gly Phe Thr Met Asp Ser Phe Ala Ile Ser
645 650 655

Ser Ile Leu Lys Ala Ala Ala Leu Ser Asp Glu Ser Ser Leu Gly Ala
660 665 670

Gln Val His Ala Tyr Ile Thr Lys Ile Gly Leu Cys Thr Glu Pro Ser
675 680 685

Val Gly Ser Ser Leu Leu Thr Met Tyr Ser Lys Phe Gly Ser Ile Asp
690 695 700

Asp Cys Cys Lys Ala Phe Ser Gln Ile Asn Gly Pro Asp Leu Ile Ala
705 710 715 720

Trp Thr Ala Leu Ile Ala Ser Tyr Ala Gln His Gly Lys Ala Asn Glu
725 730 735

Ala Leu Gln Val Tyr Asn Leu Met Lys Glu Lys Gly Phe Lys Pro Asp
740 745 750

Lys Val Thr Phe Val Gly Val Leu Ser Ala Cys Ser His Gly Gly Leu
755 760 765

Val Glu Glu Ser Tyr Phe His Leu Asn Ser Met Val Lys Asp Tyr Gly
770 775 780

Ile Glu Pro Glu Asn Arg His Tyr Val Cys Met Val Asp Ala Leu Gly
785 790 795 800

Arg Ser Gly Arg Leu Arg Glu Ala Glu Ser Phe Ile Asn Asn Met His
805 810 815

Ile Lys Pro Asp Ala Leu Val Trp Gly Thr Leu Leu Ala Ala Cys Lys
820 825 830

Ile His Gly Glu Val Glu Leu Gly Lys Val Ala Ala Lys Lys Ala Ile
835 840 845

Glu Leu Glu Pro Ser Asp Ala Gly Ala Tyr Ile Ser Leu Ser Asn Ile
850 855 860

Leu Ala Glu Val Gly Glu Trp Asp Glu Val Glu Glu Thr Arg Lys Leu
865 870 875 880

Met Lys Gly Thr Gly Val Gln Lys Glu Pro Gly Trp Ser Ser Val
885 890 895

<210> SEQ ID NO 24
<211> LENGTH: 681
<212> TYPE: PRT
<213> ORGANISM: Arabidopsis thaliana

<400> SEQUENCE: 24

Met Asn Ile Ser Lys Ala Lys Leu Leu Leu Pro Pro Pro Leu Thr
1 5 10 15

Pro Lys Leu Asn Arg Ser Leu Tyr Ser His Ser Gln Arg Arg Thr Arg
20 25 30

Ser Leu Pro His His Arg Asp Lys Pro Ile Asn Trp Asn Ser Thr His
35 40 45

Ser Phe Val Leu His Asn Pro Leu Leu Ser Leu Glu Lys Cys Lys
50 55 60

Leu Leu Leu His Leu Lys Gln Ile Gln Ala Gln Met Ile Ile Asn Gly
65 70 75 80

Leu Ile Leu Asp Pro Phe Ala Ser Ser Arg Leu Ile Ala Phe Cys Ala
85 90 95

```
Leu Ser Glu Ser Arg Tyr Leu Asp Tyr Ser Val Lys Ile Leu Lys Gly
            100                 105                 110

Ile Glu Asn Pro Asn Ile Phe Ser Trp Asn Val Thr Ile Arg Gly Phe
            115                 120                 125

Ser Glu Ser Glu Asn Pro Lys Glu Ser Phe Leu Leu Tyr Lys Gln Met
        130                 135                 140

Leu Arg His Gly Cys Cys Glu Ser Arg Pro Asp His Phe Thr Tyr Pro
145                 150                 155                 160

Val Leu Phe Lys Val Cys Ala Asp Leu Arg Leu Ser Ser Leu Gly His
                165                 170                 175

Met Ile Leu Gly His Val Leu Lys Leu Arg Leu Glu Leu Val Ser His
            180                 185                 190

Val His Asn Ala Ser Ile His Met Phe Ala Ser Cys Gly Asp Met Glu
        195                 200                 205

Asn Ala Arg Lys Val Phe Asp Glu Ser Pro Val Arg Asp Leu Val Ser
    210                 215                 220

Trp Asn Cys Leu Ile Asn Gly Tyr Lys Lys Ile Gly Glu Ala Glu Lys
225                 230                 235                 240

Ala Ile Tyr Val Tyr Lys Leu Met Glu Ser Glu Gly Val Lys Pro Asp
                245                 250                 255

Asp Val Thr Met Ile Gly Leu Val Ser Ser Cys Ser Met Leu Gly Asp
            260                 265                 270

Leu Asn Arg Gly Lys Glu Phe Tyr Glu Tyr Val Lys Glu Asn Gly Leu
        275                 280                 285

Arg Met Thr Ile Pro Leu Val Asn Ala Leu Met Asp Met Phe Ser Lys
    290                 295                 300

Cys Gly Asp Ile His Glu Ala Arg Arg Ile Phe Asp Asn Leu Glu Lys
305                 310                 315                 320

Arg Thr Ile Val Ser Trp Thr Thr Met Ile Ser Gly Tyr Ala Arg Cys
                325                 330                 335

Gly Leu Leu Asp Val Ser Arg Lys Leu Phe Asp Asp Met Glu Glu Lys
            340                 345                 350

Asp Val Val Leu Trp Asn Ala Met Ile Gly Gly Ser Val Gln Ala Lys
        355                 360                 365

Arg Gly Gln Asp Ala Leu Ala Leu Phe Gln Glu Met Gln Thr Ser Asn
    370                 375                 380

Thr Lys Pro Asp Glu Ile Thr Met Ile His Cys Leu Ser Ala Cys Ser
385                 390                 395                 400

Gln Leu Gly Ala Leu Asp Val Gly Ile Trp Ile His Arg Tyr Ile Glu
                405                 410                 415

Lys Tyr Ser Leu Ser Leu Asn Val Ala Leu Gly Thr Ser Leu Val Asp
            420                 425                 430

Met Tyr Ala Lys Cys Gly Asn Ile Ser Glu Ala Leu Ser Val Phe His
        435                 440                 445

Gly Ile Gln Thr Arg Asn Ser Leu Thr Tyr Thr Ala Ile Ile Gly Gly
    450                 455                 460

Leu Ala Leu His Gly Asp Ala Ser Thr Ala Ile Ser Tyr Phe Asn Glu
465                 470                 475                 480

Met Ile Asp Ala Gly Ile Ala Pro Asp Glu Ile Thr Phe Ile Gly Leu
                485                 490                 495

Leu Ser Ala Cys Cys His Gly Gly Met Ile Gln Thr Gly Arg Asp Tyr
            500                 505                 510
```

```
Phe Ser Gln Met Lys Ser Arg Phe Asn Leu Asn Pro Gln Leu Lys His
            515                 520                 525

Tyr Ser Ile Met Val Asp Leu Leu Gly Arg Ala Gly Leu Leu Glu Glu
        530                 535                 540

Ala Asp Arg Leu Met Glu Ser Met Pro Met Glu Ala Asp Ala Ala Val
545                 550                 555                 560

Trp Gly Ala Leu Leu Phe Gly Cys Arg Met His Gly Asn Val Glu Leu
                565                 570                 575

Gly Glu Lys Ala Ala Lys Lys Leu Leu Glu Leu Asp Pro Ser Asp Ser
            580                 585                 590

Gly Ile Tyr Val Leu Leu Asp Gly Met Tyr Gly Glu Ala Asn Met Trp
        595                 600                 605

Glu Asp Ala Lys Arg Ala Arg Arg Met Met Asn Glu Arg Gly Val Glu
610                 615                 620

Lys Ile Pro Gly Cys Ser Ser Ile Glu Val Asn Gly Ile Val Cys Glu
625                 630                 635                 640

Phe Ile Val Arg Asp Lys Ser Arg Pro Glu Ser Glu Lys Ile Tyr Asp
                645                 650                 655

Arg Leu His Cys Leu Gly Arg His Met Arg Ser Ser Leu Ser Val Leu
            660                 665                 670

Phe Ser Glu Tyr Glu Ile Thr Asn Asn
        675                 680

<210> SEQ ID NO 25
<211> LENGTH: 842
<212> TYPE: PRT
<213> ORGANISM: Arabidopsis thaliana

<400> SEQUENCE: 25

Met Ala Met Leu Gly Asn Val Leu His Leu Ser Pro Met Val Leu Ala
1               5                   10                  15

Thr Thr Thr Thr Thr Lys Pro Ser Leu Leu Asn Gln Ser Lys Cys Thr
            20                  25                  30

Lys Ala Thr Pro Ser Ser Leu Lys Asn Cys Lys Thr Ile Asp Glu Leu
        35                  40                  45

Lys Met Phe His Arg Ser Leu Thr Lys Gln Gly Leu Asp Asn Asp Val
    50                  55                  60

Ser Thr Ile Thr Lys Leu Val Ala Arg Ser Cys Glu Leu Gly Thr Arg
65                  70                  75                  80

Glu Ser Leu Ser Phe Ala Lys Glu Val Phe Glu Asn Ser Glu Ser Tyr
                85                  90                  95

Gly Thr Cys Phe Met Tyr Asn Ser Leu Ile Arg Gly Tyr Ala Ser Ser
            100                 105                 110

Gly Leu Cys Asn Glu Ala Ile Leu Phe Leu Arg Met Met Asn Ser
        115                 120                 125

Gly Ile Ser Pro Asp Lys Tyr Thr Phe Pro Phe Gly Leu Ser Ala Cys
    130                 135                 140

Ala Lys Ser Arg Ala Lys Gly Asn Gly Ile Gln Ile His Gly Leu Ile
145                 150                 155                 160

Val Lys Met Gly Tyr Ala Lys Asp Leu Phe Val Gln Asn Ser Leu Val
                165                 170                 175

His Phe Tyr Ala Glu Cys Gly Glu Leu Asp Ser Ala Arg Lys Val Phe
            180                 185                 190

Asp Glu Met Ser Glu Arg Asn Val Val Ser Trp Thr Ser Met Ile Cys
        195                 200                 205
```

-continued

Gly Tyr Ala Arg Arg Asp Phe Ala Lys Asp Ala Val Asp Leu Phe Phe
    210                 215                 220

Arg Met Val Arg Asp Glu Val Thr Pro Asn Ser Val Thr Met Val
225                 230                 235                 240

Cys Val Ile Ser Ala Cys Ala Lys Leu Glu Asp Leu Glu Thr Gly Glu
                245                 250                 255

Lys Val Tyr Ala Phe Ile Arg Asn Ser Gly Ile Glu Val Asn Asp Leu
                260                 265                 270

Met Val Ser Ala Leu Val Asp Met Tyr Met Lys Cys Asn Ala Ile Asp
            275                 280                 285

Val Ala Lys Arg Leu Phe Asp Glu Tyr Gly Ala Ser Asn Leu Asp Leu
        290                 295                 300

Cys Asn Ala Met Ala Ser Asn Tyr Val Arg Gln Gly Leu Thr Arg Glu
305                 310                 315                 320

Ala Leu Gly Val Phe Asn Leu Met Met Asp Ser Gly Val Arg Pro Asp
                325                 330                 335

Arg Ile Ser Met Leu Ser Ala Ile Ser Ser Cys Ser Gln Leu Arg Asn
                340                 345                 350

Ile Leu Trp Gly Lys Ser Cys His Gly Tyr Val Leu Arg Asn Gly Phe
            355                 360                 365

Glu Ser Trp Asp Asn Ile Cys Asn Ala Leu Ile Asp Met Tyr Met Lys
        370                 375                 380

Cys His Arg Gln Asp Thr Ala Phe Arg Ile Phe Asp Arg Met Ser Asn
385                 390                 395                 400

Lys Thr Val Val Thr Trp Asn Ser Ile Val Ala Gly Tyr Val Glu Asn
                405                 410                 415

Gly Glu Val Asp Ala Ala Trp Glu Thr Phe Glu Thr Met Pro Glu Lys
                420                 425                 430

Asn Ile Val Ser Trp Asn Thr Ile Ile Ser Gly Leu Val Gln Gly Ser
            435                 440                 445

Leu Phe Glu Glu Ala Ile Glu Val Phe Cys Ser Met Gln Ser Gln Glu
        450                 455                 460

Gly Val Asn Ala Asp Gly Val Thr Met Met Ser Ile Ala Ser Ala Cys
465                 470                 475                 480

Gly His Leu Gly Ala Leu Asp Leu Ala Lys Trp Ile Tyr Tyr Tyr Ile
                485                 490                 495

Glu Lys Asn Gly Ile Gln Leu Asp Val Arg Leu Gly Thr Thr Leu Val
            500                 505                 510

Asp Met Phe Ser Arg Cys Gly Asp Pro Glu Ser Ala Met Ser Ile Phe
        515                 520                 525

Asn Ser Leu Thr Asn Arg Asp Val Ser Ala Trp Thr Ala Ala Ile Gly
        530                 535                 540

Ala Met Ala Met Ala Gly Asn Ala Glu Arg Ala Ile Glu Leu Phe Asp
545                 550                 555                 560

Asp Met Ile Glu Gln Gly Leu Lys Pro Asp Gly Val Ala Phe Val Gly
                565                 570                 575

Ala Leu Thr Ala Cys Ser His Gly Gly Leu Val Gln Gln Gly Lys Glu
                580                 585                 590

Ile Phe Tyr Ser Met Leu Lys Leu His Gly Val Ser Pro Glu Asp Val
            595                 600                 605

His Tyr Gly Cys Met Val Asp Leu Leu Gly Arg Ala Gly Leu Leu Glu
        610                 615                 620

```
Glu Ala Val Gln Leu Ile Glu Asp Met Pro Met Glu Pro Asn Asp Val
625                 630                 635                 640

Ile Trp Asn Ser Leu Leu Ala Ala Cys Arg Val Gln Gly Asn Val Glu
            645                 650                 655

Met Ala Ala Tyr Ala Ala Glu Lys Ile Gln Val Leu Ala Pro Glu Arg
            660                 665                 670

Thr Gly Ser Tyr Val Leu Leu Ser Asn Val Tyr Ala Ser Ala Gly Arg
            675                 680                 685

Trp Asn Asp Met Ala Lys Val Arg Leu Ser Met Lys Glu Lys Gly Leu
690                 695                 700

Arg Lys Pro Pro Gly Thr Ser Ile Gln Ile Arg Gly Lys Thr His
705                 710                 715                 720

Glu Phe Thr Ser Gly Asp Glu Ser His Pro Glu Met Pro Asn Ile Glu
            725                 730                 735

Ala Met Leu Asp Glu Val Ser Gln Arg Ala Ser His Leu Gly His Val
            740                 745                 750

Pro Asp Leu Ser Asn Val Leu Met Asp Val Asp Glu Lys Glu Lys Ile
            755                 760                 765

Phe Met Leu Ser Arg His Ser Glu Lys Leu Ala Met Ala Tyr Gly Leu
770                 775                 780

Ile Ser Ser Asn Lys Gly Thr Thr Ile Arg Ile Val Lys Asn Leu Arg
785                 790                 795                 800

Val Cys Ser Asp Cys His Ser Phe Ala Lys Phe Ala Ser Lys Val Tyr
            805                 810                 815

Asn Arg Glu Ile Ile Leu Arg Asp Asn Asn Arg Phe His Tyr Ile Arg
            820                 825                 830

Gln Gly Lys Cys Ser Cys Gly Asp Phe Trp
            835                 840

<210> SEQ ID NO 26
<211> LENGTH: 859
<212> TYPE: PRT
<213> ORGANISM: Physcomitrella patens

<400> SEQUENCE: 26

Met Leu His Gln Gly Ala Gly Arg Ala Arg Gly Gly Leu Pro Ser Leu
1               5                   10                  15

Leu Leu Gly Arg Arg Phe Asp Leu Trp Ala Ser Phe Pro Trp Ser Phe
            20                  25                  30

Ser Ser Thr Ser Asp Asp Pro Ser Ser Arg Gln Ser Glu Glu Asn Ser
            35                  40                  45

Gln Thr Ile Asp Glu Leu Trp Glu Tyr Phe Ala Gly Pro Ser Gln Trp
50                  55                  60

Trp Asp Asn Arg Ile His Lys Arg Asn Pro Arg Ser Pro Asp Leu Lys
65                  70                  75                  80

His Lys Val Thr Gly Lys Ala Leu Trp Ile Asp Gly Cys Phe Thr Pro
            85                  90                  95

Glu Trp Val Lys Phe Gln Pro Val Ala Gln Val Gly Leu Gln Ser Tyr
            100                 105                 110

Ala Thr Cys Thr Thr Lys Cys Thr Glu Gly Gly Ala Gln Gly Lys Arg
            115                 120                 125

Gln Pro Lys Gly Asn Asp Gly Lys Leu Ala Thr Ala Cys Glu Ser Ala
130                 135                 140

Arg Val Leu Gly Arg Ile Ala Gln Gly Gly Ile Asn Met His Val Gln
145                 150                 155                 160
```

-continued

```
Thr Ala Asn Thr Leu Ser Glu Ala Ile Val Val Leu Met Asn Arg Leu
                165                 170                 175

Gln Arg Gly Leu Ile Thr Asp Ser Phe Met Tyr Val Glu Val Leu Lys
            180                 185                 190

Arg Cys Leu Lys Gln Lys Asp Leu Met Ala Ala Lys Gln Val His Asp
        195                 200                 205

Cys Ile Ile Lys Ser Arg Met Glu Gln Asn Ala His Val Met Asn Asn
    210                 215                 220

Leu Leu His Val Tyr Ile Glu Cys Gly Arg Leu Gln Glu Ala Arg Cys
225                 230                 235                 240

Val Phe Asp Ala Leu Val Lys Lys Ser Gly Ala Ser Trp Asn Ala Met
                245                 250                 255

Ile Ala Gly Tyr Val Glu His Lys His Ala Glu Asp Ala Met Arg Leu
            260                 265                 270

Phe Arg Glu Met Cys His Glu Gly Val Gln Pro Asn Ala Gly Thr Tyr
        275                 280                 285

Met Ile Ile Leu Lys Ala Cys Ala Ser Leu Ser Ala Leu Lys Trp Gly
    290                 295                 300

Lys Glu Val His Ala Cys Ile Arg His Gly Leu Glu Ser Asp Val
305                 310                 315                 320

Arg Val Gly Thr Ala Leu Leu Arg Met Tyr Gly Lys Cys Gly Ser Ile
                325                 330                 335

Asn Glu Ala Arg Arg Ile Phe Asp Asn Leu Met Asn His Asp Ile Ile
            340                 345                 350

Ser Trp Thr Val Met Ile Gly Ala Tyr Ala Gln Ser Gly Asn Gly Lys
        355                 360                 365

Glu Ala Tyr Arg Leu Met Leu Gln Met Glu Gln Glu Gly Phe Lys Pro
    370                 375                 380

Asn Ala Ile Thr Tyr Val Ser Ile Leu Asn Ala Cys Ala Ser Glu Gly
385                 390                 395                 400

Ala Leu Lys Trp Val Lys Arg Val His Arg His Ala Leu Asp Ala Gly
                405                 410                 415

Leu Glu Leu Asp Val Arg Val Gly Thr Ala Leu Val Gln Met Tyr Ala
            420                 425                 430

Lys Ser Gly Ser Ile Asp Asp Ala Arg Val Val Phe Asp Arg Met Lys
        435                 440                 445

Val Arg Asp Val Val Ser Trp Asn Val Met Ile Gly Ala Phe Ala Glu
    450                 455                 460

His Gly Arg Gly His Glu Ala Tyr Asp Leu Phe Leu Gln Met Gln Thr
465                 470                 475                 480

Glu Gly Cys Lys Pro Asp Ala Ile Met Phe Leu Ser Ile Leu Asn Ala
                485                 490                 495

Cys Ala Ser Ala Gly Ala Leu Glu Trp Val Lys Lys Ile His Arg His
            500                 505                 510

Ala Leu Asp Ser Gly Leu Glu Val Asp Val Arg Val Gly Thr Ala Leu
        515                 520                 525

Val His Met Tyr Ser Lys Ser Gly Ser Ile Asp Asp Ala Arg Val Val
    530                 535                 540

Phe Asp Arg Met Lys Val Arg Asn Val Val Ser Trp Asn Ala Met Ile
545                 550                 555                 560

Ser Gly Leu Ala Gln His Gly Leu Gly Gln Asp Ala Leu Glu Val Phe
                565                 570                 575
```

-continued

Arg Arg Met Thr Ala His Gly Val Lys Pro Asp Arg Val Thr Phe Val
            580                 585                 590

Ala Val Leu Ser Ala Cys Ser His Ala Gly Leu Val Asp Glu Gly Arg
        595                 600                 605

Ser Gln Tyr Leu Ala Met Thr Gln Val Tyr Gly Ile Glu Pro Asp Val
    610                 615                 620

Ser His Cys Asn Cys Met Val Asp Leu Leu Gly Arg Ala Gly Arg Leu
625                 630                 635                 640

Met Glu Ala Lys Leu Phe Ile Asp Asn Met Ala Val Asp Pro Asp Glu
            645                 650                 655

Ala Thr Trp Gly Ala Leu Leu Gly Ser Cys Arg Thr Tyr Gly Asn Val
        660                 665                 670

Glu Leu Gly Glu Leu Val Ala Lys Glu Arg Leu Lys Leu Asp Pro Lys
    675                 680                 685

Asn Ala Ala Thr Tyr Val Leu Leu Ser Asn Ile Tyr Ala Glu Ala Gly
690                 695                 700

Lys Trp Asp Met Val Ser Trp Val Arg Thr Met Met Arg Glu Arg Gly
705                 710                 715                 720

Ile Arg Lys Glu Pro Gly Arg Ser Trp Ile Glu Val Asp Asn Lys Ile
            725                 730                 735

His Asp Phe Leu Val Ala Asp Ser Ser His Pro Glu Cys Lys Glu Ile
        740                 745                 750

Asn Glu Ser Lys Asp Lys Val Ile Glu Lys Ile Lys Ala Glu Gly Tyr
    755                 760                 765

Ile Pro Asp Thr Arg Leu Val Leu Lys Asn Lys Asn Met Lys Asp Lys
770                 775                 780

Glu Leu Asp Ile Cys Ser His Ser Glu Lys Leu Ala Ile Val Tyr Gly
785                 790                 795                 800

Leu Met His Thr Pro Pro Gly Asn Pro Ile Arg Val Phe Lys Asn Leu
            805                 810                 815

Arg Val Cys Thr Asp Cys His Gly Ala Thr Lys Leu Ile Ser Lys Val
        820                 825                 830

Glu Gly Arg Glu Ile Ile Val Arg Asp Ala Asn Arg Phe His His Phe
    835                 840                 845

Lys Asp Gly Val Cys Ser Cys Gly Asp Tyr Trp
850                 855

<210> SEQ ID NO 27
<211> LENGTH: 833
<212> TYPE: PRT
<213> ORGANISM: Physcomitrella patens

<400> SEQUENCE: 27

Met Arg Val Ser Thr Arg Ile Ala Ala Asn Ile Ala Val Val Arg Arg
1               5                   10                  15

Arg Trp Phe Gly Ser Leu Gln Leu Pro Val Pro Ser Ala Arg Phe Arg
            20                  25                  30

Ser Thr Phe Thr Arg Arg Val Gly Ala Asn Asp Val Leu Gln Arg Leu
        35                  40                  45

Gly Glu Gly Gly Asn His Ile Asp Ser Arg Thr Tyr Val Lys Leu Phe
    50                  55                  60

Gln Arg Cys Thr Glu Leu Arg Asp Ala Ala Leu Gly Lys Gln Val Arg
65                  70                  75                  80

Asp His Ile Ile Gln Gly Gly Arg Gln Leu Asn Ile Tyr Glu Leu Asn
                85                  90                  95

```
Thr Leu Ile Lys Leu Tyr Ser Ile Cys Gly Asn Val Thr Glu Ala Arg
            100                 105                 110

Gln Ile Phe Asp Ser Val Glu Asn Lys Thr Val Val Thr Trp Asn Ala
            115                 120                 125

Leu Ile Ala Gly Tyr Ala Gln Val Gly His Val Lys Glu Ala Phe Ala
            130                 135                 140

Leu Phe Arg Gln Met Val Asp Glu Gly Leu Glu Pro Ser Ile Ile Thr
145                 150                 155                 160

Phe Leu Ser Val Leu Asp Ala Cys Ser Ser Pro Ala Gly Leu Asn Trp
                165                 170                 175

Gly Lys Glu Val His Ala Gln Val Val Thr Ala Gly Phe Val Ser Asp
            180                 185                 190

Phe Arg Ile Gly Thr Ala Leu Val Ser Met Tyr Val Lys Gly Gly Ser
            195                 200                 205

Met Asp Asp Ala Arg Gln Val Phe Asp Gly Leu His Ile Arg Asp Val
            210                 215                 220

Ser Thr Phe Asn Val Met Val Gly Gly Tyr Ala Lys Ser Gly Asp Trp
225                 230                 235                 240

Glu Lys Ala Phe Glu Leu Phe Tyr Arg Met Gln Gln Val Gly Leu Lys
                245                 250                 255

Pro Asn Lys Ile Ser Phe Leu Ser Ile Leu Asp Gly Cys Trp Thr Pro
            260                 265                 270

Glu Ala Leu Ala Trp Gly Lys Ala Val His Ala Gln Cys Met Asn Ala
            275                 280                 285

Gly Leu Val Asp Asp Ile Arg Val Ala Thr Ser Leu Ile Arg Met Tyr
            290                 295                 300

Thr Thr Cys Gly Ser Ile Glu Gly Ala Arg Arg Val Phe Asp Asn Met
305                 310                 315                 320

Lys Val Arg Asp Val Val Ser Trp Thr Val Met Ile Glu Gly Tyr Ala
                325                 330                 335

Glu Asn Gly Asn Ile Glu Asp Ala Phe Gly Leu Phe Ala Thr Met Gln
            340                 345                 350

Glu Glu Gly Ile Gln Pro Asp Arg Ile Thr Tyr Met His Ile Met Asn
            355                 360                 365

Ala Cys Ala Ile Ser Ala Asn Leu Asn His Ala Arg Glu Ile His Ser
            370                 375                 380

Gln Val Asp Ile Ala Gly Phe Gly Thr Asp Leu Leu Val Ser Thr Ala
385                 390                 395                 400

Leu Val His Met Tyr Ala Lys Cys Gly Ala Ile Lys Asp Ala Arg Gln
                405                 410                 415

Val Phe Asp Ala Met Pro Arg Arg Asp Val Val Ser Trp Ser Ala Met
            420                 425                 430

Ile Gly Ala Tyr Val Glu Asn Gly Tyr Gly Thr Glu Ala Phe Glu Thr
            435                 440                 445

Phe His Leu Met Lys Arg Ser Asn Ile Glu Pro Asp Gly Val Thr Tyr
            450                 455                 460

Ile Asn Leu Leu Asn Ala Cys Gly His Leu Gly Ala Leu Asp Val Gly
465                 470                 475                 480

Met Glu Ile Tyr Thr Gln Ala Ile Lys Ala Asp Leu Val Ser His Val
                485                 490                 495

Pro Leu Gly Asn Ala Leu Ile Ile Met Asn Ala Lys His Gly Ser Val
            500                 505                 510
```

```
Glu Arg Ala Arg Tyr Ile Phe Asp Thr Met Val Arg Asp Val Ile
            515                 520                 525

Thr Trp Asn Ala Met Ile Gly Gly Tyr Ser Leu His Gly Asn Ala Arg
530                 535                 540

Glu Ala Leu Tyr Leu Phe Asp Arg Met Leu Lys Glu Arg Phe Arg Pro
545                 550                 555                 560

Asn Ser Val Thr Phe Val Gly Val Leu Ser Ala Cys Ser Arg Ala Gly
                565                 570                 575

Phe Val Asp Glu Gly Arg Arg Phe Phe Thr Tyr Leu Leu Glu Gly Arg
            580                 585                 590

Gly Ile Val Pro Thr Val Lys Leu Tyr Gly Cys Met Val Asp Leu Leu
            595                 600                 605

Gly Arg Ala Gly Glu Leu Asp Glu Ala Glu Leu Leu Ile Lys Ser Met
        610                 615                 620

Pro Val Lys Pro Thr Ser Ser Ile Trp Ser Ser Leu Leu Val Ala Cys
625                 630                 635                 640

Arg Ile His Gly Asn Leu Asp Val Ala Glu Arg Ala Ala Glu Arg Cys
                645                 650                 655

Leu Met Ile Asp Pro Tyr Asp Gly Ala Val Tyr Val Gln Leu Ser His
            660                 665                 670

Met Tyr Ala Ala Ala Gly Met Trp Glu Asn Val Ala Lys Val Arg Lys
        675                 680                 685

Val Met Glu Ser Arg Gly Ile Arg Lys Glu Gln Gly Cys Thr Trp Ile
690                 695                 700

Glu Val Ala Gly Lys Val His Thr Phe Val Val Glu Asp Arg Ser His
705                 710                 715                 720

Pro Leu Val Gly Glu Ile Tyr Ala Glu Leu Ala Arg Leu Met Asn Ala
                725                 730                 735

Ile Lys Arg Glu Gly Tyr Ile Pro Ile Thr Gln Asn Val Leu His Asp
            740                 745                 750

Val Gly Glu Gln Gln Lys Glu Glu Ala Ile Ser Tyr His Ser Glu Lys
        755                 760                 765

Leu Ala Ile Ala Tyr Gly Val Leu Ser Leu Pro Ser Gly Thr Pro Ile
770                 775                 780

Arg Ile Tyr Lys Asn Leu Arg Val Cys Ser Asp Cys His Ser Ala Ser
785                 790                 795                 800

Lys Phe Ile Ser Lys Val Thr Gly Arg Glu Ile Ile Ala Arg Asp Ala
                805                 810                 815

Ser Arg Phe His His Phe Lys Asp Gly Val Cys Ser Cys Gly Asp Tyr
            820                 825                 830

Trp

<210> SEQ ID NO 28
<211> LENGTH: 1204
<212> TYPE: PRT
<213> ORGANISM: Physcomitrella patens

<400> SEQUENCE: 28

Met Tyr Arg Cys Leu Trp Arg Ser Val Ile Gln Thr His Lys Gly Ser
1               5                   10                  15

Leu Gly Arg Val Ala Gly Val Arg Glu Phe Ser Ala Arg Pro Trp Pro
                20                  25                  30

Val Glu Gln Asn Arg Ser Ser Ile Gly Ala Ala Gly Gly Glu Ser Ser
            35                  40                  45
```

```
Asn Leu Val Pro Val Lys Val Met Arg Asn Glu Arg His Cys Gly Pro
    50                  55                  60

Asp Arg Glu Asp Val Ser Asn Thr His Gln Pro Arg Pro Thr Glu Thr
65                  70                  75                  80

Asp Arg Ala Thr Tyr Val Ala Leu Leu Gln Asn Cys Thr Arg Lys Arg
                85                  90                  95

Leu Leu Met Arg Asn Glu Arg His Cys Gly Pro Asp Arg Glu Asp Val
            100                 105                 110

Ser Asn Thr His Gln Pro Arg Pro Thr Glu Thr Glu Arg Ala Thr Tyr
        115                 120                 125

Val Ala Leu Leu Gln Asn Cys Thr Arg Lys Arg Leu Leu Pro Glu Ala
    130                 135                 140

Lys Arg Ile His Ala Gln Met Val Glu Ala Trp Val Gly Pro Asp Ile
145                 150                 155                 160

Phe Leu Ser Asn Leu Leu Ile Asn Met Tyr Val Lys Cys Arg Ser Val
                165                 170                 175

Leu Asp Ala His Gln Val Phe Lys Glu Met Pro Arg Arg Asp Val Ile
            180                 185                 190

Ser Trp Asn Ser Leu Ile Ser Cys Tyr Ala Gln Gln Gly Phe Lys Lys
        195                 200                 205

Lys Ala Phe Gln Leu Phe Glu Glu Met Gln Asn Ala Gly Phe Ile Pro
    210                 215                 220

Asn Lys Ile Thr Tyr Ile Ser Ile Leu Thr Ala Cys Tyr Ser Pro Ala
225                 230                 235                 240

Glu Leu Glu Asn Gly Lys Lys Ile His Ser Gln Ile Ile Lys Ala Gly
                245                 250                 255

Tyr Gln Arg Asp Pro Arg Val Gln Asn Ser Leu Leu Ser Met Tyr Gly
            260                 265                 270

Lys Cys Gly Asp Leu Pro Arg Ala Arg Gln Val Phe Ala Gly Ile Ser
        275                 280                 285

Pro Arg Asp Val Val Ser Tyr Asn Thr Met Leu Gly Leu Tyr Ala Gln
    290                 295                 300

Lys Ala Tyr Val Lys Glu Cys Leu Gly Leu Phe Gly Gln Met Ser Ser
305                 310                 315                 320

Glu Gly Ile Ser Pro Asp Lys Val Thr Tyr Ile Asn Leu Leu Asp Ala
                325                 330                 335

Phe Thr Thr Pro Ser Met Leu Asp Glu Gly Lys Arg Ile His Lys Leu
            340                 345                 350

Thr Val Glu Glu Gly Leu Asn Ser Asp Ile Arg Val Gly Thr Ala Leu
        355                 360                 365

Val Thr Met Cys Val Arg Cys Gly Asp Val Asp Ser Ala Lys Gln Ala
    370                 375                 380

Phe Lys Gly Thr Ala Asp Arg Asp Val Val Tyr Asn Ala Leu Ile
385                 390                 395                 400

Ala Ala Leu Ala Gln His Gly His Asn Val Glu Ala Phe Glu Gln Tyr
                405                 410                 415

Tyr Arg Met Arg Ser Asp Gly Val Ala Leu Asn Arg Thr Thr Tyr Leu
            420                 425                 430

Ser Ile Leu Asn Ala Cys Ser Thr Ser Lys Ala Leu Glu Ala Gly Lys
        435                 440                 445

Leu Ile His Ser His Ile Ser Glu Asp Gly His Ser Ser Asp Val Gln
    450                 455                 460

Ile Gly Asn Ala Leu Ile Ser Met Tyr Ala Arg Cys Gly Asp Leu Pro
```

-continued

```
            465                 470                 475                 480
Lys Ala Arg Glu Leu Phe Tyr Thr Met Pro Lys Arg Asp Leu Ile Ser
                    485                 490                 495

Trp Asn Ala Ile Ile Ala Gly Tyr Ala Arg Glu Asp Arg Gly Glu
                500                 505                 510

Ala Met Arg Leu Tyr Lys Gln Met Gln Ser Glu Gly Val Lys Pro Gly
                    515                 520                 525

Arg Val Thr Phe Leu His Leu Leu Ser Ala Cys Ala Asn Ser Ser Ala
            530                 535                 540

Tyr Ala Asp Gly Lys Met Ile His Glu Asp Ile Leu Arg Ser Gly Ile
545                 550                 555                 560

Lys Ser Asn Gly His Leu Ala Asn Ala Leu Met Asn Met Tyr Arg Arg
                565                 570                 575

Cys Gly Ser Leu Met Glu Ala Gln Asn Val Phe Glu Gly Thr Gln Ala
                580                 585                 590

Arg Asp Val Ile Ser Trp Asn Ser Met Ile Ala Gly His Ala Gln His
            595                 600                 605

Gly Ser Tyr Glu Thr Ala Tyr Lys Leu Phe Gln Glu Met Gln Asn Glu
            610                 615                 620

Glu Leu Glu Pro Asp Asn Ile Thr Phe Ala Ser Val Leu Ser Gly Cys
625                 630                 635                 640

Lys Asn Pro Glu Ala Leu Glu Leu Gly Lys Gln Ile His Gly Arg Ile
                645                 650                 655

Thr Glu Ser Gly Leu Gln Leu Asp Val Asn Leu Gly Asn Ala Leu Ile
                660                 665                 670

Asn Met Tyr Ile Arg Cys Gly Ser Leu Gln Asp Ala Arg Asn Val Phe
            675                 680                 685

His Ser Leu Gln His Arg Asp Val Met Ser Trp Thr Ala Met Ile Gly
            690                 695                 700

Gly Cys Ala Asp Gln Gly Glu Asp Met Lys Ala Ile Glu Leu Phe Trp
705                 710                 715                 720

Gln Met Gln Asn Glu Gly Phe Arg Pro Val Lys Ser Thr Phe Ser Ser
                725                 730                 735

Ile Leu Lys Val Cys Thr Ser Ser Ala Cys Leu Asp Glu Gly Lys Lys
                740                 745                 750

Val Ile Ala Tyr Ile Leu Asn Ser Gly Tyr Glu Leu Asp Thr Gly Val
            755                 760                 765

Gly Asn Ala Leu Ile Ser Ala Tyr Ser Lys Ser Gly Ser Met Thr Asp
            770                 775                 780

Ala Arg Glu Val Phe Asp Lys Met Pro Ser Arg Asp Ile Val Ser Trp
785                 790                 795                 800

Asn Lys Ile Ile Ala Gly Tyr Ala Gln Asn Gly Leu Gly Gln Thr Ala
                805                 810                 815

Val Glu Phe Ala Tyr Gln Met Gln Glu Gln Asp Val Val Pro Asn Lys
                820                 825                 830

Phe Ser Phe Val Ser Leu Leu Asn Ala Cys Ser Ser Phe Ser Ala Leu
            835                 840                 845

Glu Glu Gly Lys Arg Val His Ala Glu Ile Val Lys Arg Lys Leu Gln
            850                 855                 860

Gly Asp Val Arg Val Gly Ala Ala Leu Ile Ser Met Tyr Ala Lys Cys
865                 870                 875                 880

Gly Ser Gln Gly Glu Ala Gln Glu Val Phe Asp Asn Ile Ile Glu Lys
                885                 890                 895
```

Asn Val Val Thr Trp Asn Ala Met Ile Asn Ala Tyr Ala Gln His Gly
                    900                 905                 910

Leu Ala Ser Lys Ala Leu Gly Phe Phe Asn Cys Met Glu Lys Glu Gly
            915                 920                 925

Ile Lys Pro Asp Gly Ser Thr Phe Thr Ser Ile Leu Ser Ala Cys Asn
    930                 935                 940

His Ala Gly Leu Val Leu Glu Gly Tyr Gln Ile Phe Ser Ser Met Glu
945                 950                 955                 960

Ser Glu Tyr Gly Val Leu Pro Thr Ile Glu His Tyr Gly Cys Leu Val
                965                 970                 975

Gly Leu Leu Gly Arg Ala Arg Arg Phe Gln Glu Ala Glu Thr Leu Ile
            980                 985                 990

Asn Gln Met Pro Phe Pro Pro Asp Ala Ala Val Trp Glu Thr Leu Leu
        995                 1000                1005

Gly Ala Cys Arg Ile His Gly Asn Ile Ala Leu Ala Glu His Ala
    1010                1015                1020

Ala Asn Asn Ala Leu Lys Leu Asn Ala Arg Asn Pro Ala Val Tyr
    1025                1030                1035

Ile Leu Leu Ser Asn Val Tyr Ala Ala Ala Gly Arg Trp Asp Asp
    1040                1045                1050

Val Ala Lys Ile Arg Arg Val Met Glu Gly Arg Gly Ile Arg Lys
    1055                1060                1065

Glu Pro Gly Arg Ser Trp Ile Glu Val Asp Asn Ile Ile His Glu
    1070                1075                1080

Phe Ile Ala Ala Asp Arg Ser His Pro Glu Thr Ala Glu Ile Tyr
    1085                1090                1095

Ala Glu Leu Lys Arg Leu Ser Val Glu Met Glu Glu Ala Gly Tyr
    1100                1105                1110

Phe Pro Asp Thr Gln His Val Leu His Asp Leu Gly Lys Ala His
    1115                1120                1125

Gln Glu Thr Ser Leu Cys Thr His Ser Glu Arg Leu Ala Ile Ala
    1130                1135                1140

Tyr Gly Leu Ile Lys Thr Pro Pro Gly Thr Pro Ile Arg Ile Phe
    1145                1150                1155

Lys Asn Leu Arg Ile Cys Gly Asp Cys His Thr Ala Ser Lys Phe
    1160                1165                1170

Ile Ser Lys Leu Val Gly Arg Glu Ile Ile Ala Arg Asp Ser Asn
    1175                1180                1185

Arg Phe His Ser Phe Lys Asn Gly Lys Cys Ser Cys Glu Asp Tyr
    1190                1195                1200

Trp

<210> SEQ ID NO 29
<211> LENGTH: 1042
<212> TYPE: PRT
<213> ORGANISM: Physcomitrella patens

<400> SEQUENCE: 29

Met Ser Leu Pro Trp Gly Leu Asp Phe Thr Thr Val Thr Ala Lys
1               5                   10                  15

Gln Thr Gln Ala Gly Phe Ser Val Leu Lys Lys Glu Lys His Ser Leu
            20                  25                  30

Arg Asp Asp Leu Ile Leu Ala Thr Ser Arg Gln Asn Asp Ala Gly His
        35                  40                  45

```
Lys Ile Asp Leu Val Gly Asp Ser Ala Arg Asn Phe Leu Val Lys Gln
     50                  55                  60

Ile Ala Arg Asp Ser Asp Thr Leu Val Arg Ala Asp Leu Lys Lys Glu
 65              70                  75                  80

Cys Ser Arg Ala Tyr Gly Lys Pro Ser Leu Leu Val Glu Ala His Arg
                 85                  90                  95

Ser Ser Ser Met His Ser Gln Ser Arg Val Gln Leu Cys Lys Trp Trp
                100                 105                 110

Phe Asn Thr Ser Gly Phe Arg Tyr Ser Asn Gly Lys Pro Arg Val Asn
             115                 120                 125

Lys Leu Tyr Phe His Thr Tyr Lys Asp Glu Lys Ile Met Ile Glu Lys
    130                 135                 140

Asp Gly Ala Val Asp Val Val Gln Tyr Leu Gln Gln Gly Ala Gln
145             150                 155                 160

Val Asn Ser Ser Asp Tyr Met Lys Met Leu Lys Arg Cys Ile Glu Val
                165                 170                 175

Lys Asp Leu Val Ala Gly Arg Gln Val His Gln His Ile Ile Gln His
             180                 185                 190

Arg Thr Val Pro Asp Gln Tyr Thr Val Asn Ala Leu Ile Asn Met Tyr
         195                 200                 205

Ile Gln Cys Gly Ser Ile Glu Glu Ala Arg Gln Val Trp Lys Lys Leu
     210                 215                 220

Ser Tyr Met Glu Arg Thr Val His Ser Trp Asn Ala Met Val Val Gly
225             230                 235                 240

Tyr Ile Gln Tyr Gly Tyr Ile Glu Lys Ala Leu Lys Leu Leu Arg Gln
                 245                 250                 255

Met Gln Gln His Gly Leu Ala Pro Asp Arg Thr Thr Ile Met Ser Phe
             260                 265                 270

Leu Ser Ser Cys Lys Ser Pro Gly Ala Leu Glu Trp Gly Arg Glu Ile
     275                 280                 285

His Phe Gln Ala Met Gln Ala Gly Leu Leu Phe Asp Val Lys Val Ala
    290                 295                 300

Asn Cys Ile Leu Asn Met Tyr Ala Lys Cys Gly Ser Ile Glu Glu Ala
305             310                 315                 320

Arg Glu Val Phe Asp Lys Met Glu Lys Lys Ser Val Val Ser Trp Thr
                 325                 330                 335

Ile Thr Ile Gly Gly Tyr Ala Asp Cys Gly Arg Ser Glu Thr Ala Phe
             340                 345                 350

Glu Ile Phe Gln Lys Met Glu Gln Glu Gly Val Val Pro Asn Arg Ile
    355                 360                 365

Thr Tyr Ile Ser Val Leu Asn Ala Phe Ser Ser Pro Ala Ala Leu Lys
    370                 375                 380

Trp Gly Lys Ala Val His Ser Arg Ile Leu Asn Ala Gly His Glu Ser
385             390                 395                 400

Asp Thr Ala Val Gly Thr Ala Leu Val Lys Met Tyr Ala Lys Cys Gly
                 405                 410                 415

Ser Tyr Lys Asp Cys Arg Gln Val Phe Glu Lys Leu Val Asn Arg Asp
             420                 425                 430

Leu Ile Ala Trp Asn Thr Met Ile Gly Gly Leu Ala Glu Gly Gly Tyr
         435                 440                 445

Trp Glu Glu Ala Ser Glu Val Tyr Asn Gln Met Gln Arg Glu Gly Val
450                 455                 460
```

```
Met Pro Asn Lys Ile Thr Tyr Val Ile Leu Leu Asn Ala Cys Val Asn
465                 470                 475                 480

Ser Ala Ala Leu His Trp Gly Lys Glu Ile His Ser Arg Val Ala Lys
            485                 490                 495

Ala Gly Phe Thr Ser Asp Ile Gly Val Gln Asn Ala Leu Ile Ser Met
                500                 505                 510

Tyr Ser Arg Cys Gly Ser Ile Lys Asp Ala Arg Leu Val Phe Asp Lys
            515                 520                 525

Met Val Arg Lys Asp Val Ile Ser Trp Thr Ala Met Ile Gly Gly Leu
            530                 535                 540

Ala Lys Ser Gly Phe Gly Ala Glu Ala Leu Thr Val Tyr Gln Glu Met
545                 550                 555                 560

Gln Gln Ala Gly Val Glu Pro Asn Arg Val Thr Tyr Thr Ser Ile Leu
                565                 570                 575

Asn Ala Cys Ser Ser Pro Ala Ala Leu Glu Trp Gly Arg Arg Ile His
                580                 585                 590

Gln Gln Val Val Glu Ala Gly Leu Ala Thr Asp Ala His Val Gly Asn
            595                 600                 605

Thr Leu Val Asn Met Tyr Ser Met Cys Gly Ser Val Lys Asp Ala Arg
            610                 615                 620

Gln Val Phe Asp Arg Met Ile Gln Arg Asp Ile Val Ala Tyr Asn Ala
625                 630                 635                 640

Met Ile Gly Gly Tyr Ala Ala His Asn Leu Gly Lys Glu Ala Leu Lys
                645                 650                 655

Leu Phe Asp Arg Leu Gln Glu Glu Gly Leu Lys Pro Asp Lys Val Thr
                660                 665                 670

Tyr Ile Asn Met Leu Asn Ala Cys Ala Asn Ser Gly Ser Leu Glu Trp
            675                 680                 685

Ala Arg Glu Ile His Thr Leu Val Arg Lys Gly Gly Phe Phe Ser Asp
690                 695                 700

Thr Ser Val Gly Asn Ala Leu Val Ser Thr Tyr Ala Lys Cys Gly Ser
705                 710                 715                 720

Phe Ser Asp Ala Ser Ile Val Phe Glu Lys Met Thr Lys Arg Asn Val
                725                 730                 735

Ile Ser Trp Asn Ala Ile Ile Gly Gly Ser Ala Gln His Gly Arg Gly
            740                 745                 750

Gln Asp Ala Leu Gln Leu Phe Glu Arg Met Lys Met Glu Gly Val Lys
                755                 760                 765

Pro Asp Ile Val Thr Phe Val Ser Leu Leu Ser Ala Cys Ser His Ala
770                 775                 780

Gly Leu Leu Glu Glu Gly Arg Arg Tyr Phe Cys Ser Met Ser Gln Asp
785                 790                 795                 800

Phe Ala Ile Ile Pro Thr Ile Glu His Tyr Gly Cys Met Val Asp Leu
                805                 810                 815

Leu Gly Arg Ala Gly Gln Leu Asp Glu Ala Glu Ala Leu Ile Lys Thr
            820                 825                 830

Met Pro Phe Gln Ala Asn Thr Arg Ile Trp Gly Ala Leu Leu Gly Ala
            835                 840                 845

Cys Arg Ile His Gly Asn Val Pro Val Ala Glu Arg Ala Ala Glu Ser
            850                 855                 860

Ser Leu Lys Leu Asp Leu Asp Asn Ala Val Val Tyr Val Ala Leu Ser
865                 870                 875                 880

His Met Tyr Ala Ala Ala Gly Met Trp Asp Ser Ala Ala Lys Leu Arg
```

```
                        885                 890                 895
Lys Leu Met Glu Gln Arg Gly Val Thr Lys Glu Pro Gly Arg Ser Trp
        900                 905                 910
Ile Gln Val Gly Asp Lys Leu His Tyr Phe Val Ala Glu Asp Arg Ser
        915                 920                 925
His Pro Gln Ser Glu Lys Ile Tyr Ala Glu Leu Asp Arg Leu Thr His
        930                 935                 940
Ala Met Lys Met Lys Gly Tyr Val Pro Asp Thr Arg Ser Val Met His
945                 950                 955                 960
Asp Val Asp Glu Gly Glu Lys Glu Asn Ala Val Cys His His Ser Glu
                965                 970                 975
Arg Leu Ala Ile Ala Tyr Gly Leu Ile Ser Thr Pro Gly Thr Arg
                980                 985                 990
Ile His Ile Phe Lys Asn Leu Arg Val Cys Pro Asp Cys His Thr Ala
                995                 1000                1005
Thr Lys Phe Ile Ser Lys Ile Val Asp Arg Glu Ile Ile Ala Arg
        1010                1015                1020
Asp Val Asn Arg Phe His His Phe Lys Asp Gly Val Cys Ser Cys
        1025                1030                1035
Gly Asp Tyr Trp
        1040

<210> SEQ ID NO 30
<211> LENGTH: 804
<212> TYPE: PRT
<213> ORGANISM: Physcomitrella patens

<400> SEQUENCE: 30

Met Ile Pro Thr Gly Lys Asp Gly Trp Tyr Ala Pro Ala Asp Val Leu
1               5                   10                  15
Gln Tyr Leu His Arg Lys Gly Pro Gln Val Asp Ser Tyr Asp Tyr Val
            20                  25                  30
Lys Leu Leu Gln Ser Cys Val Lys Ala Lys Asp Leu Ala Val Gly Lys
        35                  40                  45
Gln Val His Glu His Ile Leu Arg Cys Gly Val Lys Pro Asn Val Tyr
    50                  55                  60
Ile Thr Asn Thr Leu Leu Lys Leu Tyr Ala His Cys Gly Ser Val Asn
65                  70                  75                  80
Glu Ala Arg Gln Leu Phe Asp Lys Phe Ser Asn Lys Ser Val Val Ser
                85                  90                  95
Trp Asn Val Met Ile Ser Gly Tyr Ala His Arg Gly Leu Ala Gln Glu
            100                 105                 110
Ala Phe Asn Leu Phe Thr Leu Met Gln Gln Glu Arg Leu Glu Pro Asp
        115                 120                 125
Lys Phe Thr Phe Val Ser Ile Leu Ser Ala Cys Ser Ser Pro Ala Val
    130                 135                 140
Leu Asn Trp Gly Arg Glu Ile His Val Arg Val Met Glu Ala Gly Leu
145                 150                 155                 160
Ala Asn Asp Thr Thr Val Gly Asn Ala Leu Ile Ser Met Tyr Ala Lys
                165                 170                 175
Cys Gly Ser Val Arg Asp Ala Arg Arg Val Phe Asp Ala Met Ala Ser
            180                 185                 190
Arg Asp Glu Val Ser Trp Thr Thr Leu Thr Gly Ala Tyr Ala Glu Ser
        195                 200                 205
```

-continued

Gly Tyr Gly Glu Glu Ser Leu Lys Thr Tyr His Ala Met Leu Gln Glu
    210                 215                 220

Arg Val Arg Pro Ser Arg Ile Thr Tyr Met Asn Val Leu Ser Ala Cys
225                 230                 235                 240

Gly Ser Leu Ala Ala Leu Glu Lys Gly Lys Gln Ile His Ala His Ile
                245                 250                 255

Val Glu Ser Glu Tyr His Ser Asp Val Arg Val Ser Thr Ala Leu Thr
            260                 265                 270

Lys Met Tyr Met Lys Cys Gly Ala Phe Lys Asp Ala Arg Glu Val Phe
            275                 280                 285

Glu Cys Leu Ser Tyr Arg Asp Val Ile Ala Trp Asn Thr Met Ile Arg
290                 295                 300

Gly Phe Val Asp Ser Gly Gln Leu Glu Glu Ala His Gly Thr Phe His
305                 310                 315                 320

Arg Met Leu Glu Glu Gly Val Ala Pro Asp Arg Ala Thr Tyr Thr Thr
                325                 330                 335

Val Leu Ser Ala Cys Ala Arg Pro Gly Gly Leu Ala Arg Gly Lys Glu
            340                 345                 350

Ile His Ala Arg Ala Ala Lys Asp Gly Leu Val Ser Asp Val Arg Phe
        355                 360                 365

Gly Asn Ala Leu Ile Asn Met Tyr Ser Lys Ala Gly Ser Met Lys Asp
    370                 375                 380

Ala Arg Gln Val Phe Asp Arg Met Pro Lys Arg Asp Val Val Ser Trp
385                 390                 395                 400

Thr Thr Leu Leu Gly Arg Tyr Ala Asp Cys Asp Gln Val Val Glu Ser
                405                 410                 415

Phe Thr Thr Phe Lys Gln Met Leu Gln Gln Gly Val Lys Ala Asn Lys
            420                 425                 430

Ile Thr Tyr Met Cys Val Leu Lys Ala Cys Ser Asn Pro Val Ala Leu
        435                 440                 445

Lys Trp Gly Lys Glu Ile His Ala Glu Val Val Lys Ala Gly Leu Leu
    450                 455                 460

Ala Asp Leu Ala Val Thr Asn Ala Leu Met Ser Met Tyr Phe Lys Cys
465                 470                 475                 480

Gly Ser Val Glu Asp Ala Ile Arg Val Phe Glu Gly Met Ser Met Arg
                485                 490                 495

Asp Val Val Thr Trp Asn Thr Leu Ile Gly Gly Leu Gly Gln Asn Gly
            500                 505                 510

Arg Gly Leu Glu Ala Leu Gln Arg Tyr Glu Val Met Lys Ser Glu Gly
        515                 520                 525

Met Arg Pro Asn Ala Ala Thr Phe Val Asn Val Leu Ser Ala Cys Arg
    530                 535                 540

Val Cys Asn Leu Val Glu Glu Gly Arg Arg Gln Phe Ala Phe Met Ser
545                 550                 555                 560

Lys Asp Tyr Gly Ile Val Pro Thr Glu Lys His Tyr Ala Cys Met Val
                565                 570                 575

Asp Ile Leu Ala Arg Ala Gly His Leu Arg Glu Ala Glu Asp Val Ile
            580                 585                 590

Leu Thr Ile Pro Leu Lys Pro Ser Ala Ala Met Trp Gly Ala Leu Leu
        595                 600                 605

Ala Ala Cys Arg Ile His Cys Asn Val Glu Ile Gly Glu Arg Ala Ala
    610                 615                 620

Glu His Cys Leu Lys Leu Glu Pro Gln Asn Ala Gly Leu Tyr Val Ser

```
                625                 630                 635                 640
Leu Ser Ala Ile Tyr Ala Ala Ala Gly Met Trp Arg Asp Val Ala Lys
                    645                 650                 655
Leu Arg Lys Phe Met Lys Glu Arg Gly Val Lys Lys Glu Pro Gly Arg
                    660                 665                 670
Ser Trp Ile Glu Ile Ala Gly Glu Val His Ser Phe Val Ala Arg Asp
                    675                 680                 685
Gln Ser His Pro Arg Thr Gln Glu Ile Tyr Ala Glu Leu Glu Thr Leu
                    690                 695                 700
Lys Lys Gln Met Lys Ser Leu Gly Tyr Val Pro Asp Thr Arg Phe Val
705                 710                 715                 720
Met His Asp Leu Asp Asp Glu Gly Lys Glu Arg Ala Val Cys His His
                    725                 730                 735
Ser Glu Lys Leu Ala Ile Ala Tyr Gly Leu Ile Ser Thr Pro Pro Gly
                    740                 745                 750
Thr Pro Ile Arg Ile Ser Lys Asn Leu Arg Val Cys Thr Asp Cys His
                    755                 760                 765
Thr Ala Thr Lys Phe Ile Ser Lys Ile Thr Lys Arg Glu Ile Ile Ala
                    770                 775                 780
Arg Asp Ala His Arg Phe His His Phe Lys Asn Gly Glu Cys Ser Cys
785                 790                 795                 800
Gly Asp Tyr Trp

<210> SEQ ID NO 31
<211> LENGTH: 890
<212> TYPE: PRT
<213> ORGANISM: Physcomitrella patens

<400> SEQUENCE: 31

Met Leu Ser Arg Arg Phe Gly Leu Arg Arg Trp Lys Gln Val Leu Gln
1                   5                   10                  15
Asn Tyr His Val Gly Ala Met Thr Ser Ile Val Tyr Asn Asp Gly Phe
                    20                  25                  30
Ala Ser Thr Gly Lys Glu Leu Asp Gly Pro Thr Ser Val Ser Gly Gly
                    35                  40                  45
Glu Val Trp Arg Leu Cys Lys Ala Gly Arg Leu Arg Glu Ala Ile Gln
            50                  55                  60
Leu Leu Gly Ile Ile Lys Gln Arg Gly Leu Leu Val Asn Ser Asn Thr
65                  70                  75                  80
Tyr Gly Cys Val Ile Glu His Cys Ala Lys Ala Arg Arg Phe Glu Asp
                    85                  90                  95
Gly Lys Met Val His Lys Gln Leu Asp Glu Leu Gly Val Glu Ile Asp
                    100                 105                 110
Ile Tyr Leu Gly Asn Ser Leu Ile Asn Phe Tyr Ser Lys Phe Glu Asp
                    115                 120                 125
Val Ala Ser Ala Glu Gln Val Phe Arg Arg Met Thr Leu Arg Asp Val
            130                 135                 140
Val Thr Trp Ser Ser Met Ile Ala Ala Tyr Ala Gly Asn Asn His Pro
145                 150                 155                 160
Ala Lys Ala Phe Asp Thr Phe Glu Arg Met Thr Asp Ala Asn Ile Glu
                    165                 170                 175
Pro Asn Arg Ile Thr Phe Leu Ser Ile Leu Lys Ala Cys Asn Asn Tyr
                    180                 185                 190
Ser Ile Leu Glu Lys Gly Arg Lys Ile His Thr Ile Val Lys Ala Met
```

-continued

```
            195                 200                 205
Gly Met Glu Thr Asp Val Ala Val Ala Thr Ala Leu Ile Thr Met Tyr
210                 215                 220

Ser Lys Cys Gly Glu Ile Ser Val Ala Cys Glu Val Phe His Lys Met
225                 230                 235                 240

Thr Glu Arg Asn Val Val Ser Trp Thr Ala Ile Ile Gln Ala Asn Ala
                245                 250                 255

Gln His Arg Lys Leu Asn Glu Ala Phe Glu Leu Tyr Glu Gln Met Leu
                260                 265                 270

Gln Ala Gly Ile Ser Pro Asn Ala Val Thr Phe Val Ser Leu Leu Asn
                275                 280                 285

Ser Cys Asn Thr Pro Glu Ala Leu Asn Arg Gly Arg Arg Ile His Ser
290                 295                 300

His Ile Ser Glu Arg Gly Leu Glu Thr Asp Met Ile Val Ala Asn Ala
305                 310                 315                 320

Leu Ile Thr Met Tyr Cys Lys Cys Asn Ser Val Gln Glu Ala Arg Glu
                325                 330                 335

Ile Phe Asp Arg Met Ser Lys Arg Asp Val Ile Ser Trp Ser Ala Met
                340                 345                 350

Ile Ala Gly Tyr Ala Gln Ser Gly Tyr Lys Asp Lys Glu Ser Ile Asp
                355                 360                 365

Glu Val Phe Gln Leu Leu Glu Arg Met Arg Glu Gly Val Phe Pro
370                 375                 380

Asn Lys Val Thr Phe Met Ser Ile Leu Arg Ala Cys Thr Ala His Gly
385                 390                 395                 400

Ala Leu Glu Gln Gly Arg Gln Ile His Ala Glu Leu Ser Lys Val Gly
                405                 410                 415

Phe Glu Leu Asp Arg Ser Leu Gln Thr Ala Ile Phe Asn Met Tyr Ala
                420                 425                 430

Lys Cys Gly Ser Ile Tyr Glu Ala Glu Gln Val Phe Ser Lys Met Ala
                435                 440                 445

Asn Lys Asn Val Val Ala Trp Thr Ser Phe Leu Ser Met Tyr Ile Lys
                450                 455                 460

Cys Gly Asp Leu Ser Ser Ala Glu Lys Val Phe Ser Glu Met Pro Thr
465                 470                 475                 480

Arg Asn Val Val Ser Trp Asn Leu Met Ile Ala Gly Tyr Ala Gln Asn
                485                 490                 495

Gly Asp Ile Val Lys Val Phe Glu Leu Leu Ser Ser Met Lys Ala Glu
                500                 505                 510

Gly Phe Gln Pro Asp Arg Val Thr Val Ile Thr Ile Leu Glu Ala Cys
                515                 520                 525

Gly Ala Leu Ala Gly Leu Glu Arg Gly Lys Leu Val His Ala Glu Ala
530                 535                 540

Val Lys Leu Gly Leu Glu Ser Asp Thr Val Ala Thr Ser Leu Ile
545                 550                 555                 560

Gly Met Tyr Ser Lys Cys Gly Gln Val Ala Glu Ala Arg Thr Val Phe
                565                 570                 575

Asp Lys Met Ser Asn Arg Asp Thr Val Ala Trp Asn Ala Met Leu Ala
                580                 585                 590

Gly Tyr Gly Gln His Gly Asp Gly Leu Glu Ala Val Asp Leu Phe Lys
                595                 600                 605

Arg Met Leu Lys Glu Arg Val Ser Pro Asn Glu Ile Thr Leu Thr Ala
610                 615                 620
```

Val Ile Ser Ala Cys Ser Arg Ala Gly Leu Val Gln Glu Gly Arg Glu
625                 630                 635                 640

Ile Phe Arg Met Met Gln Glu Asp Phe Lys Met Thr Pro Arg Lys Gln
            645                 650                 655

His Tyr Gly Cys Met Val Asp Leu Leu Gly Arg Ala Gly Arg Leu Gln
        660                 665                 670

Glu Ala Glu Glu Phe Ile Gln Ser Met Pro Cys Glu Pro Asp Ile Ser
    675                 680                 685

Val Trp His Ala Leu Leu Gly Ala Cys Lys Ser His Asn Asn Val Gln
690                 695                 700

Leu Ala Glu Arg Ala Ala His His Ile Leu Leu Glu Pro Ser Tyr
705                 710                 715                 720

Ala Ser Val Tyr Ile Thr Leu Ser Asn Ile Tyr Ala Gln Ala Gly Arg
            725                 730                 735

Trp Asp Asp Ser Thr Lys Val Arg Arg Val Met Asp Asp Arg Gly Leu
        740                 745                 750

Lys Lys Asp Arg Gly Glu Ser Ser Ile Glu Ile Asp Gly Arg Ile His
    755                 760                 765

Thr Phe Val Ala Glu Asp Cys Ala His Pro Gly Ile Asp Ala Ile His
770                 775                 780

Ala Glu Leu Glu Thr Leu Thr Lys Glu Met Lys Glu Ala Gly Tyr Thr
785                 790                 795                 800

Pro Asp Met Arg Phe Val Leu His Asp Val Asp Asp Val Gln Lys Glu
            805                 810                 815

Lys Ala Leu Cys His His Ser Glu Lys Leu Ala Ile Ala Tyr Gly Leu
        820                 825                 830

Leu Lys Thr Pro Ser Gly Thr Pro Ile Arg Ile Met Lys Asn Leu Arg
    835                 840                 845

Val Cys Gly Asp Cys His Thr Ala Thr Lys Phe Ile Ser Lys Ile Arg
850                 855                 860

Lys Arg Glu Ile Val Ala Arg Asp Ala Asn Arg Phe His Tyr Phe Asn
865                 870                 875                 880

Asn Gly Thr Cys Ser Cys Gly Asp Phe Trp
            885                 890

<210> SEQ ID NO 32
<211> LENGTH: 31
<212> TYPE: RNA
<213> ORGANISM: Physcomitrella patens

<400> SEQUENCE: 32
cuauagguau uggaaacgua uuuaguucuu c                                   31

<210> SEQ ID NO 33
<211> LENGTH: 31
<212> TYPE: RNA
<213> ORGANISM: Physcomitrella patens

<400> SEQUENCE: 33
cuauuucaau gguuggluaag uagagauguu c                                   31

<210> SEQ ID NO 34
<211> LENGTH: 31
<212> TYPE: RNA
<213> ORGANISM: Physcomitrella patens

<400> SEQUENCE: 34

```
guagagaugu uuccacaggu gcuccuuuuu c                                31

<210> SEQ ID NO 35
<211> LENGTH: 31
<212> TYPE: RNA
<213> ORGANISM: Physcomitrella patens

<400> SEQUENCE: 35
aucccgaucc ugaggucuau auucuaauuu c                                31

<210> SEQ ID NO 36
<211> LENGTH: 31
<212> TYPE: RNA
<213> ORGANISM: Physcomitrella patens

<400> SEQUENCE: 36
acaauuacua ucaaagcuau uggacaucaa c                                31

<210> SEQ ID NO 37
<211> LENGTH: 31
<212> TYPE: RNA
<213> ORGANISM: Physcomitrella patens

<400> SEQUENCE: 37
cacuuuggcu uugaagcagc ugcuuggua c                                 31

<210> SEQ ID NO 38
<211> LENGTH: 31
<212> TYPE: RNA
<213> ORGANISM: Physcomitrella patens

<400> SEQUENCE: 38
uuauuauauu ugauuuggaa gucaccuuuu c                                31

<210> SEQ ID NO 39
<211> LENGTH: 31
<212> TYPE: RNA
<213> ORGANISM: Physcomitrella patens

<400> SEQUENCE: 39
auuuuuauau agguauagac gguaucucuu c                                31

<210> SEQ ID NO 40
<211> LENGTH: 31
<212> TYPE: RNA
<213> ORGANISM: Physcomitrella patens

<400> SEQUENCE: 40
caaacaguag acuuucgac uauuuuugcu c                                 31

<210> SEQ ID NO 41
<211> LENGTH: 31
<212> TYPE: RNA
<213> ORGANISM: Physcomitrella patens

<400> SEQUENCE: 41
ggaaaaucug cacaaauagg auugcauacu c                                31

<210> SEQ ID NO 42
<211> LENGTH: 31
<212> TYPE: RNA
<213> ORGANISM: Physcomitrella patens
```

```
<400> SEQUENCE: 42
cuaaaacaaa uauuuaaua auaaaaaaau c                                31

<210> SEQ ID NO 43
<211> LENGTH: 31
<212> TYPE: RNA
<213> ORGANISM: Physcomitrella patens

<400> SEQUENCE: 43
aaaacaaaua uuuuaauaau aaaaaaauca c                               31

<210> SEQ ID NO 44
<211> LENGTH: 31
<212> TYPE: RNA
<213> ORGANISM: Physcomitrella patens

<400> SEQUENCE: 44
aucaaauacg uuaugaauau uuuuuaaagu c                               31

<210> SEQ ID NO 45
<211> LENGTH: 31
<212> TYPE: RNA
<213> ORGANISM: Arabidopsis thaliana

<400> SEQUENCE: 45
aaaugaguag uucagaaaga aucgagcuuu c                               31

<210> SEQ ID NO 46
<211> LENGTH: 31
<212> TYPE: RNA
<213> ORGANISM: Arabidopsis thaliana

<400> SEQUENCE: 46
uuuuuuuuau cgauauucuu guuuacuacu c                               31

<210> SEQ ID NO 47
<211> LENGTH: 31
<212> TYPE: RNA
<213> ORGANISM: Arabidopsis thaliana

<400> SEQUENCE: 47
gauuuaauac cgauauuuua gcaacaaauc c                               31

<210> SEQ ID NO 48
<211> LENGTH: 31
<212> TYPE: RNA
<213> ORGANISM: Arabidopsis thaliana

<400> SEQUENCE: 48
guuuuuaugu cagcaacaga agcccaagcu c                               31

<210> SEQ ID NO 49
<211> LENGTH: 31
<212> TYPE: RNA
<213> ORGANISM: Arabidopsis thaliana

<400> SEQUENCE: 49
ccaagauuuu ucuuguucuu auauaauucu c                               31

<210> SEQ ID NO 50
<211> LENGTH: 31
<212> TYPE: RNA
<213> ORGANISM: Arabidopsis thaliana
```

-continued

<400> SEQUENCE: 50
ugauuguaug ugugauagca ucuacuauac c                                    31

<210> SEQ ID NO 51
<211> LENGTH: 31
<212> TYPE: RNA
<213> ORGANISM: Arabidopsis thaliana

<400> SEQUENCE: 51
ccuccacuag cagguuuuuu uggaaaacuc c                                    31

<210> SEQ ID NO 52
<211> LENGTH: 31
<212> TYPE: RNA
<213> ORGANISM: Arabidopsis thaliana

<400> SEQUENCE: 52
cucgaauuuu cgauauuccu uuuuauuucu c                                    31

<210> SEQ ID NO 53
<211> LENGTH: 31
<212> TYPE: RNA
<213> ORGANISM: Arabidopsis thaliana

<400> SEQUENCE: 53
cuguuacuuc gaaaguagcu gcuucagcuu c                                    31

<210> SEQ ID NO 54
<211> LENGTH: 31
<212> TYPE: RNA
<213> ORGANISM: Arabidopsis thaliana

<400> SEQUENCE: 54
uucuuucugu uacuucgaaa guagcugcuu c                                    31

<210> SEQ ID NO 55
<211> LENGTH: 31
<212> TYPE: RNA
<213> ORGANISM: Arabidopsis thaliana

<400> SEQUENCE: 55
gaauuggguu caagcuuucc cuagccccuu c                                    31

<210> SEQ ID NO 56
<211> LENGTH: 31
<212> TYPE: RNA
<213> ORGANISM: Arabidopsis thaliana

<400> SEQUENCE: 56
augggugggg caagcucuuc uauucgguu c                                     31

<210> SEQ ID NO 57
<211> LENGTH: 31
<212> TYPE: RNA
<213> ORGANISM: Arabidopsis thaliana

<400> SEQUENCE: 57
cuaacgauuu aauaacuauc uuuguagcuc c                                    31

<210> SEQ ID NO 58
<211> LENGTH: 31
<212> TYPE: RNA

<213> ORGANISM: Arabidopsis thaliana

<400> SEQUENCE: 58
uuggccuaau ucuucuucug augaucgauu c                               31

<210> SEQ ID NO 59
<211> LENGTH: 31
<212> TYPE: RNA
<213> ORGANISM: Arabidopsis thaliana

<400> SEQUENCE: 59
uccaaauaau uuaugcagcu ucaacaucuc c                               31

<210> SEQ ID NO 60
<211> LENGTH: 31
<212> TYPE: RNA
<213> ORGANISM: Arabidopsis thaliana

<400> SEQUENCE: 60
ucgguacaau ccaaauaauu uaugcagcuu c                               31

<210> SEQ ID NO 61
<211> LENGTH: 31
<212> TYPE: RNA
<213> ORGANISM: Arabidopsis thaliana

<400> SEQUENCE: 61
uuggauuucu uauugcuuuu gccgucaaau c                               31

<210> SEQ ID NO 62
<211> LENGTH: 31
<212> TYPE: RNA
<213> ORGANISM: Arabidopsis thaliana

<400> SEQUENCE: 62
uguuagcaau guacagcggu caaauaggau c                               31

<210> SEQ ID NO 63
<211> LENGTH: 31
<212> TYPE: RNA
<213> ORGANISM: Arabidopsis thaliana

<400> SEQUENCE: 63
cuuuggaccu gguguaucuu gucuuuacca c                               31

<210> SEQ ID NO 64
<211> LENGTH: 31
<212> TYPE: RNA
<213> ORGANISM: Arabidopsis thaliana

<400> SEQUENCE: 64
acuuuaucga uccacuuacu ucuauuaugu c                               31

<210> SEQ ID NO 65
<211> LENGTH: 31
<212> TYPE: RNA
<213> ORGANISM: Arabidopsis thaliana

<400> SEQUENCE: 65
uacaugauuu ucuuuuaguu uuucugggau c                               31

<210> SEQ ID NO 66
<211> LENGTH: 31

```
<212> TYPE: RNA
<213> ORGANISM: Arabidopsis thaliana

<400> SEQUENCE: 66
aaaaacauau uuuauugagu cccuucaugc c                              31

<210> SEQ ID NO 67
<211> LENGTH: 31
<212> TYPE: RNA
<213> ORGANISM: Arabidopsis thaliana

<400> SEQUENCE: 67
ggcauuccau uaauaacagg ccguuuugau c                              31

<210> SEQ ID NO 68
<211> LENGTH: 31
<212> TYPE: RNA
<213> ORGANISM: Arabidopsis thaliana

<400> SEQUENCE: 68
cuguucaugg acuagcugua ccuaccguuu c                              31

<210> SEQ ID NO 69
<211> LENGTH: 31
<212> TYPE: RNA
<213> ORGANISM: Arabidopsis thaliana

<400> SEQUENCE: 69
uggcaguuuu ugcauuaauu auuacuucau c                              31

<210> SEQ ID NO 70
<211> LENGTH: 31
<212> TYPE: RNA
<213> ORGANISM: Arabidopsis thaliana

<400> SEQUENCE: 70
aucaauauac uuuuaauguc gaaucaggau c                              31

<210> SEQ ID NO 71
<211> LENGTH: 31
<212> TYPE: RNA
<213> ORGANISM: Arabidopsis thaliana

<400> SEQUENCE: 71
uagaaggaac auguauuaca cgugcaaaau c                              31

<210> SEQ ID NO 72
<211> LENGTH: 31
<212> TYPE: RNA
<213> ORGANISM: Arabidopsis thaliana

<400> SEQUENCE: 72
auaacccaga aauaauucgu guauauauuu c                              31

<210> SEQ ID NO 73
<211> LENGTH: 31
<212> TYPE: RNA
<213> ORGANISM: Arabidopsis thaliana

<400> SEQUENCE: 73
ggaaacaaaa aauaucuauu cuaguucuau c                              31

<210> SEQ ID NO 74
```

```
<211> LENGTH: 31
<212> TYPE: RNA
<213> ORGANISM: Arabidopsis thaliana

<400> SEQUENCE: 74
acauuccuuu aaugaauucc cuuggaacuu c                              31

<210> SEQ ID NO 75
<211> LENGTH: 31
<212> TYPE: RNA
<213> ORGANISM: Arabidopsis thaliana

<400> SEQUENCE: 75
aaaaaccuac uuucuuacga uuacgagguu c                              31

<210> SEQ ID NO 76
<211> LENGTH: 31
<212> TYPE: RNA
<213> ORGANISM: Arabidopsis thaliana

<400> SEQUENCE: 76
gacauaaaaa ggaaauucuu uuugaaauau c                              31

<210> SEQ ID NO 77
<211> LENGTH: 31
<212> TYPE: RNA
<213> ORGANISM: Arabidopsis thaliana

<400> SEQUENCE: 77
aauggaaaau ucauggaaaa uuacaauccc c                              31

<210> SEQ ID NO 78
<211> LENGTH: 31
<212> TYPE: RNA
<213> ORGANISM: Arabidopsis thaliana

<400> SEQUENCE: 78
aaaaaaaaua ucauuugauu cgucgauccu c                              31

<210> SEQ ID NO 79
<211> LENGTH: 31
<212> TYPE: RNA
<213> ORGANISM: Arabidopsis thaliana

<400> SEQUENCE: 79
uuaucgcgga auuagaccug cuauuaacgu c                              31

<210> SEQ ID NO 80
<211> LENGTH: 31
<212> TYPE: RNA
<213> ORGANISM: Arabidopsis thaliana

<400> SEQUENCE: 80
ugaaagcuau gaaacaagua ugcgguaguu c                              31

<210> SEQ ID NO 81
<211> LENGTH: 31
<212> TYPE: RNA
<213> ORGANISM: Arabidopsis thaliana

<400> SEQUENCE: 81
ucaauagagg ugcaaggcug acagaaguac c                              31
```

```
<210> SEQ ID NO 82
<211> LENGTH: 31
<212> TYPE: RNA
<213> ORGANISM: Arabidopsis thaliana

<400> SEQUENCE: 82
acagaaucuc ucaauaugag aaagccauuc c                              31

<210> SEQ ID NO 83
<211> LENGTH: 31
<212> TYPE: RNA
<213> ORGANISM: Arabidopsis thaliana

<400> SEQUENCE: 83
guggauuaac uaacgaaaga aaaauggaac c                              31

<210> SEQ ID NO 84
<211> LENGTH: 31
<212> TYPE: RNA
<213> ORGANISM: Arabidopsis thaliana

<400> SEQUENCE: 84
aucggaaacu ucuauuucuc auucacaaau c                              31

<210> SEQ ID NO 85
<211> LENGTH: 31
<212> TYPE: RNA
<213> ORGANISM: Arabidopsis thaliana

<400> SEQUENCE: 85
uggcgcgaaa uccaucauug gcuaaacaau c                              31

<210> SEQ ID NO 86
<211> LENGTH: 31
<212> TYPE: RNA
<213> ORGANISM: Arabidopsis thaliana

<400> SEQUENCE: 86
cucuaaccga agcuauugca uuguuugccc c                              31

<210> SEQ ID NO 87
<211> LENGTH: 31
<212> TYPE: RNA
<213> ORGANISM: Arabidopsis thaliana

<400> SEQUENCE: 87
cucaacccga gauguuagaa ggugcaaaau c                              31

<210> SEQ ID NO 88
<211> LENGTH: 31
<212> TYPE: RNA
<213> ORGANISM: Arabidopsis thaliana

<400> SEQUENCE: 88
caauaggugc cggagcugcu acaauugcuu c                              31

<210> SEQ ID NO 89
<211> LENGTH: 31
<212> TYPE: RNA
<213> ORGANISM: Arabidopsis thaliana

<400> SEQUENCE: 89
ccuuaaugcu agguuugaa aaagacuuuu c                               31
```

<210> SEQ ID NO 90
<211> LENGTH: 31
<212> TYPE: RNA
<213> ORGANISM: Arabidopsis thaliana

<400> SEQUENCE: 90
uagguuuuga aaaagacuuu ucaugucauu c                                    31

<210> SEQ ID NO 91
<211> LENGTH: 31
<212> TYPE: RNA
<213> ORGANISM: Arabidopsis thaliana

<400> SEQUENCE: 91
aaagacuuuu caugucauuc ccauuuaggu c                                    31

<210> SEQ ID NO 92
<211> LENGTH: 31
<212> TYPE: RNA
<213> ORGANISM: Arabidopsis thaliana

<400> SEQUENCE: 92
aagacuuuuc augucauucc cauuuagguc c                                    31

<210> SEQ ID NO 93
<211> LENGTH: 31
<212> TYPE: RNA
<213> ORGANISM: Arabidopsis thaliana

<400> SEQUENCE: 93
uuuucauguc auucccauuu agguccgauu c                                    31

<210> SEQ ID NO 94
<211> LENGTH: 31
<212> TYPE: RNA
<213> ORGANISM: Arabidopsis thaliana

<400> SEQUENCE: 94
augucauucc cauuuagguc cgauucggau c                                    31

<210> SEQ ID NO 95
<211> LENGTH: 31
<212> TYPE: RNA
<213> ORGANISM: Arabidopsis thaliana

<400> SEQUENCE: 95
agaagaagua aggaaaugag acgacuuuuu c                                    31

<210> SEQ ID NO 96
<211> LENGTH: 31
<212> TYPE: RNA
<213> ORGANISM: Arabidopsis thaliana

<400> SEQUENCE: 96
ugucauuccc auuuaggucc gauucggauc c                                    31

<210> SEQ ID NO 97
<211> LENGTH: 31
<212> TYPE: RNA
<213> ORGANISM: Arabidopsis thaliana

<400> SEQUENCE: 97
auucccauuu agguccgauu cggaucccuc c                                    31

```
<210> SEQ ID NO 98
<211> LENGTH: 31
<212> TYPE: RNA
<213> ORGANISM: Arabidopsis thaliana

<400> SEQUENCE: 98
uuagguccga uucggauccc uccguuguuu c                                          31

<210> SEQ ID NO 99
<211> LENGTH: 31
<212> TYPE: RNA
<213> ORGANISM: Arabidopsis thaliana

<400> SEQUENCE: 99
cgauucggau cccuccguug uuuccuuuuc c                                          31

<210> SEQ ID NO 100
<211> LENGTH: 31
<212> TYPE: RNA
<213> ORGANISM: Arabidopsis thaliana

<400> SEQUENCE: 100
auucggaucc cuccguuguu uccuuuuccu c                                          31

<210> SEQ ID NO 101
<211> LENGTH: 31
<212> TYPE: RNA
<213> ORGANISM: Arabidopsis thaliana

<400> SEQUENCE: 101
ucccuccguu guuuccuuuu ccuccugcac c                                          31

<210> SEQ ID NO 102
<211> LENGTH: 31
<212> TYPE: RNA
<213> ORGANISM: Arabidopsis thaliana

<400> SEQUENCE: 102
ccguuguuuc cuuuuccucc ugcaccuuuu c                                          31

<210> SEQ ID NO 103
<211> LENGTH: 31
<212> TYPE: RNA
<213> ORGANISM: Arabidopsis thaliana

<400> SEQUENCE: 103
cguuguuucc uuuuccuccu gcaccuuuuc c                                          31

<210> SEQ ID NO 104
<211> LENGTH: 31
<212> TYPE: RNA
<213> ORGANISM: Arabidopsis thaliana

<400> SEQUENCE: 104
gaaaugagac gacuuuuucu ugaacuauau c                                          31

<210> SEQ ID NO 105
<211> LENGTH: 31
<212> TYPE: RNA
<213> ORGANISM: Arabidopsis thaliana

<400> SEQUENCE: 105
```

```
aagauccuac uucuacaauu ggugggucac c                                31

<210> SEQ ID NO 106
<211> LENGTH: 31
<212> TYPE: RNA
<213> ORGANISM: Arabidopsis thaliana

<400> SEQUENCE: 106
uugguggguc accggguuau ucaaauaagu c                                31

<210> SEQ ID NO 107
<211> LENGTH: 31
<212> TYPE: RNA
<213> ORGANISM: Arabidopsis thaliana

<400> SEQUENCE: 107
uuuucugugg uuuucccaug uuacaacuuu c                                31

<210> SEQ ID NO 108
<211> LENGTH: 31
<212> TYPE: RNA
<213> ORGANISM: Arabidopsis thaliana

<400> SEQUENCE: 108
ucguaccaau ucggucgauc cggaauggau c                                31

<210> SEQ ID NO 109
<211> LENGTH: 31
<212> TYPE: RNA
<213> ORGANISM: Arabidopsis thaliana

<400> SEQUENCE: 109
ggucgauccg gaauggaucg guuaaacauu c                                31

<210> SEQ ID NO 110
<211> LENGTH: 31
<212> TYPE: RNA
<213> ORGANISM: Arabidopsis thaliana

<400> SEQUENCE: 110
gucgauccgg aauggaucgg uuaaacauuc c                                31

<210> SEQ ID NO 111
<211> LENGTH: 31
<212> TYPE: RNA
<213> ORGANISM: Arabidopsis thaliana

<400> SEQUENCE: 111
auuccauuag ggagccuggu cuugacucuu c                                31

<210> SEQ ID NO 112
<211> LENGTH: 31
<212> TYPE: RNA
<213> ORGANISM: Arabidopsis thaliana

<400> SEQUENCE: 112
gucuugacuc uucugugugg uauucauucu c                                31

<210> SEQ ID NO 113
<211> LENGTH: 31
<212> TYPE: RNA
<213> ORGANISM: Arabidopsis thaliana

<400> SEQUENCE: 113
```
ugacucuucu gugugguauu cauucucguu c                                    31

<210> SEQ ID NO 114
<211> LENGTH: 31
<212> TYPE: RNA
<213> ORGANISM: Arabidopsis thaliana

<400> SEQUENCE: 114
gaaucacauc cagcaguggu uggaacagcu c                                    31

<210> SEQ ID NO 115
<211> LENGTH: 31
<212> TYPE: RNA
<213> ORGANISM: Arabidopsis thaliana

<400> SEQUENCE: 115
uccagcagug guuggaacag cucgcaaaau c                                    31

<210> SEQ ID NO 116
<211> LENGTH: 31
<212> TYPE: RNA
<213> ORGANISM: Arabidopsis thaliana

<400> SEQUENCE: 116
ccagcagugg uuggaacagc ucgcaaaauc c                                    31

<210> SEQ ID NO 117
<211> LENGTH: 31
<212> TYPE: RNA
<213> ORGANISM: Arabidopsis thaliana

<400> SEQUENCE: 117
guuggaacag cucgcaaaau ccaaccacuu c                                    31

<210> SEQ ID NO 118
<211> LENGTH: 31
<212> TYPE: RNA
<213> ORGANISM: Arabidopsis thaliana

<400> SEQUENCE: 118
cuucaccuac uuuauugccc cuaaccguuu c                                    31

<210> SEQ ID NO 119
<211> LENGTH: 31
<212> TYPE: RNA
<213> ORGANISM: Arabidopsis thaliana

<400> SEQUENCE: 119
ucaccuacuu uauugccccu aaccguuucu c                                    31

<210> SEQ ID NO 120
<211> LENGTH: 31
<212> TYPE: RNA
<213> ORGANISM: Arabidopsis thaliana

<400> SEQUENCE: 120
cuauugaaac agaauggucu cauguucuuu c                                    31

<210> SEQ ID NO 121
<211> LENGTH: 31
<212> TYPE: RNA
<213> ORGANISM: Arabidopsis thaliana

```
<400> SEQUENCE: 121
uugaaacaga augguucau guucuuucau c                              31

<210> SEQ ID NO 122
<211> LENGTH: 31
<212> TYPE: RNA
<213> ORGANISM: Arabidopsis thaliana

<400> SEQUENCE: 122
gguuucaugu cuuucaucg auugguuauu c                              31

<210> SEQ ID NO 123
<211> LENGTH: 31
<212> TYPE: RNA
<213> ORGANISM: Arabidopsis thaliana

<400> SEQUENCE: 123
uucauguucu uucaucgauu gguuauuccu c                             31

<210> SEQ ID NO 124
<211> LENGTH: 31
<212> TYPE: RNA
<213> ORGANISM: Arabidopsis thaliana

<400> SEQUENCE: 124
ucuccuccac accaaucacg aguuuucuu c                              31

<210> SEQ ID NO 125
<211> LENGTH: 31
<212> TYPE: RNA
<213> ORGANISM: Arabidopsis thaliana

<400> SEQUENCE: 125
cuccacacca aucacgaguu uucuucauu c                              31

<210> SEQ ID NO 126
<211> LENGTH: 31
<212> TYPE: RNA
<213> ORGANISM: Arabidopsis thaliana

<400> SEQUENCE: 126
cacaccaauc acgaguuuuu cuucauuccu c                             31

<210> SEQ ID NO 127
<211> LENGTH: 31
<212> TYPE: RNA
<213> ORGANISM: Arabidopsis thaliana

<400> SEQUENCE: 127
caccaaucac gaguuuuucu ucauccucu c                              31

<210> SEQ ID NO 128
<211> LENGTH: 31
<212> TYPE: RNA
<213> ORGANISM: Arabidopsis thaliana

<400> SEQUENCE: 128
ucuugguugu cuuaacagc gauggcuauu c                              31

<210> SEQ ID NO 129
<211> LENGTH: 31
<212> TYPE: RNA
<213> ORGANISM: Arabidopsis thaliana
```

```
<400> SEQUENCE: 129
cauuuaaguc uuggguagc accacuagau c                              31

<210> SEQ ID NO 130
<211> LENGTH: 31
<212> TYPE: RNA
<213> ORGANISM: Arabidopsis thaliana

<400> SEQUENCE: 130
auucucguau ucucuaugua cauguccug c                              31

<210> SEQ ID NO 131
<211> LENGTH: 31
<212> TYPE: RNA
<213> ORGANISM: Arabidopsis thaliana

<400> SEQUENCE: 131
cguauucucu auguacaugu uccugcggcu c                             31

<210> SEQ ID NO 132
<211> LENGTH: 31
<212> TYPE: RNA
<213> ORGANISM: Arabidopsis thaliana

<400> SEQUENCE: 132
uuccuauuaa caaaacaucc ccuuuaucuu c                             31

<210> SEQ ID NO 133
<211> LENGTH: 31
<212> TYPE: RNA
<213> ORGANISM: Arabidopsis thaliana

<400> SEQUENCE: 133
acguuguuua ccuuaguuac uggggguuu c                              31

<210> SEQ ID NO 134
<211> LENGTH: 31
<212> TYPE: RNA
<213> ORGANISM: Arabidopsis thaliana

<400> SEQUENCE: 134
gggaugcucg uuugaccucu guauucaucu c                             31

<210> SEQ ID NO 135
<211> LENGTH: 31
<212> TYPE: RNA
<213> ORGANISM: Arabidopsis thaliana

<400> SEQUENCE: 135
gcucguuuga ccucuguauu caucucguuu c                             31

<210> SEQ ID NO 136
<211> LENGTH: 31
<212> TYPE: RNA
<213> ORGANISM: Arabidopsis thaliana

<400> SEQUENCE: 136
aucucguuuc uuauuuaccu ggugcacug c                              31

<210> SEQ ID NO 137
<211> LENGTH: 31
<212> TYPE: RNA
```

```
<213> ORGANISM: Arabidopsis thaliana

<400> SEQUENCE: 137
cacugcguuu ucaaaagcuu ccugucgaac c                              31

<210> SEQ ID NO 138
<211> LENGTH: 31
<212> TYPE: RNA
<213> ORGANISM: Arabidopsis thaliana

<400> SEQUENCE: 138
aaaagcuucc ugucgaaccg gcuucuauuu c                              31

<210> SEQ ID NO 139
<211> LENGTH: 31
<212> TYPE: RNA
<213> ORGANISM: Arabidopsis thaliana

<400> SEQUENCE: 139
cuuccugucg aaccggcuuc uauuucaauu c                              31

<210> SEQ ID NO 140
<211> LENGTH: 31
<212> TYPE: RNA
<213> ORGANISM: Arabidopsis thaliana

<400> SEQUENCE: 140
cugucgaacc ggcuucuauu ucaauucgug c                              31

<210> SEQ ID NO 141
<211> LENGTH: 31
<212> TYPE: RNA
<213> ORGANISM: Arabidopsis thaliana

<400> SEQUENCE: 141
aaccggcuuc uauuucaauu cgugcuggac c                              31

<210> SEQ ID NO 142
<211> LENGTH: 31
<212> TYPE: RNA
<213> ORGANISM: Arabidopsis thaliana

<400> SEQUENCE: 142
ggcuucuauu ucaauucgug cuggaccgau c                              31

<210> SEQ ID NO 143
<211> LENGTH: 31
<212> TYPE: RNA
<213> ORGANISM: Arabidopsis thaliana

<400> SEQUENCE: 143
cuggaccgau cgauauacca auaauaaagu c                              31

<210> SEQ ID NO 144
<211> LENGTH: 31
<212> TYPE: RNA
<213> ORGANISM: Arabidopsis thaliana

<400> SEQUENCE: 144 uaaagcuuc agucaacugg uggaauacau c                               31

<210> SEQ ID NO 145
<211> LENGTH: 31
```

```
<212> TYPE: RNA
<213> ORGANISM: Arabidopsis thaliana

<400> SEQUENCE: 145
caucgcauca accugggagc auuagccgau c                              31

<210> SEQ ID NO 146
<211> LENGTH: 31
<212> TYPE: RNA
<213> ORGANISM: Arabidopsis thaliana

<400> SEQUENCE: 146
auuagccgau cugguacauc aauacauguu c                              31

<210> SEQ ID NO 147
<211> LENGTH: 31
<212> TYPE: RNA
<213> ORGANISM: Arabidopsis thaliana

<400> SEQUENCE: 147 gaucgguac aucaauacau guuccuaugc c                               31

<210> SEQ ID NO 148
<211> LENGTH: 31
<212> TYPE: RNA
<213> ORGANISM: Arabidopsis thaliana

<400> SEQUENCE: 148
uuccaaucuu gucuaacuuu gcuaacuucc c                              31

<210> SEQ ID NO 149
<211> LENGTH: 31
<212> TYPE: RNA
<213> ORGANISM: Arabidopsis thaliana

<400> SEQUENCE: 149
ucuugucuaa cuuugcuaac uuccccuucu c                              31

<210> SEQ ID NO 150
<211> LENGTH: 31
<212> TYPE: RNA
<213> ORGANISM: Arabidopsis thaliana

<400> SEQUENCE: 150
gucuaacuuu gcuaacuucc ccuucucaac c                              31

<210> SEQ ID NO 151
<211> LENGTH: 31
<212> TYPE: RNA
<213> ORGANISM: Arabidopsis thaliana

<400> SEQUENCE: 151
ucuaacuuug cuaacuuccc cuucucaacc c                              31

<210> SEQ ID NO 152
<211> LENGTH: 31
<212> TYPE: RNA
<213> ORGANISM: Arabidopsis thaliana

<400> SEQUENCE: 152
cuuugcuaac uuccccuucu caacccguau c                              31

<210> SEQ ID NO 153
```

<211> LENGTH: 31
<212> TYPE: RNA
<213> ORGANISM: Arabidopsis thaliana

<400> SEQUENCE: 153
guaucuuguu uguucuggaa acacgucuuc c                                           31

<210> SEQ ID NO 154
<211> LENGTH: 31
<212> TYPE: RNA
<213> ORGANISM: Arabidopsis thaliana

<400> SEQUENCE: 154
uguuuguucu ggaaacacgu cuuccuauuc c                                           31

<210> SEQ ID NO 155
<211> LENGTH: 31
<212> TYPE: RNA
<213> ORGANISM: Arabidopsis thaliana

<400> SEQUENCE: 155
cgucuuccua uuccaucuuu ucucgaaucu c                                           31

<210> SEQ ID NO 156
<211> LENGTH: 31
<212> TYPE: RNA
<213> ORGANISM: Arabidopsis thaliana

<400> SEQUENCE: 156
cuauugaaau gguucgucag uagagauguu c                                           31

<210> SEQ ID NO 157
<211> LENGTH: 31
<212> TYPE: RNA
<213> ORGANISM: Arabidopsis thaliana

<400> SEQUENCE: 157
agcacggcug aaguggcuau acauacaaau c                                           31

<210> SEQ ID NO 158
<211> LENGTH: 31
<212> TYPE: RNA
<213> ORGANISM: Arabidopsis thaliana

<400> SEQUENCE: 158
auacaaaucu auuuacggau cuauaugcuu c                                           31

<210> SEQ ID NO 159
<211> LENGTH: 31
<212> TYPE: RNA
<213> ORGANISM: Arabidopsis thaliana

<400> SEQUENCE: 159 aaguccaga acaggagguu gguauaccac c                                            31

<210> SEQ ID NO 160
<211> LENGTH: 31
<212> TYPE: RNA
<213> ORGANISM: Arabidopsis thaliana

<400> SEQUENCE: 160
guagagaugu ucccacgggu gccccuuuuu c                                           31

-continued

<210> SEQ ID NO 161
<211> LENGTH: 31
<212> TYPE: RNA
<213> ORGANISM: Arabidopsis thaliana

<400> SEQUENCE: 161
uagagauguu cccacgggug ccccuuuuuc c                                  31

<210> SEQ ID NO 162
<211> LENGTH: 31
<212> TYPE: RNA
<213> ORGANISM: Arabidopsis thaliana

<400> SEQUENCE: 162
auaaugaaac ugccuuuuau uuuuuuauu c                                   31

<210> SEQ ID NO 163
<211> LENGTH: 31
<212> TYPE: RNA
<213> ORGANISM: Arabidopsis thaliana

<400> SEQUENCE: 163
uaggauuuau guuggcuucg uugggaggcu c                                  31

<210> SEQ ID NO 164
<211> LENGTH: 31
<212> TYPE: RNA
<213> ORGANISM: Arabidopsis thaliana

<400> SEQUENCE: 164
cagcuccaaa aggauaaguu gcguuggaau c                                  31

<210> SEQ ID NO 165
<211> LENGTH: 31
<212> TYPE: RNA
<213> ORGANISM: Arabidopsis thaliana

<400> SEQUENCE: 165
cuuuuuccaa ugguacuaua auccuauuc c                                   31

<210> SEQ ID NO 166
<211> LENGTH: 31
<212> TYPE: RNA
<213> ORGANISM: Arabidopsis thaliana

<400> SEQUENCE: 166
augguacuau aauuccuauu ccuaucucuu c                                  31

<210> SEQ ID NO 167
<211> LENGTH: 31
<212> TYPE: RNA
<213> ORGANISM: Arabidopsis thaliana

<400> SEQUENCE: 167
acauaaauuc cuauuccuau cucuucauuc c                                  31

<210> SEQ ID NO 168
<211> LENGTH: 31
<212> TYPE: RNA
<213> ORGANISM: Arabidopsis thaliana

<400> SEQUENCE: 168
ccuaucucuu cauucccucu uuuggucuau c                                  31

<210> SEQ ID NO 169
<211> LENGTH: 31
<212> TYPE: RNA
<213> ORGANISM: Arabidopsis thaliana

<400> SEQUENCE: 169
cuuauuuuuu uucguucccg uucuucauuu c              31

<210> SEQ ID NO 170
<211> LENGTH: 31
<212> TYPE: RNA
<213> ORGANISM: Arabidopsis thaliana

<400> SEQUENCE: 170
uuauuuuuuu ucguucccgu ucuucauuuc c              31

<210> SEQ ID NO 171
<211> LENGTH: 31
<212> TYPE: RNA
<213> ORGANISM: Arabidopsis thaliana

<400> SEQUENCE: 171 caaggggac uucucauauu uagaaucuuu c               31

<210> SEQ ID NO 172
<211> LENGTH: 31
<212> TYPE: RNA
<213> ORGANISM: Arabidopsis thaliana

<400> SEQUENCE: 172
uucugcggug ugcucuguuu acuauucuuu c              31

<210> SEQ ID NO 173
<211> LENGTH: 31
<212> TYPE: RNA
<213> ORGANISM: Arabidopsis thaliana

<400> SEQUENCE: 173
gugcucuguu uacuauucuu ucguacuuuc c              31

<210> SEQ ID NO 174
<211> LENGTH: 31
<212> TYPE: RNA
<213> ORGANISM: Arabidopsis thaliana

<400> SEQUENCE: 174
uuuucuuuuu uauuauuuuu auggucgugc c              31

<210> SEQ ID NO 175
<211> LENGTH: 31
<212> TYPE: RNA
<213> ORGANISM: Arabidopsis thaliana

<400> SEQUENCE: 175 gcaccccau uuagauuuag aaagaagggu c               31

<210> SEQ ID NO 176
<211> LENGTH: 31
<212> TYPE: RNA
<213> ORGANISM: Arabidopsis thaliana

<400> SEQUENCE: 176
uccauuugug ggaauuugau gaucuauaaa c              31

<210> SEQ ID NO 177
<211> LENGTH: 31
<212> TYPE: RNA
<213> ORGANISM: Arabidopsis thaliana

<400> SEQUENCE: 177
agaaacaacc accagcguuu ggugcagcac c                           31

<210> SEQ ID NO 178
<211> LENGTH: 31
<212> TYPE: RNA
<213> ORGANISM: Arabidopsis thaliana

<400> SEQUENCE: 178
ggugcauucu ucuuucuuuc cuuggucuuu c                           31

<210> SEQ ID NO 179
<211> LENGTH: 31
<212> TYPE: RNA
<213> ORGANISM: Arabidopsis thaliana

<400> SEQUENCE: 179
ucuuuccuug gucuuucguu cugucauauu c                           31

<210> SEQ ID NO 180
<211> LENGTH: 31
<212> TYPE: RNA
<213> ORGANISM: Arabidopsis thaliana

<400> SEQUENCE: 180
ccaauuacaa cguauuaacc gcuaaugcac c                           31

<210> SEQ ID NO 181
<211> LENGTH: 31
<212> TYPE: RNA
<213> ORGANISM: Arabidopsis thaliana

<400> SEQUENCE: 181
aaucaugagg guaguauuuu auuauggugu c                           31

<210> SEQ ID NO 182
<211> LENGTH: 31
<212> TYPE: RNA
<213> ORGANISM: Arabidopsis thaliana

<400> SEQUENCE: 182
aggguaguau uuuauuaugg ugucggaucc c                           31

<210> SEQ ID NO 183
<211> LENGTH: 31
<212> TYPE: RNA
<213> ORGANISM: Arabidopsis thaliana

<400> SEQUENCE: 183
ugucggaucc caaauuuuua uggauuuuuu c                           31

<210> SEQ ID NO 184
<211> LENGTH: 31
<212> TYPE: RNA
<213> ORGANISM: Arabidopsis thaliana

<400> SEQUENCE: 184

-continued cagagccaua augucuuaaa acaaggaggc c    31

<210> SEQ ID NO 185
<211> LENGTH: 31
<212> TYPE: RNA
<213> ORGANISM: Arabidopsis thaliana

<400> SEQUENCE: 185
auagggaaag ucuuuuuuuu uuuuugucu c    31

<210> SEQ ID NO 186
<211> LENGTH: 31
<212> TYPE: RNA
<213> ORGANISM: Arabidopsis thaliana

<400> SEQUENCE: 186
aagucuuuuu uuuuuuuug ucucgaacuu c    31

<210> SEQ ID NO 187
<211> LENGTH: 31
<212> TYPE: RNA
<213> ORGANISM: Arabidopsis thaliana

<400> SEQUENCE: 187
acuucgugaa gaacucaauu uuaucucucc c    31

<210> SEQ ID NO 188
<211> LENGTH: 31
<212> TYPE: RNA
<213> ORGANISM: Arabidopsis thaliana

<400> SEQUENCE: 188
uauaugaauu cuuucauuau ucguuauuuc c    31

<210> SEQ ID NO 189
<211> LENGTH: 31
<212> TYPE: RNA
<213> ORGANISM: Arabidopsis thaliana

<400> SEQUENCE: 189
guucuacgaa cccuuguuga uucugaacuu c    31

<210> SEQ ID NO 190
<211> LENGTH: 31
<212> TYPE: RNA
<213> ORGANISM: Arabidopsis thaliana

<400> SEQUENCE: 190
gaaaauuaaa aauccucugg acgcuuggcg c    31

<210> SEQ ID NO 191
<211> LENGTH: 31
<212> TYPE: RNA
<213> ORGANISM: Arabidopsis thaliana

<400> SEQUENCE: 191
aaauuaaaaa uccucuggac gcuuggcgcu c    31

<210> SEQ ID NO 192
<211> LENGTH: 31
<212> TYPE: RNA
<213> ORGANISM: Arabidopsis thaliana

<400> SEQUENCE: 192
ggagcucuug gcauugcuuu guuuuucucu c                                       31

<210> SEQ ID NO 193
<211> LENGTH: 31
<212> TYPE: RNA
<213> ORGANISM: Arabidopsis thaliana

<400> SEQUENCE: 193
gagcucuugg cauugcuuug uuuuucucuc c                                       31

<210> SEQ ID NO 194
<211> LENGTH: 31
<212> TYPE: RNA
<213> ORGANISM: Arabidopsis thaliana

<400> SEQUENCE: 194
gcauugcuuu guuuuucucu ccuuuccuau c                                       31

<210> SEQ ID NO 195
<211> LENGTH: 31
<212> TYPE: RNA
<213> ORGANISM: Arabidopsis thaliana

<400> SEQUENCE: 195
ucuuuguuug uaccgaaccg cuugcagaau c                                       31

<210> SEQ ID NO 196
<211> LENGTH: 31
<212> TYPE: RNA
<213> ORGANISM: Arabidopsis thaliana

<400> SEQUENCE: 196
ccgaaccgcu ugcagaauca aauccuguuc c                                       31

<210> SEQ ID NO 197
<211> LENGTH: 31
<212> TYPE: RNA
<213> ORGANISM: Arabidopsis thaliana

<400> SEQUENCE: 197
aaucaaaucc uguuccacaa gauccuauau c                                       31

<210> SEQ ID NO 198
<211> LENGTH: 31
<212> TYPE: RNA
<213> ORGANISM: Arabidopsis thaliana

<400> SEQUENCE: 198
gaugccgccg aaaagaaugg aacgcugcuu c                                       31

<210> SEQ ID NO 199
<211> LENGTH: 31
<212> TYPE: RNA
<213> ORGANISM: Arabidopsis thaliana

<400> SEQUENCE: 199
guuggugguu uuuaaccgua ggcaucuugc c                                       31

<210> SEQ ID NO 200
<211> LENGTH: 31
<212> TYPE: RNA
<213> ORGANISM: Arabidopsis thaliana

```
<400> SEQUENCE: 200
ggaaguuggu gggcuuauca ugaauuaggu c                             31

<210> SEQ ID NO 201
<211> LENGTH: 31
<212> TYPE: RNA
<213> ORGANISM: Arabidopsis thaliana

<400> SEQUENCE: 201
caugaauuag gucggggugg cuggugguuu c                             31

<210> SEQ ID NO 202
<211> LENGTH: 31
<212> TYPE: RNA
<213> ORGANISM: Arabidopsis thaliana

<400> SEQUENCE: 202
saucccguag aaaaugcuuc uuuuaugccu c                             31

<210> SEQ ID NO 203
<211> LENGTH: 31
<212> TYPE: RNA
<213> ORGANISM: Arabidopsis thaliana

<400> SEQUENCE: 203
ucuuuuaugc cucggguauu agccacagcu c                             31

<210> SEQ ID NO 204
<211> LENGTH: 31
<212> TYPE: RNA
<213> ORGANISM: Arabidopsis thaliana

<400> SEQUENCE: 204
acagcucgua uucauucugu aauuuuaccc c                             31

<210> SEQ ID NO 205
<211> LENGTH: 31
<212> TYPE: RNA
<213> ORGANISM: Arabidopsis thaliana

<400> SEQUENCE: 205
uaauuuuacc ccuucuucau ucuuggaccu c                             31

<210> SEQ ID NO 206
<211> LENGTH: 31
<212> TYPE: RNA
<213> ORGANISM: Arabidopsis thaliana

<400> SEQUENCE: 206
ggaccucguu ucuuaauauu gugacuuuuc c                             31

<210> SEQ ID NO 207
<211> LENGTH: 31
<212> TYPE: RNA
<213> ORGANISM: Arabidopsis thaliana

<400> SEQUENCE: 207
uuaauauugu gacuuuucca ugcugugucu c                             31

<210> SEQ ID NO 208
<211> LENGTH: 31
<212> TYPE: RNA
<213> ORGANISM: Arabidopsis thaliana
```

```
<400> SEQUENCE: 208
accuuuucaa uacgguccgg auugcuagcu c                              31

<210> SEQ ID NO 209
<211> LENGTH: 31
<212> TYPE: RNA
<213> ORGANISM: Arabidopsis thaliana

<400> SEQUENCE: 209
ggugguucuu ccuucuaaug accggcauau c                              31

<210> SEQ ID NO 210
<211> LENGTH: 31
<212> TYPE: RNA
<213> ORGANISM: Arabidopsis thaliana

<400> SEQUENCE: 210
uucguaaugg aaagaaagag accacuacuu c                              31

<210> SEQ ID NO 211
<211> LENGTH: 31
<212> TYPE: RNA
<213> ORGANISM: Arabidopsis thaliana

<400> SEQUENCE: 211
agacuuacau cacgauaucu uuucuuccu c                               31

<210> SEQ ID NO 212
<211> LENGTH: 31
<212> TYPE: RNA
<213> ORGANISM: Arabidopsis thaliana

<400> SEQUENCE: 212
uuugaaaaug auuguucuaa aaugguuauu c                              31

<210> SEQ ID NO 213
<211> LENGTH: 31
<212> TYPE: RNA
<213> ORGANISM: Arabidopsis thaliana

<400> SEQUENCE: 213 uugaaauga uuguucuaaa augguuauuc c                               31

<210> SEQ ID NO 214
<211> LENGTH: 31
<212> TYPE: RNA
<213> ORGANISM: Arabidopsis thaliana

<400> SEQUENCE: 214
auuguucaug gaacuacuau cgagauucuu c                              31

<210> SEQ ID NO 215
<211> LENGTH: 31
<212> TYPE: RNA
<213> ORGANISM: Arabidopsis thaliana

<400> SEQUENCE: 215
uggaacuacu aucgagauuc uucggaccau c                              31

<210> SEQ ID NO 216
<211> LENGTH: 31
<212> TYPE: RNA
```

```
<213> ORGANISM: Arabidopsis thaliana

<400> SEQUENCE: 216
gaaaaugauu guucuaaaau gguuauuccu c                                31

<210> SEQ ID NO 217
<211> LENGTH: 31
<212> TYPE: RNA
<213> ORGANISM: Arabidopsis thaliana

<400> SEQUENCE: 217
uucuucggac caucuuuccu aguaucaucu c                                31

<210> SEQ ID NO 218
<211> LENGTH: 31
<212> TYPE: RNA
<213> ORGANISM: Arabidopsis thaliana

<400> SEQUENCE: 218
acuaucaaag cuauuggaca ucaaugguau c                                31

<210> SEQ ID NO 219
<211> LENGTH: 31
<212> TYPE: RNA
<213> ORGANISM: Arabidopsis thaliana

<400> SEQUENCE: 219
uuccagaaga agaucuagaa uugggucaau c                                31

<210> SEQ ID NO 220
<211> LENGTH: 31
<212> TYPE: RNA
<213> ORGANISM: Arabidopsis thaliana

<400> SEQUENCE: 220
uacguauuau uguaacaucu gcugauguac c                                31

<210> SEQ ID NO 221
<211> LENGTH: 31
<212> TYPE: RNA
<213> ORGANISM: Arabidopsis thaliana

<400> SEQUENCE: 221
auguaccuca uaguugggcu guaccuuccu c                                31

<210> SEQ ID NO 222
<211> LENGTH: 31
<212> TYPE: RNA
<213> ORGANISM: Arabidopsis thaliana

<400> SEQUENCE: 222
gugagauuug uggaacuaau caugccuuua c                                31

<210> SEQ ID NO 223
<211> LENGTH: 31
<212> TYPE: RNA
<213> ORGANISM: Arabidopsis thaliana

<400> SEQUENCE: 223
gugaugcagc ggaaccaugg caauuaggau c                                31

<210> SEQ ID NO 224
<211> LENGTH: 31
```

```
<212> TYPE: RNA
<213> ORGANISM: Arabidopsis thaliana

<400> SEQUENCE: 224
gccuuuacgu cuaucgucgu agaagcuguu c                          31

<210> SEQ ID NO 225
<211> LENGTH: 31
<212> TYPE: RNA
<213> ORGANISM: Arabidopsis thaliana

<400> SEQUENCE: 225
gaagcuguuc cuaggaaaga uuaugguucu c                          31

<210> SEQ ID NO 226
<211> LENGTH: 31
<212> TYPE: RNA
<213> ORGANISM: Arabidopsis thaliana

<400> SEQUENCE: 226
accaccguag gaggugugau guacaugcac c                          31

<210> SEQ ID NO 227
<211> LENGTH: 31
<212> TYPE: RNA
<213> ORGANISM: Arabidopsis thaliana

<400> SEQUENCE: 227
gacaucauac caaagucgua caauuaggac c                          31

<210> SEQ ID NO 228
<211> LENGTH: 31
<212> TYPE: RNA
<213> ORGANISM: Arabidopsis thaliana

<400> SEQUENCE: 228
aagucguaca auuaggaccu cgauaugguu c                          31

<210> SEQ ID NO 229
<211> LENGTH: 31
<212> TYPE: RNA
<213> ORGANISM: Arabidopsis thaliana

<400> SEQUENCE: 229
uuauguucuu uuuugcuuuu uuuugggcuu c                          31

<210> SEQ ID NO 230
<211> LENGTH: 31
<212> TYPE: RNA
<213> ORGANISM: Arabidopsis thaliana

<400> SEQUENCE: 230
uguucuuuuu ugcuuuuuuu ugggcuucuu c                          31

<210> SEQ ID NO 231
<211> LENGTH: 31
<212> TYPE: RNA
<213> ORGANISM: Arabidopsis thaliana

<400> SEQUENCE: 231
auccuuggga aaucccuuuu cuuaauaccc c                          31

<210> SEQ ID NO 232
```

-continued

<210> SEQ ID NO 232
<211> LENGTH: 31
<212> TYPE: RNA
<213> ORGANISM: Arabidopsis thaliana

<400> SEQUENCE: 232
aaaucccuuu ucuuaauacc ccuauucucc c                    31

<210> SEQ ID NO 233
<211> LENGTH: 31
<212> TYPE: RNA
<213> ORGANISM: Arabidopsis thaliana

<400> SEQUENCE: 233
uucggauagu auuuaugguu cuaccuuuuu c                    31

<210> SEQ ID NO 234
<211> LENGTH: 31
<212> TYPE: RNA
<213> ORGANISM: Arabidopsis thaliana

<400> SEQUENCE: 234
gcuccauuug uuacuauugg acaaauuucu c                    31

<210> SEQ ID NO 235
<211> LENGTH: 31
<212> TYPE: RNA
<213> ORGANISM: Arabidopsis thaliana

<400> SEQUENCE: 235
agcaaucuua guuauuggug ggguucggu c                     31

<210> SEQ ID NO 236
<211> LENGTH: 31
<212> TYPE: RNA
<213> ORGANISM: Arabidopsis thaliana

<400> SEQUENCE: 236
uauaugcaug cuaauggggc aaguauguuu c                    31

<210> SEQ ID NO 237
<211> LENGTH: 31
<212> TYPE: RNA
<213> ORGANISM: Arabidopsis thaliana

<400> SEQUENCE: 237
guuuaccuuc auauuuucg uggucuauau c                     31

<210> SEQ ID NO 238
<211> LENGTH: 31
<212> TYPE: RNA
<213> ORGANISM: Arabidopsis thaliana

<400> SEQUENCE: 238
gccaccuuaa aucguuuuuu uagucuucau c                    31

<210> SEQ ID NO 239
<211> LENGTH: 31
<212> TYPE: RNA
<213> ORGANISM: Arabidopsis thaliana

<400> SEQUENCE: 239
uuuauuuuag uaggcgccag ucuucuucau c                    31

```
<210> SEQ ID NO 240
<211> LENGTH: 31
<212> TYPE: RNA
<213> ORGANISM: Arabidopsis thaliana

<400> SEQUENCE: 240
auugugccgg aaugguauuu ccuaccgauc c                              31

<210> SEQ ID NO 241
<211> LENGTH: 31
<212> TYPE: RNA
<213> ORGANISM: Arabidopsis thaliana

<400> SEQUENCE: 241
acaaagcggg agguguagcc gcaauagcac c                              31

<210> SEQ ID NO 242
<211> LENGTH: 31
<212> TYPE: RNA
<213> ORGANISM: Arabidopsis thaliana

<400> SEQUENCE: 242
agccgcaaua gcaccaguuu uuauaugucu c                              31

<210> SEQ ID NO 243
<211> LENGTH: 31
<212> TYPE: RNA
<213> ORGANISM: Arabidopsis thaliana

<400> SEQUENCE: 243
uaugugcgua guucaaguuu ucgaccgauu c                              31

<210> SEQ ID NO 244
<211> LENGTH: 31
<212> TYPE: RNA
<213> ORGANISM: Arabidopsis thaliana

<400> SEQUENCE: 244
acacugggcg ggaucuauca gcagcgaauu c                              31

<210> SEQ ID NO 245
<211> LENGTH: 31
<212> TYPE: RNA
<213> ORGANISM: Arabidopsis thaliana

<400> SEQUENCE: 245
cugggcggga ucuaucagca gcgaauuccc c                              31

<210> SEQ ID NO 246
<211> LENGTH: 31
<212> TYPE: RNA
<213> ORGANISM: Arabidopsis thaliana

<400> SEQUENCE: 246
gagguaucau uagccgaaga agacccuggc c                              31

<210> SEQ ID NO 247
<211> LENGTH: 31
<212> TYPE: RNA
<213> ORGANISM: Arabidopsis thaliana

<400> SEQUENCE: 247
acgucagcga cgaagacauc guaaauuggu c                              31
```

<210> SEQ ID NO 248
<211> LENGTH: 31
<212> TYPE: RNA
<213> ORGANISM: Arabidopsis thaliana

<400> SEQUENCE: 248
cgucagcgac gaagacaucg uaaauugguc c                                31

<210> SEQ ID NO 249
<211> LENGTH: 31
<212> TYPE: RNA
<213> ORGANISM: Arabidopsis thaliana

<400> SEQUENCE: 249
uaaauugguc cgcgggcauc gcgauaaguc c                                31

<210> SEQ ID NO 250
<211> LENGTH: 31
<212> TYPE: RNA
<213> ORGANISM: Arabidopsis thaliana

<400> SEQUENCE: 250
gcgauaaguc cucuguccua cuacaggugc c                                31

<210> SEQ ID NO 251
<211> LENGTH: 31
<212> TYPE: RNA
<213> ORGANISM: Arabidopsis thaliana

<400> SEQUENCE: 251
aaccuuuauc aaguccgaac gauugucgac c                                31

<210> SEQ ID NO 252
<211> LENGTH: 31
<212> TYPE: RNA
<213> ORGANISM: Arabidopsis thaliana

<400> SEQUENCE: 252
cgaauauaau ccucaaguac uccaaagacu c                                31

<210> SEQ ID NO 253
<211> LENGTH: 31
<212> TYPE: RNA
<213> ORGANISM: Arabidopsis thaliana

<400> SEQUENCE: 253
uuucacacca ucgaccgaca ucgacucauc c                                31

<210> SEQ ID NO 254
<211> LENGTH: 31
<212> TYPE: RNA
<213> ORGANISM: Arabidopsis thaliana

<400> SEQUENCE: 254
aagagaucga cgaucccaag uucuuuuacu c                                31

<210> SEQ ID NO 255
<211> LENGTH: 31
<212> TYPE: RNA
<213> ORGANISM: Arabidopsis thaliana

<400> SEQUENCE: 255
ucccacacag uguacuacua ucggcccuac c                                31

```
<210> SEQ ID NO 256
<211> LENGTH: 31
<212> TYPE: RNA
<213> ORGANISM: Arabidopsis thaliana

<400> SEQUENCE: 256
acgaaauucc gauuguucag agagucagau c                           31

<210> SEQ ID NO 257
<211> LENGTH: 31
<212> TYPE: RNA
<213> ORGANISM: Arabidopsis thaliana

<400> SEQUENCE: 257
ugaaagaggc gaucagaaug guacucgaau c                           31

<210> SEQ ID NO 258
<211> LENGTH: 31
<212> TYPE: RNA
<213> ORGANISM: Arabidopsis thaliana

<400> SEQUENCE: 258
ucggauuguu acaaccucua gcagaugguu c                           31

<210> SEQ ID NO 259
<211> LENGTH: 31
<212> TYPE: RNA
<213> ORGANISM: Arabidopsis thaliana

<400> SEQUENCE: 259
ccagaucaug aguaaauaaa aaaucgaaaa c                           31

<210> SEQ ID NO 260
<211> LENGTH: 31
<212> TYPE: RNA
<213> ORGANISM: Arabidopsis thaliana

<400> SEQUENCE: 260
guggcuacau uuauguuaag ucggucgcu c                            31

<210> SEQ ID NO 261
<211> LENGTH: 31
<212> TYPE: RNA
<213> ORGANISM: Arabidopsis thaliana

<400> SEQUENCE: 261 ccuuugauu augguauggu auugucagau c                            31

<210> SEQ ID NO 262
<211> LENGTH: 31
<212> TYPE: RNA
<213> ORGANISM: Arabidopsis thaliana

<400> SEQUENCE: 262
cuuuugauua ugguauggua uugucagauc c                           31

<210> SEQ ID NO 263
<211> LENGTH: 31
<212> TYPE: RNA
<213> ORGANISM: Arabidopsis thaliana

<400> SEQUENCE: 263
```

-continued cuagguguuu auggaauuau uauagcgggu c  31

<210> SEQ ID NO 264
<211> LENGTH: 31
<212> TYPE: RNA
<213> ORGANISM: Arabidopsis thaliana

<400> SEQUENCE: 264
auucuuauua cuguacuaau auguguaggu c  31

<210> SEQ ID NO 265
<211> LENGTH: 31
<212> TYPE: RNA
<213> ORGANISM: Arabidopsis thaliana

<400> SEQUENCE: 265
ucuuauuacu guacuaauau guguaggucc c  31

<210> SEQ ID NO 266
<211> LENGTH: 31
<212> TYPE: RNA
<213> ORGANISM: Arabidopsis thaliana

<400> SEQUENCE: 266
cuuauuacug uacuaauaug uguagguccc c  31

<210> SEQ ID NO 267
<211> LENGTH: 31
<212> TYPE: RNA
<213> ORGANISM: Arabidopsis thaliana

<400> SEQUENCE: 267 cguacuaau auguguaggu ccccguaauu c  31

<210> SEQ ID NO 268
<211> LENGTH: 31
<212> TYPE: RNA
<213> ORGANISM: Arabidopsis thaliana

<400> SEQUENCE: 268
agauugucau ggcgcaaaag cagauauggu c  31

<210> SEQ ID NO 269
<211> LENGTH: 31
<212> TYPE: RNA
<213> ORGANISM: Arabidopsis thaliana

<400> SEQUENCE: 269
ggcgcaaaag cagauauggu cugguauucc c  31

<210> SEQ ID NO 270
<211> LENGTH: 31
<212> TYPE: RNA
<213> ORGANISM: Arabidopsis thaliana

<400> SEQUENCE: 270 auccccugu ucccuguauu gguuauguuc c  31

<210> SEQ ID NO 271
<211> LENGTH: 31
<212> TYPE: RNA
<213> ORGANISM: Arabidopsis thaliana

<400> SEQUENCE: 271

```
uucccuguau ugguuauguu ccuuauuucu c                                    31

<210> SEQ ID NO 272
<211> LENGTH: 31
<212> TYPE: RNA
<213> ORGANISM: Arabidopsis thaliana

<400> SEQUENCE: 272
cguuugaucu cccagaagcg gaagcugaau c                                    31

<210> SEQ ID NO 273
<211> LENGTH: 31
<212> TYPE: RNA
<213> ORGANISM: Arabidopsis thaliana

<400> SEQUENCE: 273
gcuauaaugu agaauauucu ucaauggggu c                                    31

<210> SEQ ID NO 274
<211> LENGTH: 31
<212> TYPE: RNA
<213> ORGANISM: Arabidopsis thaliana

<400> SEQUENCE: 274
aguaugccaa uaugaucuua augagugguc c                                    31

<210> SEQ ID NO 275
<211> LENGTH: 31
<212> TYPE: RNA
<213> ORGANISM: Arabidopsis thaliana

<400> SEQUENCE: 275
uaaugagugg uccaugcaca uuguucuuuc c                                    31

<210> SEQ ID NO 276
<211> LENGTH: 31
<212> TYPE: RNA
<213> ORGANISM: Arabidopsis thaliana

<400> SEQUENCE: 276
caugcacauu guucuuucca ggagguuggc c                                    31

<210> SEQ ID NO 277
<211> LENGTH: 31
<212> TYPE: RNA
<213> ORGANISM: Arabidopsis thaliana

<400> SEQUENCE: 277
uuguucuuuc caggagguug gccgccuauc c                                    31

<210> SEQ ID NO 278
<211> LENGTH: 31
<212> TYPE: RNA
<213> ORGANISM: Arabidopsis thaliana

<400> SEQUENCE: 278
aucuucccau uuucaagaag aucccgggcu c                                    31

<210> SEQ ID NO 279
<211> LENGTH: 31
<212> TYPE: RNA
<213> ORGANISM: Arabidopsis thaliana
```

<400> SEQUENCE: 279
ggcucgaucu gguuuaguau caagguucuu c               31

<210> SEQ ID NO 280
<211> LENGTH: 31
<212> TYPE: RNA
<213> ORGANISM: Arabidopsis thaliana

<400> SEQUENCE: 280
uaucguuaug aucaauuaau gggacuuggc c               31

<210> SEQ ID NO 281
<211> LENGTH: 31
<212> TYPE: RNA
<213> ORGANISM: Arabidopsis thaliana

<400> SEQUENCE: 281
cggaaagugu ucuugccucu aucauuagcu c               31

<210> SEQ ID NO 282
<211> LENGTH: 31
<212> TYPE: RNA
<213> ORGANISM: Arabidopsis thaliana

<400> SEQUENCE: 282
uucuugccuc uaucauuagc ucggguaguc c               31

<210> SEQ ID NO 283
<211> LENGTH: 31
<212> TYPE: RNA
<213> ORGANISM: Arabidopsis thaliana

<400> SEQUENCE: 283
uaaugacgau ggaugcauuc gccauaguuu c               31

<210> SEQ ID NO 284
<211> LENGTH: 31
<212> TYPE: RNA
<213> ORGANISM: Arabidopsis thaliana

<400> SEQUENCE: 284
ugggcgcucu agccaaaacg aauccuauuu c               31

<210> SEQ ID NO 285
<211> LENGTH: 31
<212> TYPE: RNA
<213> ORGANISM: Arabidopsis thaliana

<400> SEQUENCE: 285
acccccguua gccggcuuuu guagcaaauu c               31

<210> SEQ ID NO 286
<211> LENGTH: 31
<212> TYPE: RNA
<213> ORGANISM: Arabidopsis thaliana

<400> SEQUENCE: 286
gcuuuggguu gugggcuua cuuucuagcc c               31

<210> SEQ ID NO 287
<211> LENGTH: 31
<212> TYPE: RNA
<213> ORGANISM: Arabidopsis thaliana

<400> SEQUENCE: 287
cuuuggguug uggggcuuac uuucuagccc c                               31

<210> SEQ ID NO 288
<211> LENGTH: 31
<212> TYPE: RNA
<213> ORGANISM: Arabidopsis thaliana

<400> SEQUENCE: 288
ccagugggag uagugacuag cguuauaggu c                               31

<210> SEQ ID NO 289
<211> LENGTH: 31
<212> TYPE: RNA
<213> ORGANISM: Arabidopsis thaliana

<400> SEQUENCE: 289
uacuagcaau gacuuccuuu uucauuacuu c                               31

<210> SEQ ID NO 290
<211> LENGTH: 31
<212> TYPE: RNA
<213> ORGANISM: Arabidopsis thaliana

<400> SEQUENCE: 290
uagcaaugac uuccuuuuuc auuacuucau c                               31

<210> SEQ ID NO 291
<211> LENGTH: 31
<212> TYPE: RNA
<213> ORGANISM: Arabidopsis thaliana

<400> SEQUENCE: 291
ucucaguuac ucaucaaaug gcacucaguu c                               31

<210> SEQ ID NO 292
<211> LENGTH: 31
<212> TYPE: RNA
<213> ORGANISM: Arabidopsis thaliana

<400> SEQUENCE: 292
ucuuuuuagg agggacaauu uuacauauuu c                               31

<210> SEQ ID NO 293
<211> LENGTH: 31
<212> TYPE: RNA
<213> ORGANISM: Arabidopsis thaliana

<400> SEQUENCE: 293
cggcugguac cauuucgaug uguuucgauu c                               31

<210> SEQ ID NO 294
<211> LENGTH: 31
<212> TYPE: RNA
<213> ORGANISM: Arabidopsis thaliana

<400> SEQUENCE: 294
cugguaccau uucgaugugu uucgauucuu c                               31

<210> SEQ ID NO 295
<211> LENGTH: 31
<212> TYPE: RNA

```
<213> ORGANISM: Arabidopsis thaliana

<400> SEQUENCE: 295
uugaugcuuu ugaauucauu guauuaauuc c                            31

<210> SEQ ID NO 296
<211> LENGTH: 31
<212> TYPE: RNA
<213> ORGANISM: Arabidopsis thaliana

<400> SEQUENCE: 296 gcuuugaau ucauuguauu aauuccacuu c                             31

<210> SEQ ID NO 297
<211> LENGTH: 31
<212> TYPE: RNA
<213> ORGANISM: Arabidopsis thaliana

<400> SEQUENCE: 297
gaauucauug uauuaauucc acuuccuacu c                            31

<210> SEQ ID NO 298
<211> LENGTH: 31
<212> TYPE: RNA
<213> ORGANISM: Arabidopsis thaliana

<400> SEQUENCE: 298
acucgcggua ugcucuuuau gaucucggcu c                            31

<210> SEQ ID NO 299
<211> LENGTH: 31
<212> TYPE: RNA
<213> ORGANISM: Arabidopsis thaliana

<400> SEQUENCE: 299
cuuuaugauc ucggcucaug auuuaauugc c                            31

<210> SEQ ID NO 300
<211> LENGTH: 31
<212> TYPE: RNA
<213> ORGANISM: Arabidopsis thaliana

<400> SEQUENCE: 300
auuuaauugc cauguauuua gcuauugagc c                            31

<210> SEQ ID NO 301
<211> LENGTH: 31
<212> TYPE: RNA
<213> ORGANISM: Arabidopsis thaliana

<400> SEQUENCE: 301
aagaaagucu gaauuuucca cggaagccgg c                            31

<210> SEQ ID NO 302
<211> LENGTH: 31
<212> TYPE: RNA
<213> ORGANISM: Arabidopsis thaliana

<400> SEQUENCE: 302
gaaagucuga auuuccacg gaagccggcu c                             31

<210> SEQ ID NO 303
<211> LENGTH: 31
```

<212> TYPE: RNA
<213> ORGANISM: Arabidopsis thaliana

<400> SEQUENCE: 303
cucgaaauau uugaucuuag gugcauuuuc c              31

<210> SEQ ID NO 304
<211> LENGTH: 31
<212> TYPE: RNA
<213> ORGANISM: Arabidopsis thaliana

<400> SEQUENCE: 304
uuccucugga auauuauugu uugguuguuc c              31

<210> SEQ ID NO 305
<211> LENGTH: 31
<212> TYPE: RNA
<213> ORGANISM: Arabidopsis thaliana

<400> SEQUENCE: 305
cacacauguu caaucuuuuu uuagcgguuu c              31

<210> SEQ ID NO 306
<211> LENGTH: 31
<212> TYPE: RNA
<213> ORGANISM: Arabidopsis thaliana

<400> SEQUENCE: 306
ccacuucgau caauuagcca agauuuugac c              31

<210> SEQ ID NO 307
<211> LENGTH: 31
<212> TYPE: RNA
<213> ORGANISM: Arabidopsis thaliana

<400> SEQUENCE: 307 gaucagugg uauuuuuaug gggauucugu c              31

<210> SEQ ID NO 308
<211> LENGTH: 31
<212> TYPE: RNA
<213> ORGANISM: Arabidopsis thaliana

<400> SEQUENCE: 308
uccuuucuau ugcgccuaaa aucucuauuu c              31

<210> SEQ ID NO 309
<211> LENGTH: 31
<212> TYPE: RNA
<213> ORGANISM: Arabidopsis thaliana

<400> SEQUENCE: 309
ucucuauuuc ugcuaauauu uuacguguuu c              31

<210> SEQ ID NO 310
<211> LENGTH: 31
<212> TYPE: RNA
<213> ORGANISM: Arabidopsis thaliana

<400> SEQUENCE: 310
ccccagagau cuuuaucauu aaugcaaccu c              31

<210> SEQ ID NO 311

```
<211> LENGTH: 31
<212> TYPE: RNA
<213> ORGANISM: Arabidopsis thaliana

<400> SEQUENCE: 311
cccagagauc uuuaucauua augcaaccuc c                                   31

<210> SEQ ID NO 312
<211> LENGTH: 31
<212> TYPE: RNA
<213> ORGANISM: Arabidopsis thaliana

<400> SEQUENCE: 312
ccgccauggc ccaaacgaaa gucaaaagac c                                   31

<210> SEQ ID NO 313
<211> LENGTH: 31
<212> TYPE: RNA
<213> ORGANISM: Arabidopsis thaliana

<400> SEQUENCE: 313
gcccaaacga agucaaaag accucuagcu c                                    31

<210> SEQ ID NO 314
<211> LENGTH: 31
<212> TYPE: RNA
<213> ORGANISM: Arabidopsis thaliana

<400> SEQUENCE: 314
cauaguucaa uuggacaugu agguuauauu c                                   31

<210> SEQ ID NO 315
<211> LENGTH: 31
<212> TYPE: RNA
<213> ORGANISM: Arabidopsis thaliana

<400> SEQUENCE: 315
guucaauugg acauguaggu uauauucgua c                                   31

<210> SEQ ID NO 316
<211> LENGTH: 31
<212> TYPE: RNA
<213> ORGANISM: Arabidopsis thaliana

<400> SEQUENCE: 316
ugucggccua cgaauguggu uucgauccuu c                                   31

<210> SEQ ID NO 317
<211> LENGTH: 31
<212> TYPE: RNA
<213> ORGANISM: Arabidopsis thaliana

<400> SEQUENCE: 317
uuuuaucuug uuucaauuuu auuuuuaauc c                                   31

<210> SEQ ID NO 318
<211> LENGTH: 31
<212> TYPE: RNA
<213> ORGANISM: Arabidopsis thaliana

<400> SEQUENCE: 318
uuuaucuugu uucaauuuua uuuuuaaucc c                                   31
```

```
<210> SEQ ID NO 319
<211> LENGTH: 31
<212> TYPE: RNA
<213> ORGANISM: Arabidopsis thaliana

<400> SEQUENCE: 319
gaaguaaccu uuucuuucc uugggcagua c                             31

<210> SEQ ID NO 320
<211> LENGTH: 31
<212> TYPE: RNA
<213> ORGANISM: Arabidopsis thaliana

<400> SEQUENCE: 320
uaaccuuuuu cuuccuugg gcaguaccuc c                             31

<210> SEQ ID NO 321
<211> LENGTH: 31
<212> TYPE: RNA
<213> ORGANISM: Arabidopsis thaliana

<400> SEQUENCE: 321
cuguaaugau gucagaauuu gcaccaauuu c                            31

<210> SEQ ID NO 322
<211> LENGTH: 31
<212> TYPE: RNA
<213> ORGANISM: Arabidopsis thaliana

<400> SEQUENCE: 322
gauuucuaua ugaauggaaa agggugcuu c                             31

<210> SEQ ID NO 323
<211> LENGTH: 31
<212> TYPE: RNA
<213> ORGANISM: Arabidopsis thaliana

<400> SEQUENCE: 323
cuauaugaau ggaaaagggg ugcuucggau c                            31

<210> SEQ ID NO 324
<211> LENGTH: 31
<212> TYPE: RNA
<213> ORGANISM: Arabidopsis thaliana

<400> SEQUENCE: 324
uuagugauua gucugcuagu uucuuugauc c                            31

<210> SEQ ID NO 325
<211> LENGTH: 31
<212> TYPE: RNA
<213> ORGANISM: Arabidopsis thaliana

<400> SEQUENCE: 325
gauuagucug cuaguuucuu ugauccuacu c                            31

<210> SEQ ID NO 326
<211> LENGTH: 31
<212> TYPE: RNA
<213> ORGANISM: Arabidopsis thaliana

<400> SEQUENCE: 326
gcgagaaaac aaagugggcu guaaugaugu c                            31
```

-continued

<210> SEQ ID NO 327
<211> LENGTH: 31
<212> TYPE: RNA
<213> ORGANISM: Arabidopsis thaliana

<400> SEQUENCE: 327 uucuuugau ccuacucggu guuccuuuuc c                          31

<210> SEQ ID NO 328
<211> LENGTH: 31
<212> TYPE: RNA
<213> ORGANISM: Arabidopsis thaliana

<400> SEQUENCE: 328
acauacaggg aauuggaggu agcauucuac c                         31

<210> SEQ ID NO 329
<211> LENGTH: 31
<212> TYPE: RNA
<213> ORGANISM: Arabidopsis thaliana

<400> SEQUENCE: 329
auucuaccga uguuaaguca uggacugguu c                         31

<210> SEQ ID NO 330
<211> LENGTH: 31
<212> TYPE: RNA
<213> ORGANISM: Arabidopsis thaliana

<400> SEQUENCE: 330
uucuuuucau uccaaauuca agaauacgac c                         31

<210> SEQ ID NO 331
<211> LENGTH: 31
<212> TYPE: RNA
<213> ORGANISM: Arabidopsis thaliana

<400> SEQUENCE: 331
ccgacauaag acucgacuug uuagauauua c                         31

<210> SEQ ID NO 332
<211> LENGTH: 31
<212> TYPE: RNA
<213> ORGANISM: Arabidopsis thaliana

<400> SEQUENCE: 332
uacggagguu uagugagcac caugccgaau c                         31

<210> SEQ ID NO 333
<211> LENGTH: 31
<212> TYPE: RNA
<213> ORGANISM: Arabidopsis thaliana

<400> SEQUENCE: 333
cggagguuua gugagcacca ugccgaaucu c                         31

<210> SEQ ID NO 334
<211> LENGTH: 31
<212> TYPE: RNA
<213> ORGANISM: Arabidopsis thaliana

<400> SEQUENCE: 334
gagguuuagu gagcaccaug ccgaaucucu c                         31

```
<210> SEQ ID NO 335
<211> LENGTH: 31
<212> TYPE: RNA
<213> ORGANISM: Arabidopsis thaliana

<400> SEQUENCE: 335
ccaugccgaa ucucucuacc auuuucuuuu c                              31

<210> SEQ ID NO 336
<211> LENGTH: 31
<212> TYPE: RNA
<213> ORGANISM: Arabidopsis thaliana

<400> SEQUENCE: 336 ucuuucuuu uacuuuggcc aauaugaguu c                               31

<210> SEQ ID NO 337
<211> LENGTH: 31
<212> TYPE: RNA
<213> ORGANISM: Arabidopsis thaliana

<400> SEQUENCE: 337
ugguacuagc agcuuuaucg gggaauuucu c                              31

<210> SEQ ID NO 338
<211> LENGTH: 31
<212> TYPE: RNA
<213> ORGANISM: Arabidopsis thaliana

<400> SEQUENCE: 338
ucaagaauac gaccgauacg auuaauuggu c                              31

<210> SEQ ID NO 339
<211> LENGTH: 31
<212> TYPE: RNA
<213> ORGANISM: Arabidopsis thaliana

<400> SEQUENCE: 339
aaccugauuu ccuccauaaa uucuccgauu c                              31

<210> SEQ ID NO 340
<211> LENGTH: 31
<212> TYPE: RNA
<213> ORGANISM: Arabidopsis thaliana

<400> SEQUENCE: 340
aauucuccga uucaaauggc agagaaguuu c                              31

<210> SEQ ID NO 341
<211> LENGTH: 31
<212> TYPE: RNA
<213> ORGANISM: Arabidopsis thaliana

<400> SEQUENCE: 341
uuccauauuu auaccuuuuc uuguuggacu c                              31

<210> SEQ ID NO 342
<211> LENGTH: 31
<212> TYPE: RNA
<213> ORGANISM: Arabidopsis thaliana

<400> SEQUENCE: 342
```
auauuuauac cuuucuugu uggacucguu c                                    31

<210> SEQ ID NO 343
<211> LENGTH: 31
<212> TYPE: RNA
<213> ORGANISM: Arabidopsis thaliana

<400> SEQUENCE: 343
uuucuuguug gacucguucg gaugggguguu c                                  31

<210> SEQ ID NO 344
<211> LENGTH: 31
<212> TYPE: RNA
<213> ORGANISM: Arabidopsis thaliana

<400> SEQUENCE: 344
uucggauggg uguucacccc aaaguguucc c                                   31

<210> SEQ ID NO 345
<211> LENGTH: 31
<212> TYPE: RNA
<213> ORGANISM: Arabidopsis thaliana

<400> SEQUENCE: 345
gugccucucu uauuacuuuu uuguauucuc c                                   31

<210> SEQ ID NO 346
<211> LENGTH: 31
<212> TYPE: RNA
<213> ORGANISM: Arabidopsis thaliana

<400> SEQUENCE: 346
cucuuauuac uuuuuguau ucuccuguuc c                                    31

<210> SEQ ID NO 347
<211> LENGTH: 31
<212> TYPE: RNA
<213> ORGANISM: Arabidopsis thaliana

<400> SEQUENCE: 347
cuuauuacuu uuuguauuc uccuguuccu c                                    31

<210> SEQ ID NO 348
<211> LENGTH: 31
<212> TYPE: RNA
<213> ORGANISM: Arabidopsis thaliana

<400> SEQUENCE: 348
ggauacaauu cgacucuucu acggccaaau c                                   31

<210> SEQ ID NO 349
<211> LENGTH: 31
<212> TYPE: RNA
<213> ORGANISM: Arabidopsis thaliana

<400> SEQUENCE: 349
cuauguuaga acauuucugu gaaugcuauu c                                   31

<210> SEQ ID NO 350
<211> LENGTH: 31
<212> TYPE: RNA
<213> ORGANISM: Arabidopsis thaliana

<400> SEQUENCE: 350

| | |
|---|---|
| ugaccacauu ucugaucccu auuugcauuu c | 31 |

<210> SEQ ID NO 351
<211> LENGTH: 31
<212> TYPE: RNA
<213> ORGANISM: Arabidopsis thaliana

<400> SEQUENCE: 351

| | |
|---|---|
| guaugagaag uuaugggaaa gaguauauua c | 31 |

<210> SEQ ID NO 352
<211> LENGTH: 31
<212> TYPE: RNA
<213> ORGANISM: Arabidopsis thaliana

<400> SEQUENCE: 352

| | |
|---|---|
| gggaaagagu auauuacagc auuuuuaauu c | 31 |

<210> SEQ ID NO 353
<211> LENGTH: 31
<212> TYPE: RNA
<213> ORGANISM: Arabidopsis thaliana

<400> SEQUENCE: 353

| | |
|---|---|
| aauucgugaa uuucuaauga ucgccuguu c | 31 |

<210> SEQ ID NO 354
<211> LENGTH: 31
<212> TYPE: RNA
<213> ORGANISM: Arabidopsis thaliana

<400> SEQUENCE: 354

| | |
|---|---|
| auucgugaau uucuaaugau cgccuguuc c | 31 |

<210> SEQ ID NO 355
<211> LENGTH: 31
<212> TYPE: RNA
<213> ORGANISM: Arabidopsis thaliana

<400> SEQUENCE: 355

| | |
|---|---|
| augaucgccg uguccgcau gcuagaucuu c | 31 |

<210> SEQ ID NO 356
<211> LENGTH: 31
<212> TYPE: RNA
<213> ORGANISM: Arabidopsis thaliana

<400> SEQUENCE: 356

| | |
|---|---|
| augcuagauc uucuacuauu cuauguuuuu c | 31 |

<210> SEQ ID NO 357
<211> LENGTH: 31
<212> TYPE: RNA
<213> ORGANISM: Arabidopsis thaliana

<400> SEQUENCE: 357

| | |
|---|---|
| ugcuagaucu ucuacuauuc uauguuuuc c | 31 |

<210> SEQ ID NO 358
<211> LENGTH: 31
<212> TYPE: RNA
<213> ORGANISM: Arabidopsis thaliana

```
<400> SEQUENCE: 358
uacuauucua uguuuuccc gaaagcgugc c                            31

<210> SEQ ID NO 359
<211> LENGTH: 31
<212> TYPE: RNA
<213> ORGANISM: Arabidopsis thaliana

<400> SEQUENCE: 359
uccaaacagg aaccaccgau uuacaaauau c                           31

<210> SEQ ID NO 360
<211> LENGTH: 31
<212> TYPE: RNA
<213> ORGANISM: Arabidopsis thaliana

<400> SEQUENCE: 360
agcggcgcca aaucuuucua uggauugcuu c                           31

<210> SEQ ID NO 361
<211> LENGTH: 31
<212> TYPE: RNA
<213> ORGANISM: Arabidopsis thaliana

<400> SEQUENCE: 361
uuauucugug uccugugcua ggaagcauua c                           31

<210> SEQ ID NO 362
<211> LENGTH: 31
<212> TYPE: RNA
<213> ORGANISM: Arabidopsis thaliana

<400> SEQUENCE: 362
cggcaggauc cgucaucuug gcaggaauuc c                           31

<210> SEQ ID NO 363
<211> LENGTH: 31
<212> TYPE: RNA
<213> ORGANISM: Arabidopsis thaliana

<400> SEQUENCE: 363
uuggcaggaa uuccuuuaaa auuuggaacc c                           31

<210> SEQ ID NO 364
<211> LENGTH: 31
<212> TYPE: RNA
<213> ORGANISM: Arabidopsis thaliana

<400> SEQUENCE: 364
uacccauguu ucccgaagcg acacuuuguu c                           31

<210> SEQ ID NO 365
<211> LENGTH: 31
<212> TYPE: RNA
<213> ORGANISM: Arabidopsis thaliana

<400> SEQUENCE: 365
uccugugcua ggaagcauua cucuucuuuu c                           31

<210> SEQ ID NO 366
<211> LENGTH: 31
<212> TYPE: RNA
<213> ORGANISM: Arabidopsis thaliana
```

-continued

<400> SEQUENCE: 366
uugcuauaau auauacuucc uugaccacuu c                               31

<210> SEQ ID NO 367
<211> LENGTH: 31
<212> TYPE: RNA
<213> ORGANISM: Arabidopsis thaliana

<400> SEQUENCE: 367
ugaaucuggu gacuauuggu auguuuaguc c                               31

<210> SEQ ID NO 368
<211> LENGTH: 31
<212> TYPE: RNA
<213> ORGANISM: Arabidopsis thaliana

<400> SEQUENCE: 368
aauagacgaa auauuccuau auguucaaug c                               31

<210> SEQ ID NO 369
<211> LENGTH: 31
<212> TYPE: RNA
<213> ORGANISM: Arabidopsis thaliana

<400> SEQUENCE: 369
auauuccuau auguucaaug ccaauugaau c                               31

<210> SEQ ID NO 370
<211> LENGTH: 31
<212> TYPE: RNA
<213> ORGANISM: Arabidopsis thaliana

<400> SEQUENCE: 370
caauugaauc aauguuauua gcugugaauu c                               31

<210> SEQ ID NO 371
<211> LENGTH: 31
<212> TYPE: RNA
<213> ORGANISM: Arabidopsis thaliana

<400> SEQUENCE: 371
auucgaacuu uuugguauuu uccguuucuu c                               31

<210> SEQ ID NO 372
<211> LENGTH: 31
<212> TYPE: RNA
<213> ORGANISM: Arabidopsis thaliana

<400> SEQUENCE: 372
cggaugauau gaugggucaa guauuugcuu c                               31

<210> SEQ ID NO 373
<211> LENGTH: 31
<212> TYPE: RNA
<213> ORGANISM: Arabidopsis thaliana

<400> SEQUENCE: 373 ugaugggucaa aguauuugcu ucauugguuc c                              31

<210> SEQ ID NO 374
<211> LENGTH: 31
<212> TYPE: RNA

```
<213> ORGANISM: Arabidopsis thaliana

<400> SEQUENCE: 374
ucaaauauuu cacauuuucu augauuauuu c                                  31

<210> SEQ ID NO 375
<211> LENGTH: 31
<212> TYPE: RNA
<213> ORGANISM: Arabidopsis thaliana

<400> SEQUENCE: 375
uuuucuauga uuauuucuau uuuagguauu c                                  31

<210> SEQ ID NO 376
<211> LENGTH: 31
<212> TYPE: RNA
<213> ORGANISM: Arabidopsis thaliana

<400> SEQUENCE: 376
ggggaauccu ccuuaauaga cgaaauauuc c                                  31

<210> SEQ ID NO 377
<211> LENGTH: 31
<212> TYPE: RNA
<213> ORGANISM: Arabidopsis thaliana

<400> SEQUENCE: 377
uccuuaauag acgaaauauu ccauuaugu c                                   31

<210> SEQ ID NO 378
<211> LENGTH: 31
<212> TYPE: RNA
<213> ORGANISM: Arabidopsis thaliana

<400> SEQUENCE: 378
ugggaacuuu gcuuucuggu ugggaagugu c                                  31

<210> SEQ ID NO 379
<211> LENGTH: 31
<212> TYPE: RNA
<213> ORGANISM: Arabidopsis thaliana

<400> SEQUENCE: 379
guuuagguac caauuuuugg gccaauuccc c                                  31

<210> SEQ ID NO 380
<211> LENGTH: 31
<212> TYPE: RNA
<213> ORGANISM: Arabidopsis thaliana

<400> SEQUENCE: 380
uaucuuugau ugcuuuuuau gaagucgcac c                                  31

<210> SEQ ID NO 381
<211> LENGTH: 31
<212> TYPE: RNA
<213> ORGANISM: Arabidopsis thaliana

<400> SEQUENCE: 381
ccgaauccga guuugcugcu ccaaccauua c                                  31

<210> SEQ ID NO 382
<211> LENGTH: 31
```

```
<212> TYPE: RNA
<213> ORGANISM: Arabidopsis thaliana

<400> SEQUENCE: 382
ccaaacuaau accuauucug uuuaguacuu c                                31

<210> SEQ ID NO 383
<211> LENGTH: 31
<212> TYPE: RNA
<213> ORGANISM: Arabidopsis thaliana

<400> SEQUENCE: 383
caggugcuuu uguugcguau aauguaaauc c                                31

<210> SEQ ID NO 384
<211> LENGTH: 31
<212> TYPE: RNA
<213> ORGANISM: Arabidopsis thaliana

<400> SEQUENCE: 384
cuuucaaacu aguacuuuuu guaaucgacu c                                31

<210> SEQ ID NO 385
<211> LENGTH: 31
<212> TYPE: RNA
<213> ORGANISM: Arabidopsis thaliana

<400> SEQUENCE: 385
aguuuugaau gacuuucuag ucagaucguu c                                31

<210> SEQ ID NO 386
<211> LENGTH: 31
<212> TYPE: RNA
<213> ORGANISM: Arabidopsis thaliana

<400> SEQUENCE: 386
aucauuaugc cuuugcaaug uuacuugguu c                                31

<210> SEQ ID NO 387
<211> LENGTH: 31
<212> TYPE: RNA
<213> ORGANISM: Arabidopsis thaliana

<400> SEQUENCE: 387
uacuugguuc aacucuauuu gugaccuuuu c                                31

<210> SEQ ID NO 388
<211> LENGTH: 31
<212> TYPE: RNA
<213> ORGANISM: Arabidopsis thaliana

<400> SEQUENCE: 388
cuugguucaa cucuauugu gaccuuuucu c                                 31

<210> SEQ ID NO 389
<211> LENGTH: 31
<212> TYPE: RNA
<213> ORGANISM: Arabidopsis thaliana

<400> SEQUENCE: 389
ucuauuugug accuuucuc guauguggga c                                 31

<210> SEQ ID NO 390
```

-continued

<210> SEQ ID NO 390
<211> LENGTH: 31
<212> TYPE: RNA
<213> ORGANISM: Arabidopsis thaliana

<400> SEQUENCE: 390
acucucuauc uucuugggua gauaaucgau c          31

<210> SEQ ID NO 391
<211> LENGTH: 31
<212> TYPE: RNA
<213> ORGANISM: Arabidopsis thaliana

<400> SEQUENCE: 391
augcuucuug gggcuucuug uucgauagcc c          31

<210> SEQ ID NO 392
<211> LENGTH: 31
<212> TYPE: RNA
<213> ORGANISM: Arabidopsis thaliana

<400> SEQUENCE: 392
cgaccguagu gauguuaauu gugguuacau c          31

<210> SEQ ID NO 393
<211> LENGTH: 31
<212> TYPE: RNA
<213> ORGANISM: Arabidopsis thaliana

<400> SEQUENCE: 393
agcccucgau uuauguguua uuuauccauu c          31

<210> SEQ ID NO 394
<211> LENGTH: 31
<212> TYPE: RNA
<213> ORGANISM: Arabidopsis thaliana

<400> SEQUENCE: 394
guuauuuauc cauucuuacu uuuuuaugc c          31

<210> SEQ ID NO 395
<211> LENGTH: 31
<212> TYPE: RNA
<213> ORGANISM: Arabidopsis thaliana

<400> SEQUENCE: 395
uuaugccaau guuggugacu ggagauaacu c          31

<210> SEQ ID NO 396
<211> LENGTH: 31
<212> TYPE: RNA
<213> ORGANISM: Arabidopsis thaliana

<400> SEQUENCE: 396
uuacacgacu ucaggcagau aaagcagcua c          31

<210> SEQ ID NO 397
<211> LENGTH: 31
<212> TYPE: RNA
<213> ORGANISM: Arabidopsis thaliana

<400> SEQUENCE: 397
uaggugauuu uggauuagcu cuugggauuu c          31

```
<210> SEQ ID NO 398
<211> LENGTH: 31
<212> TYPE: RNA
<213> ORGANISM: Arabidopsis thaliana

<400> SEQUENCE: 398
gauuuuggau uagcucuugg gauuucgggu c                              31

<210> SEQ ID NO 399
<211> LENGTH: 31
<212> TYPE: RNA
<213> ORGANISM: Arabidopsis thaliana

<400> SEQUENCE: 399
caaacaguag acuuucaac cauuuuugcu c                               31

<210> SEQ ID NO 400
<211> LENGTH: 31
<212> TYPE: RNA
<213> ORGANISM: Arabidopsis thaliana

<400> SEQUENCE: 400 acuuucaac cauuuuugcu cgugcuagug c                               31

<210> SEQ ID NO 401
<211> LENGTH: 31
<212> TYPE: RNA
<213> ORGANISM: Arabidopsis thaliana

<400> SEQUENCE: 401 cuuucaacc auuuuugcuc gugcuagugc c                               31

<210> SEQ ID NO 402
<211> LENGTH: 31
<212> TYPE: RNA
<213> ORGANISM: Arabidopsis thaliana

<400> SEQUENCE: 402
gugcuagugc ccccagaaau ucuuggauuu c                              31

<210> SEQ ID NO 403
<211> LENGTH: 31
<212> TYPE: RNA
<213> ORGANISM: Arabidopsis thaliana

<400> SEQUENCE: 403
aaugccauaa gucuuauuug uauuuuacuu c                              31

<210> SEQ ID NO 404
<211> LENGTH: 31
<212> TYPE: RNA
<213> ORGANISM: Arabidopsis thaliana

<400> SEQUENCE: 404
gugcuguugg gaaauccgcg cagauaggau c                              31

<210> SEQ ID NO 405
<211> LENGTH: 31
<212> TYPE: RNA
<213> ORGANISM: Arabidopsis thaliana

<400> SEQUENCE: 405
aauccgcgca gauaggaucg cauacuuggu c                              31
```

```
<210> SEQ ID NO 406
<211> LENGTH: 31
<212> TYPE: RNA
<213> ORGANISM: Arabidopsis thaliana

<400> SEQUENCE: 406
cuauggaggg ucccacucca guauccgcuu c                                    31

<210> SEQ ID NO 407
<211> LENGTH: 31
<212> TYPE: RNA
<213> ORGANISM: Arabidopsis thaliana

<400> SEQUENCE: 407
auagcaaggu gcuccccuuu auuugaauac c                                    31

<210> SEQ ID NO 408
<211> LENGTH: 31
<212> TYPE: RNA
<213> ORGANISM: Arabidopsis thaliana

<400> SEQUENCE: 408
acccaccuac ggcuuugauu guuauuacuu c                                    31

<210> SEQ ID NO 409
<211> LENGTH: 31
<212> TYPE: RNA
<213> ORGANISM: Arabidopsis thaliana

<400> SEQUENCE: 409
cuuugauugu uauuacuucu gcaggagcua c                                    31

<210> SEQ ID NO 410
<211> LENGTH: 31
<212> TYPE: RNA
<213> ORGANISM: Arabidopsis thaliana

<400> SEQUENCE: 410
cauuccguuu uguuucccau cccagucuuu c                                    31

<210> SEQ ID NO 411
<211> LENGTH: 31
<212> TYPE: RNA
<213> ORGANISM: Arabidopsis thaliana

<400> SEQUENCE: 411
uaggucucga cuucuucgcu augaucuucc c                                    31

<210> SEQ ID NO 412
<211> LENGTH: 31
<212> TYPE: RNA
<213> ORGANISM: Arabidopsis thaliana

<400> SEQUENCE: 412
gacuucuucg cuaugaucuu cccaguaguu c                                    31

<210> SEQ ID NO 413
<211> LENGTH: 31
<212> TYPE: RNA
<213> ORGANISM: Arabidopsis thaliana

<400> SEQUENCE: 413
caguaguuca uauaggagcu auagccguuu c                                    31
```

<210> SEQ ID NO 414
<211> LENGTH: 31
<212> TYPE: RNA
<213> ORGANISM: Arabidopsis thaliana

<400> SEQUENCE: 414
guaccaugau acuuucuguu uugucgagcc c                              31

<210> SEQ ID NO 415
<211> LENGTH: 31
<212> TYPE: RNA
<213> ORGANISM: Arabidopsis thaliana

<400> SEQUENCE: 415
cauugggcaa uuuacuuuau accuacuauu c                              31

<210> SEQ ID NO 416
<211> LENGTH: 31
<212> TYPE: RNA
<213> ORGANISM: Arabidopsis thaliana

<400> SEQUENCE: 416
uauaccuacu auucugucug guuuuugguu c                              31

<210> SEQ ID NO 417
<211> LENGTH: 31
<212> TYPE: RNA
<213> ORGANISM: Arabidopsis thaliana

<400> SEQUENCE: 417
gcccugcuuu ggucucuggu uugaugguug c                              31

<210> SEQ ID NO 418
<211> LENGTH: 31
<212> TYPE: RNA
<213> ORGANISM: Arabidopsis thaliana

<400> SEQUENCE: 418
gcuaaaaauc cgguacauuc cguuuuguuu c                              31

<210> SEQ ID NO 419
<211> LENGTH: 31
<212> TYPE: RNA
<213> ORGANISM: Arabidopsis thaliana

<400> SEQUENCE: 419
cuaaaaaucc gguacauucc guuuuguuuc                                31

<210> SEQ ID NO 420
<211> LENGTH: 31
<212> TYPE: RNA
<213> ORGANISM: Arabidopsis thaliana

<400> SEQUENCE: 420
auccgguaca uuccguuuug uuucccaucc c                              31

<210> SEQ ID NO 421
<211> LENGTH: 31
<212> TYPE: RNA
<213> ORGANISM: Arabidopsis thaliana

<400> SEQUENCE: 421
cuuucugguc aguaauggaa gcaaucgucc c                               31

<210> SEQ ID NO 422
<211> LENGTH: 31
<212> TYPE: RNA
<213> ORGANISM: Arabidopsis thaliana

<400> SEQUENCE: 422
gucaguaaug gaagcaaucg ucccuaccgu c                               31

<210> SEQ ID NO 423
<211> LENGTH: 31
<212> TYPE: RNA
<213> ORGANISM: Arabidopsis thaliana

<400> SEQUENCE: 423
ccuaccgucg uaaaauaaga gcacccggcu c                               31

<210> SEQ ID NO 424
<211> LENGTH: 31
<212> TYPE: RNA
<213> ORGANISM: Arabidopsis thaliana

<400> SEQUENCE: 424
accgucguaa aauaagagca cccggcucug c                               31

<210> SEQ ID NO 425
<211> LENGTH: 31
<212> TYPE: RNA
<213> ORGANISM: Arabidopsis thaliana

<400> SEQUENCE: 425
guaaaauaag agcacccggc ucugcccauu c                               31

<210> SEQ ID NO 426
<211> LENGTH: 31
<212> TYPE: RNA
<213> ORGANISM: Arabidopsis thaliana

<400> SEQUENCE: 426
ccggcucugc ccauucacaa ggacucgauu c                               31

<210> SEQ ID NO 427
<211> LENGTH: 31
<212> TYPE: RNA
<213> ORGANISM: Arabidopsis thaliana

<400> SEQUENCE: 427
gacucgauuc uauguccaaa caucacaugc c                               31

<210> SEQ ID NO 428
<211> LENGTH: 31
<212> TYPE: RNA
<213> ORGANISM: Arabidopsis thaliana

<400> SEQUENCE: 428
guccaaacau cacaugccag cagauguggu c                               31

<210> SEQ ID NO 429
<211> LENGTH: 31
<212> TYPE: RNA
<213> ORGANISM: Arabidopsis thaliana

<400> SEQUENCE: 429

-continued ugguggaacg ugcggaacca cauauuggau c                              31

<210> SEQ ID NO 430
<211> LENGTH: 31
<212> TYPE: RNA
<213> ORGANISM: Arabidopsis thaliana

<400> SEQUENCE: 430
acaaaacuua ucuucaagcu uuaccuuauu c                              31

<210> SEQ ID NO 431
<211> LENGTH: 31
<212> TYPE: RNA
<213> ORGANISM: Arabidopsis thaliana

<400> SEQUENCE: 431
aucuucaagc uuuaccuuau ucugaucguu c                              31

<210> SEQ ID NO 432
<211> LENGTH: 31
<212> TYPE: RNA
<213> ORGANISM: Arabidopsis thaliana

<400> SEQUENCE: 432
ucaagcuuua ccuauucug aucguucaga c                               31

<210> SEQ ID NO 433
<211> LENGTH: 31
<212> TYPE: RNA
<213> ORGANISM: Arabidopsis thaliana

<400> SEQUENCE: 433
cuuucccaug acgacuagga aaaggcaaau c                              31

<210> SEQ ID NO 434
<211> LENGTH: 31
<212> TYPE: RNA
<213> ORGANISM: Arabidopsis thaliana

<400> SEQUENCE: 434
uauguuucua ugauggccca agaacacgcu c                              31

<210> SEQ ID NO 435
<211> LENGTH: 31
<212> TYPE: RNA
<213> ORGANISM: Arabidopsis thaliana

<400> SEQUENCE: 435
cuaugauggc ccaagaacac gcucauucuu c                              31

<210> SEQ ID NO 436
<211> LENGTH: 31
<212> TYPE: RNA
<213> ORGANISM: Arabidopsis thaliana

<400> SEQUENCE: 436
uuacgagcuc aauauauacg aguguuauuc c                              31

<210> SEQ ID NO 437
<211> LENGTH: 31
<212> TYPE: RNA
<213> ORGANISM: Arabidopsis thaliana

```
<400> SEQUENCE: 437
gaguguuauu ccgugaaaua acucgaauuu c                                31

<210> SEQ ID NO 438
<211> LENGTH: 31
<212> TYPE: RNA
<213> ORGANISM: Arabidopsis thaliana

<400> SEQUENCE: 438
uccgugaaau aacucgaauu ucaaaucauu c                                31

<210> SEQ ID NO 439
<211> LENGTH: 31
<212> TYPE: RNA
<213> ORGANISM: Arabidopsis thaliana

<400> SEQUENCE: 439
cuaggaaaag gcaaaucaaa aauuuuacuu c                                31

<210> SEQ ID NO 440
<211> LENGTH: 31
<212> TYPE: RNA
<213> ORGANISM: Arabidopsis thaliana

<400> SEQUENCE: 440
cuucucguau cgaugaauua gaagagaugu c                                31

<210> SEQ ID NO 441
<211> LENGTH: 31
<212> TYPE: RNA
<213> ORGANISM: Arabidopsis thaliana

<400> SEQUENCE: 441
uggggauuca gugguguaau guuaagaggu c                                31

<210> SEQ ID NO 442
<211> LENGTH: 31
<212> TYPE: RNA
<213> ORGANISM: Arabidopsis thaliana

<400> SEQUENCE: 442
uguuaagagg uccaggggua ugcugggauu c                                31

<210> SEQ ID NO 443
<211> LENGTH: 31
<212> TYPE: RNA
<213> ORGANISM: Arabidopsis thaliana

<400> SEQUENCE: 443
gauucgcgaa gagcagcacc uuacgauguu c                                31

<210> SEQ ID NO 444
<211> LENGTH: 31
<212> TYPE: RNA
<213> ORGANISM: Arabidopsis thaliana

<400> SEQUENCE: 444
gagcagcacc uuacgauguu caugaccaau c                                31

<210> SEQ ID NO 445
<211> LENGTH: 31
<212> TYPE: RNA
<213> ORGANISM: Arabidopsis thaliana
```

<400> SEQUENCE: 445
gcaccuuacg auguucauga ccaaucggau c                                31

<210> SEQ ID NO 446
<211> LENGTH: 31
<212> TYPE: RNA
<213> ORGANISM: Arabidopsis thaliana

<400> SEQUENCE: 446
cuugacguac caguagguac cagaggagau c                                31

<210> SEQ ID NO 447
<211> LENGTH: 31
<212> TYPE: RNA
<213> ORGANISM: Arabidopsis thaliana

<400> SEQUENCE: 447
gaccucaaca uccugcugcu cauggucuuu c                                31

<210> SEQ ID NO 448
<211> LENGTH: 31
<212> TYPE: RNA
<213> ORGANISM: Arabidopsis thaliana

<400> SEQUENCE: 448
cagaggagau cgcuaugauc guuacuguau c                                31

<210> SEQ ID NO 449
<211> LENGTH: 31
<212> TYPE: RNA
<213> ORGANISM: Arabidopsis thaliana

<400> SEQUENCE: 449
agaucgcuau gaucguuacu guauccguau c                                31

<210> SEQ ID NO 450
<211> LENGTH: 31
<212> TYPE: RNA
<213> ORGANISM: Arabidopsis thaliana

<400> SEQUENCE: 450
gaugucgaau gaaacuaucc auggaauccu c                                31

<210> SEQ ID NO 451
<211> LENGTH: 31
<212> TYPE: RNA
<213> ORGANISM: Arabidopsis thaliana

<400> SEQUENCE: 451
ccauuucgaa cuuuauacag aagguuuuuc c                                31

<210> SEQ ID NO 452
<211> LENGTH: 31
<212> TYPE: RNA
<213> ORGANISM: Arabidopsis thaliana

<400> SEQUENCE: 452
aauugcauac cuauacaagg guucaaguuu c                                31

<210> SEQ ID NO 453
<211> LENGTH: 31
<212> TYPE: RNA

<213> ORGANISM: Arabidopsis thaliana

<400> SEQUENCE: 453
caaguuucga ucgauauuug cggaguugau c                                    31

<210> SEQ ID NO 454
<211> LENGTH: 31
<212> TYPE: RNA
<213> ORGANISM: Arabidopsis thaliana

<400> SEQUENCE: 454
accagugcag acgaaguaac acgaauaucu c                                    31

<210> SEQ ID NO 455
<211> LENGTH: 31
<212> TYPE: RNA
<213> ORGANISM: Arabidopsis thaliana

<400> SEQUENCE: 455
ccgguaguaa gucuauuucc aucagccggc c                                    31

<210> SEQ ID NO 456
<211> LENGTH: 31
<212> TYPE: RNA
<213> ORGANISM: Arabidopsis thaliana

<400> SEQUENCE: 456
ucaucaauca uccggaucua cgccguauau c                                    31

<210> SEQ ID NO 457
<211> LENGTH: 31
<212> TYPE: RNA
<213> ORGANISM: Arabidopsis thaliana

<400> SEQUENCE: 457
gguuucgagg gucauccauu acgaaaagac c                                    31

<210> SEQ ID NO 458
<211> LENGTH: 31
<212> TYPE: RNA
<213> ORGANISM: Arabidopsis thaliana

<400> SEQUENCE: 458
aaauggaaag aucggaacau gggaauagau c                                    31

<210> SEQ ID NO 459
<211> LENGTH: 31
<212> TYPE: RNA
<213> ORGANISM: Arabidopsis thaliana

<400> SEQUENCE: 459
cuuggaaaaa aucguaguuc agauucaagu c                                    31

<210> SEQ ID NO 460
<211> LENGTH: 31
<212> TYPE: RNA
<213> ORGANISM: Arabidopsis thaliana

<400> SEQUENCE: 460
cuuggaaaaa aucguaguuc agauucaagu c                                    31

<210> SEQ ID NO 461
<211> LENGTH: 31

```
<212> TYPE: RNA
<213> ORGANISM: Arabidopsis thaliana

<400> SEQUENCE: 461
ugguuugaca ugguuuacgu guuacugguu c                              31

<210> SEQ ID NO 462
<211> LENGTH: 31
<212> TYPE: RNA
<213> ORGANISM: Arabidopsis thaliana

<400> SEQUENCE: 462
gguuugacau gguuuacgug uuacugguuc c                              31

<210> SEQ ID NO 463
<211> LENGTH: 31
<212> TYPE: RNA
<213> ORGANISM: Arabidopsis thaliana

<400> SEQUENCE: 463
cguguuacug guucccggaa gaguuaauau c                              31

<210> SEQ ID NO 464
<211> LENGTH: 31
<212> TYPE: RNA
<213> ORGANISM: Arabidopsis thaliana

<400> SEQUENCE: 464
guuacugguu cccggaagag uuaauaucuc c                              31

<210> SEQ ID NO 465
<211> LENGTH: 31
<212> TYPE: RNA
<213> ORGANISM: Arabidopsis thaliana

<400> SEQUENCE: 465
ucccggaaga guuaauaucu ccauuagcgu c                              31

<210> SEQ ID NO 466
<211> LENGTH: 31
<212> TYPE: RNA
<213> ORGANISM: Arabidopsis thaliana

<400> SEQUENCE: 466
ggaagaguua auaucuccau uagcgucacc c                              31

<210> SEQ ID NO 467
<211> LENGTH: 31
<212> TYPE: RNA
<213> ORGANISM: Arabidopsis thaliana

<400> SEQUENCE: 467
cgucacccuu ucuuacccug ccuuuugacu c                              31

<210> SEQ ID NO 468
<211> LENGTH: 31
<212> TYPE: RNA
<213> ORGANISM: Arabidopsis thaliana

<400> SEQUENCE: 468
ggagaacaaa ggacgaaaua caaucgauuc c                              31

<210> SEQ ID NO 469
```

-continued

```
<211> LENGTH: 31
<212> TYPE: RNA
<213> ORGANISM: Arabidopsis thaliana

<400> SEQUENCE: 469
gaacaaagga cgaaauacaa ucgauccuc c                           31

<210> SEQ ID NO 470
<211> LENGTH: 31
<212> TYPE: RNA
<213> ORGANISM: Arabidopsis thaliana

<400> SEQUENCE: 470
aauacaaucg auuccuccau uuaaguggu c                           31

<210> SEQ ID NO 471
<211> LENGTH: 31
<212> TYPE: RNA
<213> ORGANISM: Arabidopsis thaliana

<400> SEQUENCE: 471
uacaaucgau uccuccauuu aagugguucu c                          31

<210> SEQ ID NO 472
<211> LENGTH: 31
<212> TYPE: RNA
<213> ORGANISM: Arabidopsis thaliana

<400> SEQUENCE: 472
auuccuccau uuaagugguu cucgcuucuu c                          31

<210> SEQ ID NO 473
<211> LENGTH: 31
<212> TYPE: RNA
<213> ORGANISM: Arabidopsis thaliana

<400> SEQUENCE: 473
ucucgcuucu ucuuguuccu guuccuaacu c                          31

<210> SEQ ID NO 474
<211> LENGTH: 31
<212> TYPE: RNA
<213> ORGANISM: Arabidopsis thaliana

<400> SEQUENCE: 474
cucgcuucuu cuuguuccug uuccuaacuc c                          31

<210> SEQ ID NO 475
<211> LENGTH: 31
<212> TYPE: RNA
<213> ORGANISM: Arabidopsis thaliana

<400> SEQUENCE: 475
cgcuucuucu uguuccuguu ccuaacuccu c                          31

<210> SEQ ID NO 476
<211> LENGTH: 31
<212> TYPE: RNA
<213> ORGANISM: Arabidopsis thaliana

<400> SEQUENCE: 476
uucuucuugu uccuguuccu aacuccuccc c                          31
```

```
<210> SEQ ID NO 477
<211> LENGTH: 31
<212> TYPE: RNA
<213> ORGANISM: Arabidopsis thaliana

<400> SEQUENCE: 477 cccggucgu ucccaauguu uggcacuuuc c                              31

<210> SEQ ID NO 478
<211> LENGTH: 31
<212> TYPE: RNA
<213> ORGANISM: Arabidopsis thaliana

<400> SEQUENCE: 478
cuucgugggu gcaacaucaa caaauucgcu c                             31

<210> SEQ ID NO 479
<211> LENGTH: 31
<212> TYPE: RNA
<213> ORGANISM: Arabidopsis thaliana

<400> SEQUENCE: 479
augaucaagu uacaaccuaa gaucuaugac c                             31

<210> SEQ ID NO 480
<211> LENGTH: 31
<212> TYPE: RNA
<213> ORGANISM: Arabidopsis thaliana

<400> SEQUENCE: 480
augaccauau uauguuaacu guucguauuu c                             31

<210> SEQ ID NO 481
<211> LENGTH: 31
<212> TYPE: RNA
<213> ORGANISM: Arabidopsis thaliana

<400> SEQUENCE: 481
auuauguuaa cuguucguau uucguucauu c                             31

<210> SEQ ID NO 482
<211> LENGTH: 31
<212> TYPE: RNA
<213> ORGANISM: Arabidopsis thaliana

<400> SEQUENCE: 482
ucguauuucg uucauuccau cgguaugcuc c                             31

<210> SEQ ID NO 483
<211> LENGTH: 31
<212> TYPE: RNA
<213> ORGANISM: Arabidopsis thaliana

<400> SEQUENCE: 483
cccagguacc uguaauugug aucuguuugc c                             31

<210> SEQ ID NO 484
<211> LENGTH: 31
<212> TYPE: RNA
<213> ORGANISM: Arabidopsis thaliana

<400> SEQUENCE: 484
guaccuguaa uugugaucug uuugccagaa c                             31
```

<210> SEQ ID NO 485
<211> LENGTH: 31
<212> TYPE: RNA
<213> ORGANISM: Arabidopsis thaliana

<400> SEQUENCE: 485
uaccuguaau ugugaucugu uugccagaac c        31

<210> SEQ ID NO 486
<211> LENGTH: 31
<212> TYPE: RNA
<213> ORGANISM: Arabidopsis thaliana

<400> SEQUENCE: 486
uauauauauc cuaugaauuu aauuucgcau c        31

<210> SEQ ID NO 487
<211> LENGTH: 31
<212> TYPE: RNA
<213> ORGANISM: Arabidopsis thaliana

<400> SEQUENCE: 487
acgaacaauc gucguuuuuu gaugguuuuu c        31

<210> SEQ ID NO 488
<211> LENGTH: 31
<212> TYPE: RNA
<213> ORGANISM: Arabidopsis thaliana

<400> SEQUENCE: 488
aaucgucguu uuugauggu uuuccgcuu c        31

<210> SEQ ID NO 489
<211> LENGTH: 31
<212> TYPE: RNA
<213> ORGANISM: Arabidopsis thaliana

<400> SEQUENCE: 489
ugguuuuucc gcuucucaca gcugcucuuu c        31

<210> SEQ ID NO 490
<211> LENGTH: 31
<212> TYPE: RNA
<213> ORGANISM: Arabidopsis thaliana

<400> SEQUENCE: 490
gguuuuuccg cuucucacag cugcucuuuc c        31

<210> SEQ ID NO 491
<211> LENGTH: 31
<212> TYPE: RNA
<213> ORGANISM: Arabidopsis thaliana

<400> SEQUENCE: 491
uuccacaccu ccggauaucu ggugccaaau c        31

<210> SEQ ID NO 492
<211> LENGTH: 31
<212> TYPE: RNA
<213> ORGANISM: Arabidopsis thaliana

<400> SEQUENCE: 492
ccuccggaua ucggugcca aaucgucgcc c        31

```
<210> SEQ ID NO 493
<211> LENGTH: 31
<212> TYPE: RNA
<213> ORGANISM: Arabidopsis thaliana

<400> SEQUENCE: 493
ggauaucugg ugccaaaucg ucgcccguuu c                           31

<210> SEQ ID NO 494
<211> LENGTH: 31
<212> TYPE: RNA
<213> ORGANISM: Arabidopsis thaliana

<400> SEQUENCE: 494
ugauaauaga guuggcuauu uuuguggcau c                           31

<210> SEQ ID NO 495
<211> LENGTH: 31
<212> TYPE: RNA
<213> ORGANISM: Arabidopsis thaliana

<400> SEQUENCE: 495
auucuaggag aaguucgaau ccguuccguu c                           31

<210> SEQ ID NO 496
<211> LENGTH: 31
<212> TYPE: RNA
<213> ORGANISM: Arabidopsis thaliana

<400> SEQUENCE: 496
ccuuugcacg agucagaaac cgauguauuu c                           31

<210> SEQ ID NO 497
<211> LENGTH: 31
<212> TYPE: RNA
<213> ORGANISM: Arabidopsis thaliana

<400> SEQUENCE: 497
aaagcuuuau aaagccuuuu guaaagaucc c                           31

<210> SEQ ID NO 498
<211> LENGTH: 31
<212> TYPE: RNA
<213> ORGANISM: Arabidopsis thaliana

<400> SEQUENCE: 498
guacaaaacu ggguuuugga agauauggca c                           31

<210> SEQ ID NO 499
<211> LENGTH: 31
<212> TYPE: RNA
<213> ORGANISM: Arabidopsis thaliana

<400> SEQUENCE: 499
agauauggca cuaaaaguug uaaagcuggu c                           31

<210> SEQ ID NO 500
<211> LENGTH: 31
<212> TYPE: RNA
<213> ORGANISM: Arabidopsis thaliana

<400> SEQUENCE: 500
```
uauuuaacca uaaaaucgau uaugcuccug c         31

<210> SEQ ID NO 501
<211> LENGTH: 31
<212> TYPE: RNA
<213> ORGANISM: Arabidopsis thaliana

<400> SEQUENCE: 501
auaaaaucga uuaugcuccu gcggaaguau c         31

<210> SEQ ID NO 502
<211> LENGTH: 31
<212> TYPE: RNA
<213> ORGANISM: Arabidopsis thaliana

<400> SEQUENCE: 502
ggauugcucg uguguccacg ggacaaaucc c         31

<210> SEQ ID NO 503
<211> LENGTH: 31
<212> TYPE: RNA
<213> ORGANISM: Arabidopsis thaliana

<400> SEQUENCE: 503
gacaagccgc uacauuagcg gcucauaaac c         31

<210> SEQ ID NO 504
<211> LENGTH: 31
<212> TYPE: RNA
<213> ORGANISM: Arabidopsis thaliana

<400> SEQUENCE: 504
ccgcuacauu agcggcucau aaaccauguu c         31

<210> SEQ ID NO 505
<211> LENGTH: 31
<212> TYPE: RNA
<213> ORGANISM: Arabidopsis thaliana

<400> SEQUENCE: 505
cugcggaagu aucuacucgu uacggaaucu c         31

<210> SEQ ID NO 506
<211> LENGTH: 31
<212> TYPE: RNA
<213> ORGANISM: Arabidopsis thaliana

<400> SEQUENCE: 506
augacccuaa ucguucuucu cagaucgcuc c         31

<210> SEQ ID NO 507
<211> LENGTH: 31
<212> TYPE: RNA
<213> ORGANISM: Arabidopsis thaliana

<400> SEQUENCE: 507
aaguucgcuc cgccgcgcaa gauccucgaa c         31

<210> SEQ ID NO 508
<211> LENGTH: 31
<212> TYPE: RNA
<213> ORGANISM: Arabidopsis thaliana

<400> SEQUENCE: 508
aacgcauagc auucucuggg cacauaggau c                          31

<210> SEQ ID NO 509
<211> LENGTH: 31
<212> TYPE: RNA
<213> ORGANISM: Arabidopsis thaliana

<400> SEQUENCE: 509
aaaaauggaa aauuggcuau ggagauuccg c                          31

<210> SEQ ID NO 510
<211> LENGTH: 31
<212> TYPE: RNA
<213> ORGANISM: Arabidopsis thaliana

<400> SEQUENCE: 510
cucuccgagg gcauggaaug ucuaauuuuu c                          31

<210> SEQ ID NO 511
<211> LENGTH: 31
<212> TYPE: RNA
<213> ORGANISM: Arabidopsis thaliana

<400> SEQUENCE: 511
auggaauguc uaauuuuucg gucagaaucu c                          31

<210> SEQ ID NO 512
<211> LENGTH: 31
<212> TYPE: RNA
<213> ORGANISM: Arabidopsis thaliana

<400> SEQUENCE: 512
uuccacucaa uuuucauuac gaagauguau c                          31

<210> SEQ ID NO 513
<211> LENGTH: 31
<212> TYPE: RNA
<213> ORGANISM: Arabidopsis thaliana

<400> SEQUENCE: 513
uucauuacga agauguauca cgucaagauc c                          31

<210> SEQ ID NO 514
<211> LENGTH: 31
<212> TYPE: RNA
<213> ORGANISM: Arabidopsis thaliana

<400> SEQUENCE: 514
cuucggccaa cacacaagau gagacuuuac c                          31

<210> SEQ ID NO 515
<211> LENGTH: 31
<212> TYPE: RNA
<213> ORGANISM: Arabidopsis thaliana

<400> SEQUENCE: 515
gauguaucac gucaagaucc guugcucaaa c                          31

<210> SEQ ID NO 516
<211> LENGTH: 31
<212> TYPE: RNA
<213> ORGANISM: Arabidopsis thaliana

```
<400> SEQUENCE: 516
auguaucacg ucaagauccg uugcucaaac c                                31

<210> SEQ ID NO 517
<211> LENGTH: 31
<212> TYPE: RNA
<213> ORGANISM: Arabidopsis thaliana

<400> SEQUENCE: 517
ucacgucaag auccguugcu caaaccgaau c                                31

<210> SEQ ID NO 518
<211> LENGTH: 31
<212> TYPE: RNA
<213> ORGANISM: Arabidopsis thaliana

<400> SEQUENCE: 518
aucacgccaa cguuauggaa guuccuggau c                                31

<210> SEQ ID NO 519
<211> LENGTH: 31
<212> TYPE: RNA
<213> ORGANISM: Arabidopsis thaliana

<400> SEQUENCE: 519
auaaaugucc ccagaaaaca ggaguaugcc c                                31

<210> SEQ ID NO 520
<211> LENGTH: 31
<212> TYPE: RNA
<213> ORGANISM: Arabidopsis thaliana

<400> SEQUENCE: 520
cgagaacacc gaaaaaaccu aauuccgcuc c                                31

<210> SEQ ID NO 521
<211> LENGTH: 31
<212> TYPE: RNA
<213> ORGANISM: Arabidopsis thaliana

<400> SEQUENCE: 521
cgguugagca aucgacauga uauauuugcu c                                31

<210> SEQ ID NO 522
<211> LENGTH: 31
<212> TYPE: RNA
<213> ORGANISM: Arabidopsis thaliana

<400> SEQUENCE: 522
uugcucacau cccgggcgaa ggucauaauu c                                31

<210> SEQ ID NO 523
<211> LENGTH: 31
<212> TYPE: RNA
<213> ORGANISM: Arabidopsis thaliana

<400> SEQUENCE: 523
uguuaauaag aggagguaga gugaaagauu c                                31

<210> SEQ ID NO 524
<211> LENGTH: 31
<212> TYPE: RNA
<213> ORGANISM: Arabidopsis thaliana
```

-continued

<400> SEQUENCE: 524
guagagugaa agauucgcca gguguaaaau c                                              31

<210> SEQ ID NO 525
<211> LENGTH: 31
<212> TYPE: RNA
<213> ORGANISM: Arabidopsis thaliana

<400> SEQUENCE: 525
uagagugaaa gauucgccag guguaaaauc c                                              31

<210> SEQ ID NO 526
<211> LENGTH: 31
<212> TYPE: RNA
<213> ORGANISM: Arabidopsis thaliana

<400> SEQUENCE: 526
ggaccguacu cgagcuuugg auaaaugucc c                                              31

<210> SEQ ID NO 527
<211> LENGTH: 31
<212> TYPE: RNA
<213> ORGANISM: Arabidopsis thaliana

<400> SEQUENCE: 527
caaucaauua agggucaaau guuggaaccu c                                              31

<210> SEQ ID NO 528
<211> LENGTH: 31
<212> TYPE: RNA
<213> ORGANISM: Arabidopsis thaliana

<400> SEQUENCE: 528
gaaagagagg aauuccguac agguacaacu c                                              31

<210> SEQ ID NO 529
<211> LENGTH: 31
<212> TYPE: RNA
<213> ORGANISM: Arabidopsis thaliana

<400> SEQUENCE: 529
guaucaagau gucaaucuga gaucuuauuu c                                              31

<210> SEQ ID NO 530
<211> LENGTH: 31
<212> TYPE: RNA
<213> ORGANISM: Arabidopsis thaliana

<400> SEQUENCE: 530
guacagguac aacucuuauu uuuacgaagu c                                              31

<210> SEQ ID NO 531
<211> LENGTH: 31
<212> TYPE: RNA
<213> ORGANISM: Arabidopsis thaliana

<400> SEQUENCE: 531
uuuuuacgaa gucaaaaaaa ugcgaucuuu c                                              31

<210> SEQ ID NO 532
<211> LENGTH: 31
<212> TYPE: RNA

<213> ORGANISM: Arabidopsis thaliana

<400> SEQUENCE: 532
gucagucaaa auaaaaucug uuuaucaaag c           31

<210> SEQ ID NO 533
<211> LENGTH: 31
<212> TYPE: RNA
<213> ORGANISM: Arabidopsis thaliana

<400> SEQUENCE: 533
aaaauaaaau cuguuuauca aagcgcuucu c           31

<210> SEQ ID NO 534
<211> LENGTH: 31
<212> TYPE: RNA
<213> ORGANISM: Arabidopsis thaliana

<400> SEQUENCE: 534
aaauaaaauc uguuuaucaa agcgcuucuc c           31

<210> SEQ ID NO 535
<211> LENGTH: 31
<212> TYPE: RNA
<213> ORGANISM: Arabidopsis thaliana

<400> SEQUENCE: 535 aggggugag ggaauccgua uauguuuuc c           31

<210> SEQ ID NO 536
<211> LENGTH: 31
<212> TYPE: RNA
<213> ORGANISM: Arabidopsis thaliana

<400> SEQUENCE: 536
aaacuaaaug cuauaagcau agaaaaacuu c           31

<210> SEQ ID NO 537
<211> LENGTH: 31
<212> TYPE: RNA
<213> ORGANISM: Arabidopsis thaliana

<400> SEQUENCE: 537
acuaaaugcu auaagcauag aaaacuucu c           31

<210> SEQ ID NO 538
<211> LENGTH: 31
<212> TYPE: RNA
<213> ORGANISM: Arabidopsis thaliana

<400> SEQUENCE: 538
uauuuaacca uaaaucgau uaugcuccug c           31

<210> SEQ ID NO 539
<211> LENGTH: 31
<212> TYPE: RNA
<213> ORGANISM: Arabidopsis thaliana

<400> SEQUENCE: 539
auaaaaucga uuaugcuccu gcggaaguau c           31

<210> SEQ ID NO 540
<211> LENGTH: 31

```
<212> TYPE: RNA
<213> ORGANISM: Arabidopsis thaliana

<400> SEQUENCE: 540
cugcggaagu aucuacucgu uacggaaucu c                              31

<210> SEQ ID NO 541
<211> LENGTH: 31
<212> TYPE: RNA
<213> ORGANISM: Arabidopsis thaliana

<400> SEQUENCE: 541
uucggcuuuc gucucgguag guguauuauu c                              31

<210> SEQ ID NO 542
<211> LENGTH: 31
<212> TYPE: RNA
<213> ORGANISM: Arabidopsis thaliana

<400> SEQUENCE: 542
accgauuacc cucgauaaag aagaaucuuu c                              31

<210> SEQ ID NO 543
<211> LENGTH: 31
<212> TYPE: RNA
<213> ORGANISM: Arabidopsis thaliana

<400> SEQUENCE: 543
uacccucgau aaagaagaau cuuucuaaau c                              31

<210> SEQ ID NO 544
<211> LENGTH: 31
<212> TYPE: RNA
<213> ORGANISM: Arabidopsis thaliana

<400> SEQUENCE: 544
agcguuccug auagaaaaug acgacuccuu c                              31

<210> SEQ ID NO 545
<211> LENGTH: 31
<212> TYPE: RNA
<213> ORGANISM: Arabidopsis thaliana

<400> SEQUENCE: 545
cuuggaaaaa aucguaguuc agauucaagu c                              31

<210> SEQ ID NO 546
<211> LENGTH: 31
<212> TYPE: RNA
<213> ORGANISM: Arabidopsis thaliana

<400> SEQUENCE: 546
guucucguau cgcuuuuuuu guagaaagcu c                              31

<210> SEQ ID NO 547
<211> LENGTH: 31
<212> TYPE: RNA
<213> ORGANISM: Arabidopsis thaliana

<400> SEQUENCE: 547
cauaucccuc acgacauaag auuaaaagau c                              31

<210> SEQ ID NO 548
```

<210> SEQ ID NO 548
<211> LENGTH: 31
<212> TYPE: RNA
<213> ORGANISM: Arabidopsis thaliana

<400> SEQUENCE: 548
auaucccuca cgacauaaga uuaaaagauc c        31

<210> SEQ ID NO 549
<211> LENGTH: 31
<212> TYPE: RNA
<213> ORGANISM: Arabidopsis thaliana

<400> SEQUENCE: 549
acgacauaag auuaaaagau ccaaaccuuc c        31

<210> SEQ ID NO 550
<211> LENGTH: 31
<212> TYPE: RNA
<213> ORGANISM: Arabidopsis thaliana

<400> SEQUENCE: 550
auaagauuaa aagauccaaa ccuuccucuu c        31

<210> SEQ ID NO 551
<211> LENGTH: 31
<212> TYPE: RNA
<213> ORGANISM: Arabidopsis thaliana

<400> SEQUENCE: 551
aagagaucua uuaagaagag aaagauuuau c        31

<210> SEQ ID NO 552
<211> LENGTH: 31
<212> TYPE: RNA
<213> ORGANISM: Arabidopsis thaliana

<400> SEQUENCE: 552
uauauacaau uacaaacuac acgaaaguug c        31

<210> SEQ ID NO 553
<211> LENGTH: 31
<212> TYPE: RNA
<213> ORGANISM: Arabidopsis thaliana

<400> SEQUENCE: 553
auacaauuac aaacuacacg aaaguugccc c        31

<210> SEQ ID NO 554
<211> LENGTH: 31
<212> TYPE: RNA
<213> ORGANISM: Arabidopsis thaliana

<400> SEQUENCE: 554
uuacaaacua cacgaaaguu gccccuuuuu c        31

<210> SEQ ID NO 555
<211> LENGTH: 31
<212> TYPE: RNA
<213> ORGANISM: Arabidopsis thaliana

<400> SEQUENCE: 555
gaacaaaacg aacuucauau aucccuuuuc c        31

-continued

```
<210> SEQ ID NO 556
<211> LENGTH: 31
<212> TYPE: RNA
<213> ORGANISM: Arabidopsis thaliana

<400> SEQUENCE: 556
gaacuucaua uaucccuuuu ccacucaauc c                              31

<210> SEQ ID NO 557
<211> LENGTH: 31
<212> TYPE: RNA
<213> ORGANISM: Arabidopsis thaliana

<400> SEQUENCE: 557
ucaauccaga aacaagauuu gacguuauuc c                              31

<210> SEQ ID NO 558
<211> LENGTH: 31
<212> TYPE: RNA
<213> ORGANISM: Arabidopsis thaliana

<400> SEQUENCE: 558
acaagauuug acguuauucc gcuucgucuc c                              31

<210> SEQ ID NO 559
<211> LENGTH: 31
<212> TYPE: RNA
<213> ORGANISM: Arabidopsis thaliana

<400> SEQUENCE: 559
uucuugaaac uauuccucaa gcaaggcagc c                              31

<210> SEQ ID NO 560
<211> LENGTH: 31
<212> TYPE: RNA
<213> ORGANISM: Arabidopsis thaliana

<400> SEQUENCE: 560
aaauaaggag aucuuucuau aaagaaauuu c                              31

<210> SEQ ID NO 561
<211> LENGTH: 31
<212> TYPE: RNA
<213> ORGANISM: Arabidopsis thaliana

<400> SEQUENCE: 561
cauuaagauu ucaaacuugu cgucuacuuu c                              31

<210> SEQ ID NO 562
<211> LENGTH: 31
<212> TYPE: RNA
<213> ORGANISM: Arabidopsis thaliana

<400> SEQUENCE: 562
caaacuuguc gucuacuuuc aggaaauguu c                              31

<210> SEQ ID NO 563
<211> LENGTH: 31
<212> TYPE: RNA
<213> ORGANISM: Arabidopsis thaliana

<400> SEQUENCE: 563
ucaaaaggau cgaacuaccu acucauuauu c                              31
```

```
<210> SEQ ID NO 564
<211> LENGTH: 31
<212> TYPE: RNA
<213> ORGANISM: Arabidopsis thaliana

<400> SEQUENCE: 564
gaacuaccua cucauuauuc ggagguuaau c                                        31

<210> SEQ ID NO 565
<211> LENGTH: 31
<212> TYPE: RNA
<213> ORGANISM: Arabidopsis thaliana

<400> SEQUENCE: 565
uuaaucauag aacaccaaaa gcugugguau c                                        31

<210> SEQ ID NO 566
<211> LENGTH: 31
<212> TYPE: RNA
<213> ORGANISM: Arabidopsis thaliana

<400> SEQUENCE: 566
uaagcuauag gauaagcuua gagaaauguu c                                        31

<210> SEQ ID NO 567
<211> LENGTH: 32
<212> TYPE: DNA
<213> ORGANISM: Artificial Sequence
<220> FEATURE:
<223> OTHER INFORMATION: Enko_B-F primer

<400> SEQUENCE: 567
cgcgaattca gcggagagag ttgcgaagca gg                                       32

<210> SEQ ID NO 568
<211> LENGTH: 31
<212> TYPE: DNA
<213> ORGANISM: Artificial Sequence
<220> FEATURE:
<223> OTHER INFORMATION: Enko_B-R primer

<400> SEQUENCE: 568
cgcgtcgact catcccccaa atgatagatc c                                        31

<210> SEQ ID NO 569
<211> LENGTH: 32
<212> TYPE: DNA
<213> ORGANISM: Artificial Sequence
<220> FEATURE:
<223> OTHER INFORMATION: Kosena_B-F primer

<400> SEQUENCE: 569
cgcgaattca gcggagagag ttgcgaagca gg                                       32

<210> SEQ ID NO 570
<211> LENGTH: 31
<212> TYPE: DNA
<213> ORGANISM: Artificial Sequence
<220> FEATURE:
<223> OTHER INFORMATION: Kosena_B-R primer

<400> SEQUENCE: 570
cgcgtcgact catcccccaa atgatagatc c                                        31
```

<210> SEQ ID NO 571
<211> LENGTH: 38
<212> TYPE: DNA
<213> ORGANISM: Artificial Sequence
<220> FEATURE:
<223> OTHER INFORMATION: Enko A-F primer

<400> SEQUENCE: 571
cgcgaattca gcagggatgg agagagtggc gaagcagg            38

<210> SEQ ID NO 572
<211> LENGTH: 54
<212> TYPE: DNA
<213> ORGANISM: Artificial Sequence
<220> FEATURE:
<223> OTHER INFORMATION: Enko A-R primer

<400> SEQUENCE: 572
cgcgtcgact tcatcctcca actgatatcc cacactcatc tgcagatcct caag    54

<210> SEQ ID NO 573
<211> LENGTH: 2064
<212> TYPE: DNA
<213> ORGANISM: Raphanus sativus

<400> SEQUENCE: 573

| | | |
|---|---|---|
| atgttggcta gggtttgtgg attcaagtgt tcttcttctc ctgctgagtc tgcggctaga | 60 |
| ttgttctgta cgagatcgat tcgtgatact ctggccaagg caagcggaga gagttgcgaa | 120 |
| gcaggttttg gaggagagag tttgaagctg caaagtgggt tcatgaaat caaaggttta | 180 |
| gaggatgcga ttgatttgtt cagtgacatg cttcgatctc gtcctttacc ttctgtggtt | 240 |
| gatttctgta aattgatggg tgtggtggtg agaatggaac gcccggatct tgtgatttct | 300 |
| ctctatcaga agatggaaag gaaacagatt cgatgtgata tatacagctt caatattctg | 360 |
| ataaaatgtt tctgcagctg ctctaagctc ccctttgctt tgtctacatt tggtaagatc | 420 |
| accaagcttg gactccaccc tgatgttgtt accttcacca ccctgctcca tggattatgt | 480 |
| gtggaagata gggtttctga agccttggat tttttcatc aaatgtttga acgacatgt | 540 |
| aggcccaatg tcgtaacctt caccactttg atgaacggtc tttgccgcga gggtagaatt | 600 |
| gtcgaagccg tagctctgct tgatcggatg atggaagatg gtctccagcc tacccagatt | 660 |
| acttatggaa caatcgtaga tgggatgtgt aagaagggag atactgtgtc tgcactgaat | 720 |
| ctgctgagga agatggagga ggtgagccac atcatcacca atgttgtaat ctatagtgca | 780 |
| atcattgata gcctttgtaa agacggacgt atagcgatg cacaaaatct tttcactgaa | 840 |
| atgcaagaga aggaatctt tcccgattta tttacctaca acagtatgat agttggtttt | 900 |
| tgtagctctg gtagatggag cgacgcggag cagttgttgc aagaaatgtt agaaaggaag | 960 |
| atcagccctg atgttgtaac ttataatgct ttgatcaatg catttgtcaa ggaaggcaag | 1020 |
| ttctttgagg ctgaagaatt atacgatgag atgcttccaa ggggtataat ccctaataca | 1080 |
| atcacatata gttcaatgat cgatggattt tgcaaacaga atcgtcttga tgctgctgag | 1140 |
| cacatgtttt atttgatggc taccaagggc tgctctccca acctaatcac tttcaatact | 1200 |
| ctcatagacg atattgtgg ggctaagagg atagatgatg gaatgaact tctccatgag | 1260 |
| atgactgaaa caggattagt tgctgacaca actacttaca acactcttat tcacgggttc | 1320 |
| tatctggtgg gcgatcttaa tgctgctcta gacctttac aagagatgat ctctagtggt | 1380 |
| ttgtgccctg atatcgttac ttgtgacact ttgctggatg gtctctgcga taatgggaaa | 1440 |

```
ctaaaagatg cattggaaat gtttaaggtt atgcagaaga gtaagaagga tcttgatgct    1500
agtcacccct tcaatggtgt ggaacctgat gttcaaactt acaatatatt gatcagcggc    1560
ttgatcaatg aagggaagtt tttagaggcc gaggaattat acgaggagat gccccacagg    1620
ggtatagtcc cagatactat cacctatagc tcaatgatcg atggattatg caagcagagc    1680
cgcctagatg aggctacaca aatgtttgat tcgatgggta gcaagagctt ctctccaaac    1740
gtagtgacct ttactacact cattaatggc tactgtaagg caggaagggt tgatgatggg    1800
ctggagcttt tctgcgagat gggtcgaaga gggatagttg ctaacgcaat tacttacatc    1860
actttgattt gtggttttcg taaagtgggt aatattaatg ggctctaga cattttccag    1920 gagatgattt caagtggtgt gtatcctgat accattacca tccgcaatat gctgactggt    1980
ttatggagta agaggaact aaaaagggca gtggcaatgc ttgagaaact gcagatgagt    2040
atggatctat catttggggg atga                                           2064

<210> SEQ ID NO 574
<211> LENGTH: 2064
<212> TYPE: DNA
<213> ORGANISM: Raphanus sativus

<400> SEQUENCE: 574
atgttggcta gggtttgtgg attcaagtgt tcttcttctc ctgctgagtc tgcggctaga     60
ttgttctgta cgagatcgat tcgtgatact ctggccaagg caagcggaga gagttgcgaa    120
gcaggttttg gaggagagag tttgaagctg caaagtgggt ttcatgaaat caaaggttta    180
gaggatgcga ttgatttgtt cagtgacatg cttcgatctc gtcctttacc ttctgtggtt    240
gatttctgta aattgatggg tgtggtggtg agaatggaac gcccggatct tgtgatttct    300
ctctatcaga agatggaaag gaaacagatt cgatgtgata tatacagctt caccattctg    360
ataaaatgtt tctgcagctg ctctaagctc ccctttgctt tgtctacatt tggtaagatc    420
accaagcttg gactccaccc tgatgttgtt accttcaaca ccctgctcca cggattgtgc    480
gtggaagata gggttctga agctttgaat tgtttcatc aaatgtttga acgacatgt    540 aggcccaatg tcgtaacctt caccactttg atgaacggtc tttgccgcga gggtagaatt    600
gtcgaagccg tagctctgct tgatcggatg atggaagatg gtctccagcc tacccagatt    660
acttatggaa caatcgtaga tgggatgtgt aagaagggag atactgtgtc tgcattgaat    720
cttctgagga agatggagga ggtgagccac atcatacccca atgttgtaat ctatagtgca    780
atcattgata gccttttgtaa agacggacgt catagcgatg cacaaaatct tttcactgaa    840
atgcaagaga aaggaatctt tcccgattta tttacctaca acagtatgat agttggtttt    900
tgtagctctg gtagatggag cgacgcggag cagttgttgc aagaaatgtt agaaaggaag    960
atcagccctg atgttgtaac ttataatgct ttgatcaatg catttgtcaa ggaaggcaag   1020
ttctttgagg ctgaagaatt atacgatgag atgcttccaa ggggtataat ccctaataca   1080
atcacatata gttcaatgat cgatggattt tgcaaacaga atcgtcttga tgctgctgag   1140
cacatgtttt atttgatggc taccaagggc tgctctccca acctaatcac tttcaatact   1200
ctcatagacg atattgtgg ggctaagagg atagatgatg aatggaact tctccatgag   1260 atgactgaaa caggattagt tgctgacaca actacttaca acactcttat tcacgggttc   1320
tatctggtgg gcgatcttaa tgctgctcta gacctttac aagagatgat ctctagtggt   1380
ttgtgccctg atatcgttac ttgtgacact ttgctggatg gtctctgcga taatgggaaa   1440
ctaaaagatg cattggaaat gtttaaggtt atgcagaaga gtaagaagga tcttgatgct   1500
```

```
agtcacccct tcaatggtgt ggaacctgat gttcaaactt acaatatatt gatcagcggc      1560
ttgatcaatg aagggaagtt tttagaggcc gaggaattat acgaggagat gccccacagg      1620
ggtatagtcc cagatactat cacctatagc tcaatgatcg atggattatg caagcagagc      1680
cgcctagatg aggctacaca aatgtttgat tcgatgggta gcaagagctt ctctccaaac      1740
gtagtgacct ttactacact cattaatggc tactgtaagg caggaagggt tgatgatggg      1800
ctggagcttt tctgcgagat gggtcgaaga gggatagttg ctaacgcaat tacttacatc      1860
actttgattt gtggttttcg taaagtgggt aatattaatg gggctctaga cattttccag      1920
gagatgattt caagtggtgt gtatcctgat accattacca tccgcaatat gctgactggt      1980
ttatggagta agaggaact aaaaagggca gtggcaatgc ttgagaaact gcagatgagt      2040
atggatctat catttggggg atga                                             2064
```

<210> SEQ ID NO 575
<211> LENGTH: 2061
<212> TYPE: DNA
<213> ORGANISM: Raphanus sativus

<400> SEQUENCE: 575

```
atgttggcta gggtttgcag attcgagtct tcctcttcgt cttctgtgtc tgcggctaga        60
tttttctgta cgggatcgat tcgtcatgct ctggccgaga aaagcaggga tggagagagt       120
ggcgaagcag gttttagagg agagagtttg aaactgcgaa gtggatctta tgaaatcaaa       180
gggttagagg atgcgattga tttgttcagt gacatgcttc gatctcgtcc tttaccttct       240
gtgattgatt tcaacaagct aatgggtgcg gtggtgagaa tggaacgccc ggatcttgtg       300
atttctctct atcaaaagat ggaaaggaaa cagattcgat gtgatatata cagcttcacc       360
attctgataa aatgtttctg cagttgctct aagctcccct ttgctttgtc tacatttggt       420
aagctcacca agcttggact ccaccctgat gttgttacct tcaccaccct gctccacgga       480
ttatgtcttg atcacagggt ttctgaagcc ttggatttgt ttcatcaaat ttgtagacca       540
gatgtcctaa cgttcaccac gctgatgaat ggtctttgcc gcgagggtcg agttgtcgaa       600
gccgtagctc tgcttgatcg gatggtggaa atggtctccc agcctgacca gattacttac       660
ggaacatttg tagatgggat gtgtaagatg ggcgacactg tgtctgcatt gaatcttctg       720
aggaagatgg aggagataag ccacatcaaa cccaatgtgg ttatctatag tgccatcatt       780
gatggccttt gtaaagatgg acgccatagc gattctcata atcttttcat tgaaatgcaa       840
gacaagggaa tcttttccaaa tatagttacc tacaactgta tgatcggtgg attttgcatc       900
tctggtagat ggagtgcagc ccagcggttg ttgcaagaaa tgttagaaag gaagatcagc       960
cctaatgttg taacttataa tgctttgatc aatgcatttg tcaaggaagg caagttcttc      1020
gaggctgcag aattatacga tgagatgctt ccaagggta tcattcctaa tacaatcaca       1080
tataattcaa tgatcgatgg ttttgcaaaa caggatcgtc ttgatgctgc tgaggacatg      1140
ttttatttga tggctaccaa gggctgctct ccggacgtat tcactttcac tactctcata      1200
gacggatatt gtggggctaa gaggatagat gatggaatgg aacttctcca tgagatgcct      1260
agaagaggat tagttgctaa cacagttact tacaacactc ttattcacgg gttctgtctg      1320
gtgggcgatc ttaatgctgc tctagacctt tcacagcaga tgatttctag tggtgtgtgc      1380
cctgatatcg ttacttgtaa cactttgctg gacggtctct gcgataatgg gaaactaaaa      1440
gatgcattgg aaatgtttaa ggctatgcag aagagtaaga tggatcttga tgctagtcac      1500
```

-continued

```
ccccttcaatg gtgtggaacc tgatgttcta acttacaata tattgatctg cggcttgatc    1560
aatgaaggga agttttttaga ggccgaggaa ttatacgagg agatgccaca cagaggtata    1620
gtcccagata ctatcaccta tagctcaatg atcgatggac tatgcaagca gagccgccta    1680
gatgaggcta cacaaatgtt tgtttcgatg ggtagcaaga gcttctctcc caacgtagtg    1740
acatttaaca cactcattaa tggctactgt aaggcaggaa gggttgatga tgggctggag    1800
cttttctgcg agatgggtcg aagagggata gttgctgatg caattattta catcactttg    1860
atttatggtt ttcgtaaagt gggtaatatt aatgggctc tagacatttt ccaggagatg    1920
atttcaagtg gtgtgtatcc tgataccatt actatccgca atatgctgac tggtttttgg    1980
agtaaagagg aactagaaag ggcagtggca atgcttgagg atctgcagat gagtgtgggg    2040
tatcagttgg aggatgaatg a                                                2061
```

<210> SEQ ID NO 576
<211> LENGTH: 687
<212> TYPE: PRT
<213> ORGANISM: Raphanus sativus

<400> SEQUENCE: 576

```
Met Leu Ala Arg Val Cys Gly Phe Lys Cys Ser Ser Pro Ala Glu
1               5                   10                  15

Ser Ala Ala Arg Leu Phe Cys Thr Arg Ser Ile Arg Asp Thr Leu Ala
            20                  25                  30

Lys Ala Ser Gly Glu Ser Cys Glu Ala Gly Phe Gly Gly Glu Ser Leu
        35                  40                  45

Lys Leu Gln Ser Gly Phe His Glu Ile Lys Gly Leu Glu Asp Ala Ile
    50                  55                  60

Asp Leu Phe Ser Asp Met Leu Arg Ser Arg Pro Leu Pro Ser Val Val
65                  70                  75                  80

Asp Phe Cys Lys Leu Met Gly Val Val Arg Met Glu Arg Pro Asp
                85                  90                  95

Leu Val Ile Ser Leu Tyr Gln Lys Met Glu Arg Lys Gln Ile Arg Cys
            100                 105                 110

Asp Ile Tyr Ser Phe Asn Ile Leu Ile Lys Cys Phe Cys Ser Cys Ser
        115                 120                 125

Lys Leu Pro Phe Ala Leu Ser Thr Phe Gly Lys Ile Thr Lys Leu Gly
    130                 135                 140

Leu His Pro Asp Val Val Thr Phe Thr Thr Leu Leu His Gly Leu Cys
145                 150                 155                 160

Val Glu Asp Arg Val Ser Glu Ala Leu Asp Phe Phe His Gln Met Phe
                165                 170                 175

Glu Thr Thr Cys Arg Pro Asn Val Val Thr Phe Thr Thr Leu Met Asn
            180                 185                 190

Gly Leu Cys Arg Glu Gly Arg Ile Val Glu Ala Val Ala Leu Leu Asp
        195                 200                 205

Arg Met Met Glu Asp Gly Leu Gln Pro Thr Gln Ile Thr Tyr Gly Thr
    210                 215                 220

Ile Val Asp Gly Met Cys Lys Lys Gly Asp Thr Val Ser Ala Leu Asn
225                 230                 235                 240

Leu Leu Arg Lys Met Glu Glu Val Ser His Ile Ile Pro Asn Val Val
                245                 250                 255

Ile Tyr Ser Ala Ile Ile Asp Ser Leu Cys Lys Asp Gly Arg His Ser
            260                 265                 270
```

```
Asp Ala Gln Asn Leu Phe Thr Glu Met Gln Glu Lys Gly Ile Phe Pro
            275                 280                 285
Asp Leu Phe Thr Tyr Asn Ser Met Ile Val Gly Phe Cys Ser Ser Gly
290                 295                 300
Arg Trp Ser Asp Ala Glu Gln Leu Leu Gln Glu Met Leu Glu Arg Lys
305                 310                 315                 320
Ile Ser Pro Asp Val Val Thr Tyr Asn Ala Leu Ile Asn Ala Phe Val
                325                 330                 335
Lys Glu Gly Lys Phe Phe Glu Ala Glu Leu Tyr Asp Glu Met Leu
            340                 345                 350
Pro Arg Gly Ile Ile Pro Asn Thr Ile Thr Tyr Ser Ser Met Ile Asp
            355                 360                 365
Gly Phe Cys Lys Gln Asn Arg Leu Asp Ala Ala Glu His Met Phe Tyr
370                 375                 380
Leu Met Ala Thr Lys Gly Cys Ser Pro Asn Leu Ile Thr Phe Asn Thr
385                 390                 395                 400
Leu Ile Asp Gly Tyr Cys Gly Ala Lys Arg Ile Asp Asp Gly Met Glu
                405                 410                 415
Leu Leu His Glu Met Thr Glu Thr Gly Leu Val Ala Asp Thr Thr Thr
            420                 425                 430
Tyr Asn Thr Leu Ile His Gly Phe Tyr Leu Val Gly Asp Leu Asn Ala
            435                 440                 445
Ala Leu Asp Leu Leu Gln Glu Met Ile Ser Ser Gly Leu Cys Pro Asp
450                 455                 460
Ile Val Thr Cys Asp Thr Leu Leu Asp Gly Leu Cys Asp Asn Gly Lys
465                 470                 475                 480
Leu Lys Asp Ala Leu Glu Met Phe Lys Val Met Gln Lys Ser Lys Lys
                485                 490                 495
Asp Leu Asp Ala Ser His Pro Phe Asn Gly Val Glu Pro Asp Val Gln
            500                 505                 510
Thr Tyr Asn Ile Leu Ile Ser Gly Leu Ile Asn Glu Gly Lys Phe Leu
            515                 520                 525
Glu Ala Glu Glu Leu Tyr Glu Glu Met Pro His Arg Gly Ile Val Pro
530                 535                 540
Asp Thr Ile Thr Tyr Ser Ser Met Ile Asp Gly Leu Cys Lys Gln Ser
545                 550                 555                 560
Arg Leu Asp Glu Ala Thr Gln Met Phe Asp Ser Met Gly Ser Lys Ser
                565                 570                 575
Phe Ser Pro Asn Val Val Thr Phe Thr Thr Leu Ile Asn Gly Tyr Cys
            580                 585                 590
Lys Ala Gly Arg Val Asp Asp Gly Leu Glu Leu Phe Cys Glu Met Gly
            595                 600                 605
Arg Arg Gly Ile Val Ala Asn Ala Ile Thr Tyr Ile Thr Leu Ile Cys
610                 615                 620
Gly Phe Arg Lys Val Gly Asn Ile Asn Gly Ala Leu Asp Ile Phe Gln
625                 630                 635                 640
Glu Met Ile Ser Ser Gly Val Tyr Pro Asp Thr Ile Thr Ile Arg Asn
                645                 650                 655
Met Leu Thr Gly Leu Trp Ser Lys Glu Glu Leu Lys Arg Ala Val Ala
            660                 665                 670
Met Leu Glu Lys Leu Gln Met Ser Met Asp Leu Ser Phe Gly Gly
            675                 680                 685
```

<210> SEQ ID NO 577
<211> LENGTH: 687
<212> TYPE: PRT
<213> ORGANISM: Raphanus sativus

<400> SEQUENCE: 577

```
Met Leu Ala Arg Val Cys Gly Phe Lys Cys Ser Ser Pro Ala Glu
1               5                  10                  15

Ser Ala Ala Arg Leu Phe Cys Thr Arg Ser Ile Arg Asp Thr Leu Ala
                20                  25                  30

Lys Ala Ser Gly Glu Ser Cys Glu Ala Gly Phe Gly Gly Glu Ser Leu
            35                  40                  45

Lys Leu Gln Ser Gly Phe His Glu Ile Lys Gly Leu Glu Asp Ala Ile
    50                  55                  60

Asp Leu Phe Ser Asp Met Leu Arg Ser Arg Pro Leu Pro Ser Val Val
65                  70                  75                  80

Asp Phe Cys Lys Leu Met Gly Val Val Arg Met Glu Arg Pro Asp
                85                  90                  95

Leu Val Ile Ser Leu Tyr Gln Lys Met Glu Arg Lys Gln Ile Arg Cys
                100                 105                 110

Asp Ile Tyr Ser Phe Thr Ile Leu Ile Lys Cys Phe Cys Ser Cys Ser
            115                 120                 125

Lys Leu Pro Phe Ala Leu Ser Thr Phe Gly Lys Ile Thr Lys Leu Gly
    130                 135                 140

Leu His Pro Asp Val Val Thr Phe Asn Thr Leu Leu His Gly Leu Cys
145                 150                 155                 160

Val Glu Asp Arg Val Ser Glu Ala Leu Asn Leu Phe His Gln Met Phe
                165                 170                 175

Glu Thr Thr Cys Arg Pro Asn Val Val Thr Phe Thr Thr Leu Met Asn
                180                 185                 190

Gly Leu Cys Arg Glu Gly Arg Ile Val Glu Ala Val Ala Leu Leu Asp
            195                 200                 205

Arg Met Met Glu Asp Gly Leu Gln Pro Thr Gln Ile Thr Tyr Gly Thr
    210                 215                 220

Ile Val Asp Gly Met Cys Lys Lys Gly Asp Thr Val Ser Ala Leu Asn
225                 230                 235                 240

Leu Leu Arg Lys Met Glu Glu Val Ser His Ile Ile Pro Asn Val Val
                245                 250                 255

Ile Tyr Ser Ala Ile Ile Asp Ser Leu Cys Lys Asp Gly Arg His Ser
                260                 265                 270

Asp Ala Gln Asn Leu Phe Thr Glu Met Gln Glu Lys Gly Ile Phe Pro
            275                 280                 285

Asp Leu Phe Thr Tyr Asn Ser Met Ile Val Gly Phe Cys Ser Ser Gly
    290                 295                 300

Arg Trp Ser Asp Ala Glu Gln Leu Leu Gln Glu Met Leu Glu Arg Lys
305                 310                 315                 320

Ile Ser Pro Asp Val Val Thr Tyr Asn Ala Leu Ile Asn Ala Phe Val
                325                 330                 335

Lys Glu Gly Lys Phe Phe Glu Ala Glu Glu Leu Tyr Asp Glu Met Leu
                340                 345                 350

Pro Arg Gly Ile Ile Pro Asn Thr Ile Thr Tyr Ser Ser Met Ile Asp
            355                 360                 365

Gly Phe Cys Lys Gln Asn Arg Leu Asp Ala Ala Glu His Met Phe Tyr
    370                 375                 380
```

```
Leu Met Ala Thr Lys Gly Cys Ser Pro Asn Leu Ile Thr Phe Asn Thr
385                 390                 395                 400

Leu Ile Asp Gly Tyr Cys Gly Ala Lys Arg Ile Asp Asp Gly Met Glu
            405                 410                 415

Leu Leu His Glu Met Thr Glu Thr Gly Leu Val Ala Asp Thr Thr Thr
        420                 425                 430

Tyr Asn Thr Leu Ile His Gly Phe Tyr Leu Val Gly Asp Leu Asn Ala
            435                 440                 445

Ala Leu Asp Leu Leu Gln Glu Met Ile Ser Ser Gly Leu Cys Pro Asp
        450                 455                 460

Ile Val Thr Cys Asp Thr Leu Leu Asp Gly Leu Cys Asp Asn Gly Lys
465                 470                 475                 480

Leu Lys Asp Ala Leu Glu Met Phe Lys Val Met Gln Lys Ser Lys Lys
            485                 490                 495

Asp Leu Asp Ala Ser His Pro Phe Asn Gly Val Glu Pro Asp Val Gln
        500                 505                 510

Thr Tyr Asn Ile Leu Ile Ser Gly Leu Ile Asn Glu Gly Lys Phe Leu
            515                 520                 525

Glu Ala Glu Glu Leu Tyr Glu Glu Met Pro His Arg Gly Ile Val Pro
        530                 535                 540

Asp Thr Ile Thr Tyr Ser Ser Met Ile Asp Gly Leu Cys Lys Gln Ser
545                 550                 555                 560

Arg Leu Asp Glu Ala Thr Gln Met Phe Asp Ser Met Gly Ser Lys Ser
            565                 570                 575

Phe Ser Pro Asn Val Val Thr Phe Thr Thr Leu Ile Asn Gly Tyr Cys
        580                 585                 590

Lys Ala Gly Arg Val Asp Asp Gly Leu Glu Leu Phe Cys Glu Met Gly
            595                 600                 605

Arg Arg Gly Ile Val Ala Asn Ala Ile Thr Tyr Ile Thr Leu Ile Cys
610                 615                 620

Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
            645                 650                 655

Met Leu Thr Gly Leu Trp Ser Lys Glu Glu Leu Lys Arg Ala Val Ala
            660                 665                 670

Met Leu Glu Lys Leu Gln Met Ser Met Asp Leu Ser Phe Gly Gly
        675                 680                 685

<210> SEQ ID NO 578
<211> LENGTH: 686
<212> TYPE: PRT
<213> ORGANISM: Raphanus sativus

<400> SEQUENCE: 578

Met Leu Ala Arg Val Cys Arg Phe Glu Ser Ser Ser Ser Ser Ser Val
1               5                   10                  15

Ser Ala Ala Arg Phe Phe Cys Thr Gly Ser Ile Arg His Ala Leu Ala
            20                  25                  30

Glu Lys Ser Arg Asp Gly Glu Ser Gly Glu Ala Gly Phe Arg Gly Glu
        35                  40                  45

Ser Leu Lys Leu Arg Ser Gly Ser Tyr Glu Ile Lys Gly Leu Glu Asp
    50                  55                  60

Ala Ile Asp Leu Phe Ser Asp Met Leu Arg Ser Arg Pro Leu Pro Ser
65                  70                  75                  80
```

```
Val Ile Asp Phe Asn Lys Leu Met Gly Ala Val Val Arg Met Glu Arg
                 85                  90                  95

Pro Asp Leu Val Ile Ser Leu Tyr Gln Lys Met Glu Arg Lys Gln Ile
            100                 105                 110

Arg Cys Asp Ile Tyr Ser Phe Thr Ile Leu Ile Lys Cys Phe Cys Ser
        115                 120                 125

Cys Ser Lys Leu Pro Phe Ala Leu Ser Thr Phe Gly Lys Leu Thr Lys
130                 135                 140

Leu Gly Leu His Pro Asp Val Val Thr Phe Thr Thr Leu Leu His Gly
145                 150                 155                 160

Leu Cys Leu Asp His Arg Val Ser Glu Ala Leu Asp Leu Phe His Gln
                165                 170                 175

Ile Cys Arg Pro Asp Val Leu Thr Phe Thr Thr Leu Met Asn Gly Leu
                180                 185                 190

Cys Arg Glu Gly Arg Val Val Glu Ala Val Ala Leu Leu Asp Arg Met
            195                 200                 205

Val Glu Asn Gly Leu Gln Pro Asp Gln Ile Thr Tyr Gly Thr Phe Val
210                 215                 220

Asp Gly Met Cys Lys Met Gly Asp Thr Val Ser Ala Leu Asn Leu Leu
225                 230                 235                 240

Arg Lys Met Glu Glu Ile Ser His Ile Lys Pro Asn Val Val Ile Tyr
                245                 250                 255

Ser Ala Ile Ile Asp Gly Leu Cys Lys Asp Gly Arg His Ser Asp Ser
                260                 265                 270

His Asn Leu Phe Ile Glu Met Gln Asp Lys Gly Ile Phe Pro Asn Ile
            275                 280                 285

Val Thr Tyr Asn Cys Met Ile Gly Gly Phe Cys Ile Ser Gly Arg Trp
        290                 295                 300

Ser Ala Ala Gln Arg Leu Leu Gln Glu Met Leu Glu Arg Lys Ile Ser
305                 310                 315                 320

Pro Asn Val Val Thr Tyr Asn Ala Leu Ile Asn Ala Phe Val Lys Glu
                325                 330                 335

Gly Lys Phe Phe Glu Ala Ala Glu Leu Tyr Asp Glu Met Leu Pro Arg
                340                 345                 350

Gly Ile Ile Pro Asn Thr Ile Thr Tyr Asn Ser Met Ile Asp Gly Phe
            355                 360                 365

Cys Lys Gln Asp Arg Leu Asp Ala Ala Glu Asp Met Phe Tyr Leu Met
        370                 375                 380

Ala Thr Lys Gly Cys Ser Pro Asp Val Phe Thr Phe Thr Thr Leu Ile
385                 390                 395                 400

Asp Gly Tyr Cys Gly Ala Lys Arg Ile Asp Asp Gly Met Glu Leu Leu
                405                 410                 415

His Glu Met Pro Arg Arg Gly Leu Val Ala Asn Thr Val Thr Tyr Asn
                420                 425                 430

Thr Leu Ile His Gly Phe Cys Leu Val Gly Asp Leu Asn Ala Ala Leu
            435                 440                 445

Asp Leu Ser Gln Gln Met Ile Ser Ser Gly Val Cys Pro Asp Ile Val
        450                 455                 460

Thr Cys Asn Thr Leu Leu Asp Gly Leu Cys Asp Asn Gly Lys Leu Lys
465                 470                 475                 480

Asp Ala Leu Glu Met Phe Lys Ala Met Gln Lys Ser Lys Met Asp Leu
                485                 490                 495
```

```
Asp Ala Ser His Pro Phe Asn Gly Val Pro Glu Pro Asp Val Leu Thr Tyr
            500                 505                 510

Asn Ile Leu Ile Cys Gly Leu Ile Asn Glu Gly Lys Phe Leu Glu Ala
        515                 520                 525

Glu Glu Leu Tyr Glu Glu Met Pro His Arg Gly Ile Val Pro Asp Thr
    530                 535                 540

Ile Thr Tyr Ser Ser Met Ile Asp Gly Leu Cys Lys Gln Ser Arg Leu
545                 550                 555                 560

Asp Glu Ala Thr Gln Met Phe Val Ser Met Gly Ser Lys Ser Phe Ser
                565                 570                 575

Pro Asn Val Val Thr Phe Asn Thr Leu Ile Asn Gly Tyr Cys Lys Ala
            580                 585                 590

Gly Arg Val Asp Asp Gly Leu Glu Leu Phe Cys Glu Met Gly Arg Arg
        595                 600                 605

Gly Ile Val Ala Asp Ala Ile Ile Tyr Ile Thr Leu Ile Tyr Gly Phe
    610                 615                 620

Arg Lys Val Gly Asn Ile Asn Gly Ala Leu Asp Ile Phe Gln Glu Met
625                 630                 635                 640

Ile Ser Ser Gly Val Tyr Pro Asp Thr Ile Thr Ile Arg Asn Met Leu
                645                 650                 655

Thr Gly Phe Trp Ser Lys Glu Glu Leu Glu Arg Ala Val Ala Met Leu
            660                 665                 670

Glu Asp Leu Gln Met Ser Val Gly Tyr Gln Leu Glu Asp Glu
        675                 680                 685

<210> SEQ ID NO 579
<211> LENGTH: 41
<212> TYPE: DNA
<213> ORGANISM: Artificial Sequence
<220> FEATURE:
<223> OTHER INFORMATION: A-F primer primer

<400> SEQUENCE: 579
aatacgactc actatagaag aagaagctgc tttgtggagt g                    41

<210> SEQ ID NO 580
<211> LENGTH: 24
<212> TYPE: DNA
<213> ORGANISM: Artificial Sequence
<220> FEATURE:
<223> OTHER INFORMATION: A-R primer primer

<400> SEQUENCE: 580
tgcatttata tgctgaagaa aagc                                       24

<210> SEQ ID NO 581
<211> LENGTH: 48
<212> TYPE: DNA
<213> ORGANISM: Artificial Sequence
<220> FEATURE:
<223> OTHER INFORMATION: B-F primer primer

<400> SEQUENCE: 581
tagataatac gactcactat agggatgatt accttttcg aaaaattg              48

<210> SEQ ID NO 582
<211> LENGTH: 38
<212> TYPE: DNA
<213> ORGANISM: Artificial Sequence
<220> FEATURE:
<223> OTHER INFORMATION: B-R primer primer
```

<210> SEQ ID NO 583
<211> LENGTH: 42
<212> TYPE: DNA
<213> ORGANISM: Artificial Sequence
<220> FEATURE:
<223> OTHER INFORMATION: C-F primer primer

<400> SEQUENCE: 583
aaaccagctt agccaaatat gggccattag caaataag 38

<210> SEQ ID NO 583
<211> LENGTH: 42
<212> TYPE: DNA
<213> ORGANISM: Artificial Sequence
<220> FEATURE:
<223> OTHER INFORMATION: C-F primer primer

<400> SEQUENCE: 583
aatacgactc actatagtat ttggctaagc tggttttcta ac 42

<210> SEQ ID NO 584
<211> LENGTH: 27
<212> TYPE: DNA
<213> ORGANISM: Artificial Sequence
<220> FEATURE:
<223> OTHER INFORMATION: C-R primer primer

<400> SEQUENCE: 584
gacacctagc cacccatact gaaattc 27

<210> SEQ ID NO 585
<211> LENGTH: 667
<212> TYPE: PRT
<213> ORGANISM: Raphanus sativus

<400> SEQUENCE: 585

Met Leu Ala Arg Val Cys Arg Phe Glu Ser Ser Ser Val Pro Ala
1               5                   10                  15

Ala Arg Leu Phe Cys Thr Arg Ser Ile Arg His Thr Leu Ala Lys Lys
            20                  25                  30

Ser Ser Gly Lys Ala Gly Gly Phe Gly Gly Glu Arg Leu Lys Leu Gln
        35                  40                  45

Ser Gly Phe His Glu Ile Lys Gly Leu Asp Asp Ala Ile Asp Leu Phe
    50                  55                  60

Gly Tyr Met Val Arg Ser Arg Pro Leu Pro Cys Val Ile Asp Phe Cys
65                  70                  75                  80

Lys Leu Leu Gly Val Val Val Arg Met Glu Arg Pro Asp Val Val Ile
                85                  90                  95

Ser Leu His Arg Lys Met Glu Met Arg Arg Ile Pro Cys Asn Ile Tyr
            100                 105                 110

Ser Phe Thr Ile Leu Ile Lys Cys Phe Cys Ser Cys Ser Lys Leu Pro
        115                 120                 125

Phe Ala Leu Ser Thr Phe Gly Lys Ile Thr Lys Leu Gly Phe His Pro
    130                 135                 140

Ser Leu Val Thr Phe Ser Thr Leu Leu His Gly Leu Cys Val Glu Asp
145                 150                 155                 160

Arg Val Ser Glu Ala Leu His Phe Phe His Gln Ile Cys Lys Pro Asn
                165                 170                 175

Val Ile Ala Phe Thr Thr Leu Met Asn Gly Leu Cys Arg Glu Gly Arg
            180                 185                 190

Val Val Glu Ala Val Ala Leu Leu Asp Arg Met Val Glu Asp Gly Leu
        195                 200                 205

Gln Pro Asn Gln Ile Thr Tyr Gly Thr Ile Val Asp Gly Met Cys Lys
    210                 215                 220

-continued

```
Met Gly Asp Thr Val Ser Ala Leu Asn Leu Leu Arg Lys Met Glu Glu
225                 230                 235                 240

Val Ser Arg Ile Lys Pro Asn Val Val Ile Tyr Ser Ala Ile Ile Asp
            245                 250                 255

Gly Leu Trp Lys Asp Gly Arg Gln Thr Asp Ala Gln Asn Leu Phe Ser
        260                 265                 270

Glu Met Gln Glu Lys Gly Ile Ser Pro Asn Leu Phe Thr Tyr Asn Cys
    275                 280                 285

Met Ile Asn Gly Phe Cys Ser Ser Gly Arg Trp Ser Glu Ala Gln Arg
290                 295                 300

Leu Leu Arg Glu Met Phe Glu Arg Lys Met Ser Pro Asp Val Val Thr
305                 310                 315                 320

Phe Ser Val Leu Ile Asn Ala Leu Val Lys Glu Gly Lys Phe Phe Glu
                325                 330                 335

Ala Glu Glu Leu Tyr Asn Glu Met Leu Pro Arg Gly Ile Ile Pro Asn
            340                 345                 350

Thr Ile Thr Tyr Asn Ser Met Ile Asp Gly Phe Ser Lys Gln Asn Arg
        355                 360                 365

Leu Asp Ala Ala Glu Arg Met Phe Tyr Leu Met Ala Thr Lys Gly Cys
370                 375                 380

Ser Pro Asp Val Ile Thr Phe Ser Ile Leu Ile Asp Gly Tyr Cys Gly
385                 390                 395                 400

Ala Lys Arg Val Asp Asp Gly Met Lys Leu Leu His Glu Met Ser Arg
                405                 410                 415

Arg Gly Leu Val Ala Asn Thr Ile Thr Tyr Thr Thr Leu Ile His Gly
            420                 425                 430

Phe Cys Gln Leu Gly Asn Leu Asn Ala Ala Leu Asp Leu Leu Gln Glu
        435                 440                 445

Met Ile Ser Ser Gly Val Cys Pro Asn Val Val Thr Cys Asn Thr Leu
450                 455                 460

Leu Asp Gly Leu Cys Asn Asn Gly Lys Leu Lys Asp Ala Leu Glu Met
465                 470                 475                 480

Phe Lys Val Met Gln Lys Ser Lys Met Asp Leu Asp Ala Ser His Pro
                485                 490                 495

Phe Asn Asp Val Glu Pro Asp Val Gln Thr Tyr Asn Ile Leu Ile Cys
            500                 505                 510

Gly Leu Ile Asn Glu Gly Lys Phe Ser Glu Ala Glu Glu Leu Tyr Glu
        515                 520                 525

Glu Met Pro His Arg Gly Leu Val Pro Asp Thr Ile Thr Tyr Asn Ser
530                 535                 540

Val Ile Asp Gly Leu Cys Lys Gln Ser Arg Leu Asp Glu Ala Thr Gln
545                 550                 555                 560

Met Phe Asp Ser Met Gly Ser Lys Gly Phe Ser Pro Asp Val Val Thr
                565                 570                 575

Phe Thr Thr Leu Ile Asn Gly Tyr Cys Lys Val Gly Arg Val Gly Asp
            580                 585                 590

Gly Leu Glu Val Phe Cys Glu Met Gly Arg Arg Gly Ile Val Ala Asn
        595                 600                 605

Ala Ile Thr Tyr Arg Thr Leu Ile His Gly Phe Cys Gln Val Gly Asn
610                 615                 620

Ile Asn Gly Ala Leu Asp Ile Phe Gln Glu Met Ile Ser Ser Gly Val
625                 630                 635                 640

Tyr Pro Asp Thr Ile Thr Ile Arg Asn Met Leu Thr Gly Leu Trp Ser
```

-continued

```
                645                 650                 655
Lys Glu Glu Leu Lys Arg Ala Val Gln Cys Leu
            660                 665

<210> SEQ ID NO 586
<211> LENGTH: 683
<212> TYPE: PRT
<213> ORGANISM: Raphanus sativus

<400> SEQUENCE: 586

Met Leu Ala Arg Val Cys Arg Phe Glu Ser Ser Ser Ser Ser Val
1               5                   10                  15

Ser Ala Ala Arg Phe Phe Cys Thr Gly Ser Ile Arg His Ala Leu Ala
                20                  25                  30

Glu Lys Ser Arg Asp Gly Glu Ser Gly Glu Ala Gly Phe Arg Gly Glu
            35                  40                  45

Ser Leu Lys Leu Arg Ser Gly Ser Tyr Glu Ile Lys Gly Leu Glu Asp
        50                  55                  60

Ala Ile Asp Leu Phe Ser Asp Met Leu Arg Ser Arg Pro Leu Pro Ser
65                  70                  75                  80

Val Ile Asp Phe Asn Lys Leu Met Gly Ala Val Val Arg Met Glu Arg
                85                  90                  95

Pro Asp Leu Val Ile Ser Leu Tyr Gln Lys Met Glu Arg Lys Gln Ile
            100                 105                 110

Arg Cys Asp Ile Tyr Ser Phe Thr Ile Leu Ile Lys Cys Phe Cys Ser
        115                 120                 125

Cys Ser Lys Leu Pro Phe Ala Leu Ser Thr Phe Gly Lys Leu Thr Lys
130                 135                 140

Leu Gly Leu His Pro Asp Val Val Thr Phe Thr Thr Leu Leu His Gly
145                 150                 155                 160

Leu Cys Leu Asp His Arg Val Ser Glu Ala Leu Asp Leu Phe His Gln
                165                 170                 175

Ile Cys Arg Pro Asp Val Leu Thr Phe Thr Thr Leu Met Asn Gly Leu
            180                 185                 190

Cys Arg Glu Gly Arg Val Val Glu Ala Val Ala Leu Leu Asp Arg Met
        195                 200                 205

Val Glu Asn Gly Leu Gln Pro Asp Gln Ile Thr Tyr Gly Thr Phe Val
210                 215                 220

Asp Gly Met Cys Lys Met Gly Asp Thr Val Ser Ala Leu Asn Leu Leu
225                 230                 235                 240

Arg Lys Met Glu Glu Ile Ser His Ile Lys Pro Asn Val Val Ile Tyr
                245                 250                 255

Ser Ala Ile Ile Asp Gly Leu Cys Lys Asp Gly Arg His Ser Asp Ser
            260                 265                 270

His Asn Leu Phe Ile Glu Met Gln Asp Lys Gly Ile Phe Pro Asn Ile
        275                 280                 285

Val Thr Tyr Asn Cys Met Ile Gly Gly Phe Cys Ile Ser Gly Arg Trp
        290                 295                 300

Ser Ala Ala Gln Arg Leu Leu Gln Glu Met Leu Glu Arg Lys Ile Ser
305                 310                 315                 320

Pro Asn Val Val Thr Tyr Asn Ala Leu Ile Asn Ala Phe Val Lys Glu
                325                 330                 335

Gly Lys Phe Phe Glu Ala Glu Leu Tyr Asp Glu Met Leu Pro Arg
            340                 345                 350
```

```
Gly Ile Ile Pro Asn Thr Ile Thr Tyr Asn Ser Met Ile Asp Gly Phe
            355                 360                 365

Cys Lys Gln Asp Arg Leu Asp Ala Ala Glu Asp Met Phe Tyr Leu Met
370                 375                 380

Ala Thr Lys Gly Cys Ser Pro Asp Val Phe Thr Phe Thr Thr Leu Ile
385                 390                 395                 400

Asp Gly Tyr Cys Gly Ala Lys Arg Ile Asp Asp Gly Met Glu Leu Leu
                405                 410                 415

His Glu Met Pro Arg Arg Gly Leu Val Ala Asn Thr Val Thr Tyr Asn
            420                 425                 430

Thr Leu Ile His Gly Phe Cys Leu Val Gly Asp Leu Asn Ala Ala Leu
        435                 440                 445

Asp Leu Ser Gln Gln Met Ile Ser Ser Gly Val Cys Pro Asp Ile Val
    450                 455                 460

Thr Cys Asn Thr Leu Leu Asp Gly Leu Cys Asp Asn Gly Lys Leu Lys
465                 470                 475                 480

Asp Ala Leu Glu Met Phe Lys Ala Met Gln Lys Ser Lys Met Asp Leu
                485                 490                 495

Asp Ala Ser His Pro Phe Asn Gly Val Glu Pro Asp Val Leu Thr Tyr
            500                 505                 510

Asn Ile Leu Ile Cys Gly Leu Ile Asn Glu Gly Lys Phe Leu Glu Ala
        515                 520                 525

Glu Glu Leu Tyr Glu Glu Met Pro His Arg Gly Ile Val Pro Asp Thr
    530                 535                 540

Ile Thr Tyr Ser Ser Met Ile Asp Gly Leu Cys Lys Gln Ser Arg Leu
545                 550                 555                 560

Asp Glu Ala Thr Gln Met Phe Val Ser Met Gly Ser Lys Ser Phe Ser
                565                 570                 575

Pro Asn Val Val Thr Phe Asn Thr Leu Ile Asn Gly Tyr Cys Lys Ala
            580                 585                 590

Gly Arg Val Asp Asp Gly Leu Glu Leu Phe Cys Glu Met Gly Arg Arg
        595                 600                 605

Gly Ile Val Ala Asp Ala Ile Ile Tyr Ile Thr Leu Ile Tyr Gly Phe
    610                 615                 620

Arg Lys Val Gly Asn Ile Asn Gly Ala Leu Asp Ile Phe Gln Glu Met
625                 630                 635                 640

Ile Ser Ser Gly Val Tyr Pro Asp Thr Ile Thr Ile Arg Asn Met Leu
                645                 650                 655

Thr Gly Phe Trp Ser Lys Glu Glu Leu Glu Arg Ala Val Ala Met Leu
            660                 665                 670

Glu Asp Leu Gln Arg Tyr Gln Leu Glu Asp Glu
        675                 680

<210> SEQ ID NO 587
<211> LENGTH: 687
<212> TYPE: PRT
<213> ORGANISM: Raphanus sativus

<400> SEQUENCE: 587

Met Leu Ala Arg Val Cys Gly Phe Lys Cys Ser Ser Ser Pro Ala Glu
1               5                   10                  15

Ser Ala Ala Arg Leu Phe Cys Thr Arg Ser Ile Arg Asp Thr Leu Ala
            20                  25                  30

Lys Ala Ser Gly Glu Ser Cys Ala Gly Phe Gly Gly Glu Ser Leu
        35                  40                  45
```

```
Lys Leu Gln Ser Gly Phe His Glu Ile Lys Gly Leu Glu Asp Ala Ile
 50                  55                  60

Asp Leu Phe Ser Asp Met Leu Arg Ser Arg Pro Leu Pro Ser Val Val
 65                  70                  75                  80

Asp Phe Cys Lys Leu Met Gly Val Val Arg Met Lys Arg Pro Asp
                 85                  90                  95

Val Val Ile Ser Leu His Lys Lys Val Glu Met Arg Arg Ile Pro Cys
                100                 105                 110

Asp Ala Tyr Ser Phe Asn Ile Leu Ile Lys Cys Phe Cys Ser Cys Ser
            115                 120                 125

Lys Leu Pro Phe Ala Leu Ser Thr Phe Gly Lys Ile Thr Lys Leu Gly
        130                 135                 140

Leu His Pro Asp Val Val Thr Phe Thr Thr Leu Leu His Gly Leu Cys
145                 150                 155                 160

Val Glu Asp Arg Val Ser Glu Ala Leu Asn Leu Phe His Gln Met Phe
                165                 170                 175

Glu Thr Thr Cys Arg Pro Asn Val Val Thr Phe Thr Thr Leu Met Asn
            180                 185                 190

Gly Leu Cys Arg Glu Gly Arg Ile Val Glu Ala Val Ala Leu Leu Asp
        195                 200                 205

Arg Met Met Glu Asp Gly Leu Gln Pro Thr Gln Ile Thr Tyr Gly Thr
    210                 215                 220

Ile Val Asp Gly Met Cys Lys Lys Gly Asp Thr Val Ser Ala Leu Asn
225                 230                 235                 240

Leu Leu Arg Lys Met Glu Glu Val Ser His Ile Ile Pro Asn Val Val
                245                 250                 255

Ile Tyr Ser Ala Ile Ile Asp Ser Leu Cys Lys Asp Gly Arg His Ser
            260                 265                 270

Asp Ala Gln Asn Leu Phe Thr Glu Met Gln Glu Lys Gly Ile Phe Pro
        275                 280                 285

Asp Leu Phe Thr Tyr Asn Ser Met Ile Val Gly Phe Cys Ser Ser Gly
        290                 295                 300

Arg Trp Ser Asp Ala Glu Gln Leu Leu Gln Glu Met Leu Glu Arg Lys
305                 310                 315                 320

Ile Ser Pro Asp Val Val Thr Tyr Asn Ala Leu Ile Asn Ala Phe Val
                325                 330                 335

Lys Glu Gly Lys Phe Phe Glu Ala Glu Leu Tyr Asp Glu Met Leu
            340                 345                 350

Pro Arg Gly Ile Ile Pro Asn Thr Ile Thr Tyr Ser Ser Met Ile Asp
        355                 360                 365

Gly Phe Cys Lys Gln Asn Arg Leu Asp Ala Ala Glu Asn Met Phe Tyr
        370                 375                 380

Leu Met Ala Thr Lys Gly Cys Ser Pro Asn Leu Ile Thr Phe Asn Thr
385                 390                 395                 400

Leu Ile Asp Gly Tyr Cys Gly Ala Lys Arg Ile Asp Asp Gly Met Glu
                405                 410                 415

Leu Leu His Glu Met Thr Glu Thr Gly Leu Val Ala Asp Thr Thr Thr
            420                 425                 430

Tyr Asn Thr Leu Ile His Gly Phe Cys Leu Val Gly Asp Leu Asn Ala
        435                 440                 445

Ala Leu Asp Leu Leu Gln Glu Met Ile Ser Ser Gly Leu Cys Pro Asp
    450                 455                 460
```

```
Ile Val Thr Cys Asp Thr Leu Leu Asp Gly Leu Cys Asp Asn Gly Lys
465                 470                 475                 480

Leu Lys Asp Ala Leu Glu Met Phe Lys Val Met Gln Lys Ser Lys Lys
                485                 490                 495

Asp Leu Asp Ala Ser His Pro Phe Asn Gly Val Glu Pro Asp Val Gln
            500                 505                 510

Thr Tyr Asn Ile Leu Ile Ser Gly Leu Ile Asn Glu Gly Lys Phe Leu
            515                 520                 525

Glu Ala Glu Glu Leu Tyr Glu Glu Met Pro His Arg Gly Ile Val Pro
        530                 535                 540

Asp Thr Ile Thr Tyr Ser Ser Met Ile Asp Gly Leu Cys Lys Gln Ser
545                 550                 555                 560

Arg Leu Asp Glu Ala Thr Gln Met Phe Asp Ser Met Gly Ser Lys Ser
                565                 570                 575

Phe Ser Pro Asn Val Val Thr Phe Thr Thr Leu Ile Asn Gly Tyr Cys
            580                 585                 590

Lys Ala Gly Arg Val Asp Asp Gly Leu Glu Leu Phe Cys Glu Met Gly
        595                 600                 605

Arg Arg Gly Ile Val Ala Asn Ala Ile Thr Tyr Ile Thr Leu Ile Cys
610                 615                 620

Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
                645                 650                 655

Met Leu Thr Gly Leu Trp Ser Lys Glu Glu Leu Lys Arg Ala Val Ala
            660                 665                 670

Met Leu Glu Lys Leu Gln Met Ser Met Asp Leu Ser Phe Gly Gly
        675                 680                 685

<210> SEQ ID NO 588
<211> LENGTH: 690
<212> TYPE: PRT
<213> ORGANISM: Raphanus sativus

<400> SEQUENCE: 588

Met Leu Ala Arg Val Cys Arg Phe Glu Ser Ser Ser Ser Ser Ser Val
1               5                   10                  15

Ser Ala Ala Arg Met Phe Cys Thr Gly Ser Ile Arg His Ala Leu Ala
                20                  25                  30

Lys Lys Gly Arg Asp Gly Glu Ser Gly Glu Ala Gly Phe Gly Gly Glu
            35                  40                  45

Ser Leu Lys Leu Arg Ser Gly Phe His Glu Ile Lys Gly Leu Glu Asp
        50                  55                  60

Ala Ile Asp Leu Phe Ser Asp Met Leu Arg Ser Arg Pro Leu Pro Ser
65                  70                  75                  80

Val Ile Asp Phe Asn Lys Leu Met Gly Val Val Arg Met Glu Arg
                85                  90                  95

Pro Asp Leu Val Ile Ser Leu Tyr Gln Lys Met Glu Arg Lys Gln Ile
            100                 105                 110

Pro Cys Asp Val Tyr Ser Phe Asn Ile Leu Ile Lys Cys Phe Cys Ser
            115                 120                 125

Cys Ser Lys Leu Pro Phe Ala Leu Ser Thr Phe Gly Lys Ile Thr Lys
        130                 135                 140

Leu Gly Leu His Pro Asp Val Ala Thr Phe Asn Thr Leu Leu His Gly
145                 150                 155                 160
```

-continued

```
Leu Cys Leu Asp Lys Arg Val Ser Glu Ala Leu Asp Leu Phe His Gln
                165                 170                 175

Met Phe Glu Thr Thr Cys Arg Pro Asn Ile Ile Thr Phe Thr Thr Leu
            180                 185                 190

Met Asn Gly Leu Cys Tyr Glu Gly Arg Val Val Glu Ala Val Ala Leu
        195                 200                 205

Leu Asp Arg Met Leu Glu Asp Gly Leu Gln Pro Asp Gln Ile Thr Tyr
    210                 215                 220

Gly Thr Ile Val Asp Gly Met Cys Lys Met Gly Asp Thr Val Ser Ala
225                 230                 235                 240

Leu Asn Leu Leu Arg Lys Met Glu Glu Leu Ser His Ile Lys Pro Asn
                245                 250                 255

Val Val Ile Tyr Ser Ala Ile Ile Asp Gly Leu Trp Lys Asp Gly Arg
            260                 265                 270

His Thr Asp Ala Gln Asn Leu Phe Ser Glu Met Gln Glu Lys Gly Ile
        275                 280                 285

Phe Pro Asn Leu Phe Thr Tyr Thr Cys Met Ile Asn Gly Phe Cys Asp
    290                 295                 300

Ser Gly Arg Trp Ser Glu Ala Gln Gln Leu Leu Gln Glu Met Leu Val
305                 310                 315                 320

Arg Lys Ile Ser Pro Asn Val Val Thr Tyr Ser Ala Leu Ile Asn Ala
                325                 330                 335

Phe Val Lys Glu Gly Lys Phe Phe Glu Ala Glu Leu Tyr Asp Glu
            340                 345                 350

Met Leu Pro Arg Gly Ile Ile Pro Ser Thr Val Thr Tyr Ser Ser Met
        355                 360                 365

Ile Asp Gly Phe Cys Lys Gln Asn Arg Leu Asp Ala Ala Glu His Met
    370                 375                 380

Phe Tyr Leu Met Pro Thr Lys Gly Cys Ser Pro Asn Leu Ile Thr Phe
385                 390                 395                 400

Asn Thr Leu Ile Ala Gly Tyr Cys Arg Ala Lys Arg Val Asp Asp Gly
                405                 410                 415

Met Glu Leu Leu His Glu Met Thr Glu Thr Gly Leu Val Ala Asp Thr
            420                 425                 430

Thr Thr Tyr Asn Thr Leu Ile His Gly Phe Cys Leu Val Asp Asp Leu
        435                 440                 445

Asn Ala Ala Leu Asp Leu Ser Gln Gln Met Ile Ser Ser Gly Val Cys
    450                 455                 460

Pro Asp Ile Val Thr Cys Asn Thr Leu Leu Asp Gly Leu Cys Asp Asn
465                 470                 475                 480

Gly Lys Leu Lys Asp Ala Leu Glu Met Phe Lys Ala Met Gln Lys Ser
                485                 490                 495

Lys Met Asp Phe Asp Ala Ser His Pro Phe Asn Asp Val Glu Pro Asp
            500                 505                 510

Val Leu Thr Tyr Asn Ile Leu Ile Ser Gly Leu Ile Asn Asp Gly Lys
        515                 520                 525

Phe Leu Gly Ala Glu Glu Leu Tyr Glu Met Pro His Arg Gly Ile
    530                 535                 540

Val Pro Asp Thr Phe Thr Tyr Asn Ser Met Ile Cys Gly Leu Cys Lys
545                 550                 555                 560

Gln Asn Arg Leu Asp Glu Ala Lys Gln Met Ser Asp Ser Met Gly Ser
                565                 570                 575
```

-continued

```
Lys Ser Phe Ser Pro Asn Val Val Thr Phe Asn Thr Leu Ile Asn Gly
            580                 585                 590

Tyr Cys Lys Ala Gly Arg Val Asp Asp Gly Leu Glu Leu Phe Cys Gly
        595                 600                 605

Met Gly Gln Arg Gly Ile Val Ala Asn Ala Ile Thr Tyr Ile Thr Leu
    610                 615                 620

Ile His Gly Phe Arg Lys Val Asp Asn Ile Asn Gly Ala Leu Asp Ile
625                 630                 635                 640

Phe Gln Glu Met Ile Ser Ser Gly Val Tyr Pro Asp Thr Ile Thr Ile
                645                 650                 655

Arg Asn Met Leu Thr Gly Leu Trp Ser Lys Glu Glu Leu Lys Arg Ala
        660                 665                 670

Val Ala Met Leu Glu Asp Leu Gln Met Ser Val Gly Tyr Gln Leu Glu
        675                 680                 685

Asp Glu
    690

<210> SEQ ID NO 589
<211> LENGTH: 690
<212> TYPE: PRT
<213> ORGANISM: Raphanus sativus

<400> SEQUENCE: 589

Met Leu Ala Arg Val Cys Arg Phe Glu Ser Ser Ser Ser Ser Ser Val
1               5                   10                  15

Ser Ala Ala Arg Met Phe Cys Thr Gly Ser Ile Arg His Ala Leu Ala
                20                  25                  30

Lys Lys Gly Arg Asp Gly Glu Ser Gly Glu Ala Gly Phe Gly Gly Glu
            35                  40                  45

Ser Leu Lys Leu Arg Ser Gly Phe His Glu Ile Lys Gly Leu Glu Asp
        50                  55                  60

Ala Ile Asp Leu Phe Ser Asp Met Leu Arg Ser Arg Pro Leu Pro Ser
65                  70                  75                  80

Val Ile Asp Phe Asn Lys Leu Met Gly Val Val Arg Met Glu Arg
                85                  90                  95

Pro Asp Leu Val Ile Ser Leu Tyr Gln Lys Met Glu Arg Lys Gln Ile
            100                 105                 110

Pro Cys Asp Val Tyr Ser Phe Asn Ile Leu Ile Lys Cys Phe Cys Ser
        115                 120                 125

Cys Ser Lys Leu Pro Phe Ala Leu Ser Thr Phe Gly Lys Ile Thr Lys
    130                 135                 140

Leu Gly Leu His Pro Asp Val Ala Thr Phe Asn Thr Leu Leu His Gly
145                 150                 155                 160

Leu Cys Leu Asp Lys Arg Val Ser Glu Ala Leu Asp Leu Phe His Gln
                165                 170                 175

Met Phe Glu Thr Thr Cys Arg Pro Asn Ile Ile Thr Phe Thr Thr Leu
            180                 185                 190

Met Asn Gly Leu Cys Tyr Glu Gly Arg Val Val Glu Ala Val Ala Leu
        195                 200                 205

Leu Asp Arg Met Leu Glu Asp Gly Leu Gln Pro Asp Gln Ile Thr Tyr
    210                 215                 220

Gly Thr Ile Val Asp Gly Met Cys Lys Met Gly Asp Thr Val Ser Ala
225                 230                 235                 240

Leu Asn Leu Leu Arg Lys Met Glu Glu Leu Ser His Ile Lys Pro Asn
                245                 250                 255
```

```
Val Val Ile Tyr Ser Ala Ile Ile Asp Gly Leu Trp Lys Asp Gly Arg
            260                 265                 270

His Thr Asp Ala Gln Asn Leu Phe Ser Glu Met Gln Glu Lys Gly Ile
            275                 280                 285

Phe Pro Asn Leu Phe Thr Tyr Thr Cys Met Ile Asn Gly Phe Cys Asp
            290                 295                 300

Ser Gly Arg Trp Ser Glu Ala Gln Gln Leu Leu Gln Glu Met Leu Val
305                 310                 315                 320

Arg Lys Ile Ser Pro Asn Val Val Thr Tyr Ser Ala Leu Ile Asn Ala
                325                 330                 335

Phe Val Lys Glu Gly Lys Phe Phe Glu Ala Glu Leu Tyr Asp Glu
            340                 345                 350

Met Leu Pro Arg Gly Ile Ile Pro Ser Thr Val Thr Tyr Ser Ser Met
            355                 360                 365

Ile Asp Gly Phe Cys Lys Gln Asn Arg Leu Asp Ala Ala Glu His Met
370                 375                 380

Phe Tyr Leu Met Pro Thr Lys Gly Cys Ser Pro Asn Leu Ile Thr Phe
385                 390                 395                 400

Asn Thr Leu Ile Ala Gly Tyr Cys Arg Ala Lys Arg Val Asp Asp Gly
                405                 410                 415

Met Glu Leu Leu His Glu Met Thr Glu Thr Gly Leu Val Ala Asp Thr
            420                 425                 430

Thr Thr Tyr Asn Thr Leu Ile His Gly Phe Cys Leu Val Asp Asp Leu
            435                 440                 445

Asn Ala Ala Leu Asp Leu Ser Gln Gln Met Ile Ser Ser Gly Val Cys
            450                 455                 460

Pro Asp Ile Val Thr Cys Asn Thr Leu Leu Asp Gly Leu Cys Asp Asn
465                 470                 475                 480

Gly Lys Leu Lys Asp Ala Leu Glu Met Phe Lys Ala Met Gln Lys Ser
                485                 490                 495

Lys Met Asp Phe Asp Ala Ser His Pro Phe Asn Asp Val Glu Pro Asp
            500                 505                 510

Val Leu Thr Tyr Asn Ile Leu Ile Ser Gly Leu Ile Asn Asp Gly Lys
            515                 520                 525

Phe Leu Gly Ala Glu Glu Leu Tyr Glu Glu Met Pro His Arg Gly Ile
            530                 535                 540

Val Pro Asp Thr Val Thr Tyr Asn Ser Val Ile Asn Gly Leu Cys Lys
545                 550                 555                 560

Gln Ser Arg Leu Asn Glu Ala Lys Gln Met Ser Asp Ser Met Gly Ser
                565                 570                 575

Arg Ser Phe Ser Pro Asn Val Val Thr Phe Asn Thr Leu Ile Asn Gly
            580                 585                 590

Tyr Cys Lys Ala Gly Arg Val Asp Asp Gly Leu Glu Leu Phe Cys Glu
            595                 600                 605

Met Gly Arg Arg Gly Val Val Ala Asn Ala Ile Thr Tyr Ile Thr Leu
            610                 615                 620

Ile His Gly Phe Ser Lys Val Gly Asn Ile Asn Gly Ala Leu Asp Ile
625                 630                 635                 640

Phe Gln Glu Met Met Ala Ser Gly Val Tyr Pro Asp Thr Ile Thr Ile
            645                 650                 655

Arg Asn Met Leu Thr Gly Leu Trp Ser Lys Glu Glu Val Lys Arg Ala
            660                 665                 670
```

```
Val Ala Met Leu Glu Asp Leu Gln Met Ser Val Gly Tyr Gln Leu Glu
            675                 680                 685
Asp Glu
    690

<210> SEQ ID NO 590
<211> LENGTH: 683
<212> TYPE: PRT
<213> ORGANISM: Raphanus sativus

<400> SEQUENCE: 590

Met Leu Ala Arg Val Tyr Arg Ser Gly Ser Ser Ser Pro Ala Val
1               5                   10                  15

Ser Ala Ala Arg Leu Phe Cys Thr Arg Ser Ile Arg His Ala Leu Ala
                20                  25                  30

Lys Lys Ser Arg Asp Gly Glu Ser Gly Phe Gly Gly Glu Ser Leu Lys
            35                  40                  45

Leu Arg Ser Gly Phe His Glu Ile Lys Gly Leu Glu Asp Ala Ile Asp
        50                  55                  60

Leu Phe Gly Asp Met Val Arg Ser Arg Pro Leu Pro Ser Val Ile Asp
65                  70                  75                  80

Phe Cys Lys Leu Met Gly Val Val Arg Met Gly Arg Leu Asp Val
                85                  90                  95

Val Ile Ser Leu His Arg Lys Met Glu Met Gly Arg Val Pro Cys Asn
                100                 105                 110

Ala Tyr Ser Phe Thr Ile Leu Met Lys Cys Phe Cys Ser Cys Ser Lys
            115                 120                 125

Leu Pro Phe Ala Leu Ser Thr Phe Gly Lys Ile Thr Lys Leu Gly Leu
        130                 135                 140

His Pro Asp Val Val Thr Phe Asn Thr Leu His Gly Leu Cys Val
145                 150                 155                 160

Glu Asp Arg Val Ser Glu Ala Leu Tyr Leu Phe His Gln Met Cys Lys
                165                 170                 175

Pro Asn Val Val Thr Phe Thr Thr Leu Met Lys Gly Leu Cys Arg Glu
            180                 185                 190

Gly Arg Val Val Glu Ala Val Ala Leu Leu Asp Arg Met Val Glu Asp
        195                 200                 205

Gly Leu Gln Pro Asn Gln Ile Thr Tyr Gly Thr Ile Val Asp Gly Met
    210                 215                 220

Cys Lys Met Gly Asp Ser Val Ser Ala Leu Asp Leu Leu Arg Lys Met
225                 230                 235                 240

Glu Glu Val Ser His Ile Lys Pro Asp Val Val Ile Tyr Ser Ala Ile
                245                 250                 255

Ile Asp Gly Leu Trp Lys Asp Gly Arg His Thr Asp Ala Gln Asn Leu
            260                 265                 270

Phe Ser Glu Met Gln Asp Lys Arg Ile Phe Pro Asp Leu Phe Thr Tyr
        275                 280                 285

Ser Cys Met Ile Asp Gly Phe Cys Ser Ser Gly Arg Trp Ser Glu Ala
    290                 295                 300

Gln Gln Leu Leu Gln Glu Met Leu Glu Arg Lys Ile Ser Pro Asp Val
305                 310                 315                 320

Val Thr Tyr Asn Ala Leu Ile Asn Ala Phe Val Lys Glu Gly Lys Phe
                325                 330                 335

Phe Glu Ala Glu Glu Leu Tyr Asp Glu Met Leu Pro Arg Gly Ile Ile
            340                 345                 350
```

```
Pro Asn Thr Ile Thr Tyr Ser Ser Met Ile Asp Gly Phe Cys Lys Gln
            355                 360                 365

Asn Arg Leu Asp Ala Ala Glu His Met Phe Tyr Leu Met Ala Thr Lys
        370                 375                 380

Gly Cys Ser Pro Asp Val Phe Thr Phe Asn Thr Leu Ile Asp Gly Tyr
385                 390                 395                 400

Cys Gly Ala Lys Arg Ile Asp Asp Gly Met Glu Leu Leu His Glu Met
                405                 410                 415

Thr Glu Ala Gly Leu Val Ala Asn Thr Val Thr Tyr Thr Thr Leu Ile
            420                 425                 430

His Gly Phe Cys Gln Val Gly Asp Leu Asn Ser Ala Gln Asp Leu Leu
        435                 440                 445

Gln Glu Met Ile Ser Ser Gly Val Cys Pro Asn Val Val Thr Cys Asn
    450                 455                 460

Thr Leu Leu Asp Gly Leu Cys Asp Asn Gly Lys Leu Lys Asp Ala Leu
465                 470                 475                 480

Lys Met Phe Lys Ala Met Gln Lys Ser Lys Lys Asn Phe Asp Ala Ser
                485                 490                 495

His Pro Phe Asn Gly Val Glu Pro Asp Val Leu Thr Tyr Asn Ile Leu
            500                 505                 510

Ile Cys Gly Leu Ile Asn Glu Gly Lys Phe Ile Glu Ala Glu Glu Leu
        515                 520                 525

Tyr Glu Glu Met Pro His Arg Gly Ile Val Pro Asp Thr Ile Thr Tyr
    530                 535                 540

Ser Ser Met Ile Asp Gly Leu Cys Lys Gln Ser Arg Leu Asp Glu Ala
545                 550                 555                 560

Thr Gln Met Ser Asp Ser Met Gly Ser Lys Ser Phe Ser Pro Asn Val
                565                 570                 575

Val Thr Phe Asn Thr Leu Ile Asn Gly Tyr Cys Lys Ala Gly Arg Val
            580                 585                 590

Asp Asp Gly Leu Glu Leu Phe Cys Glu Met Gly Arg Gly Ile Val
        595                 600                 605

Ala Asn Ala Ile Thr Tyr Ile Thr Leu Ile Tyr Gly Ser Arg Lys Val
    610                 615                 620

Gly Asn Ile Asn Gly Ala Leu Asp Ile Phe Gln Glu Met Ile Ser Ser
625                 630                 635                 640

Gly Val Tyr Pro Asp Thr Ile Thr Ile Arg Asn Met Leu Thr Gly Leu
                645                 650                 655

Trp Ser Lys Glu Glu Leu Glu Arg Ala Val Ala Met Leu Glu Val Leu
            660                 665                 670

Gln Met Ser Val Gly Tyr Gln Leu Glu Asp Glu
        675                 680

<210> SEQ ID NO 591
<211> LENGTH: 686
<212> TYPE: PRT
<213> ORGANISM: Raphanus sativus

<400> SEQUENCE: 591

Met Leu Ala Arg Val Cys Arg Phe Glu Ser Ser Ser Ser Ser Ser Val
1               5                   10                  15

Ser Ala Ala Arg Leu Leu Cys Thr Arg Ser Ile His Leu Pro Leu Ala
            20                  25                  30

Glu Lys Ser Arg Asp Gly Glu Asn Gly Glu Ala Gly Ser Gly Gly Glu
```

```
                35                  40                  45
Ser Leu Lys Leu Gln Ser Gly Ser Tyr Glu Ile Lys Gly Leu Glu Asp
 50                  55                  60

Ala Ile Asp Leu Phe Ser Asp Met Leu Arg Ser Pro Leu Pro Ser
 65                  70                  75                  80

Val Ile Asp Phe Asn Lys Leu Met Gly Ala Val Arg Met Glu Arg
                 85                  90                  95

Pro Asp Leu Val Ile Ser Leu Tyr Gln Lys Met Glu Arg Lys Gln Ile
                100                 105                 110

Arg Cys Asp Ile Tyr Ser Phe Thr Ile Leu Ile Lys Cys Phe Cys Ser
                115                 120                 125

Cys Ser Lys Leu Pro Val Ala Leu Ser Thr Phe Gly Lys Leu Thr Lys
130                 135                 140

Leu Gly Leu His Pro Asp Val Val Thr Phe Thr Thr Leu Leu His Gly
145                 150                 155                 160

Leu Cys Val Glu Asp Arg Val Ser Glu Ala Leu Asp Leu Phe His Gln
                165                 170                 175

Met Cys Lys Pro Asn Val Val Thr Phe Asn Thr Leu Met Asn Gly Leu
                180                 185                 190

Cys Arg Glu Gly Arg Val Val Glu Ala Val Ala Leu Leu Asp Gln Met
                195                 200                 205

Val Glu Asn Gly Leu Gln Pro Asp Gln Ile Thr Tyr Gly Thr Ile Val
210                 215                 220

Asp Gly Met Cys Lys Met Gly Asp Thr Val Ser Ala Leu Asn Leu Leu
225                 230                 235                 240

Arg Lys Met Glu Glu Val Ser His Ile Ile Pro Asn Val Val Ile Tyr
                245                 250                 255

Ser Ala Ile Ile Asp Gly Leu Cys Lys Asp Gly Arg His Ser Asp Ala
                260                 265                 270

His Asn Leu Phe Ile Glu Met Gln Asp Lys Gly Ile Phe Pro Asn Ile
                275                 280                 285

Val Thr Tyr Asn Cys Met Ile Gly Gly Phe Cys Ile Ser Gly Arg Trp
                290                 295                 300

Ser Ala Ala Gln Arg Leu Leu Gln Glu Met Leu Val Arg Lys Ile Ser
305                 310                 315                 320

Pro Asn Val Val Thr Tyr Asn Ala Leu Ile Asn Ala Phe Val Lys Glu
                325                 330                 335

Gly Lys Phe Phe Glu Ala Glu Glu Leu Tyr Asp Glu Met Leu Pro Arg
                340                 345                 350

Gly Ile Ile Pro Asn Thr Ile Thr Tyr Asn Ser Met Ile Asp Gly Phe
                355                 360                 365

Cys Lys Gln Asn Arg Leu Asp Ala Ala Glu His Met Phe Tyr Val Met
                370                 375                 380

Ala Thr Lys Gly Cys Ser Pro Asp Val Phe Thr Phe Asn Thr Leu Ile
385                 390                 395                 400

Asp Gly Tyr Cys Gly Ala Lys Arg Ile Asp Asp Gly Met Glu Leu Leu
                405                 410                 415

His Glu Met Thr Glu Thr Gly Leu Val Ala Asp Thr Thr Tyr Asn
                420                 425                 430

Thr Leu Ile His Gly Phe Cys Leu Val Gly Asp Leu Asn Ala Ala Leu
                435                 440                 445

Asp Leu Leu Gln Glu Met Val Ser Ser Gly Val Cys Pro Asp Ile Val
450                 455                 460
```

```
Thr Cys Asn Thr Leu Leu Asp Gly Leu Cys Asp Asn Gly Lys Leu Lys
465                 470                475                480

Asp Ala Leu Glu Met Phe Lys Ala Met Gln Lys Ser Lys Met Tyr Ile
                485                490                495

Asp Ala Ser His Pro Phe Asn Gly Val Glu Pro Asp Val Leu Thr Tyr
            500                505                510

Asn Ile Leu Ile Cys Gly Leu Ile Asn Glu Gly Lys Phe Leu Glu Ala
        515                520                525

Glu Glu Leu Tyr Glu Glu Met Pro His Arg Gly Ile Val Pro Asp Thr
    530                535                540

Ile Thr Tyr Ser Ser Met Ile Asp Gly Leu Cys Lys Gln Ser Arg Leu
545                 550                555                560

Asp Glu Ala Thr Gln Met Phe Val Ser Met Gly Ser Lys Ser Phe Ser
                565                570                575

Pro Asn Val Val Thr Phe Asn Thr Leu Ile Asn Gly Tyr Cys Lys Ala
            580                585                590

Gly Arg Val Asp Asp Gly Leu Glu Leu Phe Cys Glu Met Gly Arg Arg
        595                600                605

Gly Ile Val Ala Asp Ala Ile Thr Tyr Ile Thr Leu Ile Tyr Gly Phe
        610                615                620

Arg Lys Val Gly Asn Ile Asn Gly Ala Leu Asp Ile Phe Gln Glu Met
625                 630                635                640

Met Ala Ser Gly Val Tyr Pro Asp Thr Ile Thr Ile Arg Asn Met Leu
            645                650                655

Thr Gly Leu Trp Ser Lys Glu Glu Leu Lys Arg Ala Val Ala Met Leu
            660                665                670

Glu Asp Leu Gln Met Ser Val Gly Tyr Gln Leu Glu Asp Glu
            675                680                685
```